US006555339B1

(12) United States Patent
Liaw et al.

(10) Patent No.: US 6,555,339 B1
(45) Date of Patent: Apr. 29, 2003

(54) NON-ENDOGENOUS, CONSTITUTIVELY ACTIVATED HUMAN PROTEIN-COUPLED RECEPTORS

(75) Inventors: Chen W. Liaw, San Diego, CA (US); Dominic P. Behan, San Diego, CA (US); Derek T. Chalmers, Solana Beach, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/170,496

(22) Filed: Oct. 13, 1998

Related U.S. Application Data

(63) Continuation-in-part of application No. 09/060,188, filed on Apr. 14, 1998, which is a continuation-in-part of application No. 08/839,449, filed on Apr. 14, 1997, now abandoned.
(60) Provisional application No. 60/090,783, filed on Jun. 26, 1998, and provisional application No. 60/095,677, filed on Aug. 7, 1998.

(51) Int. Cl.⁷ .......................... C12N 15/00; C12N 15/63; C07H 21/04; G06F 19/00; C07K 14/00
(52) U.S. Cl. .................. 435/69.1; 435/320.1; 435/325; 435/252.3; 435/172.3; 435/68.1; 530/333; 530/300; 530/350; 702/19; 702/20; 702/22; 536/23.1; 536/24.31
(58) Field of Search ............................. 702/19, 20, 22; 536/23.1, 24.3; 435/69.1, 320.1, 325, 252.3, 172.3, 68.1; 530/333, 300, 350

(56) References Cited

U.S. PATENT DOCUMENTS

| 5,514,578 A | 5/1996 | Hogness et al. .......... 435/240.2 |
| 5,532,157 A | 7/1996 | Fink ......................... 435/240.2 |
| 5,573,944 A | 11/1996 | Kirschner et al. ........ 435/252.3 |
| 5,639,616 A | 6/1997 | Liao et al. .................... 435/7.1 |
| 5,750,353 A | 5/1998 | Kopin et al. ................ 435/7.21 |
| 5,861,309 A | 1/1999 | Bard et al. ................... 135/325 |
| 5,891,720 A | 4/1999 | Moore et al. ............... 435/325 |
| 5,955,308 A | 9/1999 | Bergsma et al. ........... 435/69.1 |

FOREIGN PATENT DOCUMENTS

| CA | 2135253 | 5/1996 |
| EP | 0 612 845 A2 | 8/1994 |
| EP | 0 878 542 A2 | 11/1998 |
| EP | 0 892 051 A2 | 1/1999 |
| EP | 1 090 989 A1 | 4/2001 |
| EP | 1 094 076 A1 | 4/2001 |
| JP | WO/99 24569 | 5/1999 |
| WO | WO 96/05302 | 2/1996 |
| WO | WO 97/11159 | 9/1996 |
| WO | WO 97/21731 | 6/1997 |
| WO | WO 97 21731 A | 6/1997 |
| WO | WO 98 38217 A | 3/1998 |
| WO | WO 98/29439 | 7/1998 |
| WO | WO 98/00552 | 8/1998 |
| WO | WO 98/34948 | 8/1998 |
| WO | WO 98/46620 | 10/1998 |
| WO | WO 98/46995 | 10/1998 |
| WO | WO 98/56820 | 12/1998 |
| WO | WO 99/06552 | 2/1999 |
| WO | WO 99/32519 | 7/1999 |
| WO | WO 99/48921 | 9/1999 |
| WO | WO 99/52927 | 10/1999 |
| WO | WO 00/22131 | 4/2000 |
| WO | WO 01/07606 A1 | 2/2001 |
| WO | WO 01/09184 A1 | 2/2001 |
| WO | WO 01/12673 A1 | 2/2001 |
| WO | WO 01/14577 A1 | 3/2001 |
| WO | WO 01/16159 A1 | 3/2001 |
| WO | WO 01/31014 A2 | 5/2001 |
| WO | WO 01/36471 A2 | 5/2001 |

OTHER PUBLICATIONS

Shryock, John et al., "Inverse Agonists and Neutral Antagonists of Recombinant Human $A_1$ Adenosine Receptors Stably Expressed in Chinese Hamster Ovary Cells," *Molecular Pharmacology*, 1998, 53, pp. 886–893.

Wenzel–Seifert et al., "High Constitutive Activity of the Human Formyl Peptide Receptor", *Journal of Biological Chem.*, 1998, 273, pp. 24181–24189.

Forman, B.M. et al., "Androstane Metabolites Bind to and Deactivate the Nuclear Receptor CAR–β", *Nature*, 1998, 395, pp. 612–615.

(List continued on next page.)

*Primary Examiner*—Yvonne Eyler
*Assistant Examiner*—Nirmal S. Basi
(74) *Attorney, Agent, or Firm*—Cozen O'Connor, P.C.

(57) ABSTRACT

Disclosed are constitutively activated, non-endogenous versions of endogenous human GPCRs comprising the following amino acid sequence region (C-terminus to N-terminus orientation) and/or the following nucleic acid sequence region (3' to 5' orientation) transversing the transmembrane-6 (TM6) and intracellular loop-3 (IC3) regions of the GPCR:

$$P^1 AA_{15} X \qquad (a)$$

and/or $$P^{codon}(AA\text{-}codon)_{15} X_{codon}, \qquad (b)$$

respectively. In a preferred embodiment, $P^1$ and $P^{codon}$ are endogenous proline and an endogenous nucleic acid encoding region encoding proline, respectively, located within TM6 of the non-endogenous GPCR; $AA_{15}$ and (AA-codon)$_{15}$ are 15 endogenous amino acid residues and 15 codons encoding endogenous amino acid residues, respectively; and X and $X_{codon}$ are non-endogenous lysine and non-endogenous nucleic acid region encoding lysine, respectively, located within IC3 of the non-endogenous GPCR. The purified and isolated non-endogenous human GPCRs having these mutations, and the receptors incorporated into mammalian cells, are well within the present disclosure.

2 Claims, 17 Drawing Sheets

OTHER PUBLICATIONS

Seifert R. et al., Different Effects of $G_s\alpha$ Splice Variants of $\beta_2$–Adrenoreceptor–mediated Signaling, *Journal of Biological Chem.*, 1998, 273, pp. 5109–5116.

Abola, A.P., et al., "Omo sapiens chromosome 13 clone RP11–286P8, complete sequence," AC026756 XP–002175912, Apr. 24, 2000, 1–41.

Adams, M.D., et al., "CIT–HSP–2286K19.TF CIT–HSP *homo sapiens* genomic clone 2286K19, genomic survey sequence," AQ001459, XP–002175783, Aug. 24, 2001, 1 page.

Birren, B., et al., "Homo sapiens chromosome 11, clone RP11–589F4," AC027026, XP002175913, Apr. 27, 2000, 1–40.

Birren, B., et al., "Homo sapiens clone RP11–15H8, 31 unordered pieces," AC011780, XP002175781, Oct. 18, 1999, 1–46.

Birren, B., et al., "Homo sapiens clone RP11–14N15," AC016468, XP002175784, Dec. 1, 1999, 1–38.

Boyer, J.L., et al., "Molecular cloning and expression of an avian G protein–coupled P2Y receptor," *Am. Soc. For Pharmacology & Experimental Therapeutics*, XP–002175907, 1997, 928–934.

Burton, J., et al., "Human DNA sequence from clone RP11–163L4," A1161458, XP002175911, Apr. 16, 2000, 1–39.

Burton, J., "Human DNA sequence from clone RP11–15909," AL136106, XP002175785, Jan. 7, 2000.

Collier, R., "DJ68ON, 3 (G–protein coupled receptors) (fragment)," Accession Nr. Q9NTTO, XP002168498, Jan. 10, 2001, 1 page.

Doe Joint Genome Institute, "Homo sapiens chromosome 5 clone CTC–502M5, complete sequence," AC008547, XP002175786, Aug. 4, 1999, 1–30.

Doe Joint Genome Institute, "Homo sapiens chomosome 19 clone CTD–3023J11, complete sequence," AC008754, XP002175778, Aug. 4, 1999, 1–18.

Doe Joint Genome Institute, "Sequencing of human chromosome 5," ACC008728, XP002175776, Aug. 4, 1999, 1–42.

Gempscpue, "Drosophila melanogaster genome survey sequence TET3 end of BAC #BACRO8K10 of RPCI–98 library from drosophila melanogaster (fruit fly)," AL065769, XP00217590.

Hattori, M., et al., "Homo sapiens 171, 539 genomic of 11q13," AP000808, XP002175780, Dec. 3, 1999, 1–45.

Heise, C.E., et al., "Characterization of the human cysteinyl leukotriene 2 receptor," *J. Biological Chemistry*, Sep. 29, 2000, 275(39), 30531–30536.

Kjelsberg, M.A., et al., "constitutive activation of the $\alpha_{1B}$–adrenergic receptor by all amino acid substitutions at a single site," *J. Biological Chemistry*, XP–002135768, 1992, 265(3), 1430–1433.

Mahairas, G.G., et al., "Sequence–tagged connectors: A sequence approach to mapping and scanning the human genome," *Proc. Natl. Acad. Sci. USA*, Aug. 1999, 96, 9739–9744.

Marchese, A., et al., "Novel GPCRs and their endogenous ligands: expanding the boundaries of physiology and pharmacology," *TiPS*, Sep. 1999, 20, 370–375.

O'Dowd, B.F., et al., "Discovery of three novel G–protein–coupled receptor genes," *Genomics*, XP000863786, 1998, 310–313.

Ohono, M., et al., "Homo sapiens mRNA for G proteine–coupled receptor C5L2, complete cds," AB038237, XP002175947, May 4, 2000, 1 page.

Stadel, J.M., et al., "Orphan G protein–coupled receptors: a neglected opportunity for pioneer drug discovery," *TiPS*, Nov. 1997, 18, 430–437.

Stone, N., et al., "Homo sapiens chomosome 4, 16 unordered pieces," AC007104, XP002175914, Apr. 23, 1999, 1–52.

Wallis, J., "Human DNA sequence from clone RP5–1160K1," AL355310, XP002175782, May 5, 2000, 1–39.

Waterson, R.H., "homo sapiens chromosome 2 clone RP11–510c1," AC010984, XP002175915, Sep. 29, 1999, 1–50.

Weinshank, R.H., "5–hydroxytryptamine 1B receptor (–HT–1B) (serotonin receptor)," AC 008892, XP002175948, Jul. 15, 1998, 1 page.

Zhao, S., et al., "Use of BAC and sequences from library RPCI–11 for sequence–ready map building," AQ532303, XP002175779, May 18, 1999, 1 page.

Kjelsbergt, M., "Constitutive Activation of the $\alpha_{1B}$–Adrenergic Receptor by All Amino Acid Substitutions at a Single Site"; 1992; *The Journal of Biological Chemistry*; vol. 267, No. 3, Issue of Jan. 25, pp. 1430–1433.

Cotecchia, S., "Regions of the $\alpha_1$–adrenergic receptor involved in coupling to phosphatidylinositol hydrolysis and enhanced sensitivity of biological function"; 1990, *Proc. Natl. Acad. Sci. USA*, vol. 87, pp. 2896–2900.

Bergsma, D.J., et al., "Cloning and characterization of a human angiotensin II type 1 receptor," *Biochem. & Biophy. Res. Comm.*, 1992, XP–002145165, 183(3), 989–995.

Gantz, I., et al., "Molecular cloning, expression, and gene localization of a fourth melanocortin receptor," *J. Biol. Chem.*, 1993, XP–002051983, 268(20), 15174–15178.

Groblewski, T., et al., "Mutation of Asn$^{111}$ in the third transmembrane domain of the $AT_{1a}$ angiotensin II receptor induces its constitutive activation," *J. Biol. Chem.*, 1997, XP–002145162, 272(3), 1822–1826.

Koike, G., et al., "Human type 2 angiotensin II receptor gene: cloned, mapped to the X chromosome, and its mRNA is expressed in the human lung," *Biochem. And Biophy. Res. Comm.*, 1994, XP–002145166, 203(3), 1842–1850.

Kyaw, H., et al., "Cloning, characterization, and mapping of human homolog of mouse T–cell death–associated gene," *DNA and Cell Biology*, 1998, XP000929737, 17(6), 493–500.

Noda, K., et al., "The active state of the $AT_1$ angiotensin receptor is generated by angiotensin II induction," *Biochem.*, 1996, XP–002145163, 35, 16435–16442.

Reppert, S.M., et al., "Cloning of a melatonin–related receptor from human pituitary," *FEBS Letts.*, 1996, XP–002145161, 219–2254.

Scheer, A., et al., "Constitutively active G protein–coupled receptors: potential mechanisms of receptor activation," *J. Receptor & Signal Transduction Res.*, 1997, XP–000867531, 17(1–3), 57–73.

Pauwels P.J. et al., "Review: Amino Acid Domains Involved in Constitutive Activation of G–Protein–Coupled Receptors", *Molecular Neurobiology*, 1998, 17, pp. 109–135.

Watson, S. et al., The G–Protein Linked Receptor Facts Book, Academic Press, pp. 2–6 and 162–169, 1994.

Samama et al., A Mutation–induced Activated State of the Beta 2–Adrenergic Receptor, J. Biol. Chem., vol. 268, No. 7, pp. 4625–4636, 1993.

Rudinger, J et al., Peptide Hormones, ed. J. A. Parsons, University Park Press, Baltimore, pp. 1–7, 1976.

Alla, S.A. et al., "Extracellular domains of the bradykinin B2 receptor involved in ligand binding and agonist sensing defined by anti–peptide antibodies," *J. Biol. Chem.*, 1996, 271, 1748–1755.

Advenier, C. et al., "Effects of the isolated human bronchus of SR 48968, a potent and selective nonpeptide antagonist of the neurokinin A ($NK_2$) receptors," *Am. Rev. Respir. Dis.*, 1992, 146(5, Pt. 1), 1177–1181.

Alexander, W.S. et al., "Point mutations within the dimer interface homology domain of c–Mpl induce constitutive receptor activity and tumorigenicity," *EMBO J.*, 1995, 14(22), 5569–5578.

Arvanitikis, L. et al., "Human herpesvirus KSHV encodes a constitutively active G–protein–coupled receptor linked to cell proliferation," *Nature*, 1997, 385, 347–349.

Barker, E.L. et al., "Constitutively active 5–hydroxytryptamine$_{2C}$ receptors reveal novel inverse agonist activity of receptor ligands," *J. Biol. Chem.*, 1994, 269(16), 11687–11690.

Baxter, G., "5–$HT_2$ receptors: a family re–united?" *Trends Pharmacol. Sci.*, 1995, 16, 105–110.

Besmer, P. et al., "A new acute transforming feline retrovirus and relationship of its oncogene v–kit with the protein kinase gene family," *Nature*, 1986, 320, 415.

Blin, N. et al., "Mapping of single amino acid residues required for selective activation of $G_{q/11}$ by the m3 muscarinic acetylcholine receptor," *J. Biol. Chem.*, 1995, 270, 17741–17748.

Bond, R.A. et al., "Inverse agonists and G–protein–coupled receptors," in *Receptor–Based Drug Design*, Leff, P. (ed.), New York, M. Dekker, 1998, 363–377.

Boone, C. et al., "Mutations that alter the third cytoplasmic loop of the a–factor receptor lead to a constitutive and hypersensitive phenotype," *Proc. Natl. Acad. Sci. USA*, 1993, 90(21), 9921–9925.

Burstein, E.S. et al., "Constitutive activation of chimeric m2/m5 muscarinic receptors and delineation of G–protein coupling selectivity domains," *Biochem. Pharmacol.*, 1996, 51(4), 539–544.

Burstein, E.S. et al., "Amino acid side chains that define muscarinic receptor/G–protein coupling. Studies of the third intracellular loop," *J. Biol. Chem.*, 1996, 271(6), 2882–2885.

Burstein, E.S. et al., "Constitutive activation of muscarinic receptors by the G–protein $G_q$," *FEBS Lett.*, 1995, 363(3), 261–263.

Bylund, D., "International union of pharmacology nomenclature of adrenoceptors," *Pharmacol. Rev.*, 1994, 46, 121–136.

Casey, C. et al., "Constitutively active mutant 5–$HT_{2A}$ serotonin receptors: inverse agonist activity of classical 5$HT_{2A}$ antagonists," *Soc. Neurosci.*, 1996, Abstract #699.10.

Cheatham, B. et al., "Substitution of the erbB–2 oncoprotein transmembrane domain activates the insulin receptor and modulates the action of insulin–receptor substrate 1," *Proc. Natl. Acad. Sci. USA*, 1993, 90, 7336–7340.

Chen, J. et al., "Tethered Ligand Library for Discovery of Peptide Agonists," *J. Biol. Chem.*, 1995, 270, 23398–23401.

Chen, T.S. et al., "Microbial hydroxylation and glucuronidation of the angiotensin II (AII) receptor antagonist MK 954," *J. Antibiot. (Tokyo)*, 1993, 46(1), 131–134.

Chen, W. et al., "A colorimetric assay for measuring activation of $G_s$–$G_q$–coupled signaling pathways," *Anal. Biochem.*, 1995, 226(2), 349–354.

Chidiac, P. et al., "Inverse agonist activity of β–adrenergic antagonists," *J. Pharm. Exp. Ther.*, 1994, 45, 490–499.

Clozel, M. et al., "In vivo pharmacology of Ro 46–2005, the first synthetic nonpeptide endothelin receptor antagonist: implications for endothelin physiology," *J. Cardiovas. Pharmacol.*, 1993, 22(Suppl. 8), S377–S379.

Collesi, C. et al., "A splicing variant of the RON transcript induces constitutive tyrosine kinase activity and an invasive phenotype," *Mol. Cell. Biol.*, 1996, 16(2), 5518–5526.

Cooper, C.S. et al., "Molecular cloning of a new transforming gene from a chemically transformed human cell line," *Nature*, 1984, 311, 29–33.

De Dios, I. et al., "Effect of L–364,718 (CCK Receptor Antagonist) on Exocrine Pancreatic Secretion of Hydrocortison–Treated Rats," *Pancreas*, 1994, 9(2), 212–218.

Desbios–Mouthon, C. et al., "Deletion of $Asn^{281}$ in the α–subunit of the human insulin receptor causes constitutive activation of the receptor and insulin desensitization," *J. Clin. Endocrinol. Metab.*, 1996, 81(2), 719–727.

Di Renzo, M.F. et al., "Expression of the Met/HGF receptor in normal and neoplastic human tissues," *Oncogene*, 1991, 6(11), 1997–2003.

Di Renzo, M.F. et al., "Overexpression of the c–MET/HGT receptor gene in human thyroid carcinomas," *Oncogene*, 1992, 7, 2549–2553.

Duprez, L. et al., "Germline mutations of the thyrotropin receptor gene cause non–autoimmune autosomal dominant hyperethyroidism," *Nature Genetics*, 1994, 7, 396–401.

Eggericksx, D. et al., "Molecular Cloning of an Orphan G–Protein–Coupled Receptor that Constitutively Activates Adenylate Cyclase," *Biochem. J.*, 1995, 309, 837–843.

Evans, B.E. et al., "Orally Active, Nonpeptide Oxytocin Antagonists," *J. Med. Chem.*, 1992, 35, 3919–3927.

Fu, M. et al., "Functional autoimmune epitope on $α_1$–adrenergic receptors in patients with malignant hypertension," *Lancet*, 1994, 344, 1660–1663.

Furitsu, T. et al., "Identification of Mutations in the Coding Sequence of the Proto–oncogene c–kit in a Human Mast Cell Leukemia Cell Line Causing Ligand–independent Activation of c–kit Product," *J. Clin. Invest.*, 1993, 1736–1744.

Gellai, M. et al., "Nonpeptide Endothelin Receptor Antagonists V: Prevention and Reversal of Acute Renal Failure in the Rat by SB 209670," *J. Pharm. Exp. Therap.*, 1995, 275(1), 200–206.

Gitter, B. et al., "Pharmacological Characterization of LY303870: A Novel Potent and Selective Nonpeptide Substance P (Neurokinin–1) Receptor Antagonist," *J. Pharm. Exp. Therp.*, 1995, 275(2), 737–744.

Gouilleux–Gruart, V. et al., "STAT–Related Transcription Factors are Constitutively Activated in Peripheral Blood Cells from Acute Leukemia Patients," *Blood*, 1996, 87(5), 1692–1697.

Hansson, J.H. et al., "Hypertension caused by a truncated epithelial sodium channel γ subunit: genetic heterogeneity of Liddle syndrome," *Nat. Genet.*, 1995, 11(1), 76–82.

Hasegawa, H. et al., "Two Isoforms of the Prostaglandin E Receptor EP3 Subtype Different in Agonist–independent Constitutive Activity," *J. Biol. Chem.*, 1996, 271(4), 1857–1860.

Hendler, F. et al., "Human Squamous Cell Lung Cancers Express Increased Epidermal Growth Factor Receptors," *J. Clin. Invest.*, 1984, 74, 647–651.

Herrick–Davis, K. et al., "Constitutively Active 5HT2C Serotonin Receptor Created by Site–Directed Mutagenesis," *Soc. Neurosci.*, Abstract No. 699.18.

Hieble, J., "International union of pharmacology. X. Recommendation for nomenclature of 1–adrenoceptors," *Pharm. Rev.*, 1995, 47, 267–270.

Hill, S., "Distribution, Properties, and Functional Characteristics of Three Classes of Histamine Receptor," *Am. Soc. Pharm. Exp. Therap.*, 1990, 42(1), 45–83.

Högger, P. et al., "Activating and Inactivating Mutations in—and C–terminal i3 Loop Junctions of Muscarinic Acetylcholine Hm1 Receptors," *J. Biol. Chem.*, 1995, 270(13), 7405–7410.

Ikeda, H. et al., "Expression and Functional Role of the Proto–oncogene c–kit in Acute Myeloblastic Leukemia Cells," *Blood*, 1991, 78(11), 2962–2968.

Imura, R. et al., "Inhibition by HS–142–1, a novel nonpeptide atrial natriuretic peptide antagonist of microbial origin, or atrial natriuretic peptide–induced relaxation of isolated rabbit aorta through the blockade of guanylyl cyclase–linked receptors," *Mol. Pharm.*, 1992, 42, 982–990.

Jakubik, J. et al., "Constitutive activity of the $M_1$–$M_4$ subtypes of muscarinic receptors in transfected CHO cells and of muscarinic receptors in the heart cells revealed by negative antagonists," *FEBS Letts.*, 1995, 377, 275–279.

Kjelsberg, M.A. et al., "Constitutive activation of the $\alpha_{1B}$–adrenergic receptor by all amino acid substitutions at a single site," *J. Biol. Chem.*, 1992, 267(3), 1430–1433.

Knapp, R. et al., "Molecular biology and pharmacology of cloned opioid receptors," *FASEB J.*, 1995, 9, 516–525.

Kosugi, S. et al., "Characterization of heterogeneous mutations causing constitutive activation of the luteinizing hormone receptor in familial male precocious puberty," *Human Mol. Genetics*, 1995, 4(2), 183–188.

Kosugi, S. et al., "Identification of Thyroid–Stimulating Antibody–Specific Interaction Sites in the N–Terminal Region of the Thyrotropin Receptor," *Mol. Endocrinology*, 1993, 7, 114–130.

Kraus, M. et al., "Demonstration of ligand–dependent signaling by the erbB–3 tyrosine kinase and its constitutive activation in human breast tumor cells," *Proc. Natl. Acad. Sci. USA*, 1993, 90, 2900–2904.

Kudlacz, et al., "In Vitro and In Vivo Characterization of MDL 105,212A, a Nonpeptide NK–1/NK–2 Tachykinin Receptor Antagonist," *J. Pharm. Exp. Therap.*, 1996, 277(2), 840–851.

Kuriu, A. et al., "Proliferation of Human Myeloid Leukemia Cell Line Associated with the Tyrosine–Phosphorylation and Activation of the Proto–oncogene c–kit Product," *Blood*, 1991, 78(11), 2834–2840.

Labbé–Jullié, C. et al., "Effect of the nonpeptide neurotensin antagonist, SR 48692, and two enantiomeric analogs, SR 48527 and SR 49711, on neurotension binding and contractile responses in guinea pig ileum and colon," *J. Pharm. Exp. Therap.*, 1994, 271(1), 267–276.

Latronico, A. et al., "A novel mutation of the luteinizing hormone receptor gene causing male gonadotropin–independent precocious puberty," *J. Clin. Endocrinol. Metabl.*, 1995, 80(8), 2490–2494.

Laue, L. et al., "Genetic heterogeneity of constitutively activating mutations of the human luteinizing hormone receptor in familial male–limited precocious puberty," *Proc. Natl. Acad. Sci. USA*, 1995, 92, 1906–1910.

Løvlie, R. et al., "The $Ca^{2+}$–sensing receptor gene (PCAR1) mutation T151M in isolated autosomal dominant hypoparathyroidism," *Hum. Genet*, 1996, 98, 129–133.

Lefkowitz, R. et al., "Constitutive activity of receptors coupled to guanine nucleotide regulatory proteins," *Trends Pharmacol. Sci.*, 1993, 14, 300–307.

Libermann, T. et al., "Amplification, enhanced expression and possible rearrangement of EGF receptor gene in primary human brain tumours of glial origin," *Nature*, 1985, 313, 144–147.

Liu, C. et al., "Overexpression of c–met proto–oncogene but not epidermal growth factor receptor or c–erbB–2 in primary human colorectal carcinomas," *Oncogene*, 1992, 7, 181–185.

Liu, J. et al., "Molecular mechanisma involved in muscarinic acetylcholine receptor–mediated G protein activation studied by insertion mutagenesis," *J. Biol. Chem.*, 1996, 271(11), 6172–6178.

Lonardo, F. et al., "The normal erbB–2 product is an atypical receptor–like tyrosine kinase with constitutive activity in the absence of ligand," *New Biologist*, 1990, 2(11), 992–1003.

Maenhaut, C. et al., "RDC8 codes for an adenosine A2 receptor with physiological constitutive activity," *Biochem. Biophys. Res. Comm.*, 1990, 173(3), 1169–1178.

Mann, J. et al., "Increased $serotonin_2$ and β–adrenergic receptor binding in the frontal cortices of suicide victims," *Arch. Gen. Psychiatry*, 1986, 43, 954–959.

Marone, R.L. et al., "Human CRF receptor chimeras: Mapping of ligand binding determinants," 26th Meeting of the Society of Neuroscience, Washington, D.C. Nov. 16–21, 1996, Abstract No. 609.8.

Magnusson, Y. et al., "Autoimmunity in idiopathic dilated cardiomyopathy," *Circulation*, 1994, 89, 2760–2767.

Matus–Leibovitch, N. et al., "Truncation of the thyrotropin–releasing hormone receptor carboxyl tail causes constitutive activity and leads to impaired responsiveness in Xenopus Oocytes and AtT20 Cells," *J. Biol. Chem.*, 1995, 270(3), 1041–1047.

Myles, G.M. et al., "Tyrosine 569 in the c–Fms juxtamembrane domain is essential for kinase activity and macrophage colony–stimulating factor–dependent internalization," *Mol. Cell. Biol.*, 1994, 14(7), 4843–4854.

Nanevicz, T. et al., "Thrombin receptor activating mutations," *J. Biol. Chem.*, 1996, 271(2), 702–706.

Natali, P.G. et al., "Expression of the c–Met/HGF receptor in human melanocytic neoplasms: demonstration of the relationship to malignant melanoma tumour progression," *Br. J. Cancer*, 1993, 68, 746–750.

Neilson, K.M. et al., "Constitutive activation of fibroblast growth factor receptor–2 by a point mutation associated with Crouzon syndrome," *J. Biol. Chem.*, 1995, 270(44), 26037–26040.

Oda, S. et al., "Pharmacological profile of HS–142–1, a novel nonpeptide atrial natriuretic peptide (ANP) antagonist of microbial origin. II. Restoration by HS–141–1 of ANP–induced inhibition of aldosterone production in adrenal glomerulosa cells," *J. Pharm. Exp. Ther.*, 1992, 263(1), 241–245.

O'Dowd, B.F. et al., "Site–directed mutagenesis of the cytoplasmic domains of the human β2–adrenergic receptor," *J. Biol. Chem.*, 1988, 263(31), 15985–15992.

Offermanns, S. et al., "G$\alpha_{15}$ and G$\alpha_{16}$ Couple a Wide Variety of Receptors to Phospholipase C," *J. Biol. Chem.*, 1995, 270, 15175–15180.

Palkowitz, A.D. et al., "Structural evolution and pharmacology of a novel series of triacid angiotensin II receptor antagonists," *J. Med. Chem.*, 1994, 37, 4508–4521.

Parent, J. et al., "Mutations of two adjacent amino acids generate inactive and constitutively active forms of the human platelet–activating factor receptor," *J. Biol. Chem.*, 1996, 271(14), 7949–7955.

Parfitt, A.M. et al., "Hypercalcemia due to constitutive activity of the parathyroid hormone (PTH)/PTH–related peptide receptor: comparison with primary hyperparathyroidism," *J. Clin. Endocr. Metabl.*, 1996, 81, 3584–3588.

Parma, J. et al., "Somatic mutations in the thyrotropin receptor gene cause hyperfunctioning thyroid adenomas," *Nature*, 1993, 365, 649–651.

Pei, G. et al., "A constitutive active mutant β$_2$–adrenergic receptor is constitutively desensitized and phosphorylated," *Proc. Natl. Acad. Sci. USA*, 1994, 91, 2699–2702.

Pendley, C.E. et al., "The gastrin/cholecystokinin–B receptor antagonist L–365,260 reduces basal acid secretion and prevents gastrointestinal damage induced by aspirin, ethanol and cysteamine in the rat," *J. Pharmacol. Exp. Ther.*, 1993, 265(3), 1348–1354.

Peroutka, S., "Serotonin receptor subtypes. Their evolution and clinical relevance," *CNS Drugs*, 1995, 4 (Suppl. 1), 18–28.

Pettibone, D.J. et al., "Development and pharmacological assessment of novel peptide and nonpeptide oxytocin antagonists," *Regul. Pept.*, 1993, 45, 289–293.

Prat, M.P. et al., "The receptor encoded by the human c–Met oncogene is expressed in hepatocytes, epithelial cells and solid tumors," *Int. J. Cancer*, 1991, 49, 323–328.

Prezeua, L. et al., "Changes in the carboxy–terminal domain of metabotropic glutamate receptor 1 by alternate splicing generate receptors with differing agonist–independent activity," *Mol. Pharmacol.*, 1996, 49, 422–429.

Rakovska, A. et al., "Effect of loxiglumide (CR 1505) on CCK–induced contractions and $^3$H–acetylcholine release from guinea–pig gallbladder," *Neuropeptides*, 1993, 25(5), 271–276.

Ren, Q. et al., "Constitutive active mutants of the $\alpha_2$–adrenergic receptor," *J. Biol. Chem.*, 1993, 268, 16483–16487.

Reynolds, E.E. et al., "Pharmacological characterization of PD 156707, an orally active EH$_A$ receptor antagonist," *J. Pharmacol. Exp. Ther.*, 1995, 273(3), 1410–1417.

Robbins, L.S. et al., "Pigmentation phenotypes of variant extension locus alleles result from point mutations that alter MSH receptor function," *Cell*, 1993, 72, 827–834.

Rong, S. et al., "Met expression and sarcoma tumorigenicity," *Cancer*, 1993, 53(22), 5355–5360.

Samama, P. et al., "A mutation–induced activation state of the β–adrenergic receptor," *J. Biol. Chem.*, 1993, 268(7), 4625–4636.

Sautel, M. et al., "Neuropeptide Y and the nonpeptide antagonist BIBP 3226 share an overlapping binding site at the human Y1 receptor," *Am. Soc. Pharm. Exp. Ther.*, 1996, 50, 285–292.

Sawutz, D.G. et al., "Pharmacology and structure–activity relationships of the nonpeptide bradykinin receptor antagonist WIN 64338," *Can. J. Physiol. Pharmacol.*, 1995, 73, 805–811.

Scheer, A. et al., "Constitutively active G protein–coupled receptors: potential mechanisms of receptor activation," *J. Rec. Signal Transduct. Res.*, 1997, 17(1–3), 57–73.

Scheer, A. et al., "The activation process of the $\alpha_{1B}$–adrenergic receptor: Potential role of protonation and hydrophobicity of a highly conserved aspartate," *Proc. Natl. Acad. Sci. USA*, 1997, 94, 808–813.

Schwinn, D.A. et al., "Cloning and pharmacological characterization of human Alpha–1 adrenergic receptors: sequence corrections and direct comparison with other species homologues," *J. Pharmacol.*, 1995, 272(1), 134–142.

Schild, L. et al., "A mutation in the epithelial sodium channel causing Liddle disease increases channel activity in the *Xenopus laevis* oocyte expression system," *Proc. Natl. Acad. Sci. USA*, 1995, 92, 5699–5703.

Seeman, P. et al., "Dopamine receptor pharmacology," *Trends Pharmacol. Sci.*, 1994, 15, 264–270.

Seeman, P. et al., "Dopamine D4 receptors elevated in schizophrenia," *Nature*, 1993, 365, 441–445.

Serradeil–Le Gale, C. et al., "Biochemical and pharmacological properties of SR 49059, a new, potent, nonpeptide antagonist of rat and human vasopressin V$_{1a}$ receptors," *J. Clin. Invest.*, 1993, 92, 224–231.

Sharif, M. et al., "Malignant transformation by G protein–coupled hormone receptors," *Mol. Cell. Endocrinology*, 1994, 100, 115–119.

Showers, M.O. et al., "Activation of the erythropoietin receptor by the Friend spleen focus–forming virus gp55 glycoprotein induces constitutive protein tyrosine phosphorylation," *Blood*, 1992, 80(12), 3070–3078.

Skinner, R.H. et al., "Direct measurement of the binding of RAS to neurofibromin using scintillation proximity assay," *Anal. Biochem.*, 1994, 223, 259–265.

Slamon, D.J. et al., "Human breast cancer: correlation of relapse and survival with amplification of the HER–2/neu oncogene," *Science*, 1987, 235, 177–182.

Slamon, D. et al., "Studies of the HER–2/neu proto–oncogene in human breast and ovarian cancer," *Science*, 1989, 244, 707–712.

Solomon, Y. et al., "A highly sensitive adenylate cyclase assay," *Anal. Biochem.*, 1974, 58, 541–548.

Spiegel, A.M., "Defects in G protein–coupled signal transduction in human disease," *Ann. Rev. Physiol.*, 1995, 58, 143–170.

ter Laak, A. et al., "Modelling and mutation studies on the histamine H$_1$–receptor agonist binding site reveal different binding modes for H$_1$–agonists: Asp$^{116}$ (TM3) has a constitutive role in receptor stimulation," *J. Computer–Aided Mol. Design*, 1995, 9, 319–330.

Tiberi, M. et al., "High agonist–independent activity is a distinguishing feature of the dopamine D1B receptor subtype," *J. Biol. Chem.*, 1994, 269(45), 27925–27931.

Tsujimura, T. et al., "Constitutive activation of c–kit in FMA3 murine mastocytoma cells caused by deletion of seven amino acids at the juxtamembrane domain," *Blood*, 1996, 87(1), 273–283.

Wang, Z. et al., "Constitutive μ opioid receptor activation as a regulatory mechanism underlying narcotic tolerance and dependence," *Life Sci.*, 1994, 54(20), 339–350.

Watowich, S.S. et al., "Homodimerization and constitutive activation of the erythropoietin receptor," *Proc. Natl. Acad. Sci USA*, 1992, 89, 2140–2144.

Weber–Nordt, R.M. et al., "Constitutive activation of STAT proteins in primary lymphoid and myeloid leukemia cells and in Epstein–Barr virus (EBV)–related lymphoma cell lines," *Blood*, 1996, 88(3), 809–816.

Webster, M.K. et al., "Constitutive activation of fibroblast growth factor receptor 3 by the transmembrane point mutation found in achondroplasia," *EMBO J.*, 1996, 15, 520–527.

Xu, Y. et al., "Characterization of epidermal growth factor receptor gene expression in malignant and normal human cell lines," *Proc. Natl. Acad. Sci. USA*, 1984, 81, 7308–7312.

Yamada, K. et al., "Substitution of the insulin receptor transmembrane domain with the c–neu/erbB2 transmembrane domain constitutively activates the insulin receptor kinas in vitro," *J. Biol. Chem.*, 1992, 267(18), 12452–12461.

Zhang, S. et al., "Identification of Dynorphins as Endogenous Ligands for an Opioid Receptor–Like Orphan Receptor," *J. Biol. Chem.*, 1995, 270, 22772–22778.

Zhen, Z. et al., "Structural and functional domains critical for constitutive activation of the HGF–receptor (Met)," *Oncogene*, 1994, 9, 1691–1697.

(SEQ ID NOS: 287-94)

```
                                        Pst I
                                        Ava I
                                        Nci I
                                        Nci I            BsrB I
         EcoR V                         Sma I            Not I        Sac II
    Hind III   EcoR I                   BamH I Spe I Xba I  Hae III   BstX I  Sac I
    AAGCTTGATATCGAATTCCTGCAGCCCGGGGGATCCACTAGTTCTAGAGCGGCCGCCACCGCGGTGGAGCTCCAGCTTTT
    |----+----|----+----|----+----|----+----|----+----|----+----|----+----|----+----|  80
    TTCGAACTATAGCTTAAGGACGTCGGGCCCCCTAGGTGATCAAGATCTCGCCGGCGGTGGCGCCACCTCGAGGTCGAAAA K  L  D  I  E  F  L  Q  P  G  G  D  P  T  S  S  R  A  A  A  T  A  V  E  L  Q  L  L
        S  L  I  S  N  S  C  S  P  G  D  P  L  V  L  E  R  P  P  P  P  R  W  S  S  S  F
         Q  A  ·  Y  R  I  P  A  A  R  G  I  H  ·  F  ·  S  G  R  H  R  G  G  A  P  A  F
       +----+----+----+----+----+----+----+----+----+----+----+----+----+----+----+----+
       L  S  S  I  S  N  R  C  G  P  P  D  V  L  E  L  A  A  A  V  A  T  S  S  W  S  K
        L  K  I  D  F  E  Q  L  G  P  S  G  S  T  R  S  R  G  G  R  H  L  E  L  K  Q
         A  Q  Y  R  I  G  A  A  R  P  I  W  ·  N  ·  L  P  R  W  R  P  P  A  G  A  K BssH II
    GTTCCCTTTAGTGAGGGTTAATTGCGCGCTAGAGGATCTTTGTGAAGGAACCTTACTTCTGTGGTGTGACATAATTGGAC
    |----+----|----+----|----+----|----+----|----+----|----+----|----+----|----+----|  160
    CAAGGGAAATCACTCCCAATTAACGCGCGATCTCCTAGAAACACTTCCTTGGAATGAAGACACCACACTGTATTAACCTG F  P  L  V  R  V  N  C  A  L  E  D  L  C  E  G  T  L  L  L  W  C  D  I  I  G
        C  S  L  ·  ·  G  L  I  A  R  ·  R  I  F  V  K  E  P  Y  F  C  G  V  T  ·  L  D
         V  P  F  S  E  G  ·  L  R  A  R  G  S  L  ·  R  N  L  T  S  V  V  ·  H  N  W  T
       +----+----+----+----+----+----+----+----+----+----+----+----+----+----+----+----+
       N  G  K  T  L  T  L  Q  A  S  S  S  R  Q  S  P  V  K  S  R  H  H  S  M  I  P  C
        E  R  ·  H  P  N  I  A  R  ·  L  I  K  T  F  S  G  ·  K  Q  P  T  V  Y  N  S
         T  G  K  L  S  P  ·  N  R  A  L  P  D  K  H  L  F  R  V  E  T  T  H  C  L  Q  V Dra I
    AAACTACCTACAGAGATTTAAAGCTCTAAGGTAAATATAAAATTTTTAAGTGTATAATGTGTTAAACTACTGATTCTAAT
    |----+----|----+----|----+----|----+----|----+----|----+----|----+----|----+----|  240
    TTTGATGGATGTCTCTAAATTTCGAGATTCCATTTATATTTTAAAAATTCACATATTACACAATTTGATGACTAAGATTA Q  T  T  Y  R  D  L  K  L  ·  G  K  Y  K  I  F  K  C  I  M  C  ·  T  T  D  S  N
        K  L  P  T  E  I  ·  S  S  K  V  N  I  K  F  L  S  V  ·  C  V  K  L  L  I  L  I
         N  Y  L  Q  R  F  K  A  L  R  ·  I  ·  N  F  ·  V  Y  N  V  L  N  Y  ·  F  ·
       +----+----+----+----+----+----+----+----+----+----+----+----+----+----+----+----+
       V  V  ·  L  S  K  F  S  ·  P  L  Y  L  I  K  L  H  I  I  H  ·  V  V  S  E  L
        L  S  G  V  S  I  ·  L  E  L  T  F  I  F  N  K  L  T  Y  H  T  L  S  S  I  R  I
         F  ·  R  C  L  N  L  A  R  L  Y  I  Y  F  K  ·  T  Y  L  T  N  F  ·  Q  N  ·  N TGTTTGTGTATTTTAGATTCCAACCTATGGAACTGATGAATGGGAGCAGTGGTGGAATGCCTTTAATGAGGAAAACCTGT
    |----+----|----+----|----+----|----+----|----+----|----+----|----+----|----+----|  320
    ACAAACACATAAAATCTAAGGTTGGATACCTTGACTACTTACCCTCGTCACCACCTTACGGAAATTACTCCTTTTGGACA C  L  C  I  L  D  S  N  L  W  N  ·  ·  M  G  A  V  V  E  C  L  ·  G  K  P  V
        V  C  V  F  ·  I  P  T  Y  G  T  D  E  W  E  Q  W  W  N  A  F  N  E  E  N  L
         L  F  V  Y  F  R  F  Q  P  M  E  L  M  N  G  S  S  G  G  M  P  L  M  R  K  T  C
       +----+----+----+----+----+----+----+----+----+----+----+----+----+----+----+----+
       Q  K  H  I  K  S  E  L  R  H  F  Q  H  I  P  A  T  T  S  H  R  ·  H  P  F  G  T
        T  Q  T  N  ·  I  G  V  ·  P  V  S  S  H  S  C  H  H  F  A  K  L  S  S  F  R  N
         N  T  Y  K  L  N  W  G  I  S  S  I  F  P  L  L  P  P  I  G  K  I  L  F  V  Q
```

```
                BsaB I                                                Dra I
                   |                                                   |
TAGAGATCATAATCAGCCATACCACATTTGTAGAGGTTTTACTTGCTTTAAAAAAACCTCCCACACCTCCCCCTGAACCTG
+---+---+---+---+---+---+---+---+---+---+---+---+---+---+---+---+---+---+---+---+ 800
ATCTCTAGTATTAGTCGGTATGGTGTAAACATCTCCAAAATGAACGAAATTTTTTGGAGGGTGTGGAGGGGGACTTGGAC

R  S  ·  S  A  I  P  H  L  ·  R  F  Y  L  L  ·  K  T  S  H  T  S  P  P  ·  T
  R  D  H  N  Q  P  Y  H  I  C  R  G  F  T  C  F  K  K  N  P  P  T  P  P  P  E  P
L  E  I  I  I  S  H  T  T  F  V  E  V  L  L  A  L  K  N  L  P  H  L  P  L  N  L
+---+---+---+---+---+---+---+---+---+---+---+---+---+---+---+---+---+---+---+---+
    ·  L  D  Y  D  A  M  G  C  K  Y  L  N  ·  K  S  ·  F  V  E  W  V  E  G  Q  V  Q
  L  S  ·  L  ·  G  Y  W  M  Q  L  P  K  V  Q  K  L  F  G  G  V  G  G  G  S  G  S
    S  I  M  I  L  W  V  V  V  N  T  S  T  K  S  A  K  F  F  R  G  C  R  G  R  F  R

Hinc II
             Mfel       Hpa 1
                |         |
AAACATAAAATGAATGCAATTGTTGTTGTTAACTTGTTTATTGCAGCTTATAATGGTTACAAATAAAGCAATAGCATCAC
+---+---+---+---+---+---+---+---+---+---+---+---+---+---+---+---+---+---+---+---+ 880
TTTGTATTTTACTTACGTTAACAACAACAATTGAACAAATAACGTCGAATATTACCAATGTTTATTTCGTTATCGTAGTG N  I  K  ·  M  Q  L  L  L  L  T  C  L  L  Q  L  I  M  V  T  N  K  A  I  A  S
  E  T  ·  N  E  C  N  C  C  C  ·  L  V  Y  C  S  L  ·  W  L  Q  I  K  Q  ·  H  H
K  H  K  M  N  A  I  V  V  V  N  L  F  I  A  A  Y  N  G  Y  K  ·  S  N  S  I  T
+---+---+---+---+---+---+---+---+---+---+---+---+---+---+---+---+---+---+---+---+
    F  M  F  H  I  C  N  N  N  N  V  Q  K  N  C  S  I  I  T  V  F  L  A  I  A  D  C
  V  Y  F  S  H  L  Q  Q  Q  ·  S  T  ·  Q  L  K  Y  H  N  C  I  F  C  Y  C  ·
F  C  L  I  F  A  I  T  T  T  L  K  N  I  A  A  ·  L  P  ·  L  Y  L  L  L  M  V Xba 1
                                                                           |
AAATTTCACAAATAAAGCATTTTTTTCACTGCATTCTAGTTGTGGTTTGTCCAAACTCATCAATGTATCTTATCATGTCT
+---+---+---+---+---+---+---+---+---+---+---+---+---+---+---+---+---+---+---+---+ 960
TTTAAAGTGTTTATTTCGTAAAAAAAGTGACGTAAGATCAACACCAAACAGGTTTGAGTAGTTACATAGAATAGTACAGA Q  I  S  Q  I  K  H  F  F  H  C  I  L  V  V  V  C  P  N  S  S  M  Y  L  I  M  S
  K  F  H  K  ·  S  I  F  F  F  T  A  F  ·  L  W  F  V  Q  T  H  Q  C  I  L  S  C  L
N  F  T  N  K  A  F  F  S  L  H  S  S  C  G  L  S  K  L  I  N  V  S  Y  H  V
+---+---+---+---+---+---+---+---+---+---+---+---+---+---+---+---+---+---+---+---+
    I  E  C  I  F  C  K  K  ·  Q  M  R  T  T  T  Q  G  F  E  D  I  Y  R  I  M  D
L  N  ·  L  Y  L  M  K  K  K  V  A  N  ·  N  H  N  T  W  V  ·  ·  H  I  K  D  H  R
F  K  V  F  L  A  N  K  E  S  C  E  L  Q  P  K  D  L  S  M  L  T  D  ·  ·  T  ·
                                                                           Sph 1
    Bgl II                                                                 | Nsi 1
    |                                                                      | |
AGATCTTGTGGAATGTGTGTCAGTTAGGGTGTGGAAAGTCCCCAGGCTCCCCAGCAGGCAGAAGTATGCAAAGCATGCAT
+---+---+---+---+---+---+---+---+---+---+---+---+---+---+---+---+---+---+---+---+ 1040
TCTAGAACACCTTACACACAGTCAATCCCACACCTTTCAGGGGTCCGAGGGGTCGTCCGTCTTCATACGTTTCGTACGTA R  S  C  G  M  C  V  S  ·  G  V  E  S  P  Q  A  P  Q  Q  A  E  V  C  K  A  C  I
  D  L  V  E  C  V  S  V  R  V  W  K  V  P  R  L  P  S  R  Q  K  Y  A  K  H  A
·  I  L  W  N  V  C  Q  L  G  C  G  K  S  P  G  S  P  A  G  R  S  M  Q  S  M  H
+---+---+---+---+---+---+---+---+---+---+---+---+---+---+---+---+---+---+---+---+
    L  D  Q  P  I  H  T  L  ·  P  T  S  L  G  W  A  G  W  C  A  S  T  H  L  A  H  M
  S  R  T  ·  S  H  T  D  T  L  T  H  F  T  G  L  S  G  L  L  C  F  Y  A  F  C  A  D
    I  K  H  F  T  H  ·  N  P  H  P  F  D  G  P  E  G  A  P  L  L  I  C  L  M  C
```

```
                                              Ava II  Pvu I              Hae III
CGAGTTACATGATCCCCCATGTTGTGCAAAAAAGCGGTTAGCTCCTTCGGTCCTCCGATCGTTGTCAGAAGTAAGTTGGC
GCTCAATGTACTAGGGGGTACAACACGTTTTTTCGCCAATCGAGGAAGCCAGGAGGCTAGCAACAGTCTTCATTCAACCG  2960
  R V T   S P M L C K K A V S S F G P P I V V R S K L A
   E L H D P P P C C A K K R L A P S V L R S L S E V S W
 A S Y M I P H V V Q K S G . L L R S S D R C Q K . V G
  R T V H D G M N H L F A T L E K P G G I T T L L L N A
   S N C S G G H Q A F F R N A G E T R R D N D S T L Q G
    L . M I G W T T C F L P . S R R D E S R Q . F Y T P

CGCAGTGTTATCACTCATGGTTATGGCAGCACTGCATAATTCTCTTACTGTCATGCCATCCGTAAGATGCTTTTCTGTGA
GCGTCACAATAGTGAGTACCAATACCGTCGTGACGTATTAAGAGAATGACAGTACGGTAGGCATTCTACGAAAAGACACT  3040
  A V L S L M V M A A L H N S L T V M P S V R C F S V
   P Q C Y H S W L W Q H C I I L L L S C H P . D A F L .
    R S V I T H G Y G S T A . F S Y C H A I R K M L F C D
  A T N D S M T I A A S C L E R V T M G D T L H K E T V
   C H . . E H N H C C Q M I R K S D H W G Y S A K R H
    R L T I V . P . P L V A Y N E . Q . A M R L I S K Q S

Rsa I                                          Nci I  Hinc II
   Sca I
CTGGTGAGTACTCAACCAAGTCATTCTGAGAATAGTGTATGCGGCGACCGAGTTGCTCTTGCCCGGCGTCAACACGGGAT
GACCACTCATGAGTTGGTTCAGTAAGACTCTTATCACATACGCCGCTGGCTCAACGAGAACGGGCCGCAGTTGTGCCCTA  3120
  T G E Y S T K S F . E . C M R R P S C S C P A S T R D
   L V S T Q P S H S E N S V C G D R V A L A R R Q H G I
    W . V L N Q V I L R I V Y A A T E L L L P G V N T G
    P S Y E V L D N Q S Y H I R R G L Q E Q G A D V R S
   S T L V . G L . E S F L T H P S R T A R A R R . C P I
  Q H T S L W T M R L I T Y A A V S N S K G P T L V P Y Dra I              Xmn I
AATACCGCGCCACATAGCAGAACTTTAAAAGTGCTCATCATTGGAAAACGTTCTTCGGGGCGAAAACTCTCAAGGATCTT
TTATGGCGCGGTGTATCGTCTTGAAATTTTCACGAGTAGTAACCTTTTGCAAGAAGCCCCGCTTTTGAGAGTTCCTAGAA  3200
  N T A P H S R T L K V L I I G K R S S G R K L S R I L
   I P R H I A E L . K C S S L E N V L R G E N S Q G S
    . Y R A T . Q N F K S A H H W K T F F G A K T L K D L
  L V A G C L L V K F T S M M P F R E E P R F S E L I K
   I G R W M A S S . F H E D N S F T R R P S F E . P D .
    Y R A V Y C F K L L A . . Q F V N K P A F V R L S R
```

```
                                          Aat II
ACTCACGGGGATTTCCAAGTCTCCACCCCATTGACGTCAATGGGAGTTTGTTTTGGCACCAAAATCAACGGGACTTTCCA
|---+----+----+----+----+----+----+----+----+----+----+----+----+----+----+----| 3920
TGAGTGCCCCTAAAGGTTCAGAGCTGGGGTAACTGCAGTTACCCTCAAACAAAACCGTGGTTTTAGTTGCCCTGAAAGGT

T  H  G  D  F  Q  V  S  T  P  L  T  S  M  G  V  C  F  G  T  K  I  N  G  T  F  Q
    L  T  G  I  S  P  K  S  P  P  P  H  ·  R  Q  W  E  F  V  L  A  P  K  S  T  G  L  S
  D  S  R  G  F  P  S  L  H  P  I  D  V  N  G  S  L  F  W  H  Q  N  Q  R  D  F  P
|---+----+----+----+----+----+----+----+----+----+----+----+----+----+----+----|
 V  ·  P  S  K  W  T  E  V  G  N  V  D  I  P  T  Q  K  P  V  L  I  L  P  V  K  W
  S  V  P  I  E  L  D  G  G  W  Q  R  ·  H  S  N  T  K  A  G  F  D  V  P  S  E  L
   E  R  P  N  G  L  R  W  G  M  S  T  L  P  L  K  N  Q  C  W  F  ·  R  S  K  G

Rsa I                             Sac I
AAATGTCGTAACAACTCCGCCCCATTGACGCAAATGGGCGGTAGGCGTGTACGGTGGGAGGTCTATATAAGCAGAGCTCT
|---+----+----+----+----+----+----+----+----+----+----+----+----+----+----+----| 4000
TTTACAGCATTGTTGAGGCGGGGTAACTGCGTTTACCCGCCATCCGCACATGCCACCCTCCAGATATATTCGTCTCGAGA

N  V  V  T  T  P  P  H  ·  R  K  W  A  V  G  V  Y  G  G  R  S  I  ·  A  E  L
   K  M  S  ·  Q  L  R  P  I  D  A  N  G  R  ·  A  C  T  V  G  G  L  Y  K  Q  S  S
  K  C  R  N  N  S  A  P  L  T  Q  M  G  G  R  R  V  R  W  E  V  Y  I  S  R  A  L
|---+----+----+----+----+----+----+----+----+----+----+----+----+----+----+----|
    F  T  T  V  V  G  G  W  Q  R  L  H  A  T  P  T  Y  P  P  L  D  I  Y  A  S  S  E
     I  D  Y  C  S  R  G  M  S  A  F  P  R  Y  A  H  V  T  P  P  R  Y  L  C  L  E
   F  H  R  L  L  E  A  G  N  V  C  I  P  P  L  R  T  R  H  S  T  ·  I  L  L  A  R

Rsa I
CTGGCTAACTAGAGAACCCACTGCTTAACTGGCTTATCGAAATTAATACGACTCACTATAGGGAGACCC
|---+----+----+----+----+----+----+----+----+----+----+----+----|→ 4069
GACGGATTGATCTCTTGGGTGACGAATTGACCGAATAGCTTTAATTATGCTGAGTGATATCCCTCTGGG

… # NON-ENDOGENOUS, CONSTITUTIVELY ACTIVATED HUMAN PROTEIN-COUPLED RECEPTORS

CROSS-REFERENCE TO RELATED APPLICATIONS

This application is a continuation-in-part of U.S. Ser. No. 09/060,188, filed Apr. 14, 1998, which is a continuation-in-part of U.S. Ser. No. 08/839,449, filed Apr. 14, 1997 (now abandoned); this application also claims benefit of U.S. Provisional No. 60/090,783, filed Jun. 26, 1998, and U.S. Provisional No. 60/095,677, filed on Aug. 7, 1998.

FIELD OF THE INVENTION

The invention disclosed in this patent document relates to transmembrane receptors, and more particularly to human G protein-coupled receptors (GPCRs) which have been altered such that altered GPCRs are constitutively activated. Most preferably, the altered human GPCRs are used for the screening of therapeutic compounds.

BACKGROUND OF THE INVENTION

Although a number of receptor classes exist in humans, by far the most abundant and therapeutically relevant is represented by the G protein-coupled receptor (GPCR or GPCRs) class. It is estimated that there are some 100,000 genes within the human genome, and of these, approximately 2% or 2,000 genes, are estimated to code for GPCRs. Of these, there are approximately 100 GPCRs for which the endogenous ligand that binds to the GPCR has been identified. Because of the significant time-lag that exists between the discovery of an endogenous GPCR and its endogenous ligand, it can be presumed that the remaining 1,900 GPCRs will be identified and characterized long before the endogenous ligands for these receptors are identified. Indeed, the rapidity by which the Human Genome Project is sequencing the 100,000 human genes indicates that the remaining human GPCRs will be fully sequenced within the next few years. Nevertheless, and despite the efforts to sequence the human genome, it is still very unclear as to how scientists will be able to rapidly, effectively and efficiently exploit this information to improve and enhance the human condition. The present invention is geared towards this important objective.

Receptors, including GPCRs, for which the endogenous ligand has been identified are referred to as "known" receptors, while receptors for which the endogenous ligand has not been identified are referred to as "orphan" receptors. This distinction is not merely semantic, particularly in the case of GPCRs. GPCRs represent an important area for the development of pharmaceutical products: from approximately 20 of the 100 known GPCRs, 60% of all prescription pharmaceuticals have been developed. Thus, the orphan GPCRs are to the pharmaceutical industry what gold was to California in the late 19$^{th}$ century—an opportunity to drive growth, expansion, enhancement and development. A serious drawback exists, however, with orphan receptors relative to the discovery of novel therapeutics. This is because the traditional approach to the discovery and development of pharmaceuticals has required access to both the receptor and its endogenous ligand. Thus, heretofore, orphan GPCRs have presented the art with a tantalizing and undeveloped resource for the discovery of pharmaceuticals.

Under the traditional approach to the discovery of potential therapeutics, it is generally the case that the receptor is first identified. Before drug discovery efforts can be initiated, elaborate, time consuming and expensive procedures are typically put into place in order to identify, isolate and generate the receptor's endogenous ligand—this process can require from between 3 and ten years per receptor, at a cost of about $5million (U.S.) per receptor. These time and financial resources must be expended before the traditional approach to drug discovery can commence. This is because traditional drug discovery techniques rely upon so-called "competitive binding assays" whereby putative therapeutic agents are "screened" against the receptor in an effort to discover compounds that either block the endogenous ligand from binding to the receptor ("antagonists"), or enhance or mimic the effects of the ligand binding to the receptor ("agonists"). The overall objective is to identify compounds that prevent cellular activation when the ligand binds to the receptor (the antagonists), or that enhance or increase cellular activity that would otherwise occur if the ligand was properly binding with the receptor (the agonists). Because the endogenous ligands for orphan GPCRs are by definition not identified, the ability to discover novel and unique therapeutics to these receptors using traditional drug discovery techniques is not possible. The present invention, as will be set forth in greater detail below, overcomes these and other severe limitations created by such traditional drug discovery techniques.

GPCRs share a common structural motif. All these receptors have seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell. The general structure of G protein-coupled receptors is depicted in FIG. 1.

Generally, when an endogenous ligand binds with the receptor (often referred to as "activation" of the receptor), there is a change in the conformation of the intracellular region that allows for coupling between the intracellular region and an intracellular "G-protein." Although other G proteins exist, currently, Gq, Gs, Gi, and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein. A principal focus of this invention is directed to the transmembrane-6 (TM6) region and the intracellular-3 (IC3) region of the GPCR.

Under physiological conditions, GPCRs exist in the cell membrane in equilibrium between two different conformations: an "inactive" state and an "active" state. As shown schematically in FIG. 2, a receptor in an inactive state is unable to link to the intracellular signaling transduction pathway to produce a biological response. Changing the receptor conformation to the active state allows linkage to the transduction pathway (via the G-protein) and produces a biological response.

A receptor may be stabilized in an active state by an endogenous ligand or a compound such as a drug. Recent discoveries, including but not exclusively limited to modifications to the amino acid sequence of the receptor, provide means other than endogenous ligands or drugs to promote and stabilize the receptor in the active state conformation. These means effectively stabilize the receptor in an active state by simulating the effect of an endogenous ligand binding to the receptor. Stabilization by such ligand-independent means is termed "constitutive receptor activation."

As noted above, the use of an orphan receptor for screening purposes has not been possible. This is because the traditional "dogma" regarding screening of compounds mandates that the ligand for the receptor be known. By definition, then, this approach has no applicability with respect to orphan receptors. Thus, by adhering to this dogmatic approach to the discovery of therapeutics, the art, in essence, has taught and has been taught to forsake the use of orphan receptors unless and until the endogenous ligand for the receptor is discovered. Given that there are an estimated 2,000 G protein coupled receptors, the majority of which are orphan receptors, such dogma castigates a creative, unique and distinct approach to the discovery of therapeutics.

Information regarding the nucleic acid and/or amino acid sequences of a variety of GPCRs is summarized below in Table A. Because an important focus of the invention disclosed herein is directed towards orphan GPCRs, many of the below-cited references are related to orphan GPCRs. However, this list is not intended to imply, nor is this list to be construed, legally or otherwise, that the invention disclosed herein is only applicable to orphan GPCRs or the specific GPCRs listed below. Additionally, certain receptors that have been isolated are not the subject of publications per se; for example, reference is made to a G Protein-Coupled Receptor database on the "world-wide web" (neither the named inventors nor the assignee have any affiliation with this site) that lists GPCRs. Other GPCRs are the subject of patent applications owned by the present assignee and these are not listed below (including GPR3, GPR6 and GPR12; see U.S. Provisional No. 60/094879):

TABLE A

| Receptor Name | Publication Reference |
| --- | --- |
| GPR1 | 23 Genomics 609 (1994) |
| GPR4 | 14 DNA and Cell Biology 25 (1995) |
| GPR5 | 14 DNA and Cell Biology 25 (1995) |
| GPR7 | 28 Genomics 84 (1995) |
| GPR8 | 28 Genomics 84 (1995) |
| GPR9 | 184 J. Exp. Med. 963 (1996) |
| GPR10 | 29 Genomics 335 (1995) |
| GPR15 | 32 Genomics 462 (1996) |
| GPR17 | 70 J Neurochem. 1357 (1998) |
| GPR18 | 42 Genomics 462 (1997) |
| GPR20 | 187 Gene 75 (1997) |
| GPR21 | 187 Gene 75 (1997) |
| GPR22 | 187 Gene 75 (1997) |
| GPR24 | 398 FEBS Lett.253 (1996) |
| GPR30 | 45 Genomics 607 (1997) |
| GPR31 | 42 Genomics 519 (1997) |

TABLE A-continued

| Receptor Name | Publication Reference |
| --- | --- |
| GPR32 | 50 Genomics 281 (1997) |
| GPR40 | 239 Biochem. Biophys. Res. Commun. 543 (1997) |
| GPR41 | 239 Biochem. Biophys. Res. Commun. 543 (1997) |
| GPR43 | 239 Biochem. Biophys. Res. Commun. 543 (1997) |
| APJ | 136 Gene 355 (1993) |
| BLR1 | 22 Eur. J. Immnunol. 2759 (1992) |
| CEPR | 231 Biochem. Biophys. Res. Commun. 651 (1997) |
| EBI1 | 23 Genomics 643 (1994) |
| EBI2 | 67 J. Virol. 2209 (1993) |
| ETBR-LP2 | 424 FEBS Lett. 193 (1998) |
| GPCR-CNS | 54 Brain Res. Mol. Brain Res. 152 (1998); 45 Genomics 68 (1997) |
| GPR-NGA | 394 FEBS Lett. 325 (1996) |
| H9 | 386 FEBS Lett 219 (1996) |
| HBA954 | 1261 Biochim. Biophys. Acta 121 (1995) |
| HG38 | 247 Biochem Biophys Res. Commun. 266 (1998) |
| HM74 | 5 Int. Immunol. 1239 (1993) |
| OGR1 | 35 Genomics 397 (1996) |
| V28 | 163 Gene295 (1995) |

As will be set forth and disclosed in greater detail below, utilization of a mutational cassette to modify the endogenous sequence of a human GPCR leads to a constitutively activated version of the human GPCR. These non-endogenous, constitutively activated versions of human GPCRs can be utilized, inter alia, for the screening of candidate compounds to directly identify compounds of, e.g., therapeutic relevance.

SUMMARY OF THE INVENTION

Disclosed herein is a non-endogenous, human G protein-coupled receptor comprising (a) as a most preferred amino acid sequence region (C-terminus to N-terminus orientation) and/or (b) as a most preferred nucleic acid sequence region (3' to 5' orientation) transversing the transmembrane-6 (TM6) and intracellular loop-3 (IC3) regions of the GPCR:

$$P^1AA_{15}X \qquad (a)$$

wherein:

(1) $P^1$ is an amino acid residue located within the TM6 region of the GPCR, where $P^1$ is selected from the group consisting of (i) the endogenous GPCR's proline residue, and (ii) a non-endogenous amino acid residue other than proline;

(2) $AA_{15}$ are 15 amino acids selected from the group consisting of (a) the endogenous GPCR's amino acids (b) non-endogenous amino acid residues, and (c) a combination of the endogenous GPCR's amino acids and non-endogenous amino acids, excepting that none of the 15 endogenous amino acid residues that are positioned within the TM6 region of the GPCR is proline; and (3) X is a non-endogenous amino acid residue located within the IC3 region of said GPCR, preferably selected from the group consisting of lysine, hisitidine and arginine, and most preferably lysine, excepting that when the endogenous amino acid at position X is lysine, then X is an amino acid other than lysine, preferably alanine; and/or $$P^{codon}(\text{AA-codon})_{15}X_{codon} \quad \text{(b)}$$

wherein:
(1) $P^{codon}$ is a nucleic acid sequence within the TM6 region of the GPCR, where $P^{codon}$ encodes an amino acid selected from the group consisting of (i) the endogenous GPCR's proline residue, and (ii) a non-endogenous amino acid residue other than proline;
(2) (AA-codon)$_{15}$ are 15 codons encoding 15 amino acids selected from the group consisting of (a) the endogenous GPCR's amino acids (b) non-endogenous amino acid residues and (c) a combination of the endogenous GPCR's amino acids and non-endogenous amino acids, excepting that none of the 15 endogenous codons within the TM6 region of the GPCR encodes a proline amino acid residue; and
(3) $X_{codon}$ is a nucleic acid encoding region residue located within the IC3 region of said GPCR, where $X_{codon}$ encodes a non-endogenous amino acid, preferably selected from the group consisting of lysine, hisitidine and arginine, and most preferably lysine, excepting that when the endogenous encoding region at position $X_{codon}$ encodes the amino acid lysine, then $X_{codon}$ encodes an amino acid other than lysine, preferably alanine.

The terms endogenous and non-endogenous in reference to these sequence cassettes are relative to the endogenous GPCR. For example, once the endogenous proline residue is located within the TM6 region of a particular GPCR, and the 16$^{th}$ amino acid therefrom is identified for mutation to constitutively activate the receptor, it is also possible to mutate the endogenous proline residue (i.e., once the marker is located and the 16$^{th}$ amino acid to be mutated is identified, one may mutate the marker itself), although it is most preferred that the proline residue not be mutated. Similarly, and while it is most preferred that AA$_{15}$ be maintained in their endogenous forms, these amino acids may also be mutated. The only amino acid that must be mutated in the non-endogenous version of the human GPCR is X i.e., the endogenous amino acid that is 16 residues from $P^1$ cannot be maintained in its endogenous form and must be mutated, as further disclosed herein. Stated again, while it is preferred that in the non-endogenous version of the human GPCR, $P^1$ and AA$_{15}$ remain in their endogenous forms (i.e., identical to their wild-type forms), once X is identified and mutated, any and/or all of $P^1$ and AA$_{15}$ can be mutated. This applies to the nucleic acid sequences as well. In those cases where the endogenous amino acid at position X is lysine, then in the non-endogenous version of such GPCR, X is an amino acid other than lysine, preferably alanine.

Accordingly, and as a hypothetical example, if the endogenous GPCR has the following endogenous amino acid sequence at the above-noted positions:
P-AACCTTGGRRRDDDE-Q (SEQ.I.D.NO:281)
then any of the following exemplary and hypothetical cassettes would fall within the scope of the disclosure (non-endogenous amino acids are set forth in bold):
P-AACCTTGGRRRDDDE-K (SEQ.I.D.NO.:282)
P-AACCTTHIGRRDDDE-K (SEQ.I.D.NO.:283)
P-ADEETTGGRRRDDDE-A (SEQ.I.D.NO.:284)
P-LLKFMSTWZLVAAPQ-K (SEQ.I.D.NO.:285)
A-LLKFMSTWZLVAAPQ-K (SEQ I.D. NO.:286)
It is also possible to add amino acid residues within AA$_{15}$, but such an approach is not particularly advanced. Indeed, in the most preferred embodiments, the only amino acid that differs in the non-endogenous version of the human GPCR as compared with the endogenous version of that GPCR is the amino acid in position X; mutation of this amino acid itself leads to constitutive activation of the receptor.

Thus, in particularly preferred embodiments, $P^1$ and $P^{codon}$ are endogenous proline and an endogenous nucleic acid encoding region encoding proline, respectively; and X and $X_{codon}$ are non-endogenous lysine or alanine and a non-endogenous nucleic acid encoding region encoding lysine or alanine, respectively, with lysine being most preferred. Because it is most preferred that the non-endogenous versions of the human GPCRs which incorporate these mutations are incorporated into mammalian cells and utilized for the screening of candidate compounds, the non-endogenous human GPCR incorporating the mutation need not be purified and isolated per se (i.e., these are incorporated within the cellular membrane of a mammalian cell), although such purified and isolated non-endogenous human GPCRs are well within the purview of this disclosure. Gene-targeted and transgenic non-human mammals (preferably rats and mice) incorporating the non-endogenous human GPCRs are also within the purview of this invention; in particular, gene-targeted mammals are most preferred in that these animals will incorporate the non-endogenous versions of the human GPCRs in place of the non-human mammal's endogenous GPCR-encoding region (techniques for generating such non-human mammals to replace the non-human mammal's protein encoding region with a human encoding region are well known; see, for example, U.S. Pat. No. 5,777,194.)

It has been discovered that these changes to an endogenous human GPCR render the GPCR constitutively active such that, as will be further disclosed herein, the non-endogenous, constitutively activated version of the human GPCR can be utilized for, inter alia, the direct screening of candidate compounds without the need for the endogenous ligand. Thus, methods for using these materials, and products identified by these methods are also within the purview of the following disclosure.

BRIEF DESCRIPTION OF THE DRAWINGS

FIGS. 3A–3L provide a sequence diagram of the preferred vector pCMV, including restriction site locations. Nucleotide sequences are set forth as SEQ ID NOS: 287 and 288, and amino acid sequences are set forth as SEQ ID NOS: 289–294 (from top to bottom).

DETAILED DESCRIPTION

Figure 1:
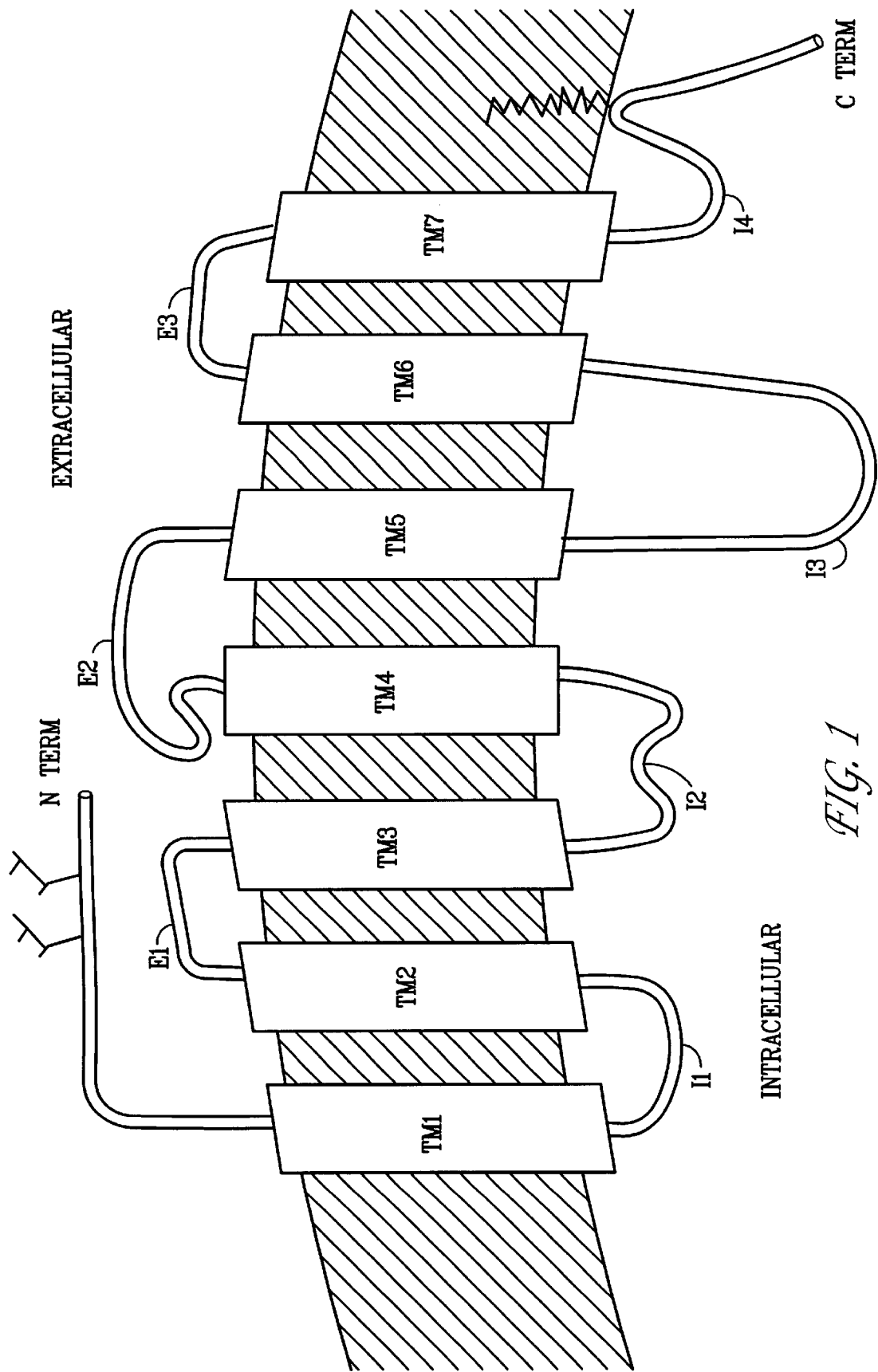
FIG. 1 shows a generalized structure of a G protein-coupled receptor with the numbers assigned to the transmembrane helixes, the intracellular loops, and the extracellular loops.
Figure 2:
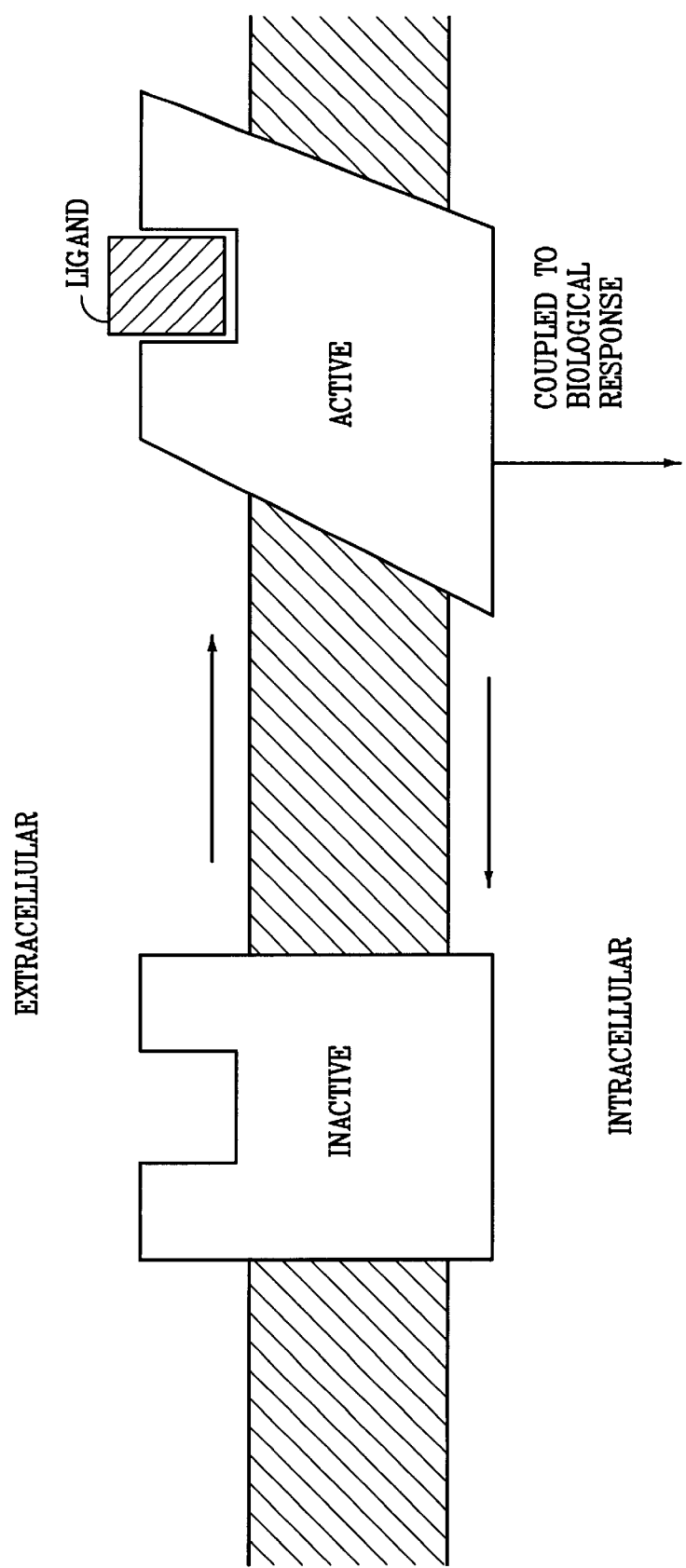
FIG. 2 schematically shows the two states, active and inactive, for a typical G protein coupled receptor and the linkage of the active state to the second messenger transduction pathway.

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean compounds that activate the intracellular response when they bind to the receptor, or enhance GTP binding to membranes.

AMINO ACID ABBREVIATIONS used herein are set below:

| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

PARTIAL AGONISTS shall mean compounds which activate the intracellular response when they bind to the receptor to a lesser degree/extent than do agonists, or enhance GTP binding to membranes to a lesser degree/extent than do agonists.

ANTAGONIST shall mean compounds that competitively bind to the receptor at the same site as the agonists but which do not activate the intracellular response initiated by the active form of the receptor, and can thereby inhibit the intracellular responses by agonists or partial agonists. ANTAGONISTS do not diminish the baseline intracellular response in the absence of an agonist or partial agonist.

CANDIDATE COMPOUND shall mean a molecule (for example, and not limitation, a chemical compound) which is amenable to a screening technique. Preferably, the phrase "candidate compound" does not include compounds which were publicly known to be compounds selected from the group consisting of inverse agonist, agonist or antagonist to a receptor, as previously determined by an indirect identification process ("indirectly identified compound"); more preferably, not including an indirectly identified compound which has previously been determined to have therapeutic efficacy in at least one mammal; and, most preferably, not including an indirectly identified compound which has previously been determined to have therapeutic utility in humans.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

COMPOUND EFFICACY shall mean a measurement of the ability of a compound to inhibit or stimulate receptor functionality, as opposed to receptor binding affinity. A preferred means of detecting compound efficacy is via measurement of, e.g., [$^{35}$S]GTPγS binding, as further disclosed in the Example section of this patent document.

CONSTITUTIVELY ACTIVATED RECEPTOR shall mean a receptor subject to constitutive receptor activation. In accordance with the invention disclosed herein, a non-endogenous, human constitutively activated G protein-coupled receptor is one that has been mutated to include the amino acid cassette $P^1AA_{15}X$, as set forth in greater detail below.

CONSTITUTIVE RECEPTOR ACTIVATION shall mean stabilization of a receptor in the active state by means other than binding of the receptor with its endogenous ligand or a chemical equivalent thereof. Preferably, a G protein-coupled receptor subjected to constitutive receptor activation in accordance with the invention disclosed herein evidences at least a 10% difference in response (increase or decrease, as the case may be) to the signal measured for constitutive activation as compared with the endogenous form of that GPCR, more preferably, about a 25% difference in such comparative response, and most preferably about a 50% difference in such comparative response. When used for the purposes of directly identifying candidate compounds, it is most preferred that the signal difference be at least about 50% such that there is a sufficient difference between the endogenous signal and the non-endogenous signal to differentiate between selected candidate compounds. In most instances, the "difference" will be an increase in signal; however, with respect to Gi-coupled GPCRS, the "difference" measured is preferably a decrease, as will be set forth in greater detail below.

CONTACT or CONTACTING shall mean bringing at least two moieties together, whether in an in vitro system or an in vivo system.

DIRECTLY IDENTIFYING or DIRECTLY IDENTIFIED, in relationship to the phrase "candidate compound", shall mean the screening of a candidate compound against a constitutively activated G protein-coupled receptor, and assessing the compound efficacy of such compound. This phrase is, under no circumstances, to be interpreted or understood to be encompassed by or to encompass the phrase "indirectly identifying" or "indirectly identified."

ENDOGENOUS shall mean a material that is naturally produced by the genome of the species. ENDOGENOUS in reference to, for example and not limitation, GPCR, shall mean that which is naturally produced by a human, an insect, a plant, a bacterium, or a virus. By contrast, the term NON-ENDOGENOUS in this context shall mean that which is not naturally produced by the genome of a species. For example, and not limitation, a receptor which is not constitutively active in its endogenous form, but when mutated by using the cassettes disclosed herein and thereafter becomes constitutively active, is most preferably referred to herein as a "non-endogenous, constitutively activated receptor." Both terms can be utilized to describe both "in vivo" and "in vitro" systems. For example, and not limitation, in a screening approach, the endogenous or non-endogenous receptor may be in reference to an in vitro screening system whereby the receptor is expressed on the cell-surface of a mammalian cell. As a further example and not limitation, where the genome of a mammal has been manipulated to include a non-endogenous constitutively activated receptor, screening of a candidate compound by means of an in vivo system is viable.

HOST CELL shall mean a cell capable of having a Plasmid and/or Vector incorporated therein. In the case of a prokaryotic Host Cell, a Plasmid is typically replicated as an autonomous molecule as the Host Cell replicates (generally, the Plasmid is thereafter isolated for introduction into a eukaryotic Host Cell); in the case of a eukaryotic Host Cell, a Plasmid is integrated into the cellular DNA of the Host Cell such that when the eukaryotic Host Cell replicates, the Plasmid replicates. Preferably, for the purposes of the invention disclosed herein, the Host Cell is eukaryotic, more preferably, mammalian, and most preferably selected from the group consisting of 293, 293T and COS-7 cells.

INDIRECTLY IDENTIFYING or INDIRECTLY IDENTIFIED means the traditional approach to the drug discovery process involving identification of an endogenous ligand specific for an endogenous receptor, screening of candidate compounds against the receptor for determination of those which interfere and/or compete with the ligand-receptor interaction, and assessing the efficacy of the compound for affecting at least one second messenger pathway associated with the activated receptor.

INHIBIT or INHIBITING, in relationship to the term "response" shall mean that a response is decreased or prevented in the presence of a compound as opposed to in the absence of the compound.

INVERSE AGONISTS shall mean compounds which bind to either the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

KNOWN RECEPTOR shall mean an endogenous receptor for which the endogenous ligand specific for that receptor has been identified.

LIGAND shall mean an endogenous, naturally occurring molecule specific for an endogenous, naturally occurring receptor.

MUTANT or MUTATION in reference to an endogenous receptor's nucleic acid and/or amino acid sequence shall mean a specified change or changes to such endogenous sequences such that a mutated form of an endogenous, non-constitutively activated receptor evidences constitutive activation of the receptor. In terms of equivalents to specific sequences, a subsequent mutated form of a human receptor is considered to be equivalent to a first mutation of the human receptor if (a) the level of constitutive activation of the subsequent mutated form of the receptor is substantially the same as that evidenced by the first mutation of the receptor; and (b) the percent sequence (amino acid and/or nucleic acid) homology between the subsequent mutated form of the receptor and the first mutation of the receptor is at least about 80%, more preferably at least about 90% and most preferably at least 95%. Ideally, and owing to the fact that the most preferred cassettes disclosed herein for achieving constitutive activation includes a single amino acid and/or codon change between the endogenous and the non-endogenous forms of the GPCR (i.e. X or $X_{codon}$), the percent sequence homology should be at least 98%.

ORPHAN RECEPTOR shall mean an endogenous receptor for which the endogenous ligand specific for that receptor has not been identified or is not known.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

PLASMID shall mean the combination of a Vector and cDNA. Generally, a Plasmid is introduced into a Host Cell for the purpose of replication and/or expression of the cDNA as a protein.

STIMULATE or STIMULATING, in relationship to the term "response" shall mean that a response is increased in the presence of a compound as opposed to in the absence of the compound.

TRANSVERSE or TRANSVERSING, in reference to either a defined nucleic acid sequence or a defined amino acid sequence, shall mean that the sequence is located within at least two different and defined regions. For example, in an amino acid sequence that is 10 amino acid moieties in length, where 3 of the 10 moieties are in the TM6 region of a GPCR and the remaining 7 moieties are in the IC3 region of the GPCR, the 10 amino acid moiety can be described as transversing the TM6 and IC3 regions of the GPCR.

VECTOR in reference to cDNA shall mean a circular DNA capable of incorporating at least one cDNA and capable of incorporation into a Host Cell.

The order of the following sections is set forth for presentational efficiency and is not intended, nor should be construed, as a limitation on the disclosure or the claims to follow.

A. Introduction

The traditional study of receptors has always proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been heretofore recognized is that it is the active state of the receptor that is most useful for discovering agonists, partial agonists, and inverse agonists of the receptor. For those diseases which result from an overly active receptor or an under-active receptor, what is desired in a therapeutic drug is a compound which acts to diminish the active state of a receptor or enhance the activity of the receptor, respectively, not necessarily a drug which is an antagonist to the endogenous ligand. This is because a compound that reduces or enhances the activity of the active receptor state need not bind at the same site as the endogenous ligand. Thus, as taught by a method of this invention, any search for therapeutic compounds should start by screening compounds against the ligand-independent active state.

Screening candidate compounds against non-endogenous, constitutively activated GPCRs allows for the direct identification of candidate compounds which act at these cell surface receptors, without requiring any prior knowledge or use of the receptor's endogenous ligand. By determining areas within the body where the endogenous version of such GPCRs are expressed and/or over-expressed, it is possible to determine related disease/disorder states which are associated with the expression and/or over-expression of these receptors; such an approach is disclosed in this patent document.

B. Disease/Disorder Identification and/or Selection

Most preferably, inverse agonists to the non-endogenous, constitutively activated GPCRs can be identified using the materials of this invention. Such inverse agonists are ideal candidates as lead compounds in drug discovery programs for treating diseases related to these receptors. Because of the ability to directly identify inverse agonists, partial agonists or agonists to these receptors, thereby allowing for the development of pharmaceutical compositions, a search, for diseases and disorders associated with these receptors is possible. For example, scanning both diseased and normal tissue samples for the presence of these receptor now becomes more than an academic exercise or one which might be pursued along the path of identifying, in the case of an orphan receptor, an endogenous ligand. Tissue scans can be conducted across a broad range of healthy and diseased tissues. Such tissue scans provide a preferred first step in associating a specific receptor with a disease and/or disorder.

Preferably, the DNA sequence of the endogenous GPCR is used to make a probe for either radiolabeled cDNA or RT-PCR identification of the expression of the GPCR in tissue samples. The presence of a receptor in a diseased tissue, or the presence of the receptor at elevated or decreased concentrations in diseased tissue compared to a normal tissue, can be preferably utilized to identify a correlation with that disease. Receptors can equally well be localized to regions of organs by this technique. Based on the known functions of the specific tissues to which the receptor is localized, the putative functional role of the receptor can be deduced.

C. A "Human GPCR Proline Marker" Algorithm and the Creation of Non-Endogenous, Constitutively-Active Human GPCRs Among the many challenges facing the biotechnology arts is the unpredictability in gleaning genetic information from one species and correlating that information to another species—nowhere in this art does this problem evidence more annoying exacerbation than in the genetic sequences that encode nucleic acids and proteins. Thus, for consistency and because of the highly unpredictable nature of this art, the following invention is limited, in terms of mammals, to human GPCRs—applicability of this invention to other mammalian species, while a potential possibility, is considered beyond mere rote application.

In general, when attempting to apply common "rules" from one related protein sequence to another or from one species to another, the art has typically resorted to sequence alignment, i.e., sequences are linearized and attempts are then made to find regions of commonality between two or more sequences. While useful, this approach does not always prove to result in meaningful information. In the case of GPCRs, while the general structural motif is identical for all GPCRs, the variations in lengths of the TMs, ECs and ICs make such alignment approaches from one GPCR to another difficult at best. Thus, while it may be desirable to apply a consistent approach to, e.g., constitutive activation from one GPCR to another, because of the great diversity in sequence length, fidelity, etc from one GPCR to the next, a generally applicable, and readily successful mutational alignment approach is in essence not possible. In an analogy, such an approach is akin to having a traveler start a journey at point A by giving the traveler dozens of different maps to point B, without any scale or distance markers on any of the maps, and then asking the traveler to find the shortest and most efficient route to destination B only by using the maps. In such a situation, the task can be readily simplified by having (a) a common "place-marker" on each map, and (b) the ability to measure the distance from the place-marker to destination B—this, then, will allow the traveler to select the most efficient from starting-point A to destination B.

In essence, a feature of the invention is to provide such coordinates within human GPCRs that readily allows for creation of a constitutively active form of the human GPCRs.

As those in the art appreciate, the transmembrane region of a cell is highly hydrophobic; thus, using standard hydrophobicity plotting techniques, those in the art are readily able to determine the TM regions of a GPCR, and specifically TM6 (this same approach is also applicable to determining the EC and IC regions of the GPCR). It has been discovered that within the TM6 region of human GPCRs, a common proline residue (generally near the middle of TM6), acts as a constitutive activation "marker." By counting 15 amino acids from the proline marker, the $16^{th}$ amino acid (which is located in the IC3 loop), when mutated from its endogenous form to a non-endogenous form, leads to constitutive activation of the receptor. For convenience, we refer to this as the "Human GPCR Proline Marker" Algorithm. Although the non-endogenous amino acid at this position can be any of the amino acids, most preferably, the non-endogenous amino acid is lysine. While not wishing to be bound by any theory, we believe that this position itself is unique and that the mutation at this location impacts the receptor to allow for constitutive activation.

We note that, for example, when the endogenous amino acid at the $16^{th}$ position is already lysine (as is the case with GPR4 and GPR32), then in order for X to be a non-endogenous amino acid, it must be other than lysine; thus, in those situations where the endogenous GPCR has an endogenous lysine residue at the $16^{th}$ position, the non-endogenous version of that GPCR preferably incorporates an amino acid other than lysine, preferably alanine, histidine and arginine, at this position. Of further note, it has been determined that GPR4 appears to be linked to Gs and active in its endogenous form (data not shown).

Because there are only 20 naturally occurring amino acids (although the use of non-naturally occurring amino acids is also viable), selection of a particular non-endogenous amino acid for substitution at this $16^{th}$ position is viable and allows for efficient selection of a non-endogenous amino acid that fits the needs of the investigator. However, as noted, the more preferred non-endogenous amino acids at the $16^{th}$ position are lysine, hisitidine, arginine and alanine; with lysine being most preferred. Those of ordinary skill in the art are credited with the ability to readily determine proficient methods for changing the sequence of a codon to achieve a desired mutation.

It has also been discovered that occasionally, but not always, the proline residue marker will be preceded in TM6 by W2 (i.e., $W2P^1AA_{15}X$) where W is tryptophan and 2 is any amino acid residue.

Our discovery, amongst other things, negates the need for unpredictable and complicated sequence alignment approaches commonly used by the art. Indeed, the strength of our discovery, while an algorithm in nature, is that it can be applied in a facile manner to human GPCRs, with dexterous simplicity by those in the art, to achieve a unique and highly useful end-product, i.e., a constitutively activated version of a human GPCR. Because many years and significant amounts of money will be required to determine the endogenous ligands for the human GPCRs that the Human Genome project is uncovering, the disclosed invention not only reduces the time necessary to positively exploit this sequence information, but at significant cost-savings. This approach truly validates the importance of the Human Genome Project because it allows for the utilization of genetic information to not only understand the role of the GPCRs in, e.g., diseases, but also provides the opportunity to improve the human condition.

D. Screening of Candidate Compounds

1. Generic GPCR Screening Assay Techniques

When a G protein receptor becomes constitutively active, it couples to a G protein (e.g., Gq, Gs, Gi, Go) and stimulates release and subsequent binding of GTP to the G protein. The G protein then acts as a GTPase and slowly hydrolyzes the GTP to GDP, whereby the receptor, under normal conditions, becomes deactivated. However, constitutively activated receptors, including the non-endogenous, human constitutively active GPCRs of the present invention, continue to exchange GDP for GTP. A non-hydrolyzable analog of GTP, [$^{35}$S]GTPγS, can be used to monitor enhanced binding to G proteins present on membranes which express constitutively activated receptors. It is reported that [$^{35}$S] GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain.

a. Gs and Gi.

Gs stimulates the enzyme adenylyl cyclase. Gi (and Go), on the other hand, inhibit this enzyme. Adenylyl cyclase catalyzes the conversion of ATP to cAMP; thus, constitutively activated GPCRs that couple the Gs protein are associated with increased cellular levels of cAMP. On the other hand, constitutively activated GPCRs that couple the Gi (or Go) protein are associated with decreased cellular levels of cAMP. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; a most preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) which then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein. The reporter protein such as β-galactosidase or luciferase can then be detected using standard biochemical assays (Chen et al. 1995). With respect to GPCRs that link to Gi (or Go), and thus decrease levels of cAMP, an approach to the screening of, e.g., inverse agonists, based upon utilization of receptors that link to Gs (and thus increase levels of cAMP) is disclosed in the Example section with respect to GPR17 and GPR30.

b. Go and Gq.

Gq and Go are associated with activation of the enzyme phospholipase C, which in turn hydrolyzes the phospholipid $PIP_2$, releasing two intracellular messengers: diacycloglycerol (DAG) and inistol 1,4,5-triphoisphate ($IP_3$). Increased accumulation of $IP_3$ is associated with activation of Gq- and Go-associated receptors. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Assays that detect $IP_3$ accumulation can be utilized to determine if a candidate compound is, e.g., an inverse agonist to a Gq- or Go-associated receptor (i.e., such a compound would decrease the levels of $IP_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

E. Medicinal Chemistry

Generally, but not always, direct identification of candidate compounds is preferably conducted in conjunction with compounds generated via combinatorial chemistry techniques, whereby thousands of compounds are randomly prepared for such analysis. Generally, the results of such screening will be compounds having unique core structures; thereafter, these compounds are preferably subjected to additional chemical modification around a preferred core structure(s) to further enhance the medicinal properties thereof. Such techniques are known to those in the art and will not be addressed in detail in this patent document.

F. Pharmaceutical Compositions

Candidate compounds selected for further development can be formulated into pharmaceutical compositions using techniques well known to those in the art. Suitable pharmaceutically-acceptable carriers are available to those in the art; for example, see Remington's Pharmaceutical Sciences, $16^{th}$ Edition, 1980, Mack Publishing Co., (Oslo et al., eds.)

G. Other Utility

Although a preferred use of the non-endogenous versions of the disclosed human GPCRs is for the direct identification of candidate compounds as inverse agonists, agonists or partial agonists (preferably for use as pharmaceutical agents), these receptors can also be utilized in research settings. For example, in vitro and in vivo systems incorporating these receptors can be utilized to further elucidate and understand the roles of the receptors in the human condition, both normal and diseased, as well understanding the role of constitutive activation as it applies to understanding the signaling cascade. A value in these non-endogenous receptors is that their utility as a research tool is enhanced in that, because of their unique features, the disclosed receptors can be used to understand the role of a particular receptor in the human body before the endogenous ligand therefor is identified. Other uses of the disclosed receptors will become apparent to those in the art based upon, inter alia, a review of this patent document.

EXAMPLES

The following examples are presented for purposes of elucidation, and not limitation, of the present invention. Following the teaching of this patent document that a mutational cassette may be utilized in the IC3 loop of human GPCRs based upon a position relative to a proline residue in TM6 to constitutively activate the receptor, and while specific nucleic acid and amino acid sequences are disclosed herein, those of ordinary skill in the art are credited with the ability to make minor modifications to these sequences while achieving the same or substantially similar results reported below. Particular approaches to sequence mutations are within the purview of the artisan based upon the particular needs of the artisan.

Example 1

Preparation of Endogenous Human GPCRs

A variety of GPCRs were utilized in the Examples to follow. Some endogenous human GPCRs were graciously provided in expression vectors (as acknowledged below) and other endogenous human GPCRs were synthesized de novo using publicly-available sequence information.

1. GPR1 (GenBank Accession Number: U13666)

The human cDNA sequence for GPR1 was provided in pRcCMV by Brian O'Dowd (University of Toronto). GPR1 cDNA (1.4 kB fragment) was excised from the pRcCMV vector as a NdeI-XbaI fragment and was subcloned into the NdeI-XbaI site of pCMV vector (see. FIG. 3). Nucleic acid (SEQ.ID.NO.: 1) and amino acid (SEQ.ID.NO.: 2) sequences for human GPR1 were thereafter determined and verified.

2. GPR4 (GenBank Accession Numbers: L36148, U35399, U21051)

The human cDNA sequence for GPR4 was provided in pRcCMV by Brian O'Dowd (University of Toronto). GPR1 cDNA (1.4 kB fragment) was excised from the pRcCMV vector as an ApaI(blunted)-XbaI fragment and was subcloned (with most of the 5' untranslated region removed) into HindIII(blunted)-XbaI site of pCMV vector. Nucleic acid (SEQ.ID.NO.: 3) and amino acid (SEQ.ID.NO.: 4) sequences for human GPR4 were thereafter determined and verified.

3. GPR5 (GenBank Accession Number: L36149)

The cDNA for human GPR5 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 64° C. for 1 min; and 72° C. for 1.5 min. The 5' PCR primer contained an EcoRI site with the sequence:
5'-TATGAATTCAGATGCTCTAAACGTCCCTGC-3' (SEQ.ID.NO.: 5)

and the 3' primer contained BamHI site with the sequence:
5'-TCCGGATCCACCTGCACCTGCGCCTGCACC-3' (SEQ.ID.NO.: 6).

The 1.1 kb PCR fragment was digested with EcoRI and BamHI and cloned into EcoRI-BamHI site of PCMV expression vector. Nucleic acid (SEQ.ID.NO.: 7) and amino acid (SEQ.ID.NO.: 8) sequences for human GPR5 were thereafter determined and verified.

4. GPR7 (GenBank Accession Number: U22491)

The cDNA for human GPR7 was generated and cloned into pCMV expression vector as follows: PCR condition- PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer contained a HindIII site with the sequence:
5'-GCAAGCTTGGGGGACGCCAGGTCGCCGGCT-3' (SEQ.ID.NO.: 9)

and the 3' primer contained a BamHI site with the sequence:
5'-GCGGATCCGGACGCTGGGGGAGTCAGGCTGC-3' (SEQ.ID.NO.: 10).

The 1.1 kb PCR fragment was digested with HindIII and BamHI and cloned into HindIII-BamHI site of pCMV expression vector. Nucleic acid (SEQ.ID.NO.: 11) and amino acid (SEQ.ID.NO.: 12) sequences for human GPR7 were thereafter determined and verified.

5. GPR8 (GenBank Accession Number: U22492)

The cDNA for human GPR8 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 62° C. for 1 min; and 72 ° C. for 1 min and 20 sec. The 5' PCR primer contained an EcoRI site with the sequence:
5'-CGGAATTCGTCAACGGTCCCAGCTACAATG-3' (SEQ.ID.NO.: 13)

and the 3' primer contained a BamHI site with the sequence:
5'-ATGGATCCCAGGCCCTTCAGCACCGCAATAT-3' (SEQ.ID.NO.: 14).

The 1.1 kb PCR fragment was digested with EcoRI and BamHI and cloned into EcoRI-BamHI site of PCMV expression vector. All 4 cDNA clones sequenced contained a possible polymorphism involving a change of amino acid 206 from Arg to Gln. Aside from this difference, nucleic acid (SEQ.ID.NO.: 15) and amino acid (SEQ.ID.NO.: 16) sequences for human GPR8 were thereafter determined and verified.

6. GPR9 (GenBank Accession Number: X95876)

The cDNA for human GPR9 was generated and cloned into pCMV expression vector as follows: PCR was performed using a clone (provided by Brian O'Dowd) as template and pfu polymerase (Stratagene) with the buffer system provided by the manufacturer supplemented with 10% DMSO, 0.25 µM of each primer, and 0.5 mM of each of the 4 nucleotides. The cycle condition was 25 cycles of: 94° C. for 1 min; 56° C. for 1 min; and 72° C. for 2.5 min. The 5' PCR primer contained an EcoRI site with the sequence:
5'-ACGAATTCAGCCATGGTCCTTGAGGTGAGTGAC CACCAAGTGCTAAAT-3' (SEQ.ID.NO.: 17)

and the 3' primer contained a BamHI site with the sequence:
5'-GAGGATCCTGGAATGCGGGGAAGTCAG-3' (SEQ.ID.NO.: 18).

The 1.2 kb PCR fragment was digested with EcoRI and cloned into EcoRI-SmaI site of PCMV expression vector. Nucleic acid (SEQ.ID.NO.: 19) and amino acid (SEQ.ID.NO.: 20) sequences for human GPR9 were thereafter determined and verified.

7. GPR9-6 (GenBank Accession Number: U45982)

The cDNA for human GPR9-6 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer was kinased with the sequence:

5'-TTAAGCTTGACCTAATGCCATCTTGTGTCC-3' (SEQ.ID.NO.: 21)

and the 3' primer contained a BamHI site with the sequence:
5'-TTGGATCCAAAAGAACCATGCACCTCAGAG-3' (SEQ.ID.NO.: 22).

The 1.2 kb PCR fragment was digested with BamHI and cloned into EcoRV-BamHI site of pCMV expression vector. Nucleic acid (SEQ.ID.NO.: 23) and amino acid (SEQ.ID.NO.: 24) sequences for human GPR9-6 were thereafter determined and verified.

8. GPR10 (GenBank Accession Number: U32672)

The human cDNA sequence for GPR10 was provided in pRcCMV by Brian O'Dowd (University of Toronto). GPR10 cDNA (1.3 kB fragment) was excised from the pRcCMV vector as an EcoRI-XbaI fragment and was subcloned into EcoRI-XbaI site of pCMV vector. Nucleic acid (SEQ.ID.NO.: 25) and amino acid (SEQ.ID.NO.: 26) sequences for human GPR10 were thereafter determined and verified.

9. GPR15 (GenBank Accession Number: U34806)

The human cDNA sequence for GPR15 was provided in pcDNA3 by Brian O'Dowd (University of Toronto). GPR15 cDNA (1.5 kB fragment) was excised from the pCDNA3 vector as a HindIII-Bam fragment and was subcloned into HindIII-Bam site of pCMV vector. Nucleic acid (SEQ.ID.NO.: 27) and amino acid (SEQ.ID.NO.: 28) sequences for human GPR15 were thereafter determined and verified.

10. GPR17 (GenBank Accession Number: Z94154)

The cDNA for human GPR17 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each 4 nucleotides. The cycle condition was 30 cycles of: 94° C. for 1 min; 56° C. for 1 min and 72° C. for 1 min and 20 sec. The 5' PCR primer contained an EcoRI site with the sequence:

5'-CTAGAATTCTGACTCCAGCCAAAGCATGAAT-3' (SEQ.ID.NO.: 29)and the 3'
primer contained a BamHI site with the sequence:
5'-GCTGGATCCTAAACAGTCTGCGCTCGGCCT-3' (SEQ.ID.NO.: 30).

The 1.1 kb PCR fragment was digested with EcoRI and BamHI and cloned into EcoRI-BamHI site of pCMV expression vector. Nucleic acid (SEQ.ID.NO.: 31) and amino acid (SEQ.ID.NO.: 32) sequences for human GPR17 were thereafter determined and verified.

11. GPR18 (GenBank Accession Number: L42324)

The cDNA for human GPR18 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 54° C. for 1 min; and 72° C. for 1 min and 20 sec. The 5' PCR primer was kinased with the sequence:

5'-ATAAGATGATCACCCTGAACAATCAAGAT-3' (SEQ.ID.NO.: 33)

and the 3' primer contained an EcoRI site with the sequence:
5'-TCCGAATTCATAACATTTCACTGTTTATATTGC-3' (SEQ.ID.NO.: 34).

The 1.0 kb PCR fragment was digested with EcoRI and cloned into blunt-EcoRI site of pCMV expression vector. All 8 cDNA clones sequenced contained 4 possible polymorphisms involving changes of amino acid 12 from Thr to Pro, amino acid 86 from Ala to Glu, amino acid 97 from Ile to Leu and amino acid 310 from Leu to Met. Aside from these changes, nucleic acid (SEQ.ID.NO.: 35) and amino acid (SEQ.ID.NO.: 36) sequences for human GPR18 were thereafter determined and verified.

12. GPR20 (GenBank Accession Number: U66579)

The cDNA for human GPR20 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer was kinased with the sequence:

5'-CCAAGCTTCCAGGCCTGGGGTGTGCTGG-3' (SEQ.ID.NO.: 37)

and the 3' primer contained a BamHI site with the sequence:
5'-ATGGATCCTGACCTTCGGCCCCTGGCAGA-3' (SEQ.ID.NO.: 38).

The 1.2 kb PCR fragment was digested with BamHI and cloned into EcoRV-BamHI site of PCMV expression vector. Nucleic acid (SEQ.ID.NO.: 39) and amino acid (SEQ.ID.NO.: 40) sequences for human GPR20 were thereafter determined and verified.

13. GPR21 (GenBank Accession Number: U66580)

The cDNA for human GPR21 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer was kinased with the sequence:

5'-GAGAATTCACTCCTGAGCTCAAGATGAACT-3' (SEQ.ID.NO.: 41)

and the 3' primer contained a BamHI site with the sequence:
5'-CGGGATCCCCGTAACTGAGCCACTTCAGAT-3' (SEQ.ID.NO.: 42).

The 1.1 kb PCR fragment was digested with BamHI and cloned into EcoRV-BamHI site of pCMV expression vector. Nucleic acid (SEQ.ID.NO.: 43) and amino acid (SEQ.ID.NO.: 44) sequences for human GPR21 were thereafter determined and verified.

14. GPR22 (GenBank Accession Number: U66581)

The cDNA for human GPR22 was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 50° C. for 1 min; and 72° C. for 1.5 min. The 5' PCR primer was kinased with the sequence:
5'-TCCCCCGGGAAAAAAACCAACTGCTCCAAA-3' (SEQ.ID.NO.: 45)
and the 3' primer contained a BamHI site with the sequence:
5'-TAGGATCCATTTGAATGTGGATTTGGTGAAA-3' (SEQ.ID.NO.: 46).
The 1.38 kb PCR fragment was digested with BamHI and cloned into EcoRV-BamHI site of pCMV expression vector. Nucleic acid (SEQ.ID.NO.: 47) and amino acid (SEQ.ID.NO.: 48) sequences for human GPR22 were thereafter determined and verified.

15. GPR24 (GenBank Accession Number: U71092)

The cDNA for human GPR24 was generated and cloned into pCMV expression vector as follows: PCR was performed using genomic DNA as template and rTth polymerase (Perkin Elmer) with the buffer system provided by the manufacturer, 0.25 $\mu$M of each primer, and 0.2 mM of each 4 nucleotides. The cycle condition was 30 cycles of: 94° C. for 1 min; 56° C. for 1 min; and 72° C. for 1 min and 20 sec. The 5' PCR primer contains a HindIII site with the sequence:
5'-GTGAAGCTTGCCTCTGGTGCCTGCAGGAGG-3' (SEQ.ID.NO.: 49)
and the 3' primer contains an EcoRI site with the sequence:
5'-GCAGAATTCCCGGTGGCGTGTTGTGGTGCCC-3' (SEQ.ID.NO.: 50).
The 1.3 kb PCR fragment was digested with HindIII and EcoRI and cloned into HindIII-EcoRI site of pCMV expression vector. The nucleic acid (SEQ.ID.NO.: 51) and amino acid sequence (SEQ.ID.NO.: 52) for human GPR24 were thereafter determined and verified.

16. GPR30 (GenBank Accession Number: U63917)

The cDNA for human GPR30 was generated and cloned as follows: the coding sequence of GPR30 (1128 bp in length) was amplified from genomic DNA using the primers:
5'-GGCGGATCCATGGATGTGACTTCCCAA-3' (SEQ.ID.NO.: 53) and
5'-GGCGGATCCCTACACGGCACTGCTGAA-3' (SEQ.ID.NO.: 54).
The amplified product was then cloned into a commercially available vector, pCR2.1 (Invitrogen), using a "TOPO-TA Cloning Kit" (Invitrogen, #K4500-01), following manufacturer instructions. The full-length GPR30 insert was liberated by digestion with BamH1, separated from the vector by agarose gel electrophoresis, and purified using a Sephaglas Bandprep™ Kit (Pharmacia, # 27-9285-01) following manufacturer instructions. The nucleic acid (SEQ.ID.NO.: 55) and amino acid sequence (SEQ.ID.NO.: 56) for human GPR30 were thereafter determined and verified.

17. GPR31 (GenBank Accession Number: U65402)

The cDNA for human GPR31 was generated and cloned into pCMV expression vector as follows: PCR was performed using genomic DNA as template and rTth polymerase (Perkin Elmer) with the buffer system provided by the manufacturer, 0.25 $\mu$M of each primer, and 0.2 mM of each of the 4 nucleotides. The cycle condition was 30 cycles of: 94° C. for 1 min;. 58° C. for 1 min; and 72° C. for 2 min. The 5' PCR primer contained an EcoRI site with the sequence:
5'-AAGGAATTCACGGCCGGGTGATGCCATTCCC-3' (SEQ.ID.NO.: 57)
and the 3' primer contained a BamHI site with the sequence:
5'-GGTGGATCCATAAACACGGGCGTTGAGGAC-3' (SEQ.ID.NO.: 58).
The 1.0 kb PCR fragment was digested with EcoRI and BamHI and cloned into EcoRI-BamHI site of pCMV expression vector. Nucleic acid (SEQ.ID.NO.: 59) and amino acid (SEQ.ID.NO.: 60) sequences for human GPR31 were thereafter determined and verified.

18. GPR32 (GenBank Accession Number: AF045764)

The cDNA for human GPR32 was generated and cloned into pCMV expression vector as follows: PCR was performed using genomic DNA as template and rTth polymerase (Perkin Elmer) with the buffer system provided by the manufacturer, 0.25 $\mu$M of each primer, and 0.2 mM of each 4 nucleotides. The cycle condition was 30 cycles of: 94° C. for 1 min; 56° C. for 1 min; and 72° C. for 1 min and 20 sec. The 5' PCR primer contained an EcoRI site with the sequence:
5'-TAAGAATTCCATAAAAATTATGGAATGG-3' (SEQ.ID.NO.:243)
and the 3' primer contained a BamHI site with the sequence:
5'-CCAGGATCCAGCTGAAGTCTTCCATCATTC-3' (SEQ.ID.NO.: 244).
The 1.1 kb PCR fragment was digested with EcoRI and BamHI and cloned into EcoRI-BamHI site of pCMV expression vector. Nucleic acid (SEQ.ID.NO.: 245) and amino acid (SEQ.ID.NO.: 246) sequences for human GPR32 were thereafter determined and verified.

19. GPR40 (GenBank Accession Number: AF024687)

The cDNA for human GPR40 was generated and cloned into pCMV expression vector as follows: PCR was performed using genomic DNA as template and rTth polymerase (Perkin Elmer) with the buffer system provided by the manufacturer, 0.25 $\mu$M of each primer, and 0.2 mM of each 4 nucleotides. The cycle condition was 30 cycles of: 94° C. for 1 min, 65° C. for 1 min and 72° C. for 1 min and 10 sec. The 5' PCR primer contained an EcoRI site with the sequence
5'-GCAGAATTCGGCGGCCCCATGGACCTGCCCCC-3' (SEQ.ID.NO.: 247)
and the 3' primer contained a BamHI site with the sequence
5'-GCTGGATCCCCCGAGCAGTGGCGTTACTTC-3' (SEQ.ID.NO.: 248).
The 1 kb PCR fragment was digested with EcoRI and BamHI and cloned into EcoRI-BamHI site of pCMV expression vector. Nucleic acid (SEQ.ID.NO.: 249) and amino acid (SEQ.ID.NO.: 250) sequences for human GPR40 were thereafter determined and verified.

20. GPR41 (GenBank Accession Number AF024688)

The cDNA for human GPR41 was generated and cloned into pCMV expression vector as follows: PCR was performed using genomic DNA as template and rTth polymerase (Perkin Elmer) with the buffer system provided by the manufacturer, 0.25 $\mu$M of each primer, and 0.2 mM of each 4 nucleotides. The cycle condition was 30 cycles of 94° C. for 1 min, 65° C. for 1 min and 72° C. for 1 min and 10 sec. The 5' PCR primer contained an HindIII site with the sequence:
5'-CTCAAGCTTACTCTCTCTCACCAGTGGCCAC-3' (SEQ.ID.NO.: 251)
and the 3' primer was kinased with the sequence
5'-CCCTCCTCCCCCGGAGGACCTAGC-3' (SEQ.ID.NO.: 252).
The 1 kb PCR fragment was digested with HindIII and cloned into HindIII-blunt site of pCMV expression vector. Nucleic acid (SEQ.ID.NO.: 253) and amino acid (SEQ.ID.NO.: 254) sequences for human GPR41 were thereafter determined and verified.

21. GPR43 (GenBank Accession Number: AF024690)

The cDNA for human GPR43 was generated and cloned into pCMV expression vector as follows: PCR was performed using genomic DNA as template and rTth polymerase (Perkin Elmer) with the buffer system provided by the manufacturer, 0.25 μM of each primer, and 0.2 mM of each 4 nucleotides. The cycle condition was 30 cycles of: 94° C. for 1 min; 65° C. for 1 min; and 72° C. for 1 min and 10 sec. The 5' PCR primer contains an HindIII site with the sequence:
5'-TTTAAGCTTCCCCTCCAGGATGCTGCCGGAC-3' (SEQ.ID.NO.: 255)
and the 3' primer contained an EcoRI site with the sequence:
5'-GGCGAATTCTGAAGGTCCAGGGAAACTGCTA-3' (SEQ.ID.NO. 256).
The 1 kb PCR fragment was digested with HindIII and EcoRI and cloned into HindIII-EcoRI site of pCMV expression vector. Nucleic acid (SEQ.ID.NO.: 257) and amino acid (SEQ.ID.NO.: 258) sequences for human GPR43 were thereafter determined and verified.

22. APJ (GenBank Accession Number: U03642)

Human APJ cDNA (in pRcCMV vector) was provided by Brian O'Dowd (University of Toronto). The human APJ cDNA was excised from the pRcCMV vector as an EcoRI-XbaI (blunted) fragment and was subcloned into EcoRI-SmaI site of pCMV vector. Nucleic acid (SEQ.ID.NO.: 61) and amino acid (SEQ.ID.NO.: 62) sequences for human APJ were thereafter determined and verified.

23. BLR1 (GenBank Accession Number: X68149)

The cDNA for human BLR1 was generated and cloned into pCMV expression vector as follows: PCR was performed using thymus cDNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer contained an EcoRI site with the sequence:
5'-TGAGAATTCTGGTGACTCACAGCCGGCACAG-3' (SEQ.ID.NO.: 63):
and the 3' primer contained a BamHI site with the sequence:
5'-GCCGGATCCAAGCAAAAGCAGCAATAAAAGG-3' (SEQ.ID.NO.: 64). The 1.2 kb PCR fragment was digested with EcoRI and BamHI and cloned into EcoR-BamHI site of pCMV expression vector. Nucleic acid (SEQ.ID.NO.: 65) and amino acid (SEQ.ID.NO.: 66) sequences for human BLR1 were thereafter determined and verified.

24. CEPR (GenBank Accession Number: U77827)

The cDNA for human CEPR was generated and cloned into pCMV expression vector as follows: PCR was performed using genomic DNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1 min and 20 sec. The 5' PCR primer was kinased with the sequence:
5'-CAAAGCTTGAAAGCTGCACGGTGCAGAGAC-3' (SEQ.ID.NO.:67)
and the 3' primer contained a BamHI site with the sequence:
5'-GCGGATCCCGAGTCACACCCTGGCTGGGCC-3' (SEQ.ID.NO.: 68).
The 1.2 kb PCR fragment was digested with BamHI and cloned into EcoRV-BamHI site of pCMV expression vector. Nucleic acid (SEQ.ID.NO.: 69) and amino acid (SEQ.ID.NO.: 70) sequences for human CEPR were thereafter determined and verified.

25. EBI1 (GenBank Accession Number: L31581)

The cDNA for human EBI1 was generated and cloned into pCMV expression vector as follows: PCR was performed using thymus cDNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 62° C. for 1 min; and 72° C. for 1 min and 20 sec. The 5' PCR primer contained an EcoRI site with the sequence:
5'-ACAGAATTCCTGTGTGGTTTTACCGCCCAG-3' (SEQ.ID.NO.: 71)
and the 3' primer contained a BamHI site with the sequence:
5'-CTCGGATCCAGGCAGAAGAGTCGCCTATGG-3' (SEQ.ID.NO.: 72).
The 1.2 kb PCR fragment was digested with EcoRI and BamHI and cloned into EcoRI-BamHI site of PCMV expression vector. Nucleic acid (SEQ.ID.NO.: 73) and amino acid (SEQ.ID.NO.: 74) sequences for human EBI1 were thereafter determined and verified.

26. EBI2 (GenBank Accession Number: L08177)

The cDNA for human EBI2 was generated and cloned into pCMV expression vector as follows: PCR was performed using cDNA clone (graciously provided by Kevin Lynch, University of Virginia Health Sciences Center; the vector utilized was not identified by the source) as template and pfu polymerase (Stratagene) with the buffer system provided by the manufacturer supplemented with 10% DMSO, 0.25 μM of each primer, and 0.5 mM of each of the 4 nucleotides. The cycle condition was 30 cycles of: 94° C. for 1 min; 60° C. for 1 min; and 72° C. for 1 min and 20 sec. The 5' PCR primer contained an EcoRI site with the sequence:
5'-CTGGAATTCACCTGGACCACCACCAATGGATA-3' (SEQ.ID.NO.: 75)
and the 3' primer contained a BamHI site with the sequence
5'-CTCGGATCCTGCAAAGTTTGTCATACAG TT-3' (SEQ.ID.NO.: 76).
The 1.2 kb PCR fragment was digested with EcoRI and BamHI and cloned into EcoRI-BamHI site of pCMV expression vector. Nucleic acid (SEQ.ID.NO.: 77) and amino acid (SEQ.ID.NO.: 78) sequences for human EBI2 were thereafter determined and verified.

27. ETBR-LP2 (GenBank Accession Number: D38449)

The cDNA for human ETBR-LP2 was generated and cloned into pCMV expression vector as follows: PCR was performed using brain cDNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1.5 min. The 5' PCR contained an EcoRI site with the sequence:
5'-CTGGAATTCTCCTGCTCATCCAGCCATGCGG-3' (SEQ.ID.NO.: 79)
and the 3' primer contained a BamHI site with the sequence:
5'-CCTGGATCCCCACCCCTACTGGGGCCTCAG-3' (SEQ.ID.NO.: 80).
The 1.5 kb PCR fragment was digested with EcoRI and BamHI and cloned into EcoRI-BamHI site of pCMV expression vector. Nucleic acid (SEQ.ID.NO.: 81) and amino acid (SEQ.ID.NO.: 82) sequences for human ETBR-LP2 were thereafter determined and verified.

28. GHSR (GenBank Accession Number: U60179)

The cDNA for human GHSR was generated and cloned into pCMV expression vector as follows: PCR was performed using hippocampus cDNA as template and TaqPlus Precision polymerase (Stratagene) with the buffer system provided by the manufacturer, 0.25 μM of each primer, and 0.2 mM of each of the 4 nucleotides. The cycle condition was 30 cycles of: 94° C. for 1 min; 68° C. for 1 min; and 72°

C. for 1 min and 10 sec. For first round PCR, the 5' PCR primer sequence was:
5'-ATGTGGAACGCGACGCCCAGCG-3' (SEQ.ID.NO.: 83)
and the 3' primer sequence was:
5'-TCATGTATTAATACTAGATTCT-3' (SEQ.ID.NO.: 84).
Two microliters of the first round PCR was used as template for the second round PCR where the 5' primer was kinased with sequence:
5'-TACCATGTGGAACGCGACGCCCAGCGAAGAGC CGGGGT-3'(SEQ.ID.NO.:85)
and the 3' primer contained an EcoRI site with the sequence:
5'-CGGAATTCATGTATTAATACTAGATTCTGTCCAG GCCCG-3'(SEQ.ID.NO. :86).
The 1.1 kb PCR fragment was digested with EcoRI and cloned into blunt-EcoRI site of pCMV expression vector. Nucleic acid (SEQ.ID.NO.: 87) and amino acid (SEQ.ID.NO.: 88) sequences for human GHSR were thereafter determined and verified.

29. GPCR-CNS (GenBank Accession Number: AFO17262)

The cDNA for human GPCR-CNS was generated and cloned into pCMV expression vector as follows: PCR was performed using brain cDNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 65° C. for 1 min; and 72° C. for 2 min. The 5' PCR primer contained a HindIII site with the sequence:
5'-GCAAGCTTGTGCCCTCACCAAGCCATGCGAG CC-3' (SEQ.ID.NO.: 89)
and the 3' primer contained an EcoRI site with the sequence:
5'-CGGAATTCAGCAATGAGTTCCGACAGAAGC-3' (SEQ.ID.NO.: 90).
The 1.9 kb PCR fragment was digested with HindIII and EcoRI and cloned into HindIII-EcoRI site of pCMV expression vector. All nine clones sequenced contained a potential polymorphism involving a S284C change. Aside from this difference, nucleic acid (SEQ.ID.NO.: 91) and amino acid (SEQ.ID.NO.: 92) sequences for human GPCR-CNS were thereafter determined and verified.

30. GPR-NGA (GenBank Accession Number: U55312)

The cDNA for human GPR-NGA was generated and cloned into pCMV expression vector as follows: PCR was performed using genomic DNA as template and rTth polymerase (Perkin Elmer) with the buffer system provided by the manufacturer, 0.25 µM of each primer, and 0.2 mM of each of the 4 nucleotides. The cycle condition was 30 cycles of 94° C. for 1 min, 56° C. for 1 min and 72° C. for 1.5 min. The 5' PCR primer contained an EcoRI site with the sequence:
5'-CAGAATTCAGAGAAAAAAGTGAATATGGTTT TT-3' (SEQ.ID.NO.: 93)
and the 3' primer contained a BamHI site with the sequence:
5'-TTGGATCCCTGGTGCATAACAATTGAAAGAAT-3' (SEQ.ID.NO.: 94).
The 1.3 kb PCR fragment was digested with EcoRI and BamHI and cloned into EcoRI-BamHI site of pCMV expression vector. Nucleic acid (SEQ.ID.NO.: 95) and amino acid (SEQ.ID.NO.: 96) sequences for human GPR-NGA were thereafter determined and verified.

31. H9 (GenBank Accession Number: U52219)

The cDNA for human HB954 was generated and cloned into pCMV expression vector as follows: PCR was performed using pituitary cDNA as template and rTth polymerase (Perkin Elmer) with the buffer system provided by the manufacturer, 0.25 µM of each primer, and 0.2 mM of each 4 nucleotides. The cycle condition was 30 cycles of: 94° C. for 1 min, 62° C. for 1 min and 72° C. for 2 min. The 5' PCR primer contains a HindIII site with the sequence:
5'-GGAAAGCTTAACGATCCCCAGGAGCAACAT-3' (SEQ.ID.NO.: 97)
and the 3' primer contains a BamHI site with the sequence:
5'-CTGGGATCCTACGAGAGCATTTTTCACACAG-3' (SEQ.ID.NO.: 98).
The 1.9 kb PCR fragment was digested with HindIII and BamHI and cloned into HindIII-BamHI site of pCMV expression vector. When compared to the published sequences, a different isoform with 12 bp in frame insertion in the cytoplasmic tail was also identified and designated "H9b." Both isoforms contain two potential polymorphisms involving changes of amino acid P320S and amino acid G448A. Isoform H9a contained another potential polymorphism of amino acid S493N, while isoform H9b contained two additional potential polymorphisms involving changes of amino acid I502T and amino acid A532T (corresponding to amino acid 528 of isoform H9a). Nucleic acid (SEQ.ID.NO.: 99) and amino acid (SEQ.ID.NO.: 100) sequences for human H9 were thereafter-determined and verified (in the section below, both isoforms were mutated in accordance with the Human GPCR Proline Marker Algorithm).

32. HB954 (GenBank Accession Number: D38449)

The cDNA for human HB954 was generated and cloned into pCMV expression vector as follows: PCR was performed using brain cDNA as template and rTth polymerase (Perkin Elmer) with the buffer system provided by the manufacturer, 0.25 µM of each primer, and 0.2 mM of each of the 4 nucleotides. The cycle condition was 30 cycles of 94° C. for 1 min, 58° C. for 1 min and 72° C. for 2 min. The 5' PCR contained a HindIII site with the sequence:
5'-TCCAAGCTTCGCCATGGGACATAACGGGAGCT-3' (SEQ.ID.NO.: 101)
and the 3' primer contained an EcoRI site with the sequence:
5'-CGTGAATTCCAAGAATTTACAATCCTTGCT-3' (SEQ.ID.NO.: 102).
The 1.6 kb PCR fragment was digested with HindIII and EcoRI and cloned into HindIII-EcoRI site of pCMV expression vector. Nucleic acid (SEQ.ID.NO.: 103) and amino acid (SEQ.ID.NO.: 104) sequences for human HB954 were thereafter determined and verified.

33. HG38 (GenBank Accession Number: AF062006)

The cDNA for human HG38 was generated and cloned into pCMV expression vector as follows: PCR was performed using brain cDNA as template and rTth polymerase (Perkin Elmer) with the buffer system provided by the manufacturer, 0.25 µM of each primer, and 0.2 mM of each 4 nucleotides. The cycle condition was 30 cycles of 94° C. for 1 min, 56° C. for 1 min and 72° C. for 1 min and 30 sec. Two PCR reactions were performed to separately obtain the 5' and 3' fragment. For the 5' fragment, the 5' PCR primer contained an HindIII site with the sequence:
5'-CCCAAGCTTCGGGCACCATGGACACCTCCC-3' (SEQ.ID.NO.: 259)
and the 3' primer contained a BamHIsite with the sequence:
5'-ACAGGATCCAAATGCACAGCACTGGTAAGC-3' (SEQ.ID.NO.: 260).
This 5' 1.5 kb PCR fragment was digested with HindIII and BamHI and cloned into an HindII-BamHI site of pCMV. For the 3' fragment, the 5' PCR primer was kinased with the sequence:
5'-CTATAACTGGGTTACATGGTTTAAC-3' (SEQ.ID.NO. 261)

and the 3' primer contained an EcoRI site with the sequence:
5'-TTTGAATTCACATATTAATTAGAGACATGG-3' (SEQ.ID.NO.: 262).
The 1.4 kb 3' PCR fragment was digested with EcoRI and subcloned into a blunt-EcoRI site of pCMV vector. The 5' and 3' fragments were then ligated together through a common EcoRV site to generate the full length cDNA clone. Nucleic acid (SEQ.ID.NO.: 263) and amino acid (SEQ.ID.NO.: 264) sequences for human HG38 were thereafter determined and verified.

34. HM74 (GenBank Accession Number: D10923)

The cDNA for human HM74 was generated and cloned into pCMV expression vector as follows: PCR was performed using either genomic DNA or thymus cDNA (pooled) as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1 min and 20 sec. The 5' PCR primer contained an EcoRI site with the sequence:
5'-GGAGAATTCACTAGGCGAGGCGCTCCATC-3' (SEQ.ID.NO.: 105)
and the 3' primer was kinased with the sequence:
5'-GGAGGATCCAGGAAACCTTAGGCCGAGTCC-3' (SEQ.ID.NO.: 106).
The 1.3 kb PCR fragment was digested with EcoRI and cloned into EcoRI-SmaI site of pCMV expression vector. Clones sequenced revealed a potential polymorphism involving a N94K change. Aside from this difference, nucleic acid (SEQ.ID.NO.: 107) and amino acid (SEQ.ID.NO.: 108) sequences for human HM74 were thereafter determined and verified.

35. MIG (GenBank Accession Numbers: AFO44600 and AFO44601)

The cDNA for human MIG was generated and cloned into pCMV expression vector as follows: PCR was performed using genomic DNA as template and TaqPlus Precision polymerase (Stratagene) for first round PCR or pfu polymerase (Stratagene) for second round PCR with the buffer system provided by the manufacturer, 0.25 μM of each primer, and 0.2 mM (TaqPlus Precision) or 0.5 mM (pfu) of each of the 4 nucleotides. When pfu was used, 10% DMSO was included in the buffer. The cycle condition was 30 cycles of: 94° C. for 1 min; 65° C. for 1 min; and 72° C. for: (a) 1 min for first round PCR; and (b) 2 min for second round PCR. Because there is an intron in the coding region, two sets of primers were separately used to generate overlapping 5' and 3' fragments. The 5' fragment PCR primers were:
5'-ACCATGGCTTGCAATGGCAGTGCGGCCAGGGG GCACT-3' (external sense) (SEQ.ID.NO.: 109) and
5'-CGACCAGGACAAACAGCATCTTGGTCACTTGT CTCCGGC-3'(internal antisense) (SEQ.ID.NO.: 110).
The 3' fragment PCR primers were:
5'-GACCAAGATGCTGTTTGTCCTGGTCGTGGTGT TTGGCAT-3' (internal sense) (SEQ.ID.NO.: 111) and
5'-CGGAATTCAGGATGGATCGGTCTCTTGCTGCG CCT-3' (external antisense with an EcoRI site) (SEQ.ID.NO.: 112).
The 5' and 3' fragments were ligated together by using the first round PCR as template and the kinased external sense primer and external antisense primer to perform second round PCR. The 1.2 kb PCR fragment was digested with EcoRI and cloned into the blunt-EcoRI site of pCMV expression vector. Nucleic acid (SEQ.ID.NO.: 113) and amino acid (SEQ.ID.NO.: 114) sequences for human MIG were thereafter determined and verified.

36. OGR1 (GenBank Accession Number: U48405)

The cDNA for human OGR1 was generated and cloned into pCMV expression vector as follows: PCR was performed using genomic DNA as template and rTth polymerase (Perkin Elmer) with the buffer system provided by the manufacturer, 0.25 μM of each primer, and 0.2 mM of each of the 4 nucleotides. The cycle condition was 30 cycles of: 94° C. for 1 min; 65° C. for 1 min; and 72° C. for 1 min and 20 sec. The 5' PCR primer was kinased with the sequence:
5'-GGAAGCTTCAGGCCCAAAGATGGGGAACAT-3' (SEQ.ID.NO.: 115)
and the 3' primer contained a BamHI site with the sequence:
5'-GTGGATCCACCCGCGGAGGACCCAGGCTAG-3' (SEQ.ID.NO.: 116).
The 1.1 kb PCR fragment was digested with BamHI and cloned into the EcoRV-BamHI site of pCMV expression vector. Nucleic acid (SEQ.ID.NO.: 117) and amino acid (SEQ.ID.NO.: 118) sequences for human OGR1 were thereafter determined and verified.

37. Serotonin 5HT$_{2A}$

The cDNA encoding endogenous human 5HT$_{2A}$ receptor was obtained by RT-PCR using human brain poly-A$^+$ RNA; a 5' primer from the 5' untranslated region with an Xho I restriction site:
5'-GACCTCGAGTCCTTCTACACCTCATC-3' (SEQ.ID.NO: 119)
and a 3' primer from the 3' untranslated region containing an Xba I site:
5'-TGCTCTAGATTCCAGATAGGTGAAAACTTG-3' (SEQ.ID.NO: 120).
PCR was performed using either TaqPlus™ precision polymerase (Stratagene) or rTth™ polymerase (Perkin Elmer) with the buffer system provided by the manufacturers, 0.25 μM of each primer, and 0.2 mM of each of the 4 nucleotides. The cycle condition was 30 cycles of: 94° C. for 1 min; 57° C. for 1 min; and 72° C. for 2 min. The 1.5 kb PCR fragmen was digested with Xba I and subcloned into Eco RV-Xba I site of pBluescript. The resulting cDNA clones were fully sequenced and found to encode two amino acid changes from the published sequences. The first one was a T25N mutation in the N-terminal extracellular domain; the second is an H452Y mutation. Because cDNA clones derived from two independent PCR reactions using Taq polymerase from two different commercial sources (TaqPlus™ from Stratagene and rTth™ Perkin Elmer) contained the same two mutations, these mutations are likely to represent sequence polymorphisms rather than PCR errors. With these exceptions, the nucleic acid (SEQ.ID.NO.: 121) and amino acid (SEQ.ID.NO.: 122) sequences for human 5HT$_{2A}$ were thereafter determined and verified.

38. Serotonin 5HT$_{2C}$

The cDNA encoding endogenous human 5HT$_{2C}$ receptor was obtained from human brain poly-A$^+$ RNA by RT-PCR. The 5' and 3' primers were derived from the 5' and 3' untranslated regions and contained the following sequences:
5'-GACCTCGAGGTTGCTTAAGACTGAAGC-3' (SEQ.ID.NO.: 123)
5'-ATTTCTAGACATATGTAGCTTGTACCG-3' (SEQ.ID.NO.: 124).
Nucleic acid (SEQ.ID.NO.: 125) and amino acid (SEQ.ID.NO.: 126) sequences for human 5HT$_{2C}$ were thereafter determined and verified.

39. V28 (GenBank Accession Number: U20350)

The cDNA for human V28 was generated and cloned into pCMV expression vector as follows: PCR was performed using brain cDNA as template and rTth polymerase (Perkin Elmer) with the buffer system provided by the manufacturer, 0.25 µM of each primer, and 0.2 mM of each of the 4 nucleotides. The cycle condition was 30 cycles of: 94° C. for 1 min; 65° C. for 1 min; and 72° C. for 1 min and 20 sec. The 5' PCR primer contained a HindIII site with the sequence:
5'-GGTAAGCTTGGCAGTCCACGCCAGGCCTTC-3' (SEQ.ID.NO.: 127)
and the 3' primer contained an EcoRI site with the sequence:
5'-TCCGAATTCTCTGTAGACACAAGGCTTTGG-3' (SEQ.ID.NO.: 128).
The 1.1 kb PCR fragment was digested with HindIII and EcoRI and cloned into HindIII-EcoRI site of pCMV expression vector. Nucleic acid (SEQ.ID.NO.: 129) and amino acid (SEQ.ID.NO.: 130) sequences for human V28 were thereafter determined and verified.

Example 2

Preparation of Non-Endogenous Human GPCRs

1. Site-Directed Mutagenesis

Mutagenesis based upon the Human GPCR Proline Marker approach disclosed herein was performed on the foregoing endogenous human GPCRs using Transformer Site-Directed Mutagenesis Kit (Clontech) according to the manufacturer instructions. For this mutagenesis approach, a Mutation Probe and a Selection Marker Probe (unless otherwise indicated, the probe of SEQ.ID.NO.: 132 was the same throughout) were utilized, and the sequences of these for the specified sequences are listed below in Table B (the parenthetical number is the SEQ. ID.NO.). For convenience, the codon mutation incorporated into the human GPCR is also noted, in standard form:

TABLE B

| Receptor Identifier (Codon Mutation) | Mutation Probe Sequence (5'-3') (SEQ. ID. NO.) | Selection Marker Probe Sequence (5'-3') (SEQ. ID. NO.) |
| --- | --- | --- |
| GPR1 (F245K) | GATCTCCAGTAGGCATAAGT GGACAATTCTGG (131) | CTCCTTCGGTCCTCCTATCG TTGTCAGAAG (132) |
| GPR4 (K223A) | AGAAGGCCAAGATCGCGCG GCTGGCCCTCA (133) | CTCCTTCGGTCCTCCTATCG TTGTCAGAAGT |
| GPR5 (V224K) | CGGCGCCACCGCACGAAAA AGCTCATCTTC (134) | CTCCTTCGGTCCTCCTATCG TTGTCAGAAGT |
| GPR7 (T250K) | GCCAAGAAGCGGGTGAAGT TCCTGGTGGTGGCA (135) | CTCCTTCGGTCCTCCTATCG TTGTCAGAAGT |
| GPR8 (T259K) | CAGGCGGAAGGTGAAAGTC CTGGTCCTCGT (136) | CTCCTTCGGTCCTCCTATCG TTGTCAGAAGT |
| GPR9 (M254K) | CGGCGCCTGCGGGCCAAGC GGCTGGTGGTGGTG (137) | CTCCTTCGGTCCTCCTATCG TTGTCAGAAGT |
| GPR9-6 (L241K) | CCAAGCACAAAGCCAAGAA AGTGACCATCAC (138) | CTCCTTCGGTCCTCCTATCG TTGTCAGAAGT |
| GPR10 (F276K) | GCGCCGGCGCACCAAATGC TTGCTGGTGGT (139) | CTCCTTCGGTCCTCCTATCG TTGTCAGAAGT |
| GPR15 (I240K) | CAAAAAGCTGAAGAAATCT AAGAAGATCATCTTTATTGT CG (140) | CTCCTTCGGTCCTCCTATCG TTGTCAGAAGT |
| GPR17 (V234K) | CAAGACCAAGGCAAAACGC ATGATCGCCAT (141) | CTCCTTCGGTCCTCCTATCG TTGTCAGAAGT |
| GPR18 (I231K) | GTCAAGGAGAAGTCCAAAA GGATCATCATC (142) | CTCCTTCGGTCCTCCTATCG TTGTCAGAAGT |
| GPR20 (M240K) | CGCCGCGTGCGGGCCAAGC AGCTCCTGCTC (143) | CTCCTTCGGTCCTCCTATCG TTGTCAGAAGT |
| GPR21 (A251K) | CCTGATAAGCGCTATAAAAT GGTCCTGTTTCGA (144) | CTCCTTCGGTCCTCCTATCG TTGTCAGAAGT |
| GPR22 (F312K) | GAAAGACAAAAGAGAGTCA AGAGGATGTCTTTATTG (145) | CTCCTTCGGTCCTCCTATCG TTGTCAGAAGT |
| GPR24 (T304K) | CGGAGAAAGAGGGTGAAAC GCACAGCCATCGCC (146) | CTCCTTCGGTCCTCCTATCG TTGTCAGAAGT |
| GPR30 (L258K) | alternate approach; see below | alternate approach; see below |
| GPR31 (Q221K) | AAGCTTCAGCGGGCCAAGG CACTGGTCACC (147) | CTCCTTCGGTCCTCCTATCG TTGTCAGAAGT |

TABLE B-continued

| Receptor Identifier (Codon Mutation) | Mutation Probe Sequence (5'-3') (SEQ. ID. NO.) | Selection Marker Probe Sequence (5'-3') (SEQ. ID. NO.) |
|---|---|---|
| GPR32 (K255A) | CATGCCAACCGGCCCGCGAGGCTGCTGCTGGT (279) | ACCAGCAGCAGCCTCGCGGGCCGGTTGGCATG (280) |
| GPR40 (A223K) | CGGAAGCTGCGGGCCAAATGGGTGGCCGGC (265) | CTCCTTCGGTCCTCCTATCGTTGTCAGAAGT |
| GPR41 (A223K) | CAGAGGAGGGTGAAGGGCTGTTGGCG (266) | CTCCTTCGGTCCTCCTATCGTTGTCAGAAGT |
| GPR43 (V221K) | GGCGGCGCCGAGCCAAGGGGCTGGCTGTGG (267) | CTCCTTCGGTCCTCCTATCGTTGTCAGAAGT |
| APJ (L247K) | alternate approach; see below | alternate approach; see below |
| BLR1 (V258K) | CAGCGGCAGAAGGCAAAAAGGGTGGCCATC (148) | CTCCTTCGGTCCTCCTATCGTTGTCAGAAGT |
| CEPR (L258K) | CGGCAGAAGGCGAAGCGCATGATCCTCGCG (149) | CTCCTTCGGTCCTCCTATCGTTGTCAGAAGT |
| EBI1 (I262K) | GAGCGCAACAAGGCCAAAAAGGTGATCATC (150) | CTCCTTCGGTCCTCCTATCGTTGTCAGAAGT |
| EBI2 (L243K) | GGTGTAAACAAAAAGGCTAAAAACACAATTATTCTTATT (151) | CTCCTTCGGTCCTCCTATCGTTGTCAGAAGT |
| ETBR-LP2 (N358K) | GAGAGCCAGCTCAAGAGCACCGTGGTG (152) | CTCCTTCGGTCCTCCTATCGTTGTCAGAAGT |
| GHSR (V262K) | CCACAAGCAAACCAAGAAAATGCTGGCTGT (153) | CTCCTTCGGTCCTCCTATCGTTGTCAGAAGT |
| GPCR-CNS (N491K) | CTAGAGAGTCAGATGAAGTGTACAGTAGTGGCAC (155) | CTCCTTCGGTCCTCCTATCGTTGTCAGAAGT |
| GPR-NGA (I275K) | CGGACAAAAGTGAAAACTAAAAAGATGTTCCTCATT (156) | CTCCTTCGGTCCTCCTATCGTTGTCAGAAGT |
| H9a and H9b (F236K) | GCTGAGGTTCGCAATAAACTAACCATGTTTGTG (157) | CTCCTTCGGTCCTCCTATCGTTGTCAGAAGT |
| HB954 (H265K) | GGGAGGCCGAGCTGAAAGCCACCCTGCTC (158) | CTCCTTCGGTCCTCCTATCGTTGTCAGAAGT |
| HG38 (V765K) | GGGACTGCTCTATGAAAAAACACATTGCCCTG (268) | CATCAAGTGTATCATGTGCCAAGTACGCCC (154) |
| HM74 (I230K) | CAAGATCAAGAGAGCCAAAACCTTCATCATG (159) | CTCCTTCGGTCCTCCTATCGTTGTCAGAAGT |
| MIG (T273K) | CCGGAGACAAGTGAAGAAGATGCTGTTTGTC (160) | CTCCTTCGGTCCTCCTATCGTTGTCAGAAGT |
| OGR1 (Q227K) | GCAAGGACCAGATCAAGCGGCTGGTGCTCA (161) | CTCCTTCGGTCCTCCTATCGTTGTCAGAAGT |
| Serotonin 5HT$_{2A}$ (C322K) | alternate approach; see below | alternate approach; see below |
| Serotonin 5HT$_{2C}$ (S310K) | alternate approach; see below | alternate approach; see below |
| V28 (I230K) | CAAGAAAGCCAAAGCCAAGAAACTGATCCTTCTG 162 | CTCCTTCGGTCCTCCTATCGTTGTCAGAAGT |

The non-endogenous human GPCRs were then sequenced and the derived and verified nucleic acid and amino acid sequences are listed in the accompanying "Sequence Listing" appendix to this patent document, as summarized in Table C below:

TABLE C

| Mutated GPCR | Nucleic Acid Sequence Listing | Amino Acid Sequence Listing |
|---|---|---|
| GPR1 (F245K) | SEQ. ID. NO.: 163 | SEQ. ID. NO.: 164 |
| GPR4 (K223A) | SEQ. ID. NO.: 165 | SEQ. ID. NO.: 166 |
| GPR5 (V224K) | SEQ. ID. NO.: 167 | SEQ. ID. NO.: 168 |
| GPR7 (T250K) | SEQ. ID. NO.: 169 | SEQ. ID. NO.: 170 |
| GPR8 (T259K) | SEQ. ID. NO.: 171 | SEQ. ID. NO.: 172 |
| GPR9 (M254K) | SEQ. ID. NO.: 173 | SEQ. ID. NO.: 174 |
| GPR9-6 (L241K) | SEQ. ID. NO.: 175 | SEQ. ID. NO.: 176 |
| GPR10 (F276K) | SEQ. ID. NO.: 177 | SEQ. ID. NO.: 178 |
| GPR15 (I240K) | SEQ. D. NO.: 179 | SEQ. ID. NO.: 180 |
| GPR17 (V234K) | SEQ. ID. NO.: 181 | SEQ. ID. NO.: 182 |
| GPR18 (I231K) | SEQ. ID. NO.: 183 | SEQ. ID. NO.: 184 |
| GPR20 (M240K) | SEQ. ID. NO.: 185 | SEQ. ID. NO.: 186 |
| GPR21 (A251K) | SEQ. ID. NO.: 187 | SEQ. ID. NO.: 188 |
| GPR22 (F312K) | SEQ. ID. NO.: 189 | SEQ. ID. NO.: 190 |
| GPR24 (T304K)) | SEQ. ID. NO.: 191 | SEQ. ID. NO.: 192 |
| GPR30 (L258K) | SEQ. ID. NO.: 193 | SEQ. ID. NO.: 194 |
| GPR31 (Q221K) | SEQ. ID. NO.: 195 | SEQ. ID. NO.: 196 |
| GPR32 (K255A) | SEQ. ID. NO.: 269 | SEQ. ID. NO.: 270 |
| GPR40 (A223K) | SEQ. ID. NO.: 271 | SEQ. ID. NO.: 272 |
| GPR41 (A223K) | SEQ. ID. NO.: 273 | SEQ. ID. NO.: 274 |
| GPR43 (V221K) | SEQ. ID. NO.: 275 | SEQ. ID. NO.: 276 |
| APJ (L247K) | SEQ. ID. NO.: 197 | SEQ. ID. NO.: 198 |
| BLR1 (V258K) | SEQ. ID. NO.: 199 | SEQ. ID. NO.: 200 |
| CEPR (L258K) | SEQ. ID. NO.: 201 | SEQ. ID. NO.: 202 |
| EBI1 (I262K) | SEQ. ID. NO.: 203 | SEQ. ID. NO.: 204 |
| EBI2 (L243K) | SEQ. ID. NO.: 205 | SEQ. ID. NO.: 206 |
| ETBR-LP2 (N358K) | SEQ. ID. NO.: 207 | SEQ. ID. NO.: 208 |
| GHSR (V262K) | SEQ. ID. NO.: 209 | SEQ. ID. NO.: 210 |
| GPCR-CNS (N491K) | SEQ. ID. NO.: 211 | SEQ. ID. NO.: 212 |
| GPR-NGA (I275K | SEQ. ID. NO.: 213 | SEQ. ID. NO.: 214 |
| H9a (F236K) | SEQ. ID. NO.: 215 | SEQ. ID. NO.: 216 |
| H9b (F236K) | SEQ. ID. NO.: 217 | SEQ. ID. NO.: 218 |
| HB954 (H265K) | SEQ. ID. NO.: 219 | SEQ. ID. NO.: 220 |
| HG38 (V765K) | SEQ. ID. NO.: 277 | SEQ. ID. NO.: 278 |
| HM74 (I230K) | SEQ. ID. NO.: 221 | SEQ. ID. NO.: 222 |
| MIG (T273K) | SEQ. ID. NO.: 223 | SEQ. ID. NO.: 224 |
| OGR1 (Q227K) | SEQ. ID. NO.: 225 | SEQ. ID. NO.: 226 |
| Serotonin $5HT_{2A}$ (C322K) | SEQ. ID. NO.: 227 | SEQ. ID. NO.: 228 |
| Serotonin $5HT_{2C}$ (S310K) | SEQ. ID. NO.: 229 | SEQ. ID. NO.: 230 |
| V28 (I230K) | SEQ. ID. NO.: 231 | SEQ. ID. NO.: 232 |

2. Alternate Mutation Approaches for Employment of the Proline Marker Algorithm: APJ; Serotonin $5HT_{2A}$; Serotonin $5HT_{2C}$; and GPR30

Although the above site-directed mutagenesis approach is particularly preferred, other approaches can be utilized to create such mutations; those skilled in the art are readily credited with selecting approaches to mutating a GPCR that fits within the particular needs of the artisan.

a. APJ

Preparation of the non-endogenous, human APJ receptor was accomplished by mutating L247K. Two oligonucleotides containing this mutation were synthesized:

5'-GGCTTAAGAGCATCATCGTGGTGCTGGTG-3' (SEQ.ID.NO.: 233)

5'-GTCACCACCAGCACCACGATGATGCTCTTAAG CC-3' (SEQ.ID.NO.: 234).

The two oligonucleotides were annealed and used to replace the NaeI-BstEII fragment of human, endogenous APJ to generate the non-endogenous, version of human APJ.

b. Serotonin $5HT_{2A}$ cDNA containing the point mutation C322K was constructed by utilizing the restriction enzyme site Sph I which encompasses amino acid 322. A primer containing the C322K mutation:

5'-CAAAGAAAGTACTGGGCATCGTCTTCTTCCT-3' (SEQ.ID.NO: 235)

was used along with the primer from the 3' untranslated region of the receptor:

5'-TGCTCTAGATTCCAGATAGGTGAAAACTTG-3' (SEQ.ID.NO.: 236).

to perform PCR (under the conditions described above). The resulting PCR fragment was then used to replace the 3' end of endogenous $5HT_{2A}$ cDNA through the T4 polymerase blunted Sph I site.

C. Serotonin $5HT_{2C}$

The cDNA containing a S310K mutation was constructed by replacing the Sty I restriction fragment containing amino acid 310 with synthetic double stranded oligonucleotides that encode the desired mutation. The sense strand sequence utilized had the following sequence:

5'-CTAGGGGCACCATGCAGGCTATCAACAATGAA AGAAAAGCTAAGAAAGTC-3' (SEQ. ID.NO.: 237)

and the antisense strand sequence utilized had the following sequence:

5'-CAAGGACTTTCTTAGCTTTTCTTTCATTGTTGA TAGCCTGCATGGTGCCC-3' (SEQ. ID. NO.: 238).

d. GPR30

Prior to generating non-endogenous GPR30, several independent pCR2.1/GPR30 isolates were sequenced in their entirety in order to identify clones with no PCR-generated mutations. A clone having no mutations was digested with EcoRI and the endogenous GPR30 cDNA fragment was transferred into the CMV-driven expression plasmid pCI-neo (Promega), by digesting pCI-Neo with EcoRI and subcloning the EcoRI-liberated GPR30 fragment from pCR2.1/GPR30, to generate pCI/GPR30. Thereafter, the leucine at codon 258 was mutated to a lysine using a Quick-Change™ Site-Directed Mutagenesis Kit (Stratagene, #200518), according to manufacturer's instructions, and the following primers:

5'-CGGCGGCAGAAGGCGAAACGCATGATCCTCG CGGT-3' (SEQ.ID.NO.: 239) and
5'-ACCGCGAGGATCATGCGTTTCGCCTTCTGC CGCCG-3' (SEQ.ID.NO.: 240).

Example 3

Receptor (Endogenous and Mutated) Expression

Although a variety of cells are available to the art for the expression of proteins, it is most preferred that mammalian cells be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells. Of the mammalian cells, COS-7, 293 and 293T cells are particularly preferred, although the specific mammalian cell utilized can be predicated upon the particular needs of the artisan.

Unless otherwise noted herein, the following protocol was utilized for the expression of the endogenous and non-endogenous human GPCRs. Table D lists the mammalian cell and number utilized (per 150 mm plate) for GPCR expression.

TABLE D

| Receptor Name (Endogenous or Non-Endogenous) | Mammalian Cell (Number Utilized) |
| --- | --- |
| GPR17 | 293 ($2 \times 10^4$) |
| GPR30 | 293 ($4 \times 10^4$) |
| APJ | COS-7 ($5 \times 10^6$) |
| ETBR-LP2 | 293 ($1 \times 10^7$) |
|  | 293T ($1 \times 10^7$) |
| GHSR | 293 ($1 \times 10^7$) |
|  | 293T ($1 \times 10^7$) |
| MIG | 293 ($1 \times 10^7$) |
| Serotonin $5HT_{2A}$ | 293T ($1 \times 10^7$) |
| Serotonin $5HT_{2c}$ | 293T ($1 \times 10^7$) |

On day one, mammalian cells were plated out. On day two, two reaction tubes were prepared (the proportions to follow for each tube are per plate): tube A was prepared by mixing 20 µg DNA (e.g., pCMV vector; pCMV vector with endogenous receptor cDNA, and pCMV vector with non-endogenous receptor cDNA.) in 1.2 ml serum free DMEM (Irvine Scientific, Irvine, Calif.); tube B was prepared by mixing 120 µl lipofectamine (Gibco BRL) in 1.2 ml serum free DMEM. Tubes A and B were then admixed by inversions (several times), followed by incubation at room temperature for 30–45 min. The admixture is referred to as the "transfection mixture". Plated cells were washed with 1XPBS, followed by addition of 10 ml serum free DMEM. 2.4 ml of the transfection mixture was then added to the cells, followed by incubation for 4 hrs at 37° C./5% $CO_2$. The transfection mixture was then removed by aspiration, followed by the addition of 25 ml of DMEM/10% Fetal Bovine Serum. Cells were then incubated at 37° C./5% $CO_2$. After 72 hr incubation, cells were then harvested and utilized for analysis.

1. Gi-Coupled Receptors: Co-Transfection with Gs-Coupled Receptors

In the case of GPR30, it has been determined that this receptor couples the G protein Gi. Gi is known to inhibit the enzyme adenylyl cyclase, which is necessary for catalyzing the conversion of ATP to cAMP. Thus, a non-endogenous, constitutively activated form of GPR30 would be expected to be associated with decreased levels of cAMP. Assay confirmation of a non-endogenous, constitutively activated form of GPR30 directly via measurement of decreasing levels of cAMP, while viable, can be preferably measured by cooperative use of a Gs-coupled receptor. For example, a receptor that is Gs-coupled will stimulate adenylyl cyclase, and thus will be associated with an increase in cAMP. The assignee of the present application has discovered that the orphan receptor GPR6 is an endogenous, constitutively activated GPCR. GPR6 couples to the Gs protein. Thus when co-transfected, one can readily verify that a putative GPR30-mutation leads to constitutive activation thereof: i.e., an endogenous, constitutively activated GPR6/endogenous, non-constitutively activated GPR30 cell will evidence an elevated level of cAMP when compared with an endogenous, constitutively active GPR6/non-endogenous, constitutively activated GPR30 (the latter evidencing a comparatively lower level of cAMP). Assays that detect cAMP can be utilized to determine if a candidate compound is e.g., an inverse agonist to a Gs-associated receptor (i.e., such a compound would decrease the levels of cAMP) or a Gi-associated receptor (or a Go-associated receptor) (i.e., such a candidate compound would increase the levels of cAMP). A variety of approaches known in the art for measuring cAMP can be utilized; a preferred approach relies upon the use of anti-cAMP antibodies. Another approach, and most preferred, utilizes a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) which then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated receptor such as GPR6 causes the accumulation of cAMP which then activates the gene and expression of the reporter protein. Most preferably, 293 cells are co-transfected with GPR6 (or another Gs-linked receptor) and GPR30 (or another Gi-linked receptor) plasmids, preferably in a 1:1 ratio, most preferably in a 1:4 ratio. Because GPR6 is an endogenous, constitutively active receptor that stimulates the production of cAMP, GPR6 strongly activates the reporter gene and its expression. The reporter protein such as β-galactosidase or luciferase can then be detected using standard biochemical assays (Chen et al. 1995). Co-transfection of endogenous, constitutively active GPR6 with endogenous, non-constitutively active GPR30 evidences an increase in the luciferase reporter protein. Conversely, co-transfection of endogenous, constitutively active GPR6 with non-endogenous, constitutively active GPR30 evidences a drastic decrease in expression of luciferase. Several reporter plasmids are known and available in the art for measuring a second messenger assay. It is considered well within the skilled artisan to determine an appropriate reporter plasmid for a particular gene expression based primarily upon the particular need of the artisan. Although a variety of cells are available for expression, mammalian cells are most preferred, and of these types, 293 cells are most preferred. 293 cells were transfected with the reporter plasmid pCRE-Luc/GPR6 and non-endogenous, constitutively activated GPR30 using a Mammalian Transfection™ Kit (Stratagene, #200285) $CaPO_4$ precipitation protocol according to the manufacturer's instructions (see, 28 Genomics 347 (1995) for the published endogenous GPR6 sequence). The precipitate contained 400 ng reporter, 80 ng CMV-expression plasmid (having a 1:4 GPR6 to endogenous GPR30 or non-endogenous GPR30 ratio) and 20 ng CMV-SEAP (a transfection control plasmid encoding secreted alkaline phosphatase). 50% of the precipitate was split into 3 wells of a 96-well tissue culture dish (containing $4 \times 10^4$ cells/well); the remaining 50% was discarded. The following morning, the media was changed. 48 hr after the start of the transfection, cells were lysed and examined for luciferase activity using a Luclite™ Kit (Packard, Cat. # 6016911) and Trilux 1450 Microbeta™ liquid scintillation and luminescence counter (Wallac) as per the vendor's instructions. The data were analyzed using GraphPad Prism 2.0a (GraphPad Software Inc.).

With respect to GPR17, which has also been determined to be Gi-linked, a modification of the foregoing approach was utilized, based upon, inter alia, use of another Gs-linked endogenous receptor, GPR3 (see 23 Genomics 609 (1994) and 24 Genomics 391 (1994)). Most preferably, 293 cells are utilized. These cells were plated-out on 96 well plates at a density of $2 \times 10^4$ cells per well and were transfected using Lipofectamine Reagent (BRL) the following day according to manufacturer instructions. A DNA/lipid mixture was prepared for each 6-well transfection as follows: 260 ng of plasmid DNA in 100 µl of DMEM were gently mixed with 2 µl of lipid in 100 µl of DMEM (the 260 ng of plasmid DNA consisted of 200 ng of a 8×CRE-Luc reporter plasmid (see below), 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared- as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 (see 7 Human Gene Therapy 1883 (1996)) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture was diluted with 400 µl of DMEM and 100 µl of the diluted mixture was added to each well. 100 µl of DMEM with 10% FCS were added to each well after a 4 hr incubation in a cell culture incubator. The next morning the transfected cells were changed with 200 µl/well of DMEM with 10% FCS. Eight (8) hours later, the wells were changed to 100 µl/well of DMEM without phenol red, after one wash with PBS. Luciferase activity were measured the next day using the LucLite™ reporter gene assay kit (Packard) following manufacturer instructions and read on a 1450 MicroBeta™ scintillation and luminescence counter (Wallac).

Figure 4:
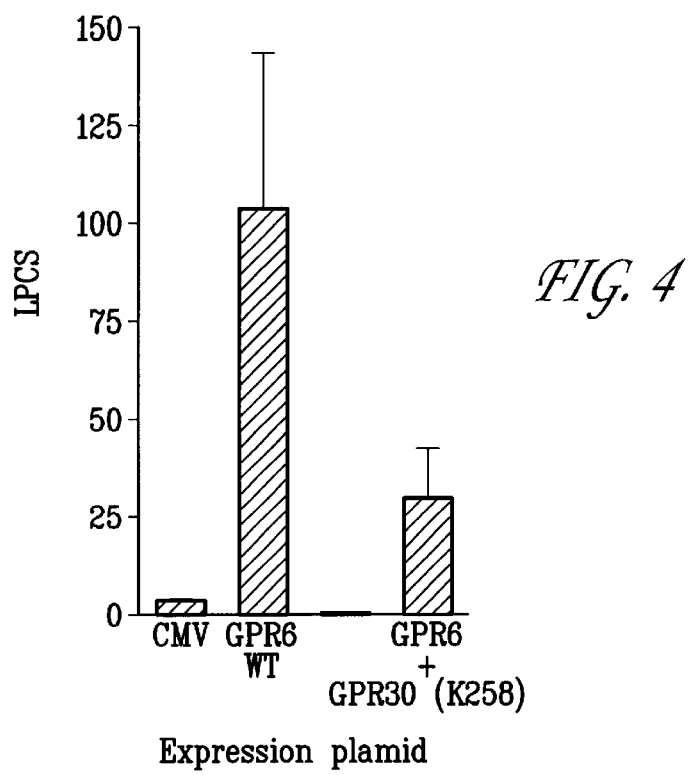
FIG. 4 is a diagrammatic representation of the signal measured comparing pCMV, non-endogenous, constitutively active GPR30 inhibition of GPR6-mediated activation of CRE-Luc reporter with endogenous GPR30 inhibition of GPR6-mediated activation of CRE-Luc reporter.
Figure 5:
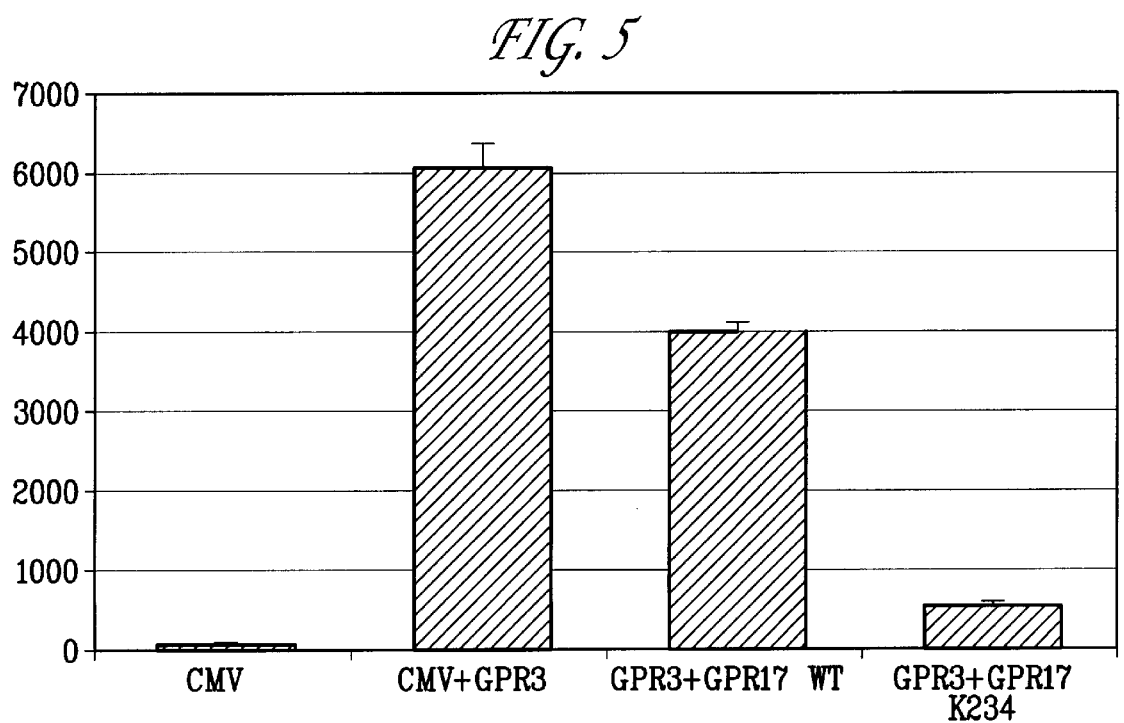
FIG. 5 is a diagrammatic representation of the signal measured comparing pCMV, non-endogenous, constitutively activated GPR17 inhibition of GPR3-mediated activation of CRE-Luc reporter with endogenous GPR17 inhibition of GPR3-mediated activation of CRE-Luc reporter.

FIG. 4 evidences that constitutively active GPR30 inhibits GPR6-mediated activation of CRE-Luc reporter in 293 cells. Luciferase was measured at about 4.1 relative light units in the expression vector pCMV. Endogenous GPR30 expressed luciferase at about 8.5 relative light units, whereas the non-endogenous, constitutively active GPR30 (L258K), expressed luciferase at about 3.8 and 3.1 relative light units, respectively. Co-transfection of endogenous GPR6 with endogenous GPR30, at a 1:4 ratio, drastically increased luciferase expression to about 104.1 relative light units. Co-transfection of endogenous GPR6 with non-endogenous GPR30 (L258K), at the same ratio, drastically decreased the expression, which is evident at about 18.2 and 29.5 relative light units, respectively. Similar results were observed with respect to GPR17 with respect to co-transfection with GPR3, as set forth in FIG. 5.

Example 4

Assays for Determination of Constitutive Activity of Non-Endogenous GPCRs

A. Membrane Binding Assays

1. [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Constitutively activated receptors continue to exchange GDP for GTP. The non-hydrolyzable GTP analog, [$^{35}$S]GTPγS, can be utilized to demonstrate enhanced binding of [$^{35}$S]GTPγS to membranes expressing constitutively activated receptors. The advantage of using [$^{35}$S]GTPγS binding to measure constitutive activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to known, orphan and constitutively activated G protein-coupled receptors. The assay is generic and has application to drug discovery at all G protein-coupled receptors. The [$^{35}$S]GTPγS assay was incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 µg membrane protein (e.g, COS-7 cells expressing the receptor; this amount can be adjusted for optimization, although 75 µg is preferred) and 1 µM GDP (this amount can be changed for optimization) for 1 hour. Wheatgerm agglutinin beads (25 µl; Amersham) were then added and the mixture was incubated for another 30 minutes at room temperature. The tubes were then centrifuged at 1500×g for 5 minutes at room temperature and then counted in a scintillation counter.

A less costly but equally applicable alternative has been identified which also meets the needs of large scale screening. Flash plates™ and Wallac™ scintistrips may be utilized to format a high throughput [$^{35}$S]GTPγS binding assay. Furthermore, using this technique, the assay can be utilized for known GPCRs to simultaneously monitor tritiated ligand binding to the receptor at the same time as monitoring the efficacy via [$^{35}$S]GTPγS binding. This is possible because the Wallac beta counter can switch energy windows to look at both tritium and $^{35}$S-labeled probes. This assay may also be used to detect other types of membrane activation events resulting in receptor activation. For example, the assay may be used to monitor $^{32}$P phosphorylation of a variety of receptors (both G protein coupled and tyrosine kinase receptors). When the membranes are centrifuged to the bottom of the well, the bound [$^{35}$S]GTPγS or the $^{32}$P-phosphorylated receptor will activate the scintillant which is coated of the wells. Scinti® strips (Wallac) have been used to demonstrate this principle. In addition, the assay also has utility for measuring ligand binding to receptors using radioactively labeled ligands. In a similar manner, when the radiolabeled bound ligand is centrifuged to the bottom of the well, the scintistrip label comes into proximity with the radiolabeled ligand resulting in activation and detection.

Figure 6:
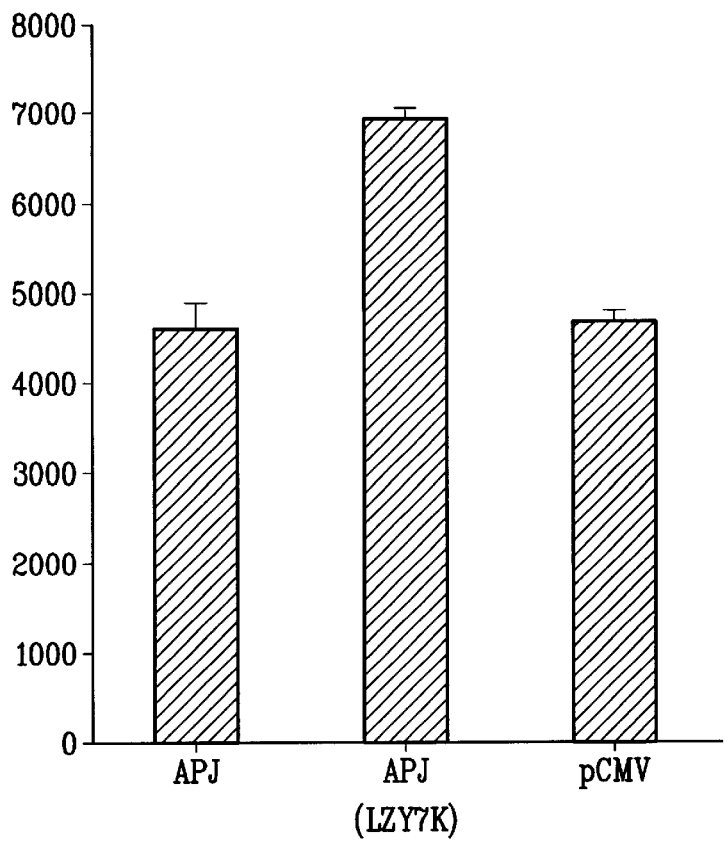
FIG. 6 provides diagrammatic results of the signal measured comparing control pCMV, endogenous APJ and non-endogenous APJ.

Representative results of graph comparing Control (pCMV), Endogenous APJ and Non-Endogenous APJ, based upon the foregoing protocol, are set forth in FIG. 6.

2. Adenylyl Cyclase

A Flash Plate™ Adenylyl Cyclase kit (New England Nuclear; Cat. No. SMP004A) designed for cell-based assays was modified for use with crude plasma membranes. The Flash Plate wells contain a scintillant coating which also contains a specific antibody recognizing cAMP. The cAMP generated in the wells was quantitated by a direct competition for binding of radioactive cAMP tracer to the cAMP antibody. The following serves as a brief protocol for the measurement of changes in cAMP levels in membranes that express the receptors.

Transfected cells were harvested approximately three days after transfection. Membranes were prepared by homogenization of suspended cells in buffer containing 20 mM HEPES, pH 7.4 and 10 mM $MgCl_2$. Homogenization was performed on ice using a Brinkman Polytron™ for approximately 10 seconds. The resulting homogenate was centrifuged at 49,000×g for 15 minutes at 4° C. The resulting pellet was then resuspended in buffer containing 20 mM HEPES, pH 7.4 and 0.1 mM EDTA, homogenized for 10 seconds, followed by centrifugation at 49,000×g for 15 minutes at 4° C. The resulting pellet can be stored at −80° C. until utilized. On the day of measurement, the membrane pellet was slowly thawed at room temperature, resuspended in buffer containing 20 mM HEPES, pH 7.4 and 10 mM $MgCl_2$ (these amounts can be optimized, although the values listed herein are prefereed), to yield a final protein concentration of 0.60 mg/ml (the resuspended membranes were placed on ice until use).

cAMP standards and Detection Buffer (comprising 2 μCi of tracer [$^{125}$I cAMP (100 μl] to 11 ml Detection Buffer) were prepared and maintained in accordance with the manufacturer's instructions. Assay Buffer was prepared fresh for screening and contained 20 mM HEPES, pH 7.4, 10 mM $MgCl_2$, 20 mM (Sigma), 0.1 units/ml creatine phosphokinase (Sigma), 50 μM GTP (Sigma), and 0.2 mM ATP (Sigma); Assay Buffer can be stored on ice until utilized. The assay was initiated by addition of 50 μl of assay buffer followed by addition of 50 μl of membrane suspension to the NEN Flash Plate. The resultant assay mixture is incubated for 60 minutes at room temperature followed by addition of 100 μl of detection buffer. Plates are then incubated an additional 2–4 hours followed by counting in a Wallac MicroBeta scintillation counter. Values of cAMP/well are extrapolated from a standard cAMP curve which is contained within each assay plate. The foregoing assay was utilized with respect to analysis of MIG.

B. Reporter-Based Assays

1. CREB Reporter Assay (Gs-associated Receptors)

A method to detect Gs stimulation depends on the known property of the transcription factor CREB, which is activated in a cAMP-dependent manner. A PathDetect CREB trans-Reporting System (Stratagene, Catalogue # 219010) was utilized to assay for Gs coupled activity in 293 or 293T cells. Cells were transfected with the plasmids components of this above system and the indicated expression plasmid encoding endogenous or mutant receptor using a Mammalian Transfection Kit (Stratagene, Catalogue #200285) according to the manufacurer's instructions. Briefly, 400 ng pFR-Luc (luciferase reporter plasmid containing Gal4 recognition sequences), 40 ng pFA2-CREB (Gal4-CREB fusion protein containing the Gal4 DNA-binding domain), 80 ng CMV-receptor expression plasmid (comprising the receptor) and 20 ng CMV-SEAP (secreted alkaline phosphatase expression plasmid; alkaline phosphatase activity is measured in the media of transfected cells to control for variations in transfection efficiency between samples) were combined in a calcium phosphate precipitate as per the Kit's instructions. Half of the precipitate was equally distributed over 3 wells in a 96-well plate, kept on the cells overnight, and replaced with fresh medium the following morning. Forty-eight (48) hr after the start of the transfection, cells were treated and assayed for luciferase activity as set forth with resepct to the GPR30 system, above. This assay was used with respect to GHSR.

2. AP1 Reporter Assay (Gq-associated Receptors)

A method to detect Gq stimulation depends on the known property of Gq-dependent phospholipase C to cause the activation of genes containing AP1 elements in their promoter. A Pathdetect AP-1 cis-Reporting System (Stratagene, Catalogue # 219073) was utilized following the protocl set forth above with respect to the CREB reporter assay, except that the components of the calcium phosphate precipitate were 410 ng pAP1-Luc, 80 ng receptor expression plasmid, and 20 ng CMV-SEAP. This assay was used with respect to ETBR-LP2 .

C. Intracellular IP3 Accumulation Assay

On day 1, cells comprising the serotonin receptors (endogenous and mutated) were plated onto 24 well plates, usually 1×10$^5$ cells/well. On day 2 cells were transfected by firstly mixing 0.25 ug DNA in 50 ul serumfree DMEM/well and 2 ul lipofectamine in 50 μl serumfree DMEM/well. The solutions were gently mixed and incubated for 15–30 min at room temperature. Cells were washed with 0.5 ml PBS and 400 μl of serum free media was mixed with the transfection media and added to the cells. The cells were then incubated for 3–4 hrs at 37° C./5%$CO_2$ and then the transfection media was removed and replaced with 1 ml/well of regular growth media. On day 3 the cells were labeled with $^3$H-myo-inositol. Briefly, the media was removed the cells were washed with 0.5 ml PBS. Then 0.5 ml inositol-free/serumfree media (GIBCO BRL) was added/well with 0.25 μCi of $^3$H-myo-inositol/well and the cells were incubated for 16–18 hrs o/n at 37° C./5%$CO_2$. On Day 4 the cells were washed with 0.5 ml PBS and 0.45 ml of assay medium was added containing inositol-free/serum free media 10 μM pargyline 10 mM lithium chloride or 0.4 ml of assay medium and 50 ul of 10×ketanserin (ket) to final concentration of 10 μM. The cells were then incubated for 30 min at 37° C. The cells were then washed with 0.5 ml PBS and 200 ul of fresh/icecold stop solution (1M KOH; 18 mM Na-borate; 3.8 mM EDTA) was added/well. The solution was kept on ice for 5–10 min or until cells were lysed and then neutralized by 200 μl of fresh/ice cold neutralization sol. (7.5%

HCL). The lysate was then transferred into 1.5 ml eppendorf tubes and 1 ml of chloroform/methanol (1:2) was added/tube. The solution was vortexed for 15 sec and the upper phase was applied to a Biorad AG1-X8 anion exchange resin (100–200 mesh). Firstly, the resin was washed with water at 1:1.25 W/V and 0.9 ml of upper phase was loaded onto the column. The column was washed with 10 mls of 5 mM myo-inositol and 10 ml of 5 mM Na-borate/60 mM Na-formate. The inositol tris phosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd $H_2O$ and stored at 4° C. in water.

Figure 7:
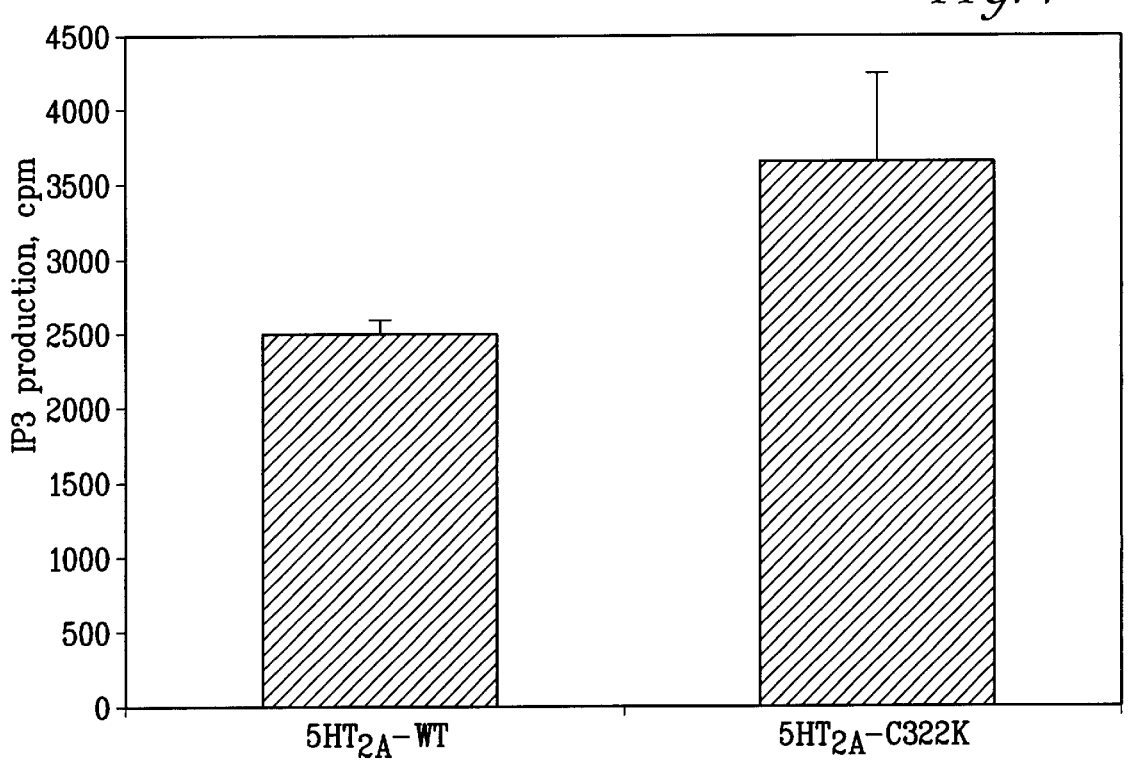
FIG. 7 provides an illustration of $IP_3$ production from non-endogenous human $5\text{-}HT_{2A}$ receptor as compared to the endogenous version of this receptor.

FIG. 7 provides an illustration of IP3 production from the human 5-$HT_{2A}$ receptor that incorporates the C322K mutation. While these results evidence that the Proline Mutation Algorithm approach constitutively activates this receptor, for purposes of using such a receptor for screening for identification of potential therapeutics, a more robust difference would be preferred. However, because the activated receptor can be utilized for understanding and elucidating the role of constitutive activation and for the identification of compounds that can be further examined, we believe that this difference is itself useful in differentiating between the endogenous and non-endogenous versions of the human $5HT_{2A}$ receptor.

D. Result Summary

The results for the GPCRs tested are set forth in Table E where the Per-Cent Increase indicates the percentage difference in results observed for the non-endogenous GPCR as compared to the endogenous GPCR; these values are followed by parenthetical indications as to the type of assay utilized. Additionally, the assay system utilized is parenthetically listed (and, in cases where different Host Cells were used, both are listed). As these results indicate, a variety of assays can be utilized to determine constitutive activity of the non-endogenous versions of the human GPCRs. Those skilled in the art, based upon the foregoing and with reference to information available to the art, are creditied with the ability to selelect and/ot maximize a particular assay approach that suites the particualr needs of the investigator.

TABLE E

| Receptor Identifier (Codon Mutation) | Per-Cent Difference |
|---|---|
| GPR17 | 74.5 |
| (V234K) | (CRE-Luc) |
| GPR30 | 71.6 |
| (L258K) | (CREB) |
| APJ | 49.0 |
| (L247K) | (GTPγS) |
| ETBR-LP2 | 48.4(AP1-Luc-293) |
| (N358K) | 61.1 AP1-Luc – 293T |
| GHSR | 58.9(CREB – 293) |
| (V262K) | 35.6(CREB – 293T) |
| MIG | 39 (cAMP) |
| (I230K) | |
| Serotonin $5HT_{2A}$ | 33.2($IP_3$) |
| (C322K) | |
| Serotonin $5HT_{2C}$ | 39.1($IP_3$) |
| (S310K) | |

Example 5

Tissue Distribution of Endogenous Orphan GPCRs

Using a commercially available human-tissue dot-blot format, endogenous orphan GPCRs were probed for a determination of the areas where such receptors are localized. Except as indicate below, the entire receptor cDNA (radiolabelled) was used as the probe: radiolabeled probe was generated using the complete receptor cDNA (excised from the vector) using a Prime-It II™ Random Primer Labeling Kit (Stratagene, #300385), according to manufacturer's instructions. A human RNA Master Blot™ (Clontech, #7770-1) was hybridized with the GPCR radiolabeled probe and washed under stringent conditions according manufacturer's instructions. The blot was exposed to Kodak BioMax Autoradiography film overnight at –80° C.

Figure 8A:
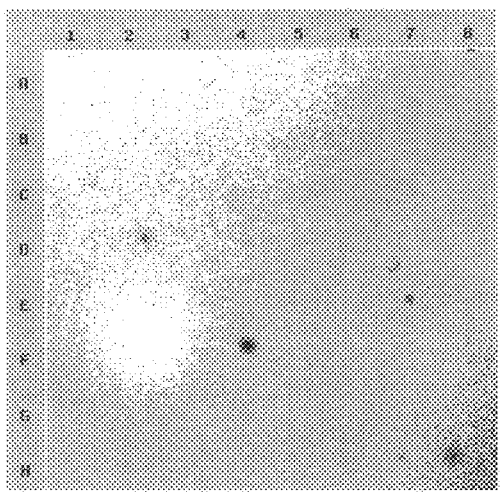
FIGS. 8A–8C are dot-blot format results for GPR1 (8A), GPR30 (8B) and APJ (8C).
Figure 8B:
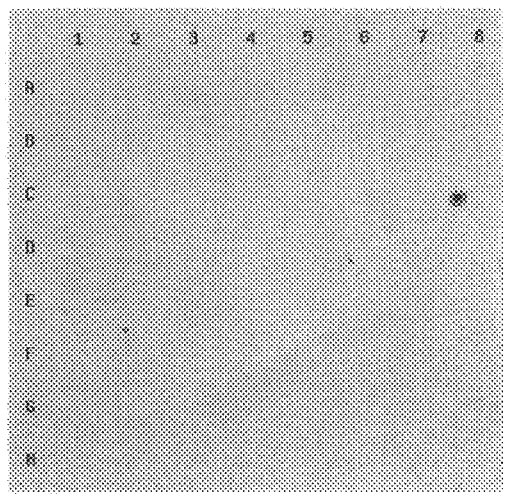
Figure 8C:
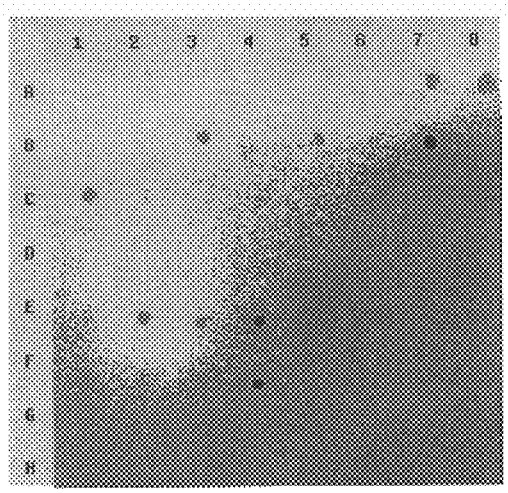

Representative dot-blot format results are presented in FIG. 8 for GPR1 (8A), GPR30 (8B), and APJ (8C), with results being summarized for all receptors in Table F

TABLE F

| GPCR | Tissue Distribution (highest levels, relative to other tissues in the dot-blot) |
|---|---|
| GPR1 | Placenta, Ovary, Adrenal |
| GPR4 | Broad; highest in Heart, Lung, Adrenal, Thyroid, Spinal Cord |
| GPR5 | Placenta, Thymus, Fetal Thymus Lesser levels in spleen, fetal spleen |
| GPR7 | Liver, Spleen, Spinal Cord, Placenta |
| GPR8 | No expression detected |
| GPR9-6 | Thymus, Fetal Thymus Lesser levels in Small Intestine |
| GPR18 | Spleen, Lymph Node, Fetal Spleen, Testis |
| GPR20 | Broad |
| GPR21 | Broad; very low abundance |
| GPR22 | Heart, Fetal Heart Lesser levels in Brain |
| GPR30 | Stomach |
| GPR31 | Broad |
| BLR1 | Spleen |
| CEPR | Stomach, Liver, Thyroid, Putamen |
| EBI1 | Pancreas Lesser levels in Lymphoid Tissues |
| EBI2 | Lymphoid Tissues, Aorta, Lung, Spinal Cord |
| ETBR-LP2 | Broad; Brain Tissue |
| GPCR-CNS | Brain Lesser levels in Testis, Placenta |
| GPR-NGA | Pituitary Lesser levels in Brain |
| H9 | Pituitary |
| HB954 | Aorta, Cerebellum Lesser levels in most other tissues |
| HM74 | Spleen, Leukocytes, Bone marrow, Mammary Glands, Lung, Trachea |
| MIG | Low levels in Kidney, Liver, Pancreas, Lung, Spleen |
| ORG1 | Pituitary, Stomach, Placenta |
| V28 | Brain, Spleen, Peripheral Leukocytes |

Based upon the foregoing information, it is noted that human GPCRs can also be assessed for distribution in diseased tissue; comparative assessments between "normal" and diseased tissue can then be utilized to determine the potential for over-expression or under-expression of a particular receptor in a diseased state. In those circumstances where it is desirable to utilize the non-endogenous versions of the humarn GPCRs for the purpose of screening to directly identify candidate compounds of potential therapeutic relevance, it is noted that inverse agonists are useful in the treatment of diseases and disorders where a particular human GPCR is over-expressed, whereas agonists or partial agonists are useful in the treatment of diseases and disorders where a particular human GPCR is under-expressed.

As desired, more detailed, cellular localization of the recepotrs, using techniques well-known to those in the art (e.g., in-situ hybridization) can be utilized to identify particualr cells within these tissues where the receptor of interest is expressed.

References cited throughout this patent document, unless otherwise indicated, are incorporated herein by reference. Modifications and extension of the disclosed inventions that are within the purview of the skilled artisan are encompassed within the above disclosure and the claims that follow.

Although a variety of expression vectors are available to those in the art, for purposes of utilization for both the endogenous and non-endogenous human GPCRs, it is most preferred that the vector utilized be pCMV. This vector has been deposited with the American Type Culture Collection (ATCC) on Oct. 13, 1998 (10801 University Blvd., Manassas, Va. 20110-2209 USA) under the provsions of the Budapest Treaty for the International Recognition of the Deposit of Microorganisms for the Purpose of patent Procedure. The vector was determined to be viable. The ATCC has assigned the following deposit number to pCMV: ATCC#20335.

SEQUENCE LISTING

<160> NUMBER OF SEQ ID NOS: 294

<210> SEQ ID NO 1
<211> LENGTH: 1068
<212> TYPE: DNA
<213> ORGANISM: Homo sapiens

<400> SEQUENCE: 1

```
atgaagatt tggaggaaac attatttgaa gaatttgaaa actattccta tgacctagac      60
tattactctc tggagtctga tttggaggag aaagtccagc tgggagttgt tcactgggtc     120
tccctggtgt tatattgttt ggcttttgtt ctgggaattc aggaaatgc catcgtcatt      180 tggttcacgg ggctcaagtg gaagaagaca gtcaccactc tgtggttcct caatctagcc    240
attgcggatt tcatttttct tctctttctg cccctgtaca tctcctatgt ggccatgaat    300
ttccactggc cctttggcat ctggctgtgc aaagccaatt ccttcactgc ccagttgaac    360
atgtttgcca gtgttttttt cctgacagtg atcagcctgg accactatat ccacttgatc    420
catcctgtct tatctcatcg gcatcgaacc ctcaagaact ctctgattgt cattatattc    480
atctggcttt tggcttctct aattggcggt cctgccctgt acttccggga cactgtggag    540
ttcaataatc atactctttg ctataacaat tttcagaagc atgatcctga cctcactttg    600
atcaggcacc atgttctgac ttgggtgaaa tttatcattg gctatctctt ccctttgcta    660
acaatgagta tttgctactt gtgtctcatc ttcaaggtga agaagcgaac agtcctgatc    720
tccagtaggc atttctggac aattctggtt gtggttgtgg cctttgtggt ttgctggact    780
ccttatcacc tgtttagcat ttgggagctc accattcacc acaatagcta ttcccaccat    840
gtgatgcagg ctggaatccc cctctccact ggtttggcat tcctcaatag ttgcttgaac    900
cccatccttt atgtcctaat tagtaagaag ttccaagctc gcttccggtc ctcagttgct    960
gagatactca agtacacact gtgggaagtc agctgttctg gcacagtgag tgaacagctc   1020
aggaactcag aaaccaagaa tctgtgtctc ctggaaacag ctcaataa                1068
```

<210> SEQ ID NO 2
<211> LENGTH: 355
<212> TYPE: PRT
<213> ORGANISM: Homo sapiens

<400> SEQUENCE: 2

Met Glu Asp Leu Glu Glu Thr Leu Phe Glu Glu Phe Glu Asn Tyr Ser
1               5                   10                  15

Tyr Asp Leu Asp Tyr Tyr Ser Leu Glu Ser Asp Leu Glu Glu Lys Val
                20                  25                  30

Gln Leu Gly Val Val His Trp Val Ser Leu Val Leu Tyr Cys Leu Ala
            35                  40                  45

```
Phe Val Leu Gly Ile Pro Gly Asn Ala Ile Val Ile Trp Phe Thr Gly
 50                  55                  60

Leu Lys Trp Lys Lys Thr Val Thr Thr Leu Trp Phe Leu Asn Leu Ala
 65                  70                  75                  80

Ile Ala Asp Phe Ile Phe Leu Leu Phe Leu Pro Leu Tyr Ile Ser Tyr
                     85                  90                  95

Val Ala Met Asn Phe His Trp Pro Phe Gly Ile Trp Leu Cys Lys Ala
                100                 105                 110

Asn Ser Phe Thr Ala Gln Leu Asn Met Phe Ala Ser Val Phe Phe Leu
            115                 120                 125

Thr Val Ile Ser Leu Asp His Tyr Ile His Leu Ile His Pro Val Leu
        130                 135                 140

Ser His Arg His Arg Thr Leu Lys Asn Ser Leu Ile Val Ile Ile Phe
145                 150                 155                 160

Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Leu Ile Arg His His Val Leu Thr Trp
        195                 200                 205

Val Lys Phe Ile Ile Gly Tyr Leu Phe Pro Leu Leu Thr Met Ser Ile
210                 215                 220

Cys Tyr Leu Cys Leu Ile Phe Lys Val Lys Lys Arg Thr Val Leu Ile
225                 230                 235                 240

Ser Ser Arg His Phe Trp Thr Ile Leu Val Val Val Ala Phe Val
                245                 250                 255

Val Cys Trp Thr Pro Tyr His Leu Phe Ser Ile Trp Glu Leu Thr Ile
            260                 265                 270

His His Asn Ser Tyr Ser His His Val Met Gln Ala Gly Ile Pro Leu
        275                 280                 285

Ser Thr Gly Leu Ala Phe Leu Asn Ser Cys Leu Asn Pro Ile Leu Tyr
290                 295                 300

Val Leu Ile Ser Lys Lys Phe Gln Ala Arg Phe Arg Ser Ser Val Ala
305                 310                 315                 320

Glu Ile Leu Lys Tyr Thr Leu Trp Glu Val Ser Cys Ser Gly Thr Val
                325                 330                 335

Ser Glu Gln Leu Arg Asn Ser Glu Thr Lys Asn Leu Cys Leu Leu Glu
            340                 345                 350

Thr Ala Gln
        355

<210> SEQ ID NO 3
<211> LENGTH: 1089
<212> TYPE: DNA
<213> ORGANISM: Homo sapiens

<400> SEQUENCE: 3
atgggcaacc acacgtggga gggctgccac gtggactcgc gcgtggacca cctctttccg    60
ccatccctct acatctttgt catcggcgtg gggctgccca ccaactgcct ggctctgtgg   120
gcggcctacc gccaggtgca acagcgcaac gagctgggcg tctacctgat gaacctcagc   180
atcgccgacc tgctgtacat ctgcacgctg ccgctgtggg tggactactt cctgcaccac   240
gacaactgga tccacggccc cgggtcctgc aagctctttg ggttcatctt ctacaccaat   300
atctacatca gcatcgcctt cctgtgctgc atctcggtgg accgctacct ggctgtggcc   360
```

-continued

```
cacccactcc gcttcgcccg cctgcgccgc gtcaagaccg ccgtggccgt gagctccgtg      420
gtctgggcca cggagctggg cgccaactcg gcgcccctgt tccatgacga gctcttccga      480
gaccgctaca accacacctt ctgctttgag aagttcccca tggaaggctg ggtggcctgg      540
atgaacctct atcgggtgtt cgtgggcttc ctcttcccgt gggcgctcat gctgctgtcg      600 taccgggca tcctgcgggc cgtgcggggc agcgtgtcca ccgagcgcca ggagaaggcc       660
aagatcaagc ggctggccct cagcctcatc gccatcgtgc tggtctgctt tgcgccctat      720
cacgtgctct tgctgtcccg cagcgccatc tacctgggcc gccctggga ctgcggcttc       780 gaggagcgcg tcttttctgc ataccacagc tcactggctt tcaccagcct caactgtgtg      840
gcggacccca tcctctactg cctggtcaac gagggcgccc gcagcgatgt ggccaaggcc      900
ctgcacaacc tgctccgctt tctggccagc gacaagcccc aggagatggc caatgcctcg      960
ctcaccctgg agaccccact cacctccaag aggaacagca cagccaaagc catgactggc     1020
agctgggcgg ccactccgcc ttcccagggg gaccaggtgc agctgaagat gctgccgcca     1080
gcacaatga                                                             1089
```

<210> SEQ ID NO 4
<211> LENGTH: 362
<212> TYPE: PRT
<213> ORGANISM: Homo sapiens

<400> SEQUENCE: 4

```
Met Gly Asn His Thr Trp Glu Gly Cys His Val Asp Ser Arg Val Asp
1               5                   10                  15

His Leu Phe Pro Pro Ser Leu Tyr Ile Phe Val Ile Gly Val Gly Leu
            20                  25                  30

Pro Thr Asn Cys Leu Ala Leu Trp Ala Ala Tyr Arg Gln Val Gln Gln
        35                  40                  45

Arg Asn Glu Leu Gly Val Tyr Leu Met Asn Leu Ser Ile Ala Asp Leu
    50                  55                  60

Leu Tyr Ile Cys Thr Leu Pro Leu Trp Val Asp Tyr Phe Leu His His
65                  70                  75                  80

Asp Asn Trp Ile His Gly Pro Gly Ser Cys Lys Leu Phe Gly Phe Ile
                85                  90                  95

Phe Tyr Thr Asn Ile Tyr Ile Ser Ile Ala Phe Leu Cys Cys Ile Ser
            100                 105                 110

Val Asp Arg Tyr Leu Ala Val Ala His Pro Leu Arg Phe Ala Arg Leu
        115                 120                 125

Arg Arg Val Lys Thr Ala Val Ala Val Ser Ser Val Val Trp Ala Thr
    130                 135                 140

Glu Leu Gly Ala Asn Ser Ala Pro Leu Phe His Asp Glu Leu Phe Arg
145                 150                 155                 160

Asp Arg Tyr Asn His Thr Phe Cys Phe Glu Lys Phe Pro Met Glu Gly
                165                 170                 175

Trp Val Ala Trp Met Asn Leu Tyr Arg Val Phe Val Gly Phe Leu Phe
            180                 185                 190

Pro Trp Ala Leu Met Leu Leu Ser Tyr Arg Gly Ile Leu Arg Ala Val
        195                 200                 205

Arg Gly Ser Val Ser Thr Glu Arg Gln Glu Lys Ala Lys Ile Lys Arg
    210                 215                 220

Leu Ala Leu Ser Leu Ile Ala Ile Val Leu Val Cys Phe Ala Pro Tyr
225                 230                 235                 240
```

```
His Val Leu Leu Leu Ser Arg Ser Ala Ile Tyr Leu Gly Arg Pro Trp
                245                 250                 255

Asp Cys Gly Phe Glu Glu Arg Val Phe Ser Ala Tyr His Ser Ser Leu
            260                 265                 270

Ala Phe Thr Ser Leu Asn Cys Val Ala Asp Pro Ile Leu Tyr Cys Leu
        275                 280                 285

Val Asn Glu Gly Ala Arg Ser Asp Val Ala Lys Ala Leu His Asn Leu
    290                 295                 300

Leu Arg Phe Leu Ala Ser Asp Lys Pro Gln Glu Met Ala Asn Ala Ser
305                 310                 315                 320

Leu Thr Leu Glu Thr Pro Leu Thr Ser Lys Arg Asn Ser Thr Ala Lys
                325                 330                 335

Ala Met Thr Gly Ser Trp Ala Ala Thr Pro Pro Ser Gln Gly Asp Gln
            340                 345                 350

Val Gln Leu Lys Met Leu Pro Pro Ala Gln
        355                 360
```

```
<210> SEQ ID NO 5
<211> LENGTH: 30
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: Novel Sequence

<400> SEQUENCE: 5
tatgaattca gatgctctaa acgtccctgc                                        30

<210> SEQ ID NO 6
<211> LENGTH: 30
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: Novel Sequence

<400> SEQUENCE: 6
tccggatcca cctgcacctg cgcctgcacc                                        30

<210> SEQ ID NO 7
<211> LENGTH: 1002
<212> TYPE: DNA
<213> ORGANISM: Homo sapiens

<400> SEQUENCE: 7
atggagtcct caggcaaccc agagagcacc accttttttt actatgacct tcagagccag       60
ccgtgtgaga accaggcctg ggtctttgct accctcgcca ccactgtcct gtactgcctg      120
gtgtttctcc tcagcctagt gggcaacagc ctggtcctgt gggtcctggt gaagtatgag      180
agcctggagt ccctcaccaa catcttcatc ctcaacctgt gcctctcaga cctggtgttc      240
gcctgcttgt tgcctgtgtg gatctcccca taccactggg gctgggtgct gggagacttc      300
ctctgcaaac tcctcaatat gatcttctcc atcagcctct acagcagcat cttcttcctg      360
accatcatga ccatccaccg ctacctgtcg gtagtgagcc ccctctccac cctgcgcgtc      420 cccacccctcc gctgccgggt gctggtgacc atggctgtgt gggtagccag catcctgtcc      480
tccatcctcg acaccatctt ccacaaggtg ctttcttcgg gctgtgatta ttccgaactc      540
```

```
acgtggtacc tcacctccgt ctaccagcac aacctcttct tcctgctgtc cctggggatt      600
atcctgttct gctacgtgga gatcctcagg accctgttcc gctcacgctc caagcggcgc      660
caccgcacgg tcaagctcat cttcgccatc gtggtggcct acttcctcag ctggggtccc      720
tacaacttca ccctgtttct gcagacgctg tttcggaccc agatcatccg gagctgcgag      780
gccaaacagc agctagaata cgccctgctc atctgccgca acctcgcctt ctcccactgc      840
tgctttaacc cggtgctcta tgtcttcgtg ggggtcaagt tccgcacaca cctgaaacat      900
gttctccggc agttctggtt ctgccggctg caggcaccca gcccagcctc gatcccccac      960
tcccctggtg ccttcgccta tgagggcgcc tccttctact ga                         1002
```

<210> SEQ ID NO 8
<211> LENGTH: 333
<212> TYPE: PRT
<213> ORGANISM: Homo sapiens

<400> SEQUENCE: 8

```
Met Glu Ser Ser Gly Asn Pro Glu Ser Thr Thr Phe Phe Tyr Tyr Asp
 1               5                  10                  15

Leu Gln Ser Gln Pro Cys Glu Asn Gln Ala Trp Val Phe Ala Thr Leu
            20                  25                  30

Ala Thr Thr Val Leu Tyr Cys Leu Val Phe Leu Leu Ser Leu Val Gly
        35                  40                  45

Asn Ser Leu Val Leu Trp Val Leu Val Lys Tyr Glu Ser Leu Glu Ser
    50                  55                  60

Leu Thr Asn Ile Phe Ile Leu Asn Leu Cys Leu Ser Asp Leu Val Phe
65                  70                  75                  80

Ala Cys Leu Leu Pro Val Trp Ile Ser Pro Tyr His Trp Gly Trp Val
                85                  90                  95

Leu Gly Asp Phe Leu Cys Lys Leu Leu Asn Met Ile Phe Ser Ile Ser
            100                 105                 110

Leu Tyr Ser Ser Ile Phe Phe Leu Thr Ile Met Thr Ile His Arg Tyr
        115                 120                 125

Leu Ser Val Val Ser Pro Leu Ser Thr Leu Arg Val Pro Thr Leu Arg
    130                 135                 140

Cys Arg Val Leu Val Thr Met Ala Val Trp Val Ala Ser Ile Leu Ser
145                 150                 155                 160

Ser Ile Leu Asp Thr Ile Phe His Lys Val Leu Ser Ser Gly Cys Asp
                165                 170                 175

Tyr Ser Glu Leu Thr Trp Tyr Leu Thr Ser Val Tyr Gln His Asn Leu
            180                 185                 190

Phe Phe Leu Leu Ser Leu Gly Ile Ile Leu Phe Cys Tyr Val Glu Ile
        195                 200                 205

Leu Arg Thr Leu Phe Arg Ser Arg Ser Lys Arg Arg His Arg Thr Val
    210                 215                 220

Lys Leu Ile Phe Ala Ile Val Val Ala Tyr Phe Leu Ser Trp Gly Pro
225                 230                 235                 240

Tyr Asn Phe Thr Leu Phe Leu Gln Thr Leu Phe Arg Thr Gln Ile Ile
                245                 250                 255

Arg Ser Cys Glu Ala Lys Gln Gln Leu Glu Tyr Ala Leu Leu Ile Cys
            260                 265                 270

Arg Asn Leu Ala Phe Ser His Cys Cys Phe Asn Pro Val Leu Tyr Val
        275                 280                 285

Phe Val Gly Val Lys Phe Arg Thr His Leu Lys His Val Leu Arg Gln
```

```
                         290                 295                 300
Phe Trp Phe Cys Arg Leu Gln Ala Pro Ser Pro Ala Ser Ile Pro His
305                 310                 315                 320

Ser Pro Gly Ala Phe Ala Tyr Glu Gly Ala Ser Phe Tyr
                325                 330
```

<210> SEQ ID NO 9
<211> LENGTH: 30
<212> TYPE: DNA
<213> ORGANISM: Artificial Sequence
<220> FEATURE:
<223> OTHER INFORMATION: Novel Sequence

<400> SEQUENCE: 9
gcaagcttgg gggacgccag gtcgccggct                                    30

<210> SEQ ID NO 10
<211> LENGTH: 31
<212> TYPE: DNA
<213> ORGANISM: Artificial Sequence
<220> FEATURE:
<223> OTHER INFORMATION: Novel Sequence

<400> SEQUENCE: 10
gcggatccgg acgctggggg agtcaggctg c                                  31

<210> SEQ ID NO 11
<211> LENGTH: 987
<212> TYPE: DNA
<213> ORGANISM: Homo sapiens

<400> SEQUENCE: 11
atggacaacg cctcgttctc ggagccctgg cccgccaacg catcgggccc ggacccggcg    60
ctgagctgct ccaacgcgtc gactctggcg ccgctgccgg cgccgctggc ggtggctgta   120
ccagttgtct acgcggtgat ctgcgccgtg gtctggcggg caactccgc cgtgctgtac    180
gtgttgctgc gggcgccccg catgaagacc gtcaccaacc tgttcatcct caacctggcc   240
atcgccgacg agctcttcac gctggtgctg cccatcaaca tcgccgactt cctgctgcgg   300
cagtggccct cggggagct catgtgcaag ctcatcgtgg ctatcgacca gtacaacacc   360
ttctccagcc tctacttcct caccgtcatg agcgccgacc gctacctggt ggtgttggcc   420
actgcggagt cgcgccgggt ggccggccgc acctacagcg ccgcgcgcgc ggtgagcctg   480
gccgtgtggg ggatcgtcac actcgtcgtg ctgcccttcg cagtcttcgc ccggctagac   540
gacgagcagg gccggcgcca gtgcgtgcta gtctttccgc agcccgaggc cttctggtgg   600
cgcgcgagcc gcctctacac gctcgtgctg ggcttcgcca tccccgtgtc caccatctgt   660
gtcctctata ccaccctgct gtgccggctg catgccatgc ggctggacag ccacgccaag   720
gccctggagc gcgccaagaa gcgggtgacc ttcctggtgg tggcaatcct ggcggtgtgc   780
ctcctctgct ggacgcccta ccacctgagc accgtggtgg cgctcaccac cgacctcccg   840
cagacgccgc tggtcatcgc tatctcctac ttcatcacca gcctgacgta cgccaacagc   900
tgcctcaacc ccttcctcta cgccttcctg acgccagct tccgcaggaa cctccgccag   960
ctgataactt gccgcgcggc agcctga                                       987

<210> SEQ ID NO 12
<211> LENGTH: 328
<212> TYPE: PRT
<213> ORGANISM: Homo sapiens

<400> SEQUENCE: 12

```
Met Asp Asn Ala Ser Phe Ser Glu Pro Trp Pro Ala Asn Ala Ser Gly
1               5                   10                  15

Pro Asp Pro Ala Leu Ser Cys Ser Asn Ala Ser Thr Leu Ala Pro Leu
            20                  25                  30

Pro Ala Pro Leu Ala Val Ala Val Pro Val Val Tyr Ala Val Ile Cys
        35                  40                  45

Ala Val Gly Leu Ala Gly Asn Ser Ala Val Leu Tyr Val Leu Leu Arg
    50                  55                  60

Ala Pro Arg Met Lys Thr Val Thr Asn Leu Phe Ile Leu Asn Leu Ala
65                  70                  75                  80

Ile Ala Asp Glu Leu Phe Thr Leu Val Leu Pro Ile Asn Ile Ala Asp
                85                  90                  95

Phe Leu Leu Arg Gln Trp Pro Phe Gly Glu Leu Met Cys Lys Leu Ile
            100                 105                 110

Val Ala Ile Asp Gln Tyr Asn Thr Phe Ser Ser Leu Tyr Phe Leu Thr
        115                 120                 125

Val Met Ser Ala Asp Arg Tyr Leu Val Val Leu Ala Thr Ala Glu Ser
    130                 135                 140

Arg Arg Val Ala Gly Arg Thr Tyr Ser Ala Ala Arg Ala Val Ser Leu
145                 150                 155                 160

Ala Val Trp Gly Ile Val Thr Leu Val Val Leu Pro Phe Ala Val Phe
                165                 170                 175

Ala Arg Leu Asp Asp Glu Gln Gly Arg Arg Gln Cys Val Leu Val Phe
            180                 185                 190

Pro Gln Pro Glu Ala Phe Trp Trp Arg Ala Ser Arg Leu Tyr Thr Leu
        195                 200                 205

Val Leu Gly Phe Ala Ile Pro Val Ser Thr Ile Cys Val Leu Tyr Thr
    210                 215                 220

Thr Leu Leu Cys Arg Leu His Ala Met Arg Leu Asp Ser His Ala Lys
225                 230                 235                 240

Ala Leu Glu Arg Ala Lys Lys Arg Val Thr Phe Leu Val Val Ala Ile
                245                 250                 255

Leu Ala Val Cys Leu Leu Cys Trp Thr Pro Tyr His Leu Ser Thr Val
            260                 265                 270

Val Ala Leu Thr Thr Asp Leu Pro Gln Thr Pro Leu Val Ile Ala Ile
        275                 280                 285

Ser Tyr Phe Ile Thr Ser Leu Thr Tyr Ala Asn Ser Cys Leu Asn Pro
    290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325
```

<210> SEQ ID NO 13
<211> LENGTH: 30
<212> TYPE: DNA
<213> ORGANISM: Artificial Sequence
<220> FEATURE:
<223> OTHER INFORMATION: Novel Sequence

<400> SEQUENCE: 13
cggaattcgt caacggtccc agctacaatg        30

<210> SEQ ID NO 14
<211> LENGTH: 31
<212> TYPE: DNA
<213> ORGANISM: Artificial Sequence
<220> FEATURE:
<223> OTHER INFORMATION: Novel Sequence

<400> SEQUENCE: 14

```
atggatccca ggcccttcag caccgcaata t                              31
```

<210> SEQ ID NO 15
<211> LENGTH: 1002
<212> TYPE: DNA
<213> ORGANISM: Homo sapiens

<400> SEQUENCE: 15

```
atgcaggccg ctgggcaccc agagcccctt gacagcaggg gctccttctc cctccccacg    60
atgggtgcca acgtctctca ggacaatggc actggccaca atgccacctt ctccgagcca   120
ctgccgttcc tctatgtgct cctgcccgcc gtgtactccg ggatctgtgc tgtggggctg   180
actggcaaca cggccgtcat ccttgtaatc ctaaggcgc ccaagatgaa gacggtgacc    240
aacgtgttca tcctgaacct ggccgtcgcc gacgggctct tcacgctggt actgcccgtc   300
aacatcgcgg agcacctgct gcagtactgg cccttcgggg agctgctctg caagctggtg   360
ctggccgtcg accactacaa catcttctcc agcatctact tcctagccgt gatgagcgtg   420
gaccgatacc tggtggtgct ggccaccgtg aggtcccgcc acatgccctg cgcacctac    480
cggggggcga aggtcgccag cctgtgtgtc tggctgggcg tcacggtcct ggttctgccc   540
ttcttctctt tcgctggcgt ctacagcaac gagctgcagg tcccaagctg tgggctgagc   600
ttcccgtggc ccgagcgggt ctggttcaag gccagccgtg tctacacttt ggtcctgggc   660
ttcgtgctgc ccgtgtgcac catctgtgtg ctctacacag acctcctgcg caggctgcgg   720
gccgtgcggc tccgctctgg agccaaggct ctaggcaagg ccaggcggaa ggtgaccgtc   780
ctggtcctcg tcgtgctggc cgtgtgcctc tctgctggat cgcccttcca cctggcctct   840
gtcgtggccc tgaccacgga cctgcccag acccactgg tcatcagtat gtcctacgtc    900
atcaccagcc tcacgtacgc caactcgtgc ctgaaccct tcctctacgc ctttctagat   960
gacaacttcc ggaagaactt ccgcagcata ttgcggtgct ga                    1002
```

<210> SEQ ID NO 16
<211> LENGTH: 333
<212> TYPE: PRT
<213> ORGANISM: Homo sapiens

<400> SEQUENCE: 16

```
Met Gln Ala Ala Gly His Pro Glu Pro Leu Asp Ser Arg Gly Ser Phe
 1               5                  10                  15

Ser Leu Pro Thr Met Gly Ala Asn Val Ser Gln Asp Asn Gly Thr Gly
             20                  25                  30

His Asn Ala Thr Phe Ser Glu Pro Leu Pro Phe Leu Tyr Val Leu Leu
         35                  40                  45

Pro Ala Val Tyr Ser Gly Ile Cys Ala Val Gly Leu Thr Gly Asn Thr
     50                  55                  60

Ala Val Ile Leu Val Ile Leu Arg Ala Pro Lys Met Lys Thr Val Thr
 65                  70                  75                  80

Asn Val Phe Ile Leu Asn Leu Ala Val Ala Asp Gly Leu Phe Thr Leu
                 85                  90                  95
```

-continued

```
Val Leu Pro Val Asn Ile Ala Glu His Leu Leu Gln Tyr Trp Pro Phe
            100                 105                 110
Gly Glu Leu Leu Cys Lys Leu Val Ala Val Asp His Tyr Asn Ile
        115                 120                 125
Phe Ser Ser Ile Tyr Phe Leu Ala Val Met Ser Val Asp Arg Tyr Leu
    130                 135                 140
Val Val Leu Ala Thr Val Arg Ser Arg His Met Pro Trp Arg Thr Tyr
145                 150                 155                 160
Arg Gly Ala Lys Val Ala Ser Leu Cys Val Trp Leu Gly Val Thr Val
                165                 170                 175
Leu Val Leu Pro Phe Phe Ser Phe Ala Gly Val Tyr Ser Asn Glu Leu
            180                 185                 190
Gln Val Pro Ser Cys Gly Leu Ser Phe Pro Trp Pro Glu Arg Val Trp
        195                 200                 205
Phe Lys Ala Ser Arg Val Tyr Thr Leu Val Leu Gly Phe Val Leu Pro
    210                 215                 220
Val Cys Thr Ile Cys Val Leu Tyr Thr Asp Leu Leu Arg Arg Leu Arg
225                 230                 235                 240
Ala Val Arg Leu Arg Ser Gly Ala Lys Ala Leu Gly Lys Ala Arg Arg
                245                 250                 255
Lys Val Thr Val Leu Val Leu Val Val Leu Ala Val Cys Leu Leu Cys
            260                 265                 270
Trp Thr Pro Phe His Leu Ala Ser Val Val Ala Leu Thr Thr Asp Leu
        275                 280                 285
Pro Gln Thr Pro Leu Val Ile Ser Met Ser Tyr Val Ile Thr Ser Leu
    290                 295                 300
Thr Tyr Ala Asn Ser Cys Leu Asn Pro Phe Leu Tyr Ala Phe Leu Asp
305                 310                 315                 320
Asp Asn Phe Arg Lys Asn Phe Arg Ser Ile Leu Arg Cys
                325                 330
```

<210> SEQ ID NO 17
<211> LENGTH: 48
<212> TYPE: DNA
<213> ORGANISM: Artificial Sequence
<220> FEATURE:
<223> OTHER INFORMATION: Novel Sequence

<400> SEQUENCE: 17
acgaattcag ccatggtcct tgaggtgagt gaccaccaag tgctaaat                48

<210> SEQ ID NO 18
<211> LENGTH: 27
<212> TYPE: DNA
<213> ORGANISM: Artificial Sequence
<220> FEATURE:
<223> OTHER INFORMATION: Novel Sequence

<400> SEQUENCE: 18
gaggatcctg gaatgcgggg aagtcag                                       27

<210> SEQ ID NO 19
<211> LENGTH: 1107
<212> TYPE: DNA
<213> ORGANISM: Homo sapiens

<400> SEQUENCE: 19
atggtccttg aggtgagtga ccaccaagtg ctaaatgacg ccgaggttgc cgccctcctg    60

-continued

```
gagaacttca gctcttccta tgactatgga gaaaacgaga gtgactcgtg ctgtacctcc      120
ccgccctgcc cacaggactt cagcctgaac ttcgaccggg ccttcctgcc agccctctac      180
agcctcctct ttctgctggg gctgctgggc aacggcgcgg tggcagccgt gctgctgagc      240
cggcggacag ccctgagcag caccgacacc ttcctgctcc acctagctgt agcagacacg      300
ctgctggtgc tgacactgcc gctctgggca gtggacgctg ccgtccagtg ggtctttggc      360
tctggcctct gcaaagtggc aggtgccctc ttcaacatca acttctacgc aggagccctc      420
ctgctggcct gcatcagctt tgaccgctac ctgaacatag ttcatgccac ccagctctac      480
cgccgggggc ccccggcccg cgtgaccctc acctgcctgg ctgtctgggg gctctgcctg      540
cttttcgccc tccagactt catcttcctg tcggcccacc acgacgagcg cctcaacgcc      600
acccactgcc aatacaactt cccacaggtg ggccgcacgg ctctgcgggt gctgcagctg      660
gtggctggct tctgctgcc cctgctggtc atggcctact gctatgccca catcctggcc      720
gtgctgctgg tttccagggg ccagcggcgc ctgcgggcca tgcggctggt ggtggtggtc      780
gtggtggcct ttgccctctg ctggaccccc atcacctggg tggtgctggt ggacatcctc      840
atggacctgg gcgctttggc ccgcaactgt ggccgagaaa gcaggtaga cgtggccaag      900
tcggtcacct caggcctggg ctacatgcac tgctgcctca cccgctgct ctatgccttt      960
gtaggggtca agttccggga gcggatgtgg atgctgctct tgcgcctggg ctgccccaac     1020
cagagagggc tccagaggca gccatcgtct ccccgccggg attcatcctg gtctgagacc     1080
tcagaggcct cctactcggg cttgtga                                        1107
```

<210> SEQ ID NO 20
<211> LENGTH: 368
<212> TYPE: PRT
<213> ORGANISM: Homo sapiens

<400> SEQUENCE: 20

```
Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190
```

```
His His Asp Glu Arg Leu Asn Ala Thr His Cys Gln Tyr Asn Phe Pro
            195                 200                 205

Gln Val Gly Arg Thr Ala Leu Arg Val Leu Gln Leu Val Ala Gly Phe
        210                 215                 220

Leu Leu Pro Leu Leu Val Met Ala Tyr Cys Tyr Ala His Ile Leu Ala
225                 230                 235                 240

Val Leu Leu Val Ser Gly Gln Arg Arg Leu Arg Ala Met Arg Leu
                245                 250                 255

Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
    275                 280                 285

Asn Cys Gly Arg Glu Ser Arg Val Asp Val Ala Lys Ser Val Thr Ser
290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
                340                 345                 350

Arg Asp Ser Ser Trp Ser Glu Thr Ser Glu Ala Ser Tyr Ser Gly Leu
            355                 360                 365

<210> SEQ ID NO 21
<211> LENGTH: 30
<212> TYPE: DNA
<213> ORGANISM: Artificial Sequence
<220> FEATURE:
<223> OTHER INFORMATION: Novel Sequence

<400> SEQUENCE: 21
ttaagcttga cctaatgcca tcttgtgtcc                                      30

<210> SEQ ID NO 22
<211> LENGTH: 30
<212> TYPE: DNA
<213> ORGANISM: Artificial Sequence
<220> FEATURE:
<223> OTHER INFORMATION: Novel Sequence

<400> SEQUENCE: 22
ttggatccaa aagaaccatg cacctcagag                                      30

<210> SEQ ID NO 23
<211> LENGTH: 1074
<212> TYPE: DNA
<213> ORGANISM: Homo sapiens

<400> SEQUENCE: 23
atggctgatg actatggctc tgaatccaca tcttccatgg aagactacgt taacttcaac      60
ttcactgact tctactgtga gaaaacaat gtcaggcagt tgcgagcca tttcctccca      120 cccttgtact ggctcgtgtt catcgtgggt gccttgggca acagtcttgt tatccttgtc     180
tactggtact gcacaagagt gaagaccatg accgacatgt tccttttgaa tttggcaatt     240
gctgacctcc tctttcttgt cactcttccc ttctgggcca tgctgctgc tgaccagtgg     300 aagttccaga ccttcatgtg caaggtggtc aacagcatgt acaagatgaa cttctacagc     360
tgtgtgttgc tgatcatgtg catcagcgtg gacaggtaca ttgccattgc ccaggccatg     420
```

-continued

```
agagcacata cttggaggga gaaaaggctt ttgtacagca aaatggtttg ctttaccatc      480
tgggtattgg cagctgctct ctgcatccca gaaatcttat acagccaaat caaggaggaa      540
tccggcattg ctatctgcac catggtttac cctagcgatg agagcaccaa actgaagtca      600
gctgtcttga ccctgaaggt cattctgggg ttcttccttc ccttcgtggt catggcttgc      660
tgctatacca tcatcattca caccctgata caagccaaga agtcttccaa gcacaaagcc      720
ctaaaagtga ccatcactgt cctgaccgtc tttgtcttgt ctcagtttcc ctacaactgc      780
attttgttgg tgcagaccat tgacgcctat gccatgttca tctccaactg tgccgtttcc      840
accaacattg acatctgctt ccaggtcacc cagaccatcg ccttcttcca cagttgcctg      900
aaccctgttc tctatgtttt tgtgggtgag agattccgcc gggatctcgt gaaaaccctg      960
aagaacttgg gttgcatcag ccaggcccag tgggtttcat ttacaaggag agagggaagc     1020
ttgaagctgt cgtctatgtt gctggagaca acctcaggag cactctccct ctga           1074
```

<210> SEQ ID NO 24
<211> LENGTH: 357
<212> TYPE: PRT
<213> ORGANISM: Homo sapiens

<400> SEQUENCE: 24

```
Met Ala Asp Asp Tyr Gly Ser Glu Ser Thr Ser Ser Met Glu Asp Tyr
1               5                   10                  15

Val Asn Phe Asn Phe Thr Asp Phe Tyr Cys Glu Lys Asn Asn Val Arg
            20                  25                  30

Gln Phe Ala Ser His Phe Leu Pro Pro Leu Tyr Trp Leu Val Phe Ile
        35                  40                  45

Val Gly Ala Leu Gly Asn Ser Leu Val Ile Leu Val Tyr Trp Tyr Cys
    50                  55                  60

Thr Arg Val Lys Thr Met Thr Asp Met Phe Leu Leu Asn Leu Ala Ile
65                  70                  75                  80

Ala Asp Leu Leu Phe Leu Val Thr Leu Pro Phe Trp Ala Ile Ala Ala
                85                  90                  95

Ala Asp Gln Trp Lys Phe Gln Thr Phe Met Cys Lys Val Val Asn Ser
            100                 105                 110

Met Tyr Lys Met Asn Phe Tyr Ser Cys Val Leu Leu Ile Met Cys Ile
        115                 120                 125

Ser Val Asp Arg Tyr Ile Ala Ile Ala Gln Ala Met Arg Ala His Thr
    130                 135                 140

Trp Arg Glu Lys Arg Leu Leu Tyr Ser Lys Met Val Cys Phe Thr Ile
145                 150                 155                 160

Trp Val Leu Ala Ala Ala Leu Cys Ile Pro Glu Ile Leu Tyr Ser Gln
                165                 170                 175

Ile Lys Glu Glu Ser Gly Ile Ala Ile Cys Thr Met Val Tyr Pro Ser
            180                 185                 190

Asp Glu Ser Thr Lys Leu Lys Ser Ala Val Leu Thr Leu Lys Val Ile
        195                 200                 205

Leu Gly Phe Phe Leu Pro Phe Val Val Met Ala Cys Cys Tyr Thr Ile
    210                 215                 220

Ile Ile His Thr Leu Ile Gln Ala Lys Lys Ser Ser Lys His Lys Ala
225                 230                 235                 240

Leu Lys Val Thr Ile Thr Val Leu Thr Val Phe Val Leu Ser Gln Phe
                245                 250                 255
```

```
Pro Tyr Asn Cys Ile Leu Leu Val Gln Thr Ile Asp Ala Tyr Ala Met
            260                 265                 270

Phe Ile Ser Asn Cys Ala Val Ser Thr Asn Ile Asp Ile Cys Phe Gln
        275                 280                 285

Val Thr Gln Thr Ile Ala Phe Phe His Ser Cys Leu Asn Pro Val Leu
    290                 295                 300

Tyr Val Phe Val Gly Glu Arg Phe Arg Arg Asp Leu Val Lys Thr Leu
305                 310                 315                 320

Lys Asn Leu Gly Cys Ile Ser Gln Ala Gln Trp Val Ser Phe Thr Arg
                325                 330                 335

Arg Glu Gly Ser Leu Lys Leu Ser Ser Met Leu Leu Glu Thr Thr Ser
            340                 345                 350

Gly Ala Leu Ser Leu
        355
```

<210> SEQ ID NO 25
<211> LENGTH: 1110
<212> TYPE: DNA
<213> ORGANISM: Homo sapiens

<400> SEQUENCE: 25

| | | | | | |
|---|---|---|---|---|---|
| atggcctcat | cgaccactcg | gggcccagg | gtttctgact | tattttctgg | gctgccgccg | 60 |
| gcggtcacaa | ctcccgccaa | ccagagcgca | gaggcctcgg | cgggcaacgg | gtcggtggct | 120 |
| ggcgcggacg | ctccagccgt | cacgcccttc | cagagcctgc | agctggtgca | tcagctgaag | 180 |
| gggctgatcg | tgctgctcta | cagcgtcgtg | gtggtcgtgg | ggctggtggg | caactgcctg | 240 |
| ctggtgctgg | tgatcgcgcg | ggtgccgcgg | ctgcacaacg | tgacgaactt | cctcatcggc | 300 |
| aacctggcct | tgtccgacgt | gctcatgtgc | accgcctgcg | tgccgctcac | gctggcctat | 360 |
| gccttcgagc | cacgcggctg | ggtgttcggc | ggcggcctgt | gccacctggt | cttcttcctg | 420 |
| cagccggtca | ccgtctatgt | gtcggtgttc | acgctcacca | ccatcgcagt | ggaccgctac | 480 |
| gtcgtgctgg | tgcacccgct | gaggcgcgca | tctcgctgcg | cctcagccta | cgctgtgctg | 540 |
| gccatctggg | cgctgtccgc | ggtgctggcg | ctgccgcccg | ccgtgcacac | ctatcacgtg | 600 |
| gagctcaagc | cgcacgacgt | gcgcctctgc | gaggagttct | ggggctccca | ggagcgccag | 660 |
| cgccagctct | acgcctgggg | gctgctgctg | gtcacctacc | tgctccctct | gctggtcatc | 720 |
| ctcctgtctt | acgtccgggt | gtcagtgaag | ctccgcaacc | gcgtggtgcc | gggctgcgtg | 780 |
| acccagagcc | aggccgactg | gaccgcgct | cggcgccggc | gcaccttctg | cttgctggtg | 840 |
| gtggtcgtgg | tggtgttcgc | cgtctgctgg | ctgccgctgc | acgtcttcaa | cctgctgcgg | 900 |
| gacctcgacc | cccacgccat | cgaccttac | gcctttgggc | tggtgcagct | gctctgccac | 960 |
| tggctcgcca | tgagttcggc | ctgctacaac | cccttcatct | acgcctggct | gcacgacagc | 1020 |
| ttccgcgagg | agctgcgcaa | actgttggtc | gcttggcccc | gcaagatagc | ccccatggc | 1080 |
| cagaatatga | ccgtcagcgt | ggtcatctga | | | | 1110 |

<210> SEQ ID NO 26
<211> LENGTH: 369
<212> TYPE: PRT
<213> ORGANISM: Homo sapiens

<400> SEQUENCE: 26

```
Met Ala Ser Ser Thr Thr Arg Gly Pro Arg Val Ser Asp Leu Phe Ser
1               5                   10                  15

Gly Leu Pro Pro Ala Val Thr Thr Pro Ala Asn Gln Ser Ala Glu Ala
```

```
                    20                  25                  30
Ser Ala Gly Asn Gly Ser Val Ala Gly Ala Asp Ala Pro Ala Val Thr
         35                  40                  45

Pro Phe Gln Ser Leu Gln Leu Val His Gln Leu Lys Gly Leu Ile Val
 50                  55                  60

Leu Leu Tyr Ser Val Val Val Val Gly Leu Val Gly Asn Cys Leu
 65                  70                  75                  80

Leu Val Leu Val Ile Ala Arg Val Pro Arg Leu His Asn Val Thr Asn
                 85                  90                  95

Phe Leu Ile Gly Asn Leu Ala Leu Ser Asp Val Leu Met Cys Thr Ala
                100                 105                 110

Cys Val Pro Leu Thr Leu Ala Tyr Ala Phe Glu Pro Arg Gly Trp Val
            115                 120                 125

Phe Gly Gly Gly Leu Cys His Leu Val Phe Phe Leu Gln Pro Val Thr
        130                 135                 140

Val Tyr Val Ser Val Phe Thr Leu Thr Thr Ile Ala Val Asp Arg Tyr
145                 150                 155                 160

Val Val Leu Val His Pro Leu Arg Arg Ala Ser Arg Cys Ala Ser Ala
                165                 170                 175

Tyr Ala Val Leu Ala Ile Trp Ala Leu Ser Ala Val Leu Ala Leu Pro
                180                 185                 190

Pro Ala Val His Thr Tyr His Val Glu Leu Lys Pro His Asp Val Arg
            195                 200                 205

Leu Cys Glu Glu Phe Trp Gly Ser Gln Glu Arg Gln Arg Gln Leu Tyr
        210                 215                 220

Ala Trp Gly Leu Leu Leu Val Thr Tyr Leu Leu Pro Leu Leu Val Ile
225                 230                 235                 240

Leu Leu Ser Tyr Val Arg Val Ser Val Lys Leu Arg Asn Arg Val Val
                245                 250                 255

Pro Gly Cys Val Thr Gln Ser Gln Ala Asp Trp Asp Arg Ala Arg Arg
                260                 265                 270

Arg Arg Thr Phe Cys Leu Leu Val Val Val Val Val Phe Ala Val
            275                 280                 285

Cys Trp Leu Pro Leu His Val Phe Asn Leu Leu Arg Asp Leu Asp Pro
        290                 295                 300

His Ala Ile Asp Pro Tyr Ala Phe Gly Leu Val Gln Leu Leu Cys His
305                 310                 315                 320

Trp Leu Ala Met Ser Ser Ala Cys Tyr Asn Pro Phe Ile Tyr Ala Trp
                325                 330                 335

Leu His Asp Ser Phe Arg Glu Glu Leu Arg Lys Leu Leu Val Ala Trp
            340                 345                 350

Pro Arg Lys Ile Ala Pro His Gly Gln Asn Met Thr Val Ser Val Val
        355                 360                 365

Ile

<210> SEQ ID NO 27
<211> LENGTH: 1083
<212> TYPE: DNA
<213> ORGANISM: Homo sapiens

<400> SEQUENCE: 27
atggacccag aagaaacttc agtttatttg gattattact atgctacgag cccaaactct      60
gacatcaggg agacccactc ccatgttcct tacacctctg tcttccttcc agtcttttac     120
```

```
acagctgtgt tcctgactgg agtgctgggg aaccttgttc tcatgggagc gttgcatttc    180
aaacccggca gccgaagact gatcgacatc tttatcatca atctggctgc ctctgacttc    240
atttttcttg tcacattgcc ctctgggtg gataaagaag catctctagg actgtggagg     300
acgggctcct tcctgtgcaa agggagctcc tacatgatct ccgtcaatat gcactgcagt    360
gtcctcctgc tcacttgcat gagtgttgac cgctacctgg ccattgtgtg gccagtcgta    420
tccaggaaat tcagaaggac agactgtgca tatgtagtct gtgccagcat ctggtttatc    480
tcctgcctgc tggggttgcc tactcttctg tccagggagc tcacgctgat tgatgataag    540
ccatactgtg cagagaaaaa ggcaactcca attaaactca tatggtccct ggtggcctta    600
attttcacct tttttgtccc tttgttgagc attgtgacct gctactgttg cattgcaagg    660
aagctgtgtg cccattacca gcaatcagga agcacaaca aaaagctgaa gaaatctata    720
aagatcatct ttattgtcgt ggcagccttt cttgtctcct ggctgccctt caatactttc    780
aagttcctgg ccattgtctc tgggttgcgg caagaacact atttaccctc agctattctt    840
cagcttggta tggaggtgag tggacccttg gcatttgcca acagctgtgt caacccttc    900
atttactata tcttcgacag ctacatccgc cgggccattg tccactgctt gtgcccttgc    960
ctgaaaaact atgactttgg gagtagcact gagacatcag atagtcacct cactaaggct   1020
ctctccacct tcattcatgc agaagatttt gccaggagga ggaagaggtc tgtgtcactc   1080
taa                                                                 1083

<210> SEQ ID NO 28
<211> LENGTH: 360
<212> TYPE: PRT
<213> ORGANISM: Homo sapiens

<400> SEQUENCE: 28

Met Asp Pro Glu Glu Thr Ser Val Tyr Leu Asp Tyr Tyr Ala Thr
  1               5                  10                  15

Ser Pro Asn Ser Asp Ile Arg Glu Thr His Ser His Val Pro Tyr Thr
                 20                  25                  30

Ser Val Phe Leu Pro Val Phe Tyr Thr Ala Val Phe Leu Thr Gly Val
         35                  40                  45

Leu Gly Asn Leu Val Leu Met Gly Ala Leu His Phe Lys Pro Gly Ser
     50                  55                  60

Arg Arg Leu Ile Asp Ile Phe Ile Ile Asn Leu Ala Ala Ser Asp Phe
 65                  70                  75                  80

Ile Phe Leu Val Thr Leu Pro Leu Trp Val Asp Lys Glu Ala Ser Leu
                 85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Leu Thr Cys Met Ser
        115                 120                 125

Val Asp Arg Tyr Leu Ala Ile Val Trp Pro Val Ser Arg Lys Phe
    130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175

Ile Asp Asp Lys Pro Tyr Cys Ala Glu Lys Lys Ala Thr Pro Ile Lys
            180                 185                 190

Leu Ile Trp Ser Leu Val Ala Leu Ile Phe Thr Phe Phe Val Pro Leu
```

```
                195                 200                 205
Leu Ser Ile Val Thr Cys Tyr Cys Ile Ala Arg Lys Leu Cys Ala
        210                 215                 220

His Tyr Gln Gln Ser Gly Lys His Asn Lys Lys Leu Lys Lys Ser Ile
225                 230                 235                 240

Lys Ile Ile Phe Ile Val Val Ala Ala Phe Leu Val Ser Trp Leu Pro
                245                 250                 255

Phe Asn Thr Phe Lys Phe Leu Ala Ile Val Ser Gly Leu Arg Gln Glu
            260                 265                 270

His Tyr Leu Pro Ser Ala Ile Leu Gln Leu Gly Met Glu Val Ser Gly
        275                 280                 285

Pro Leu Ala Phe Ala Asn Ser Cys Val Asn Pro Phe Ile Tyr Tyr Ile
        290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Thr Ser Asp Ser His
                325                 330                 335

Leu Thr Lys Ala Leu Ser Thr Phe Ile His Ala Glu Asp Phe Ala Arg
            340                 345                 350

Arg Arg Lys Arg Ser Val Ser Leu
        355                 360

<210> SEQ ID NO 29
<211> LENGTH: 31
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: Novel Sequence

<400> SEQUENCE: 29
ctagaattct gactccagcc aaagcatgaa t                               31

<210> SEQ ID NO 30
<211> LENGTH: 30
<212> TYPE: DNA
<213> ORGANISM: Artificial Sequence
<220> FEATURE:
<223> OTHER INFORMATION: Novel Sequence

<400> SEQUENCE: 30
gctggatcct aaacagtctg cgctcggcct                                 30

<210> SEQ ID NO 31
<211> LENGTH: 1020
<212> TYPE: DNA
<213> ORGANISM: Homo sapiens

<400> SEQUENCE: 31
atgaatggcc ttgaagtggc tccccaggt ctgatcacca acttctccct ggccacggca    60
gagcaatgtg gccaggagac gccactggag aacatgctgt tcgcctcctt ctaccttctg   120
gattttatcc tggctttagt tggcaatacc ctggctctgt ggcttttcat ccgagaccac   180
aagtccggga ccccggccaa cgtgttcctg atgcatctgg ccgtggccga cttgtcgtgc   240
gtgctggtcc tgcccacccg cctggtctac cacttctctg ggaaccactg gccatttggg   300
gaaatcgcat gccgtctcac cggcttcctc ttctacctca acatgtacgc cagcatctac   360
ttcctcacct gcatcagcgc cgaccgtttc ctggccattg tgcacccggt caagtccctc   420
```

```
aagctccgca ggcccctcta cgcacacctg gcctgtgcct tcctgtgggt ggtggtggct    480
gtggccatgg ccccgctgct ggtgagccca cagaccgtgc agaccaacca cacggtggtc    540
tgcctgcagc tgtaccggga aaggcctcc caccatgccc tggtgtccct ggcagtggcc    600
ttcaccttcc cgttcatcac cacggtcacc tgctacctgc tgatcatccg cagcctgcgg    660
cagggcctgc gtgtggagaa gcgcctcaag accaaggcag tgcgcatgat cgccatagtg    720
ctggccatct tcctggtctg cttcgtgccc taccacgtca accgctccgt ctacgtgctg    780
cactaccgca gccatgggc ctcctgcgcc acccagcgca tcctggccct ggcaaaccgc    840
atcacctcct gcctcaccag cctcaacggg gcactcgacc ccatcatgta tttcttcgtg    900
gctgagaagt tccgccacgc cctgtgcaac ttgctctgtg gcaaaaggct caagggcccg    960
ccccccagct tcgaagggaa aaccaacgag agctcgctga gtgccaagtc agagctgtga   1020
```

<210> SEQ ID NO 32
<211> LENGTH: 339
<212> TYPE: PRT
<213> ORGANISM: Homo sapiens

<400> SEQUENCE: 32

```
Met Asn Gly Leu Glu Val Ala Pro Pro Gly Leu Ile Thr Asn Phe Ser
 1               5                  10                  15

Leu Ala Thr Ala Glu Gln Cys Gly Gln Glu Thr Pro Leu Glu Asn Met
                20                  25                  30

Leu Phe Ala Ser Phe Tyr Leu Leu Asp Phe Ile Leu Ala Leu Val Gly
            35                  40                  45

Asn Thr Leu Ala Leu Trp Leu Phe Ile Arg Asp His Lys Ser Gly Thr
        50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Ala Cys Arg Leu Thr Gly Phe Leu Phe Tyr
               100                 105                 110

Leu Asn Met Tyr Ala Ser Ile Tyr Phe Leu Thr Cys Ile Ser Ala Asp
           115                 120                 125

Arg Phe Leu Ala Ile Val His Pro Val Lys Ser Leu Lys Leu Arg Arg
       130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
    210                 215                 220

Val Glu Lys Arg Leu Lys Thr Lys Ala Val Arg Met Ile Ala Ile Val
225                 230                 235                 240

Leu Ala Ile Phe Leu Val Cys Phe Val Pro Tyr His Val Asn Arg Ser
                245                 250                 255

Val Tyr Val Leu His Tyr Arg Ser His Gly Ala Ser Cys Ala Thr Gln
            260                 265                 270
```

-continued

```
Arg Ile Leu Ala Leu Ala Asn Arg Ile Thr Ser Cys Leu Thr Ser Leu
            275                 280                 285

Asn Gly Ala Leu Asp Pro Ile Met Tyr Phe Phe Val Ala Glu Lys Phe
    290                 295                 300

Arg His Ala Leu Cys Asn Leu Leu Cys Gly Lys Arg Leu Lys Gly Pro
305                 310                 315                 320

Pro Pro Ser Phe Glu Gly Lys Thr Asn Glu Ser Ser Leu Ser Ala Lys
                325                 330                 335

Ser Glu Leu

<210> SEQ ID NO 33
<211> LENGTH: 29
<212> TYPE: DNA
<213> ORGANISM: Artificial Sequence
<220> FEATURE:
<223> OTHER INFORMATION: Novel Sequence

<400> SEQUENCE: 33
ataagatgat caccctgaac aatcaagat                                    29

<210> SEQ ID NO 34
<211> LENGTH: 33
<212> TYPE: DNA
<213> ORGANISM: Artificial Sequence
<220> FEATURE:
<223> OTHER INFORMATION: Novel Sequence

<400> SEQUENCE: 34
tccgaattca taacatttca ctgtttatat tgc                               33

<210> SEQ ID NO 35
<211> LENGTH: 996
<212> TYPE: DNA
<213> ORGANISM: Homo sapiens

<400> SEQUENCE: 35
atgatcaccc tgaacaatca agatcaacct gtcactttta acagctcaca tccagatgaa    60
tacaaaattg cagcccttgt cttctatagc tgtatcttca taattggatt atttgttaac   120
atcactgcat tatgggtttt cagttgtacc accaagaaga gaaccacggt aaccatctat   180
atgatgaatg tggcattagt ggacttgata tttataatga ctttacccct tcgaatgttt   240
tattatgcaa aagatgcatg gccatttgga gagtacttct gccagattat tggagctctc   300
acagtgtttt acccaagcat tgctttatgg cttcttgcct ttattagtgc tgacagatac   360
atggccattg tacagccgaa gtacgccaaa gaacttaaaa acacgtgcaa agccgtgctg   420
gcgtgtgtgg gagtctggat aatgaccctg accacgacca ccctctgct actgctctat   480 aaagacccag ataagactc cactcccgcc acctgcctca agatttctga catcatctat   540
ctaaaagctg tgaacgtgct gaacctcact cgactgacat tttttttctt gattcctttg   600
ttcatcatga ttgggtgcta cttggtcatt attcataatc tccttcacgg caggacgtct   660
aagctgaaac ccaaagtcaa ggagaagtcc ataaggatca tcatcacgct gctggtgcag   720
gtgctcgtct gctttatgcc cttccacatc tgtttcgctt tcctgatgct gggaacgggg   780
gagaacagtt acaatccctg gggagccttt accaccttcc tcatgaacct cagcacgtgt   840
ctggatgtga ttctctacta catcgtttca aaacaatttc aggctcgagt cattagtgtc   900
atgctatacc gtaattacct tcgaagcctg cgcagaaaaa gtttccgatc tggtagtcta   960
```

-continued aggtcactaa gcaatataaa cagtgaaatg ttatga                                996

<210> SEQ ID NO 36
<211> LENGTH: 331
<212> TYPE: PRT
<213> ORGANISM: Homo sapiens

<400> SEQUENCE: 36

Met Ile Thr Leu Asn Asn Gln Asp Gln Pro Val Thr Phe Asn Ser Ser
1               5                   10                  15

His Pro Asp Glu Tyr Lys Ile Ala Ala Leu Val Phe Tyr Ser Cys Ile
            20                  25                  30

Phe Ile Ile Gly Leu Phe Val Asn Ile Thr Ala Leu Trp Val Phe Ser
        35                  40                  45

Cys Thr Thr Lys Lys Arg Thr Thr Val Thr Ile Tyr Met Met Asn Val
    50                  55                  60

Ala Leu Val Asp Leu Ile Phe Ile Met Thr Leu Pro Phe Arg Met Phe
65                  70                  75                  80

Tyr Tyr Ala Lys Asp Ala Trp Pro Phe Gly Glu Tyr Phe Cys Gln Ile
                85                  90                  95

Ile Gly Ala Leu Thr Val Phe Tyr Pro Ser Ile Ala Leu Trp Leu Leu
            100                 105                 110

Ala Phe Ile Ser Ala Asp Arg Tyr Met Ala Ile Val Gln Pro Lys Tyr
        115                 120                 125

Ala Lys Glu Leu Lys Asn Thr Cys Lys Ala Val Leu Ala Cys Val Gly
    130                 135                 140

Val Trp Ile Met Thr Leu Thr Thr Thr Pro Leu Leu Leu Leu Tyr
145                 150                 155                 160

Lys Asp Pro Asp Lys Asp Ser Thr Pro Ala Thr Cys Leu Lys Ile Ser
                165                 170                 175

Asp Ile Ile Tyr Leu Lys Ala Val Asn Val Leu Asn Leu Thr Arg Leu
            180                 185                 190

Thr Phe Phe Phe Leu Ile Pro Leu Phe Ile Met Ile Gly Cys Tyr Leu
        195                 200                 205

Val Ile Ile His Asn Leu Leu His Gly Arg Thr Ser Lys Leu Lys Pro
    210                 215                 220

Lys Val Lys Glu Lys Ser Ile Arg Ile Ile Thr Leu Leu Val Gln
225                 230                 235                 240

Val Leu Val Cys Phe Met Pro Phe His Ile Cys Phe Ala Phe Leu Met
                245                 250                 255

Leu Gly Thr Gly Glu Asn Ser Tyr Asn Pro Trp Gly Ala Phe Thr Thr
            260                 265                 270

Phe Leu Met Asn Leu Ser Thr Cys Leu Asp Val Ile Leu Tyr Tyr Ile
        275                 280                 285

Val Ser Lys Gln Phe Gln Ala Arg Val Ile Ser Val Met Leu Tyr Arg
    290                 295                 300

Asn Tyr Leu Arg Ser Leu Arg Arg Lys Ser Phe Arg Ser Gly Ser Leu
305                 310                 315                 320

Arg Ser Leu Ser Asn Ile Asn Ser Glu Met Leu
                325                 330

<210> SEQ ID NO 37
<211> LENGTH: 28
<212> TYPE: DNA
<213> ORGANISM: Artificial Sequence
<220> FEATURE:

```
<223> OTHER INFORMATION: Novel Sequence

<400> SEQUENCE: 37
ccaagcttcc aggcctgggg tgtgctgg                                              28

<210> SEQ ID NO 38
<211> LENGTH: 29
<212> TYPE: DNA
<213> ORGANISM: Artificial Sequence
<220> FEATURE:
<223> OTHER INFORMATION: Novel Sequence

<400> SEQUENCE: 38
atggatcctg accttcggcc cctggcaga                                             29

<210> SEQ ID NO 39
<211> LENGTH: 1077
<212> TYPE: DNA
<213> ORGANISM: Homo sapiens

<400> SEQUENCE: 39
atgccctctg tgtctccagc ggggccctcg gccggggcag tccccaatgc caccgcagtg          60
acaacagtgc ggaccaatgc cagcgggctg gaggtgcccc tgttccacct gtttgcccgg         120
ctggacgagg agctgcatgg caccttccca ggcctgtgcg tggcgctgat ggcggtgcac         180
ggagccatct tcctggcagg gctggtgctc aacgggctgg cgctgtacgt cttctgctgc         240
cgcacccggg ccaagacacc ctcagtcatc tacaccatca acctggtggt gaccgatcta         300
ctggtagggc tgtccctgcc cacgcgcttc gctgtgtact acggcgccag gggctgcctg         360
cgctgtgcct cccgcacgt  cctcggttac ttcctcaaca tgcactgctc catcctcttc         420
ctcacctgca tctgcgtgga ccgctacctg gccatcgtgc ggcccgaagg ctcccgccgc         480
tgccgccagc tgcctgtgc cagggccgtg tgcgccttcg tgtggctggc cgccggtgcc         540
gtcaccctgt cggtgctggg cgtgacaggc agccggccct gctgccgtgt ctttgcgctg         600
actgtcctgg agttcctgct gccccctgctg gtcatcagcg tgtttaccgg ccgcatcatg         660
tgtgcactgt cgcggccggg tctgctccac cagggtcgcc agcgccgcgt gcgggccatg         720
cagctcctgc tcacggtgct catcatcttt ctcgtctgct tcacgccctt ccacgcccgc         780
caagtggccg tggcgctgtg gcccgacatg ccacaccaca cgagcctcgt ggtctaccac         840
gtggccgtga ccctcagcag cctcaacagc tgcatggacc ccatcgtcta ctgcttcgtc         900
accagtggct ccaggccac cgtccgaggc ctcttcggcc agcacggaga gcgtgagccc         960
agcagcggtg acgtggtcag catgcacagg agctccaagg gctcaggccg tcatcacatc        1020
ctcagtgccg ccctcacgc cctcacccag gccctggcta atgggcccga ggcttag            1077

<210> SEQ ID NO 40
<211> LENGTH: 358
<212> TYPE: PRT
<213> ORGANISM: Homo sapiens

<400> SEQUENCE: 40

Met Pro Ser Val Ser Pro Ala Gly Pro Ser Ala Gly Ala Val Pro Asn
1               5                   10                  15

Ala Thr Ala Val Thr Thr Val Arg Thr Asn Ala Ser Gly Leu Glu Val
                20                  25                  30

Pro Leu Phe His Leu Phe Ala Arg Leu Asp Glu Glu Leu His Gly Thr
            35                  40                  45
```

-continued

```
Phe Pro Gly Leu Cys Val Ala Leu Met Ala Val His Gly Ala Ile Phe
 50                  55                  60

Leu Ala Gly Leu Val Leu Asn Gly Leu Ala Leu Tyr Val Phe Cys Cys
 65                  70                  75                  80

Arg Thr Arg Ala Lys Thr Pro Ser Val Ile Tyr Thr Ile Asn Leu Val
                 85                  90                  95

Val Thr Asp Leu Leu Val Gly Leu Ser Leu Pro Thr Arg Phe Ala Val
                100                 105                 110

Tyr Tyr Gly Ala Arg Gly Cys Leu Arg Cys Ala Phe Pro His Val Leu
                115                 120                 125

Gly Tyr Phe Leu Asn Met His Cys Ser Ile Leu Phe Leu Thr Cys Ile
                130                 135                 140

Cys Val Asp Arg Tyr Leu Ala Ile Val Arg Pro Glu Ala Pro Ala Ala
145                 150                 155                 160

Cys Arg Gln Pro Ala Cys Ala Arg Ala Val Cys Ala Phe Val Trp Leu
                165                 170                 175

Ala Ala Gly Ala Val Thr Leu Ser Val Leu Gly Val Thr Gly Ser Arg
                180                 185                 190

Pro Cys Cys Arg Val Phe Ala Leu Thr Val Leu Glu Phe Leu Leu Pro
195                 200                 205

Leu Leu Val Ile Ser Val Phe Thr Gly Arg Ile Met Cys Ala Leu Ser
                210                 215                 220

Arg Pro Gly Leu Leu His Gln Gly Arg Gln Arg Val Arg Ala Met
225                 230                 235                 240

Gln Leu Leu Leu Thr Val Leu Ile Ile Phe Leu Val Cys Phe Thr Pro
                245                 250                 255

Phe His Ala Arg Gln Val Ala Val Ala Leu Trp Pro Asp Met Pro His
                260                 265                 270

His Thr Ser Leu Val Val Tyr His Val Ala Val Thr Leu Ser Ser Leu
                275                 280                 285

Asn Ser Cys Met Asp Pro Ile Val Tyr Cys Phe Val Thr Ser Gly Phe
290                 295                 300

Gln Ala Thr Val Arg Gly Leu Phe Gly Gln His Gly Glu Arg Glu Pro
305                 310                 315                 320

Ser Ser Gly Asp Val Val Ser Met His Arg Ser Lys Gly Ser Gly
                325                 330                 335

Arg His His Ile Leu Ser Ala Gly Pro His Ala Leu Thr Gln Ala Leu
                340                 345                 350

Ala Asn Gly Pro Glu Ala
                355

<210> SEQ ID NO 41
<211> LENGTH: 30
<212> TYPE: DNA
<213> ORGANISM: Artificial Sequence
<220> FEATURE:
<223> OTHER INFORMATION: Novel Sequence

<400> SEQUENCE: 41
gagaattcac tcctgagctc aagatgaact                                      30

<210> SEQ ID NO 42
<211> LENGTH: 30
<212> TYPE: DNA
<213> ORGANISM: Artificial Sequence
<220> FEATURE:
<223> OTHER INFORMATION: Novel Sequence
```

-continued

<400> SEQUENCE: 42
cgggatcccc gtaactgagc cacttcagat                                              30

<210> SEQ ID NO 43
<211> LENGTH: 1050
<212> TYPE: DNA
<213> ORGANISM: Homo sapiens

<400> SEQUENCE: 43
atgaactcca ccttggatgg taatcagagc agccacccct tttgcctctt ggcatttggc      60
tatttggaaa ctgtcaattt tgccttttg gaagtattga ttattgtctt tctaactgta       120
ttgattattt ctggcaacat cattgtgatt tttgtatttc actgtgcacc tttgttgaac      180
catcacacta aagttatttt tatccagact atggcatatg ctgaccttt tgttggggtg      240 agctgcgtgg tcccttcttt atcactcctc catcaccccc ttccagtaga ggagtccttg      300
acttgccaga tatttggttt tgtagtatca gttctgaaga gcgtctccat ggcttctctg      360
gcctgtatca gcattgatag atacattgcc attactaaac cttaaccta taatactctg       420 gttacaccct ggagactacg cctgtgtatt ttcctgattt ggctatactc gaccctggtc      480
ttcctgcctt cctttttcca ctggggcaaa cctggatatc atggagatgt gtttcagtgg      540
tgtgcggagt cctggcacac cgactcctac ttcaccctgt tcatcgtgat gatgttatat      600
gccccagcag cccttattgt ctgcttcacc tatttcaaca tcttccgcat ctgccaacag      660
cacacaaagg atatcagcga aaggcaagcc cgcttcagca gccagagtgg ggagactggg      720
gaagtgcagg cctgtcctga taagcgctat gccatggtcc tgtttcgaat cactagtgta      780
ttttacatcc tctggttgcc atatatcatc tacttcttgt tggaaagctc cactggccac      840
agcaaccgct tcgcatcctt cttgaccacc tggcttgcta ttagtaacag tttctgcaac      900
tgtgtaattt atagtctctc caacagtgta ttccaaagag gactaaagcg cctctcaggg      960
gctatgtgta cttcttgtgc aagtcagact acagccaacg acccttacac agttagaagc      1020
aaaggccctc ttaatggatg tcatatctga                                       1050

<210> SEQ ID NO 44
<211> LENGTH: 349
<212> TYPE: PRT
<213> ORGANISM: Homo sapiens

<400> SEQUENCE: 44

Met Asn Ser Thr Leu Asp Gly Asn Gln Ser Ser His Pro Phe Cys Leu
1               5                   10                  15

Leu Ala Phe Gly Tyr Leu Glu Thr Val Asn Phe Cys Leu Leu Glu Val
                20                  25                  30

Leu Ile Ile Val Phe Leu Thr Val Leu Ile Ile Ser Gly Asn Ile Ile
            35                  40                  45

Val Ile Phe Val Phe His Cys Ala Pro Leu Leu Asn His His Thr Thr
        50                  55                  60

Ser Tyr Phe Ile Gln Thr Met Ala Tyr Ala Asp Leu Phe Val Gly Val
65                  70                  75                  80

Ser Cys Val Val Pro Ser Leu Ser Leu Leu His His Pro Leu Pro Val
                85                  90                  95

Glu Glu Ser Leu Thr Cys Gln Ile Phe Gly Phe Val Ser Val Leu
                100                 105                 110

Lys Ser Val Ser Met Ala Ser Leu Ala Cys Ile Ser Ile Asp Arg Tyr

```
            115                 120                 125
Ile Ala Ile Thr Lys Pro Leu Thr Tyr Asn Thr Leu Val Thr Pro Trp
130                 135                 140

Arg Leu Arg Leu Cys Ile Phe Leu Ile Trp Leu Tyr Ser Thr Leu Val
145                 150                 155                 160

Phe Leu Pro Ser Phe Phe His Trp Gly Lys Pro Gly Tyr His Gly Asp
                165                 170                 175

Val Phe Gln Trp Cys Ala Glu Ser Trp His Thr Asp Ser Tyr Phe Thr
            180                 185                 190

Leu Phe Ile Val Met Met Leu Tyr Ala Pro Ala Leu Ile Val Cys
        195                 200                 205

Phe Thr Tyr Phe Asn Ile Phe Arg Ile Cys Gln Gln His Thr Lys Asp
210                 215                 220

Ile Ser Glu Arg Gln Ala Arg Phe Ser Ser Gln Ser Gly Glu Thr Gly
225                 230                 235                 240

Glu Val Gln Ala Cys Pro Asp Lys Arg Tyr Ala Met Val Leu Phe Arg
                245                 250                 255

Ile Thr Ser Val Phe Tyr Ile Leu Trp Leu Pro Tyr Ile Ile Tyr Phe
            260                 265                 270

Leu Leu Glu Ser Ser Thr Gly His Ser Asn Arg Phe Ala Ser Phe Leu
        275                 280                 285

Thr Thr Trp Leu Ala Ile Ser Asn Ser Phe Cys Asn Cys Val Ile Tyr
290                 295                 300

Ser Leu Ser Asn Ser Val Phe Gln Arg Gly Leu Lys Arg Leu Ser Gly
305                 310                 315                 320

Ala Met Cys Thr Ser Cys Ala Ser Gln Thr Thr Ala Asn Asp Pro Tyr
                325                 330                 335

Thr Val Arg Ser Lys Gly Pro Leu Asn Gly Cys His Ile
            340                 345

<210> SEQ ID NO 45
<211> LENGTH: 30
<212> TYPE: DNA
<213> ORGANISM: Artificial Sequence
<220> FEATURE:
<223> OTHER INFORMATION: Novel Sequence

<400> SEQUENCE: 45
tcccccggga aaaaaaccaa ctgctccaaa                                    30

<210> SEQ ID NO 46
<211> LENGTH: 31
<212> TYPE: DNA
<213> ORGANISM: Artificial Sequence
<220> FEATURE:
<223> OTHER INFORMATION: Novel Sequence

<400> SEQUENCE: 46
taggatccat ttgaatgtgg atttggtgaa a                                  31

<210> SEQ ID NO 47
<211> LENGTH: 1302
<212> TYPE: DNA
<213> ORGANISM: Homo sapiens

<400> SEQUENCE: 47
atgtgttttt ctcccattct ggaaatcaac atgcagtctg aatctaacat tacagtgcga    60
gatgacattg atgacatcaa caccaatatg taccaaccac tatcatatcc gttaagctttt   120
```

```
caagtgtctc tcaccggatt tcttatgtta gaaattgtgt tgggacttgg cagcaacctc      180
actgtattgg tactttactg catgaaatcc aacttaatca actctgtcag taacattatt      240
acaatgaatc ttcatgtact tgatgtaata atttgtgtgg gatgtattcc tctaactata      300
gttatccttc tgctttcact ggagagtaac actgctctca tttgctgttt ccatgaggct      360
tgtgtatctt tgcaagtgt ctcaacagca atcaacgttt tgctatcac tttggacaga       420 tatgacatct ctgtaaaacc tgcaaaccga attctgacaa tgggcagagc tgtaatgtta      480
atgatatcca tttggatttt ttcttttttc tctttcctga ttccttttat tgaggtaaat      540
tttttcagtc ttcaaagtgg aaatacctgg gaaaacaaga cacttttatg tgtcagtaca      600
aatgaatact acactgaact gggaatgtat tatcaccgt tagtacagat cccaatattc       660
tttttcactg ttgtagtaat gttaatcaca tacaccaaaa tacttcaggc tcttaatatt      720
cgaataggca caagatttc aacagggcag aagaagaaag caagaaagaa aaagacaatt       780
tctctaacca cacaacatga ggctacagac atgtcacaaa gcagtggtgg gagaaatgta      840
gtctttggtg taagaactc agtttctgta ataattgccc tccggcgagc tgtgaaacga       900
caccgtgaac gacgagaaag acaaaagaga gtcttcagga tgtctttatt gattatttct      960
acatttcttc tctgctggac accaatttct gttttaaata ccaccatttt atgtttaggc     1020
ccaagtgacc ttttagtaaa attaagattg tgttttttag tcatggctta tggaacaact     1080
atatttcacc ctctattata tgcattcact agacaaaaat ttcaaaaggt cttgaaaagt     1140
aaaatgaaaa agcgagttgt ttctatagta gaagctgatc ccctgcctaa taatgctgta     1200
atacacaact cttggataga tcccaaaaga aacaaaaaaa ttacctttga agatagtgaa     1260
ataagagaaa aacgtttagt gcctcaggtt gtcacagact ag                        1302
```

<210> SEQ ID NO 48
<211> LENGTH: 433
<212> TYPE: PRT
<213> ORGANISM: Homo sapiens

<400> SEQUENCE: 48

```
Met Cys Phe Ser Pro Ile Leu Glu Ile Asn Met Gln Ser Glu Ser Asn
1               5                   10                  15

Ile Thr Val Arg Asp Asp Ile Asp Asp Ile Asn Thr Asn Met Tyr Gln
            20                  25                  30

Pro Leu Ser Tyr Pro Leu Ser Phe Gln Val Ser Leu Thr Gly Phe Leu
        35                  40                  45

Met Leu Glu Ile Val Leu Gly Leu Gly Ser Asn Leu Thr Val Leu Val
    50                  55                  60

Leu Tyr Cys Met Lys Ser Asn Leu Ile Asn Ser Val Ser Asn Ile Ile
65                  70                  75                  80

Thr Met Asn Leu His Val Leu Asp Val Ile Cys Val Gly Cys Ile
                85                  90                  95

Pro Leu Thr Ile Val Ile Leu Leu Ser Leu Glu Ser Asn Thr Ala
            100                 105                 110

Leu Ile Cys Cys Phe His Glu Ala Cys Val Ser Phe Ala Ser Val Ser
        115                 120                 125

Thr Ala Ile Asn Val Phe Ala Ile Thr Leu Asp Arg Tyr Asp Ile Ser
    130                 135                 140

Val Lys Pro Ala Asn Arg Ile Leu Thr Met Gly Arg Ala Val Met Leu
145                 150                 155                 160
```

-continued

```
Met Ile Ser Ile Trp Ile Phe Ser Phe Ser Phe Leu Ile Pro Phe
                165                 170                 175

Ile Glu Val Asn Phe Phe Ser Leu Gln Ser Gly Asn Thr Trp Glu Asn
            180                 185                 190

Lys Thr Leu Leu Cys Val Ser Thr Asn Glu Tyr Tyr Thr Glu Leu Gly
        195                 200                 205

Met Tyr Tyr His Leu Leu Val Gln Ile Pro Ile Phe Phe Phe Thr Val
    210                 215                 220

Val Val Met Leu Ile Thr Tyr Thr Lys Ile Leu Gln Ala Leu Asn Ile
225                 230                 235                 240

Arg Ile Gly Thr Arg Phe Ser Thr Gly Gln Lys Lys Ala Arg Lys
                245                 250                 255

Lys Lys Thr Ile Ser Leu Thr Thr Gln His Glu Ala Thr Asp Met Ser
            260                 265                 270

Gln Ser Ser Gly Gly Arg Asn Val Val Phe Gly Val Arg Thr Ser Val
        275                 280                 285

Ser Val Ile Ile Ala Leu Arg Arg Ala Val Lys Arg His Arg Glu Arg
    290                 295                 300

Arg Glu Arg Gln Lys Arg Val Phe Arg Met Ser Leu Leu Ile Ile Ser
305                 310                 315                 320

Thr Phe Leu Leu Cys Trp Thr Pro Ile Ser Val Leu Asn Thr Thr Ile
                325                 330                 335

Leu Cys Leu Gly Pro Ser Asp Leu Leu Val Lys Leu Arg Leu Cys Phe
            340                 345                 350

Leu Val Met Ala Tyr Gly Thr Thr Ile Phe His Pro Leu Leu Tyr Ala
        355                 360                 365

Phe Thr Arg Gln Lys Phe Gln Lys Val Leu Lys Ser Lys Met Lys Lys
    370                 375                 380

Arg Val Val Ser Ile Val Glu Ala Asp Pro Leu Pro Asn Asn Ala Val
385                 390                 395                 400

Ile His Asn Ser Trp Ile Asp Pro Lys Arg Asn Lys Lys Ile Thr Phe
                405                 410                 415

Glu Asp Ser Glu Ile Arg Glu Lys Arg Leu Val Pro Gln Val Val Thr
            420                 425                 430

Asp
```

<210> SEQ ID NO 49
<211> LENGTH: 30
<212> TYPE: DNA
<213> ORGANISM: Artificial Sequence
<220> FEATURE:
<223> OTHER INFORMATION: Novel Sequence

<400> SEQUENCE: 49
gtgaagcttg cctctggtgc ctgcaggagg         30

<210> SEQ ID NO 50
<211> LENGTH: 31
<212> TYPE: DNA
<213> ORGANISM: Artificial Sequence
<220> FEATURE:
<223> OTHER INFORMATION: Novel Sequence

<400> SEQUENCE: 50
gcagaattcc cggtggcgtg ttgtggtgcc c        31

<210> SEQ ID NO 51

```
<211> LENGTH: 1209
<212> TYPE: DNA
<213> ORGANISM: Homo sapiens

<400> SEQUENCE: 51
atgttgtgtc cttccaagac agatggctca gggcactctg gtaggattca ccaggaaact      60
catggagaag ggaaaaggga caagattagc aacagtgaag ggagggagaa tggtgggaga     120
ggattccaga tgaacggtgg gtcgctggag gctgagcatg ccagcaggat gtcagttctc     180
agagcaaagc ccatgtcaaa cagccaacgc ttgctccttc tgtccccagg atcacctcct     240
cgcacgggga gcatctccta catcaacatc atcatgcctt cggtgttcgg caccatctgc     300
ctcctgggca tcatcgggaa ctccacggtc atcttcgcgg tcgtgaagaa gtccaagctg     360
cactggtgca acaacgtccc cgacatcttc atcatcaacc tctcggtagt agatctcctc     420
tttctcctgg gcatgccctt catgatccac cagctcatgg gcaatggggt gtggcacttt     480
ggggagacca tgtgcaccct catcacggcc atggatgcca atagtcagtt caccagcacc     540
tacatcctga ccgccatggc cattgaccgc tacctggcca ctgtccaccc catctcttcc     600
acgaagttcc ggaagccctc tgtggccacc ctggtgatct gcctcctgtg ggccctctcc     660
ttcatcagca tcacccctgt gtggctgtat gccagactca tccccttccc aggaggtgca     720
gtgggctgcg gcatacgcct gcccaaccca gacactgacc tctactggtt cacccctgtac    780
cagttttttcc tggcctttgc cctgcctttt gtggtcatca cagccgcata cgtgaggatc     840
ctgcagcgca tgacgtcctc agtggccccc gcctcccagc gcagcatccg gctgcggaca     900
aagagggtga cccgcacagc catcgccatc tgtctggtct tctttgtgtg ctgggcaccc     960
tactatgtgc tacagctgac ccagttgtcc atcagccgcc cgaccctcac ctttgtctac    1020
ttatacaatg cggccatcag cttgggctat gccaacagct gcctcaaccc ctttgtgtac    1080
atcgtgctct gtgagacgtt ccgcaaacgc ttggtcctgt cggtgaagcc tgcagcccag    1140
gggcagcttc gcgctgtcag caacgctcag acggctgacg aggagaggac agaaagcaaa    1200
ggcacctga                                                            1209

<210> SEQ ID NO 52
<211> LENGTH: 402
<212> TYPE: PRT
<213> ORGANISM: Homo sapiens

<400> SEQUENCE: 52

Met Leu Cys Pro Ser Lys Thr Asp Gly Ser Gly His Ser Gly Arg Ile
1               5                   10                  15

His Gln Glu Thr His Gly Glu Gly Lys Arg Asp Lys Ile Ser Asn Ser
            20                  25                  30

Glu Gly Arg Glu Asn Gly Gly Arg Gly Phe Gln Met Asn Gly Gly Ser
        35                  40                  45

Leu Glu Ala Glu His Ala Ser Arg Met Ser Val Leu Arg Ala Lys Pro
    50                  55                  60

Met Ser Asn Ser Gln Arg Leu Leu Leu Leu Ser Pro Gly Ser Pro Pro
65                  70                  75                  80

Arg Thr Gly Ser Ile Ser Tyr Ile Asn Ile Ile Met Pro Ser Val Phe
                85                  90                  95

Gly Thr Ile Cys Leu Leu Gly Ile Ile Gly Asn Ser Thr Val Ile Phe
            100                 105                 110

Ala Val Val Lys Lys Ser Lys Leu His Trp Cys Asn Asn Val Pro Asp
        115                 120                 125
```

```
Ile Phe Ile Ile Asn Leu Ser Val Val Asp Leu Leu Phe Leu Leu Gly
    130                 135                 140

Met Pro Phe Met Ile His Gln Leu Met Gly Asn Gly Val Trp His Phe
145                 150                 155                 160

Gly Glu Thr Met Cys Thr Leu Ile Thr Ala Met Asp Ala Asn Ser Gln
                165                 170                 175

Phe Thr Ser Thr Tyr Ile Leu Thr Ala Met Ala Ile Asp Arg Tyr Leu
            180                 185                 190

Ala Thr Val His Pro Ile Ser Ser Thr Lys Phe Arg Lys Pro Ser Val
            195                 200                 205

Ala Thr Leu Val Ile Cys Leu Leu Trp Ala Leu Ser Phe Ile Ser Ile
        210                 215                 220

Thr Pro Val Trp Leu Tyr Ala Arg Leu Ile Pro Phe Pro Gly Gly Ala
225                 230                 235                 240

Val Gly Cys Gly Ile Arg Leu Pro Asn Pro Asp Thr Asp Leu Tyr Trp
                245                 250                 255

Phe Thr Leu Tyr Gln Phe Phe Leu Ala Phe Ala Leu Pro Phe Val Val
            260                 265                 270

Ile Thr Ala Ala Tyr Val Arg Ile Leu Gln Arg Met Thr Ser Ser Val
        275                 280                 285

Ala Pro Ala Ser Gln Arg Ser Ile Arg Leu Arg Thr Lys Arg Val Thr
    290                 295                 300

Arg Thr Ala Ile Ala Ile Cys Leu Val Phe Phe Val Cys Trp Ala Pro
305                 310                 315                 320

Tyr Tyr Val Leu Gln Leu Thr Gln Leu Ser Ile Ser Arg Pro Thr Leu
                325                 330                 335

Thr Phe Val Tyr Leu Tyr Asn Ala Ala Ile Ser Leu Gly Tyr Ala Asn
            340                 345                 350

Ser Cys Leu Asn Pro Phe Val Tyr Ile Val Leu Cys Glu Thr Phe Arg
        355                 360                 365

Lys Arg Leu Val Leu Ser Val Lys Pro Ala Ala Gln Gly Gln Leu Arg
    370                 375                 380

Ala Val Ser Asn Ala Gln Thr Ala Asp Glu Glu Arg Thr Glu Ser Lys
385                 390                 395                 400

Gly Thr

<210> SEQ ID NO 53
<211> LENGTH: 27
<212> TYPE: DNA
<213> ORGANISM: Artificial Sequence
<220> FEATURE:
<223> OTHER INFORMATION: Novel Sequence

<400> SEQUENCE: 53
ggcggatcca tggatgtgac ttcccaa                                        27

<210> SEQ ID NO 54
<211> LENGTH: 27
<212> TYPE: DNA
<213> ORGANISM: Artificial Sequence
<220> FEATURE:
<223> OTHER INFORMATION: Novel Sequence

<400> SEQUENCE: 54
ggcggatccc tacacggcac tgctgaa                                        27
```

<210> SEQ ID NO 55
<211> LENGTH: 1128
<212> TYPE: DNA
<213> ORGANISM: Homo sapiens

<400> SEQUENCE: 55

| | | | | | |
|---|---|---|---|---|---|
| atggatgtga | cttcccaagc | ccggggcgtg | ggcctggaga | tgtacccagg | caccgcgcac | 60 |
| gctgcggccc | ccaacaccac | ctcccccgag | ctcaacctgt | cccacccgct | cctgggcacc | 120 |
| gccctggcca | atgggacagg | tgagctctcg | agcaccagc | agtacgtgat | cggcctgttc | 180 |
| ctctcgtgcc | tctacaccat | cttcctcttc | cccatcggct | ttgtgggcaa | catcctgatc | 240 |
| ctggtggtga | acatcagctt | ccgcgagaag | atgaccatcc | ccgacctgta | cttcatcaac | 300 |
| ctggcggtgg | cggacctcat | cctggtggcc | gactccctca | ttgaggtgtt | caacctgcac | 360 |
| gagcggtact | acgacatcgc | cgtcctgtgc | accttcatgt | cgctcttcct | gcaggtcaac | 420 |
| atgtacagca | gcgtcttctt | cctcacctgg | atgagcttcg | accgctacat | cgccctggcc | 480 |
| agggccatgc | gctgcagcct | gttccgcacc | aagcaccacg | cccggctgag | ctgtggcctc | 540 |
| atctggatgc | atccgtgtc | agccacgctg | gtgcccttca | ccgccgtgca | cctgcagcac | 600 |
| accgacgagg | cctgcttctg | tttcgcggat | gtccgggagg | tgcagtggct | cgaggtcacg | 660 |
| ctgggcttca | tcgtgccctt | cgccatcatc | ggcctgtgct | actccctcat | tgtccgggtg | 720 |
| ctggtcaggg | cgcaccggca | ccgtgggctg | cggccccggc | ggcagaaggc | gctccgcatg | 780 |
| atcctcgcgg | tggtgctggt | cttcttcgtc | tgctggctgc | cggagaacgt | cttcatcagc | 840 |
| gtgcacctcc | tgcagcggac | gcagcctggg | gccgctccct | gcaagcagtc | tttccgccat | 900 |
| gcccaccccc | tcacgggcca | cattgtcaac | ctcgccgcct | ctccaacag | ctgcctaaac | 960 |
| cccctcatct | acagctttct | cggggagacc | ttcagggaca | agctgaggct | gtacattgag | 1020 |
| cagaaaacaa | atttgccggc | cctgaaccgc | ttctgtcacg | ctgccctgaa | ggccgtcatt | 1080 |
| ccagacagca | ccgagcagtc | ggatgtgagg | ttcagcagtg | ccgtgtga | | 1128 |

<210> SEQ ID NO 56
<211> LENGTH: 375
<212> TYPE: PRT
<213> ORGANISM: Homo sapiens

<400> SEQUENCE: 56

Met Asp Val Thr Ser Gln Ala Arg Gly Val Gly Leu Glu Met Tyr Pro
1               5                   10                  15

Gly Thr Ala His Ala Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140

```
Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
            165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
            195                 200                 205

Ala Asp Val Arg Glu Val Gln Trp Leu Glu Val Thr Leu Gly Phe Ile
            210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
            245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
            275                 280                 285

Pro Gly Ala Ala Pro Cys Lys Gln Ser Phe Arg His Ala His Pro Leu
            290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
            325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
            355                 360                 365

Val Arg Phe Ser Ser Ala Val
            370                 375

<210> SEQ ID NO 57
<211> LENGTH: 31
<212> TYPE: DNA
<213> ORGANISM: Artificial Sequence
<220> FEATURE:
<223> OTHER INFORMATION: Novel Sequence

<400> SEQUENCE: 57
aaggaattca cggccgggtg atgccattcc c                              31

<210> SEQ ID NO 58
<211> LENGTH: 30
<212> TYPE: DNA
<213> ORGANISM: Artificial Sequence
<220> FEATURE:
<223> OTHER INFORMATION: Novel Sequence

<400> SEQUENCE: 58
ggtggatcca taaacacggg cgttgaggac                                30

<210> SEQ ID NO 59
<211> LENGTH: 960
<212> TYPE: DNA
<213> ORGANISM: Homo sapiens

<400> SEQUENCE: 59
atgccattcc caaactgctc agcccccagc actgtggtgg ccacagctgt gggtgtcttg    60
```

-continued

```
ctggggctgg agtgtgggct gggtctgctg ggcaacgcgg tggcgctgtg gaccttcctg      120
ttccgggtca gggtgtggaa gccgtacgct gtctacctgc tcaacctggc cctggctgac      180
ctgctgttgg ctgcgtgcct gccttctg gccgccttct acctgagcct ccaggcttgg       240
catctgggcc gtgtgggctg ctgggccctg cgcttcctgc tggacctcag ccgcagcgtg      300
gggatggcct tcctggccgc cgtggctttg gaccggtacc tccgtgtggt ccaccctcgg      360
cttaaggtca acctgctgtc tcctcaggcg gccctggggg tctcgggcct cgtctggctc      420
ctgatggtcg ccctcacctg cccgggcttg ctcatctctg aggccgccca gaactccacc      480
aggtgccaca gtttctactc cagggcagac ggctccttca gcatcatctg gcaggaagca      540
ctctcctgcc ttcagtttgt cctcccctt ggcctcatcg tgttctgcaa tgcaggcatc       600
atcagggctc tccagaaaag actccgggag cctgagaaac agcccaagct tcagcgggcc      660
caggcactgg tcaccttggt ggtggtgctg tttgctctgt gctttctgcc ctgcttcctg      720
gccagagtcc tgatgcacat cttccagaat ctggggagct gcagggccct tgtgcagtg       780 gctcataccctt cggatgtcac gggcagcctc acctacctgc acagtgtcgt caaccccgtg    840
gtatactgct tctccagccc caccttcagg agctcctatc ggagggtctt ccacaccctc      900
cgaggcaaag gcaggcagc agagccccca gatttcaacc ccagagactc ctattcctga       960
```

<210> SEQ ID NO 60
<211> LENGTH: 319
<212> TYPE: PRT
<213> ORGANISM: Homo sapiens

<400> SEQUENCE: 60

```
Met Pro Phe Pro Asn Cys Ser Ala Pro Ser Thr Val Val Ala Thr Ala
1               5                   10                  15

Val Gly Val Leu Leu Gly Leu Glu Cys Gly Leu Gly Leu Leu Gly Asn
            20                  25                  30

Ala Val Ala Leu Trp Thr Phe Leu Phe Arg Val Arg Val Trp Lys Pro
        35                  40                  45

Tyr Ala Val Tyr Leu Leu Asn Leu Ala Leu Ala Asp Leu Leu Leu Ala
    50                  55                  60

Ala Cys Leu Pro Phe Leu Ala Ala Phe Tyr Leu Ser Gln Ala Trp
65                  70                  75                  80

His Leu Gly Arg Val Gly Cys Trp Ala Leu Arg Phe Leu Leu Asp Leu
                85                  90                  95

Ser Arg Ser Val Gly Met Ala Phe Leu Ala Ala Val Ala Leu Asp Arg
            100                 105                 110

Tyr Leu Arg Val Val His Pro Arg Leu Lys Val Asn Leu Leu Ser Pro
        115                 120                 125

Gln Ala Ala Leu Gly Val Ser Gly Leu Val Trp Leu Leu Met Val Ala
    130                 135                 140

Leu Thr Cys Pro Gly Leu Leu Ile Ser Glu Ala Ala Gln Asn Ser Thr
145                 150                 155                 160

Arg Cys His Ser Phe Tyr Ser Arg Ala Asp Gly Ser Phe Ser Ile Ile
                165                 170                 175

Trp Gln Glu Ala Leu Ser Cys Leu Gln Phe Val Leu Pro Phe Gly Leu
            180                 185                 190

Ile Val Phe Cys Asn Ala Gly Ile Ile Arg Ala Leu Gln Lys Arg Leu
        195                 200                 205

Arg Glu Pro Glu Lys Gln Pro Lys Leu Gln Arg Ala Gln Ala Leu Val
```

```
                210                 215                 220
Thr Leu Val Val Val Leu Phe Ala Leu Cys Phe Leu Pro Cys Phe Leu
225                 230                 235                 240

Ala Arg Val Leu Met His Ile Phe Gln Asn Leu Gly Ser Cys Arg Ala
                245                 250                 255

Leu Cys Ala Val Ala His Thr Ser Asp Val Thr Gly Ser Leu Thr Tyr
                260                 265                 270

Leu His Ser Val Val Asn Pro Val Tyr Cys Phe Ser Ser Pro Thr
                275                 280                 285

Phe Arg Ser Ser Tyr Arg Arg Val Phe His Thr Leu Arg Gly Lys Gly
                290                 295                 300

Gln Ala Ala Glu Pro Pro Asp Phe Asn Pro Arg Asp Ser Tyr Ser
305                 310                 315
```

<210> SEQ ID NO 61
<211> LENGTH: 1143
<212> TYPE: DNA
<213> ORGANISM: Homo sapiens

<400> SEQUENCE: 61

| | | | | |
|---|---|---|---|---|
| atggaggaag | gtggtgattt | tgacaactac | tatggggcag | acaaccagtc tgagtgtgag | 60 |
| tacacagact | ggaaatcctc | ggggggccctc | atccctgcca | tctacatgtt ggtcttcctc | 120 |
| ctgggcacca | cggaaaacgg | tctggtgctc | tggaccgtgt | tcggagcag ccggagaag | 180 |
| aggcgctcag | ctgatatctt | cattgctagc | ctggcggtgg | ctgacctgac cttcgtggtg | 240 |
| acgctgcccc | tgtgggctac | ctacacgtac | cgggactatg | actggccctt tgggaccttc | 300 |
| ttctgcaagc | tcagcagcta | cctcatcttc | gtcaacatgt | acgccagcgt cttctgcctc | 360 |
| accggcctca | gcttcgaccg | ctacctggcc | atcgtgaggc | cagtggccaa tgctcggctg | 420 |
| aggctgcggg | tcagcggggc | cgtggccacg | gcagttcttt | gggtgctggc cgccctcctg | 480 |
| gccatgcctg | tcatggtgtt | acgcaccacc | ggggacttgg | agaacaccac taaggtgcag | 540 |
| tgctacatgg | actactccat | ggtggccact | gtgagctcag | agtgggcctg ggaggtgggc | 600 |
| cttgggtgtct | cgtccaccac | cgtgggcttt | gtggtgccct | tcaccatcat gctgacctgt | 660 |
| tacttcttca | tcgcccaaac | catcgctggc | cacttccgca | aggaacgcat cgagggcctg | 720 |
| cggaagcggc | gccggctgct | cagcatcatc | gtggtgctgg | tggtgacctt tgccctgtgc | 780 |
| tggatgccct | accacctggt | gaagacgctg | tacatgctgg | gcagcctgct gcactggccc | 840 |
| tgtgactttg | acctcttcct | catgaacatc | ttccccctact | gcacctgcat cagctacgtc | 900 |
| aacagctgcc | tcaaccctt | cctctatgcc | tttttcgacc | ccgcttccg ccaggcctgc | 960 |
| acctccatgc | tctgctgtgg | ccagagcagg | tgcgcaggca | cctcccacag cagcagtggg | 1020 |
| gagaagtcag | ccagctactc | ttcggggcac | agccagggggc | ccggcccccaa catgggcaag | 1080 |
| ggtggagaac | agatgcacga | gaaatccatc | ccctacagcc | aggagaccct tgtggttgac | 1140 |
| tag | | | | | 1143 |

<210> SEQ ID NO 62
<211> LENGTH: 380
<212> TYPE: PRT
<213> ORGANISM: Homo sapiens

<400> SEQUENCE: 62

```
Met Glu Glu Gly Gly Asp Phe Asp Asn Tyr Tyr Gly Ala Asp Asn Gln
1               5                   10                  15
```

-continued

```
Ser Glu Cys Glu Tyr Thr Asp Trp Lys Ser Ser Gly Ala Leu Ile Pro
             20                  25                  30

Ala Ile Tyr Met Leu Val Phe Leu Leu Gly Thr Thr Gly Asn Gly Leu
         35                  40                  45

Val Leu Trp Thr Val Phe Arg Ser Ser Arg Glu Lys Arg Arg Ser Ala
 50                  55                  60

Asp Ile Phe Ile Ala Ser Leu Ala Val Ala Asp Leu Thr Phe Val Val
 65                  70                  75                  80

Thr Leu Pro Leu Trp Ala Thr Tyr Thr Tyr Arg Asp Tyr Asp Trp Pro
                 85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
370                 375                 380
```

<210> SEQ ID NO 63
<211> LENGTH: 31
<212> TYPE: DNA
<213> ORGANISM: Artificial Sequence
<220> FEATURE:
<223> OTHER INFORMATION: Novel Sequence

<400> SEQUENCE: 63

-continued

```
tgagaattct ggtgactcac agccggcaca g                               31

<210> SEQ ID NO 64
<211> LENGTH: 31
<212> TYPE: DNA
<213> ORGANISM: Artificial Sequence
<220> FEATURE:
<223> OTHER INFORMATION: Novel Sequence

<400> SEQUENCE: 64
gccggatcca aggaaaagca gcaataaaag g                               31

<210> SEQ ID NO 65
<211> LENGTH: 1119
<212> TYPE: DNA
<213> ORGANISM: Homo sapiens

<400> SEQUENCE: 65
atgaactacc cgctaacgct ggaaatggac ctcgagaacc tggaggacct gttctgggaa    60
ctggacagat tggacaacta taacgacacc tccctggtgg aaaatcatct ctgccctgcc   120
acagagggtc ccctcatggc ctccttcaag gccgtgttcg tgcccgtggc ctacagcctc   180
atcttcctcc tgggcgtgat cggcaacgtc ctggtgctgg tgatcctgga gcggcaccgg   240
cagacacgca gttccacgga gaccttcctg ttccacctgc ccgtgccgga cctcctgctg   300
gtcttcatct tgcccttgc cgtggccgag ggctctgtgg ctgggtcct ggggaccttc    360 ctctgcaaaa ctgtgattgc cctgcacaaa gtcaacttct actgcagcag cctgctcctg   420
gcctgcatcg ccgtggaccg ctacctggcc attgtccacg ccgtccatgc ctaccgccac   480
cgccgcctcc tctccatcca catcacctgt gggaccatct ggctggtggg cttcctcctt   540
gccttgccag agattctctt cgccaaagtc agccaaggcc atcacaacaa ctccctgcca   600
cgttgcacct ctcccaaga gaccaagca gaaacgcatg cctggttcac ctcccgattc   660
ctctaccatg tggcgggatt cctgctgccc atgctggtga tgggctggtg ctacgtgggg   720
gtagtgcaca ggttgcgcca ggcccagcgg cgccctcagc ggcagaaggc agtcagggtg   780
gccatcctgg tgacaagcat cttcttcctc tgctggtcac cctaccacat cgtcatcttc   840
ctggacaccc tggcgaggct gaaggccgtg gacaatacct gcaagctgaa tggctctctc   900
cccgtggcca tcaccatgtg tgagttcctg ggcctggccc actgctgcct caaccccatg   960
ctctacactt tcgccggcgt gaagttccgc agtgacctgt cgcggctcct gaccaagctg   1020
ggctgtaccg gccctgcctc cctgtgccag ctcttcccta gctggcgcag gagcagtctc   1080
tctgagtcag agaatgccac ctctctcacc acgttctag                         1119

<210> SEQ ID NO 66
<211> LENGTH: 372
<212> TYPE: PRT
<213> ORGANISM: Homo sapiens

<400> SEQUENCE: 66

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60
```

```
Gly Val Ile Gly Asn Val Leu Val Leu Val Ile Leu Glu Arg His Arg
 65                  70                  75                  80

Gln Thr Arg Ser Ser Thr Glu Thr Phe Leu Phe His Leu Ala Val Ala
                 85                  90                  95

Asp Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Ala Cys Ile Ala
        130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370

<210> SEQ ID NO 67
<211> LENGTH: 30
<212> TYPE: DNA
<213> ORGANISM: Artificial Sequence
<220> FEATURE:
<223> OTHER INFORMATION: Novel Sequence

<400> SEQUENCE: 67
caaagcttga aagctgcacg gtgcagagac                                    30

<210> SEQ ID NO 68
<211> LENGTH: 30
<212> TYPE: DNA
<213> ORGANISM: Artificial Sequence
<220> FEATURE:
```

<223> OTHER INFORMATION: Novel Sequence

<400> SEQUENCE: 68
gcggatcccg agtcacaccc tggctgggcc                                30

<210> SEQ ID NO 69
<211> LENGTH: 1128
<212> TYPE: DNA
<213> ORGANISM: Homo sapiens

<400> SEQUENCE: 69
atggatgtga cttcccaagc ccggggcgtg ggcctggaga tgtacccagg caccgcgcag    60
cctgcggccc caacaccac ctcccccgag ctcaacctgt cccacccgct cctgggcacc   120
gccctggcca atgggacagg tgagctctcg gagcaccagc agtacgtgat cggcctgttc   180
ctctcgtgcc tctacaccat cttcctcttc cccatcggct tgtgggcaa catcctgatc   240
ctggtggtga acatcagctt ccgcgagaag atgaccatcc ccgacctgta cttcatcaac   300
ctggcggtgg cggacctcat cctggtggcc gactccctca ttgaggtgtt caacctgcac   360
gagcggtact acgacatcgc cgtcctgtgc accttcatgt cgctcttcct gcaggtcaac   420
atgtacagca gcgtcttctt cctcacctgg atgagcttcg accgctacat cgccctggcc   480
agggccatgc gctgcagcct gttccgcacc aagcaccacg cccggctgag ctgtggcctc   540
atctggatgg catccgtgtc agccacgctg gtgcccttca ccgccgtgca cctgcagcac   600
accgacgagg cctgcttctg tttcgcggat gtccgggagg tgcagtggct cgaggtcacg   660
ctgggcttca tcgtgccctt cgccatcatc ggcctgtgct actccctcat tgtccgggtg   720
ctggtcaggg cgcaccggca ccgtgggctg cggcccggc ggcagaaggc gctccgcatg   780
atcctcgcgg tggtgctggt cttcttcgtc tgctggctgc cggagaacgt cttcatcagc   840
gtgcacctcc tgcagcggac gcagcctggg gccgctccct gcaagcagtc tttccgccat   900
gcccaccccc tcacgggcca cattgtcaac ctcaccgcct tctccaacag ctgcctaaac   960
cccctcatct acagctttct cggggagacc ttcagggaca agctgaggct gtacattgag  1020
cagaaaacaa atttgccggc cctgaaccgc ttctgtcacg ctgccctgaa ggccgtcatt  1080
ccagacagca ccgagcagtc ggatgtgagg ttcagcagtg ccgtgtag              1128

<210> SEQ ID NO 70
<211> LENGTH: 375
<212> TYPE: PRT
<213> ORGANISM: Homo sapiens

<400> SEQUENCE: 70

Met Asp Val Thr Ser Gln Ala Arg Gly Val Gly Leu Glu Met Tyr Pro
1               5                   10                  15

Gly Thr Ala Gln Pro Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser

```
                    100                 105                 110
Leu Ile Glu Val Phe Asn Leu His Glu Arg Tyr Tyr Asp Ile Ala Val
        115                 120                 125
Leu Cys Thr Phe Met Ser Leu Phe Leu Gln Val Asn Met Tyr Ser Ser
    130                 135                 140
Val Phe Leu Thr Trp Met Ser Phe Asp Arg Tyr Ile Ala Leu Ala
145                 150                 155                 160
Arg Ala Met Arg Cys Ser Leu Phe Arg Thr Lys His His Ala Arg Leu
                165                 170                 175
Ser Cys Gly Leu Ile Trp Met Ala Ser Val Ser Ala Thr Leu Val Pro
            180                 185                 190
Phe Thr Ala Val His Leu Gln His Thr Asp Glu Ala Cys Phe Cys Phe
        195                 200                 205
Ala Asp Val Arg Glu Val Gln Trp Leu Glu Val Thr Leu Gly Phe Ile
210                 215                 220
Val Pro Phe Ala Ile Ile Gly Leu Cys Tyr Ser Leu Ile Val Arg Val
225                 230                 235                 240
Leu Val Arg Ala His Arg His Arg Gly Leu Arg Pro Arg Arg Gln Lys
                245                 250                 255
Ala Leu Arg Met Ile Leu Ala Val Val Leu Val Phe Phe Val Cys Trp
            260                 265                 270
Leu Pro Glu Asn Val Phe Ile Ser Val His Leu Leu Gln Arg Thr Gln
        275                 280                 285
Pro Gly Ala Ala Pro Cys Lys Gln Ser Phe Arg His Ala His Pro Leu
    290                 295                 300
Thr Gly His Ile Val Asn Leu Thr Ala Phe Ser Asn Ser Cys Leu Asn
305                 310                 315                 320
Pro Leu Ile Tyr Ser Phe Leu Gly Glu Thr Phe Arg Asp Lys Leu Arg
                325                 330                 335
Leu Tyr Ile Glu Gln Lys Thr Asn Leu Pro Ala Leu Asn Arg Phe Cys
            340                 345                 350
His Ala Ala Leu Lys Ala Val Ile Pro Asp Ser Thr Glu Gln Ser Asp
        355                 360                 365
Val Arg Phe Ser Ser Ala Val
    370                 375

<210> SEQ ID NO 71
<211> LENGTH: 30
<212> TYPE: DNA
<213> ORGANISM: Artificial Sequence
<220> FEATURE:
<223> OTHER INFORMATION: Novel Sequence

<400> SEQUENCE: 71
acagaattcc tgtgtggttt taccgcccag                                    30

<210> SEQ ID NO 72
<211> LENGTH: 30
<212> TYPE: DNA
<213> ORGANISM: Artificial Sequence
<220> FEATURE:
<223> OTHER INFORMATION: Novel Sequence

<400> SEQUENCE: 72
ctcggatcca ggcagaagag tcgcctatgg                                    30

<210> SEQ ID NO 73
```

-continued

```
<211> LENGTH: 1137
<212> TYPE: DNA
<213> ORGANISM: Homo sapiens

<400> SEQUENCE: 73
atggacctgg ggaaaccaat gaaaagcgtg ctggtggtgg ctctccttgt cattttccag      60
gtatgcctgt gtcaagatga ggtcacggac gattacatcg agacaacaca cacagtggac     120
tacactttgt tcgagtcttt gtgctccaag aaggacgtgc ggaactttaa agcctggttc     180
ctccctatca tgtactccat catttgtttc gtgggcctac tgggcaatgg gctggtcgtg     240
ttgacctata tctatttcaa gaggctcaag accatgaccg atacctacct gctcaacctg     300
gcggtggcag acatcctctt cctcctgacc cttcccttct gggcctacag cgcggccaag     360
tcctgggtct tcggtgtcca cttttgcaag ctcatctttg ccatctacaa gatgagcttc     420
ttcagtggca tgctcctact tctttgcatc agcattgacc gctacgtggc catcgtccag     480
gctgtctcag ctcaccgcca ccgtgcccgc gtccttctca tcagcaagct gtcctgtgtg     540
ggcatctgga tactagccac agtgctctcc atcccagagc tcctgtacag tgacctccag     600
aggagcagca gtgagcaagc gatgcgatgc tctctcatca cagagcatgt ggaggccttt     660
atcaccatcc aggtgcccca gatggtgatc ggctttctgg tccccctgct ggccatgagc     720
ttctgttacc ttgtcatcat ccgcacectg ctccaggcac gcaactttga gcgcaacaag     780
gccatcaagg tgatcatcgc tgtggtcgtg gtcttcatag tcttccagct gcectacaat     840 ggggtggtcc tggcccagac ggtggccaac ttcaacatca ccagtagcac ctgtgagctc     900
agtaagcaac tcaacatcgc ctacgacgtc acctacagcc tggcctgcgt ccgctgctgc     960 gtcaacccett tcttgtacgc cttcatcggc gtcaagttcc gcaacgatct cttcaagctc    1020
ttcaaggacc tgggctgcct cagccaggag cagctccggc agtggtcttc ctgtcggcac    1080
atccggcgct cctccatgag tgtggaggcc gagaccacca ccaccttctc cccatag        1137

<210> SEQ ID NO 74
<211> LENGTH: 378
<212> TYPE: PRT
<213> ORGANISM: Homo sapiens

<400> SEQUENCE: 74

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140
```

```
Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
            165                 170                 175

Leu Ser Cys Val Gly Ile Trp Ile Leu Ala Thr Val Leu Ser Ile Pro
        180                 185                 190

Glu Leu Leu Tyr Ser Asp Leu Gln Arg Ser Ser Glu Gln Ala Met
    195                 200                 205

Arg Cys Ser Leu Ile Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
370                 375

<210> SEQ ID NO 75
<211> LENGTH: 32
<212> TYPE: DNA
<213> ORGANISM: Artificial Sequence
<220> FEATURE:
<223> OTHER INFORMATION: Novel Sequence

<400> SEQUENCE: 75
ctggaattca cctggaccac caccaatgga ta                              32

<210> SEQ ID NO 76
<211> LENGTH: 30
<212> TYPE: DNA
<213> ORGANISM: Artificial Sequence
<220> FEATURE:
<223> OTHER INFORMATION: Novel Sequence

<400> SEQUENCE: 76
ctcggatcct gcaaagtttg tcatacagtt                                 30

<210> SEQ ID NO 77
<211> LENGTH: 1086
<212> TYPE: DNA
<213> ORGANISM: Homo sapiens

<400> SEQUENCE: 77
atggatatac aaatggcaaa caattttact ccgccctctg caactcctca gggaaatgac    60
```

```
tgtgacctct atgcacatca cagcacggcc aggatagtaa tgcctctgca ttacagcctc    120
gtcttcatca ttgggctcgt gggaaactta ctagccttgg tcgtcattgt tcaaaacagg    180
aaaaaaatca actctaccac cctctattca acaaatttgg tgatttctga tatacttttt    240
accacggctt tgcctacacg aatagcctac tatgcaatgg gctttgactg gagaatcgga    300
gatgccttgt gtaggataac tgcgctagtg ttttacatca acacatatgc aggtgtgaac    360
tttatgacct gcctgagtat tgaccgcttc attgctgtgg tgcaccctct acgctacaac    420
aagataaaaa ggattgaaca tgcaaaaggc gtgtgcatat ttgtctggat tctagtattt    480
gctcagacac tcccactcct catcaaccct atgtcaaagc aggaggctga aggattaca     540 tgcatggagt atccaaactt tgaagaaact aaatctcttc cctggattct gcttggggca    600
tgtttcatag gatatgtact tccacttata atcattctca tctgctattc tcagatctgc    660
tgcaaactct tcagaactgc caaacaaaac ccactcactg agaaatctgg tgtaaacaaa    720
aaggctctca acacaattat tcttattatt gttgtgtttg ttctctgttt cacaccttac    780
catgttgcaa ttattcaaca tatgattaag aagcttcgtt tctctaattt cctggaatgt    840
agccaaagac attcgttcca gatttctctg cactttacag tatgcctgat gaacttcaat    900
tgctgcatgg acccttttat ctacttcttt gcatgtaaag ggtataagag aaaggttatg    960
aggatgctga aacggcaagt cagtgtatcg atttctagtg ctgtgaagtc agcccctgaa    1020
gaaaattcac gtgaaatgac agaaacgcag atgatgatac attccaagtc ttcaaatgga    1080
aagtga                                                              1086
```

<210> SEQ ID NO 78
<211> LENGTH: 361
<212> TYPE: PRT
<213> ORGANISM: Homo sapiens

<400> SEQUENCE: 78

```
Met Asp Ile Gln Met Ala Asn Asn Phe Thr Pro Pro Ser Ala Thr Pro
1               5                   10                  15

Gln Gly Asn Asp Cys Asp Leu Tyr Ala His His Ser Thr Ala Arg Ile
            20                  25                  30

Val Met Pro Leu His Tyr Ser Leu Val Phe Ile Ile Gly Leu Val Gly
        35                  40                  45

Asn Leu Leu Ala Leu Val Val Ile Val Gln Asn Arg Lys Lys Ile Asn
    50                  55                  60

Ser Thr Thr Leu Tyr Ser Thr Asn Leu Val Ile Ser Asp Ile Leu Phe
65                  70                  75                  80

Thr Thr Ala Leu Pro Thr Arg Ile Ala Tyr Tyr Ala Met Gly Phe Asp
                85                  90                  95

Trp Arg Ile Gly Asp Ala Leu Cys Arg Ile Thr Ala Leu Val Phe Tyr
            100                 105                 110

Ile Asn Thr Tyr Ala Gly Val Asn Phe Met Thr Cys Leu Ser Ile Asp
        115                 120                 125

Arg Phe Ile Ala Val Val His Pro Leu Arg Tyr Asn Lys Ile Lys Arg
    130                 135                 140

Ile Glu His Ala Lys Gly Val Cys Ile Phe Val Trp Ile Leu Val Phe
145                 150                 155                 160

Ala Gln Thr Leu Pro Leu Leu Ile Asn Pro Met Ser Lys Gln Glu Ala
                165                 170                 175

Glu Arg Ile Thr Cys Met Glu Tyr Pro Asn Phe Glu Glu Thr Lys Ser
            180                 185                 190
```

```
Leu Pro Trp Ile Leu Leu Gly Ala Cys Phe Ile Gly Tyr Val Leu Pro
            195                 200                 205

Leu Ile Ile Ile Leu Ile Cys Tyr Ser Gln Ile Cys Cys Lys Leu Phe
        210                 215                 220

Arg Thr Ala Lys Gln Asn Pro Leu Thr Glu Lys Ser Gly Val Asn Lys
225                 230                 235                 240

Lys Ala Leu Asn Thr Ile Ile Leu Ile Ile Val Val Phe Val Leu Cys
                245                 250                 255

Phe Thr Pro Tyr His Val Ala Ile Ile Gln His Met Ile Lys Lys Leu
            260                 265                 270

Arg Phe Ser Asn Phe Leu Glu Cys Ser Gln Arg His Ser Phe Gln Ile
        275                 280                 285

Ser Leu His Phe Thr Val Cys Leu Met Asn Phe Asn Cys Cys Met Asp
        290                 295                 300

Pro Phe Ile Tyr Phe Phe Ala Cys Lys Gly Tyr Lys Arg Lys Val Met
305                 310                 315                 320

Arg Met Leu Lys Arg Gln Val Ser Val Ser Ile Ser Ser Ala Val Lys
                325                 330                 335

Ser Ala Pro Glu Glu Asn Ser Arg Glu Met Thr Glu Thr Gln Met Met
            340                 345                 350

Ile His Ser Lys Ser Ser Asn Gly Lys
            355                 360

<210> SEQ ID NO 79
<211> LENGTH: 31
<212> TYPE: DNA
<213> ORGANISM: Artificial Sequence
<220> FEATURE:
<223> OTHER INFORMATION: Novel Sequence

<400> SEQUENCE: 79
ctggaattct cctgctcatc cagccatgcg g                              31

<210> SEQ ID NO 80
<211> LENGTH: 30
<212> TYPE: DNA
<213> ORGANISM: Artificial Sequence
<220> FEATURE:
<223> OTHER INFORMATION: Novel Sequence

<400> SEQUENCE: 80
cctggatccc caccectact ggggcctcag                                30

<210> SEQ ID NO 81
<211> LENGTH: 1446
<212> TYPE: DNA
<213> ORGANISM: Homo sapiens

<400> SEQUENCE: 81
atgcggtggc tgtggcccct ggctgtctct cttgctgtga ttttggctgt ggggctaagc    60
agggtctctg ggggtgcccc cctgcacctg gcaggcaca gagccgagac ccaggagcag    120
cagagccgat ccaagagggg caccgaggat gaggaggcca agggcgtgca gcagtatgtg    180
cctgaggagt gggcggagta ccccggccc attcaccctg ctggcctgca gccaaccaag    240
cccttggtgg ccaccagccc taaccccgac aaggatgggg caccccaga cagtgggcag    300 gaactgaggg gcaatctgac aggggcacca gggcagaggc tacagatcca gaacccctg    360 tatccggtga ccgagagctc ctacagtgcc tatgccatca tgcttctggc gctggtggtg    420
```

```
tttgcggtgg gcattgtggg caacctgtcg gtcatgtgca tcgtgtggca cagctactac    480
ctgaagagcg cctggaactc catccttgcc agcctggccc tctgggattt tctggtcctc    540
tttttctgcc tccctattgt catcttcaac gagatcacca agcagaggct actgggtgac    600
gtttcttgtc gtgccgtgcc cttcatggag gtctcctctc tgggagtcac gactttcagc    660
ctctgtgccc tgggcattga ccgcttccac gtggccacca gcaccctgcc caaggtgagg    720
cccatcgagc ggtgccaatc catcctggcc aagttggctg tcatctgggt gggctccatg    780
acgctggctg tgcctgagct cctgctgtgg cagctggcac aggagcctgc ccccaccatg    840
ggcaccctgg actcatgcat catgaaaccc tcagccagcc tgcccgagtc cctgtattca    900
ctggtgatga cctaccagaa cgcccgcatg tggtggtact ttggctgcta cttctgcctg    960
cccatcctct tcacagtcac ctgccagctg gtgacatggc gggtgcgagg ccctccaggg    1020
aggaagtcag agtgcagggc cagcaagcac gagcagtgtg agagccagct caacagcacc    1080
gtggtgggcc tgaccgtggt ctacgccttc tgcaccctcc cagagaacgt ctgcaacatc    1140
gtggtggcct acctctccac cgagctgacc cgccagaccc tggacctcct gggcctcatc    1200
aaccagttct ccaccttctt caagggcgcc atcacccag tgctgctcct ttgcatctgc    1260
aggccgctgg gccaggcctt cctggactgc tgctgctgct gctgctgtga ggagtgcggc    1320
ggggcttcgg aggcctctgc tgccaatggg tcggacaaca agctcaagac cgaggtgtcc    1380
tcttccatct acttccacaa gcccagggag tcaccccac tcctgcccct gggcacacct    1440
tgctga                                                              1446

<210> SEQ ID NO 82
<211> LENGTH: 481
<212> TYPE: PRT
<213> ORGANISM: Homo sapiens

<400> SEQUENCE: 82

Met Arg Trp Leu Trp Pro Leu Ala Val Ser Leu Ala Val Ile Leu Ala
1               5                   10                  15

Val Gly Leu Ser Arg Val Ser Gly Gly Ala Pro Leu His Leu Gly Arg
            20                  25                  30

His Arg Ala Glu Thr Gln Glu Gln Gln Ser Arg Ser Lys Arg Gly Thr
        35                  40                  45

Glu Asp Glu Glu Ala Lys Gly Val Gln Gln Tyr Val Pro Glu Glu Trp
50                  55                  60

Ala Glu Tyr Pro Arg Pro Ile His Pro Ala Gly Leu Gln Pro Thr Lys
65                  70                  75                  80

Pro Leu Val Ala Thr Ser Pro Asn Pro Asp Lys Asp Gly Gly Thr Pro
                85                  90                  95

Asp Ser Gly Gln Glu Leu Arg Gly Asn Leu Thr Gly Ala Pro Gly Gln
            100                 105                 110

Arg Leu Gln Ile Gln Asn Pro Leu Tyr Pro Val Thr Glu Ser Ser Tyr
        115                 120                 125

Ser Ala Tyr Ala Ile Met Leu Leu Ala Leu Val Val Phe Ala Val Gly
    130                 135                 140

Ile Val Gly Asn Leu Ser Val Met Cys Ile Val Trp His Ser Tyr Tyr
145                 150                 155                 160

Leu Lys Ser Ala Trp Asn Ser Ile Leu Ala Ser Leu Ala Leu Trp Asp
                165                 170                 175

Phe Leu Val Leu Phe Phe Cys Leu Pro Ile Val Ile Phe Asn Glu Ile
```

```
                    180                 185                 190
Thr Lys Gln Arg Leu Leu Gly Asp Val Ser Cys Arg Ala Val Pro Phe
        195                 200                 205
Met Glu Val Ser Ser Leu Gly Val Thr Thr Phe Ser Leu Cys Ala Leu
    210                 215                 220
Gly Ile Asp Arg Phe His Val Ala Thr Ser Thr Leu Pro Lys Val Arg
225                 230                 235                 240
Pro Ile Glu Arg Cys Gln Ser Ile Leu Ala Lys Leu Ala Val Ile Trp
                245                 250                 255
Val Gly Ser Met Thr Leu Ala Val Pro Glu Leu Leu Trp Gln Leu
            260                 265                 270
Ala Gln Glu Pro Ala Pro Thr Met Gly Thr Leu Asp Ser Cys Ile Met
        275                 280                 285
Lys Pro Ser Ala Ser Leu Pro Glu Ser Leu Tyr Ser Leu Val Met Thr
    290                 295                 300
Tyr Gln Asn Ala Arg Met Trp Trp Tyr Phe Gly Cys Tyr Phe Cys Leu
305                 310                 315                 320
Pro Ile Leu Phe Thr Val Thr Cys Gln Leu Val Thr Trp Arg Val Arg
                325                 330                 335
Gly Pro Pro Gly Arg Lys Ser Glu Cys Arg Ala Ser Lys His Glu Gln
            340                 345                 350
Cys Glu Ser Gln Leu Asn Ser Thr Val Val Gly Leu Thr Val Val Tyr
        355                 360                 365
Ala Phe Cys Thr Leu Pro Glu Asn Val Cys Asn Ile Val Val Ala Tyr
    370                 375                 380
Leu Ser Thr Glu Leu Thr Arg Gln Thr Leu Asp Leu Leu Gly Leu Ile
385                 390                 395                 400
Asn Gln Phe Ser Thr Phe Phe Lys Gly Ala Ile Thr Pro Val Leu Leu
                405                 410                 415
Leu Cys Ile Cys Arg Pro Leu Gly Gln Ala Phe Leu Asp Cys Cys Cys
            420                 425                 430
Cys Cys Cys Cys Glu Glu Cys Gly Gly Ala Ser Glu Ala Ser Ala Ala
        435                 440                 445
Asn Gly Ser Asp Asn Lys Leu Lys Thr Glu Val Ser Ser Ser Ile Tyr
    450                 455                 460
Phe His Lys Pro Arg Glu Ser Pro Pro Leu Leu Pro Leu Gly Thr Pro
465                 470                 475                 480
Cys

<210> SEQ ID NO 83
<211> LENGTH: 22
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: Novel Sequence

<400> SEQUENCE: 83
atgtggaacg cgacgcccag cg                                         22

<210> SEQ ID NO 84
<211> LENGTH: 22
<212> TYPE: DNA
<213> ORGANISM: Artificial Sequence
<220> FEATURE:
<223> OTHER INFORMATION: Novel Sequence
```

<400> SEQUENCE: 84
tcatgtatta atactagatt ct                                           22

<210> SEQ ID NO 85
<211> LENGTH: 38
<212> TYPE: DNA
<213> ORGANISM: Artificial Sequence
<220> FEATURE:
<223> OTHER INFORMATION: Novel Sequence

<400> SEQUENCE: 85
taccatgtgg aacgcgacgc ccagcgaaga gccggggt                          38

<210> SEQ ID NO 86
<211> LENGTH: 39
<212> TYPE: DNA
<213> ORGANISM: Artificial Sequence
<220> FEATURE:
<223> OTHER INFORMATION: Novel Sequence

<400> SEQUENCE: 86
cggaattcat gtattaatac tagattctgt ccaggcccg                         39

<210> SEQ ID NO 87
<211> LENGTH: 1101
<212> TYPE: DNA
<213> ORGANISM: Homo sapiens

<400> SEQUENCE: 87
atgtggaacg cgacgcccag cgaagagccg gggttcaacc tcacactggc cgacctggac    60
tgggatgctt cccccggcaa cgactcgctg ggcgacgagc tgctgcagct cttccccgcg   120
ccgctgctgg cgggcgtcac agccacctgc gtggcactct tcgtggtggg tatcgctggc   180
aacctgctca ccatgctggt ggtgtcgcgc ttccgcgagc tgcgcaccac caccaacctc   240
tacctgtcca gcatggcctt ctccgatctg ctcatcttcc tctgcatgcc cctggacctc   300
gttcgcctct ggcagtaccg gccctggaac ttcggcgacc tcctctgcaa actcttccaa   360
ttcgtcagtg agagctgcac ctacgccacg gtgctcacca tcacagcgct gagcgtcgag   420
cgctacttcg ccatctgctt cccactccgg gccaaggtgg tggtcaccaa ggggcgggtg   480
aagctggtca tcttcgtcat ctgggccgtg gccttctgca gcgccgggcc catcttcgtg   540
ctagtcgggg tggagcacga aacggcacc gaccttggg acaccaacga gtgccgcccc   600
accgagtttg cggtgcgctc tggactgctc acggtcatgg tgtgggtgtc cagcatcttc   660
ttcttccttc ctgtcttctg tctcacggtc tctacagtc tcatcggcag gaagctgtgg   720
cggaggaggc gcggcgatgc tgtcgtgggt gcctcgctca gggaccagaa ccacaagcaa   780
accgtgaaaa tgctggctgt agtggtgttt gccttcatcc tctgctggct ccccttccac   840
gtagggcgat atttattttc caaatccttt gagcctggct ccttggagat tgctcagatc   900
agccagtact gcaacctcgt gtcctttgtc ctcttctacc tcagtgctgc catcaacccc   960
attctgtaca catcatgtc caagaagtac cgggtggcag tgttcagact tctgggattc  1020
gaacccttct cccagagaaa gctctccact ctgaaagatg aaagttctcg ggcctggaca  1080
gaatctagta ttaatacatg a                                           1101

<210> SEQ ID NO 88
<211> LENGTH: 366
<212> TYPE: PRT

```
<213> ORGANISM: Homo sapiens

<400> SEQUENCE: 88

Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
130                 135                 140

Ile Cys Phe Pro Leu Arg Ala Lys Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Leu Pro
210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Ala Val Val Phe Ala Phe
            260                 265                 270

Ile Leu Cys Trp Leu Pro Phe His Val Gly Arg Tyr Leu Phe Ser Lys
        275                 280                 285

Ser Phe Glu Pro Gly Ser Leu Glu Ile Ala Gln Ile Ser Gln Tyr Cys
290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
                325                 330                 335

Leu Leu Gly Phe Glu Pro Phe Ser Gln Arg Lys Leu Ser Thr Leu Lys
            340                 345                 350

Asp Glu Ser Ser Arg Ala Trp Thr Glu Ser Ser Ile Asn Thr
        355                 360                 365

<210> SEQ ID NO 89
<211> LENGTH: 33
<212> TYPE: DNA
<213> ORGANISM: Artificial Sequence
<220> FEATURE:
```

<223> OTHER INFORMATION: Novel Sequence

<400> SEQUENCE: 89
gcaagcttgt gccctcacca agccatgcga gcc         33

<210> SEQ ID NO 90
<211> LENGTH: 30
<212> TYPE: DNA
<213> ORGANISM: Artificial Sequence
<220> FEATURE:
<223> OTHER INFORMATION: Novel Sequence

<400> SEQUENCE: 90
cggaattcag caatgagttc cgacagaagc         30

<210> SEQ ID NO 91
<211> LENGTH: 1842
<212> TYPE: DNA
<213> ORGANISM: Homo sapiens

<400> SEQUENCE: 91

| | |
|---|---:|
| atgcgagccc cgggcgcgct ctcgcccgc atgtcgcggc tactgcttct gctactgctc | 60 |
| aaggtgtctg cctcttctgc cctcggggtc gccctgcgt ccagaaacga aacttgtctg | 120 |
| ggggagagct gtgcacctac agtgatccag cgccgcggca gggacgcctg gggaccggga | 180 |
| aattctgcaa gagacgttct gcgagcccga gcacccaggg aggagcaggg ggcagcgttt | 240 |
| cttgcgggac cctcctggga cctgccgcg gccccggggcc gtgacccggc tgcaggcaga | 300 |
| ggggcggagg cgtcggcagc cggaccccccg ggacctccaa ccaggccacc tggcccctgg | 360 |
| aggtggaaag gtgctcgggg tcaggagcct tctgaaactt tggggagagg gaaccccacg | 420 |
| gccctccagc tcttccttca gatctcagag gaggaagaga agggtcccag aggcgctggc | 480 |
| atttccgggc gtagccagga gcagagtgtg aagacagtcc ccggagccag cgatcttttt | 540 |
| tactggccaa ggagagccgg gaaactccag ggttcccacc acaagcccct gtccaagacg | 600 |
| gccaatggac tggcggggca cgaagggtgg acaattgcac tcccgggccg ggcgctggcc | 660 |
| cagaatggat ccttgggtga aggaatccat gagcctgggg gtccccgccg gggaaacagc | 720 |
| acgaaccggc gtgtgagact gaagaacccc ttctacccgc tgacccagga gtcctatgga | 780 |
| gcctacgcgg tcatgtgtct gtccgtggtg atcttcggga ccggcatcat tggcaacctg | 840 |
| gcggtgatga gcatcgtgtg ccacaactac tacatgcgga gcatctccaa ctccctcttg | 900 |
| gccaacctgg ccttctggga ctttctcatc atcttcttct gccttccgct ggtcatcttc | 960 |
| cacgagctga ccaagaagtg gctgctggag gacttctcct gcaagatcgt gcctatata | 1020 |
| gaggtcgctt ctctgggagt caccactttc accttatgtg ctctgtgcat agaccgcttc | 1080 |
| cgtgctgcca ccaacgtaca gatgtactac gaaatgatcg aaaactgttc ctcaacaact | 1140 |
| gccaaacttg ctgttatatg ggtgggagct ctattgttag cacttccaga agttgttctc | 1200 |
| cgccagctga gcaaggagga tttgggggttt agtggccgag ctccggcaga aaggtgcatt | 1260 |
| attaagatct ctcctgattt accagacacc atctatgttc tagccctcac ctacgacagt | 1320 |
| gcgagactgt ggtggtattt tggctgttac ttttgtttgc ccacgcttttt caccatcacc | 1380 |
| tgctctctag tgactgcgag gaaaatccgc aaagcagaga aagcctgtac ccgagggaat | 1440 |
| aaacggcaga ttcaactaga gagtcagatg aactgtacag tagtggcact gaccatttta | 1500 |
| tatggatttt gcattattcc tgaaaatatc tgcaacattg ttactgccta catggctaca | 1560 |
| ggggtttcac agcagacaat ggacctcctt aatatcatca gccagttcct tttgttcttt | 1620 |

-continued

```
aagtcctgtg tcaccccagt cctccttttc tgtctctgca aacccttcag tcgggccttc    1680
atggagtgct gctgctgttg ctgtgaggaa tgcattcaga agtcttcaac ggtgaccagt    1740
gatgacaatg acaacgagta caccacggaa ctcgaactct cgcctttcag taccatacgc    1800
cgtgaaatgt ccacttttgc ttctgtcgga actcattgct ga                      1842
```

<210> SEQ ID NO 92
<211> LENGTH: 613
<212> TYPE: PRT
<213> ORGANISM: Homo sapiens

<400> SEQUENCE: 92

```
Met Arg Ala Pro Gly Ala Leu Leu Ala Arg Met Ser Arg Leu Leu Leu
1               5                   10                  15

Leu Leu Leu Lys Val Ser Ala Ser Ser Ala Leu Gly Val Ala Pro
            20                  25                  30

Ala Ser Arg Asn Glu Thr Cys Leu Gly Glu Ser Cys Ala Pro Thr Val
        35                  40                  45

Ile Gln Arg Arg Gly Arg Asp Ala Trp Gly Pro Gly Asn Ser Ala Arg
    50                  55                  60

Asp Val Leu Arg Ala Arg Ala Pro Arg Glu Glu Gln Gly Ala Ala Phe
65                  70                  75                  80

Leu Ala Gly Pro Ser Trp Asp Leu Pro Ala Ala Pro Gly Arg Asp Pro
                85                  90                  95

Ala Ala Gly Arg Gly Ala Glu Ala Ser Ala Ala Gly Pro Pro Gly Pro
            100                 105                 110

Pro Thr Arg Pro Pro Gly Pro Trp Arg Trp Lys Gly Ala Arg Gly Gln
        115                 120                 125

Glu Pro Ser Glu Thr Leu Gly Arg Gly Asn Pro Thr Ala Leu Gln Leu
    130                 135                 140

Phe Leu Gln Ile Ser Glu Glu Glu Lys Gly Pro Arg Gly Ala Gly
145                 150                 155                 160

Ile Ser Gly Arg Ser Gln Glu Gln Ser Val Lys Thr Val Pro Gly Ala
                165                 170                 175

Ser Asp Leu Phe Tyr Trp Pro Arg Arg Ala Gly Lys Leu Gln Gly Ser
            180                 185                 190

His His Lys Pro Leu Ser Lys Thr Ala Asn Gly Leu Ala Gly His Glu
        195                 200                 205

Gly Trp Thr Ile Ala Leu Pro Gly Arg Ala Leu Ala Gln Asn Gly Ser
    210                 215                 220

Leu Gly Glu Gly Ile His Glu Pro Gly Gly Pro Arg Arg Gly Asn Ser
225                 230                 235                 240

Thr Asn Arg Arg Val Arg Leu Lys Asn Pro Phe Tyr Pro Leu Thr Gln
                245                 250                 255

Glu Ser Tyr Gly Ala Tyr Ala Val Met Cys Leu Ser Val Val Ile Phe
            260                 265                 270

Gly Thr Gly Ile Ile Gly Asn Leu Ala Val Met Ser Ile Val Cys His
        275                 280                 285

Asn Tyr Tyr Met Arg Ser Ile Ser Asn Ser Leu Leu Ala Asn Leu Ala
    290                 295                 300

Phe Trp Asp Phe Leu Ile Ile Phe Phe Cys Leu Pro Leu Val Ile Phe
305                 310                 315                 320

His Glu Leu Thr Lys Lys Trp Leu Leu Glu Asp Phe Ser Cys Lys Ile
                325                 330                 335
```

-continued

```
Val Pro Tyr Ile Glu Val Ala Ser Leu Gly Val Thr Thr Phe Thr Leu
            340                 345                 350

Cys Ala Leu Cys Ile Asp Arg Phe Arg Ala Ala Thr Asn Val Gln Met
        355                 360                 365

Tyr Tyr Glu Met Ile Glu Asn Cys Ser Ser Thr Thr Ala Lys Leu Ala
    370                 375                 380

Val Ile Trp Val Gly Ala Leu Leu Ala Leu Pro Glu Val Val Leu
385                 390                 395                 400

Arg Gln Leu Ser Lys Glu Asp Leu Gly Phe Ser Gly Arg Ala Pro Ala
                405                 410                 415

Glu Arg Cys Ile Ile Lys Ile Ser Pro Asp Leu Pro Asp Thr Ile Tyr
            420                 425                 430

Val Leu Ala Leu Thr Tyr Asp Ser Ala Arg Leu Trp Trp Tyr Phe Gly
        435                 440                 445

Cys Tyr Phe Cys Leu Pro Thr Leu Phe Thr Ile Thr Cys Ser Leu Val
    450                 455                 460

Thr Ala Arg Lys Ile Arg Lys Ala Glu Lys Ala Cys Thr Arg Gly Asn
465                 470                 475                 480

Lys Arg Gln Ile Gln Leu Glu Ser Gln Met Asn Cys Thr Val Val Ala
                485                 490                 495

Leu Thr Ile Leu Tyr Gly Phe Cys Ile Ile Pro Glu Asn Ile Cys Asn
            500                 505                 510

Ile Val Thr Ala Tyr Met Ala Thr Gly Val Ser Gln Gln Thr Met Asp
        515                 520                 525

Leu Leu Asn Ile Ile Ser Gln Phe Leu Leu Phe Phe Lys Ser Cys Val
    530                 535                 540

Thr Pro Val Leu Leu Phe Cys Leu Cys Lys Pro Phe Ser Arg Ala Phe
545                 550                 555                 560

Met Glu Cys Cys Cys Cys Cys Cys Glu Glu Cys Ile Gln Lys Ser Ser
                565                 570                 575

Thr Val Thr Ser Asp Asp Asn Asp Asn Glu Tyr Thr Thr Glu Leu Glu
            580                 585                 590

Leu Ser Pro Phe Ser Thr Ile Arg Arg Glu Met Ser Thr Phe Ala Ser
        595                 600                 605

Val Gly Thr His Cys
    610
```

<210> SEQ ID NO 93
<211> LENGTH: 34
<212> TYPE: DNA
<213> ORGANISM: Artificial Sequence
<220> FEATURE:
<223> OTHER INFORMATION: Novel Sequence

<400> SEQUENCE: 93
cagaattcag agaaaaaaag tgaatatggt tttt                      34

<210> SEQ ID NO 94
<211> LENGTH: 32
<212> TYPE: DNA
<213> ORGANISM: Artificial Sequence
<220> FEATURE:
<223> OTHER INFORMATION: Novel Sequence

<400> SEQUENCE: 94
ttggatccct ggtgcataac aattgaaaga at                        32

-continued

<210> SEQ ID NO 95
<211> LENGTH: 1248
<212> TYPE: DNA
<213> ORGANISM: Homo sapiens

<400> SEQUENCE: 95

```
atggtttttg ctcacagaat ggataacagc aagccacatt tgattattcc tacacttctg      60
gtgcccctcc aaaaccgcag ctgcactgaa acagccacac ctctgccaag ccaatacctg     120
atggaattaa gtgaggagca cagttggatg agcaaccaaa cagaccttca ctatgtgctg     180
aaacccgggg aagtggccac agccagcatc ttctttggga ttctgtggtt gttttctatc     240
ttcggcaatt ccctggtttg tttggtcatc cataggagta ggaggactca gtctaccacc     300
aactactttg tggtctccat ggcatgtgct gaccttctca tcagcgttgc cagcacgcct     360
ttcgtcctgc tccagttcac cactggaagg tggacgctgg gtagtgcaac gtgcaaggtt     420
gtgcgatatt ttcaatatct cactccaggt gtccagatct acgttctcct ctccatctgc     480
atagaccggt tctacaccat cgtctatcct ctgagcttca aggtgtccag agaaaaagcc     540
aagaaaatga ttgcggcatc gtggatcttt gatgcaggct ttgtgacccc tgtgctcttt     600
ttctatggct ccaactggga cagtcattgt aactatttcc tcccctcctc ttgggaaggc     660
actgcctaca ctgtcatcca cttcttggtg ggctttgtga ttccatctgt cctcataatt     720
ttatttttacc aaaaggtcat aaaatatatt tggagaatag gcacagatgg ccgaacggtg     780
aggaggacaa tgaacattgt ccctcggaca aaagtgaaaa ctatcaagat gttcctcatt     840
ttaaatctgt tgttttttgct ctcctggctg ccttttcatg tagctcagct atggcacccc     900
catgaacaag actataagaa aagttcccctt gttttcacag ctatcacatg gatatccttt     960
agttcttcag cctctaaacc tactctgtat tcaatttata tgccaatttt tcggagaggg    1020
atgaaagaga cttttttgcat gtcctctatg aaatgttacc gaagcaatgc ctatactatc    1080
acaacaagtt caaggatggc caaaaaaaac tacgttggca tttcagaaat cccttccatg    1140
gccaaaacta ttaccaaaga ctcgatctat gactcatttg acagagaagc caaggaaaaa    1200
aagcttgctt ggcccattaa ctcaaatcca ccaaatactt ttgtctaa                  1248
```

<210> SEQ ID NO 96
<211> LENGTH: 415
<212> TYPE: PRT
<213> ORGANISM: Homo sapiens

<400> SEQUENCE: 96

```
Met Val Phe Ala His Arg Met Asp Asn Ser Lys Pro His Leu Ile Ile
1               5                  10                  15

Pro Thr Leu Leu Val Pro Leu Gln Asn Arg Ser Cys Thr Glu Thr Ala
            20                  25                  30

Thr Pro Leu Pro Ser Gln Tyr Leu Met Glu Leu Ser Glu Glu His Ser
        35                  40                  45

Trp Met Ser Asn Gln Thr Asp Leu His Tyr Val Leu Lys Pro Gly Glu
    50                  55                  60

Val Ala Thr Ala Ser Ile Phe Phe Gly Ile Leu Trp Leu Phe Ser Ile
65                  70                  75                  80

Phe Gly Asn Ser Leu Val Cys Leu Val Ile His Arg Ser Arg Arg Thr
                85                  90                  95

Gln Ser Thr Thr Asn Tyr Phe Val Val Ser Met Ala Cys Ala Asp Leu
            100                 105                 110
```

```
Leu Ile Ser Val Ala Ser Thr Pro Phe Val Leu Gln Phe Thr Thr
        115                 120                 125

Gly Arg Trp Thr Leu Gly Ser Ala Thr Cys Lys Val Val Arg Tyr Phe
130                 135                 140

Gln Tyr Leu Thr Pro Gly Val Gln Ile Tyr Val Leu Leu Ser Ile Cys
145                 150                 155                 160

Ile Asp Arg Phe Tyr Thr Ile Val Tyr Pro Leu Ser Phe Lys Val Ser
                165                 170                 175

Arg Glu Lys Ala Lys Lys Met Ile Ala Ala Ser Trp Ile Phe Asp Ala
            180                 185                 190

Gly Phe Val Thr Pro Val Leu Phe Phe Tyr Gly Ser Asn Trp Asp Ser
            195                 200                 205

His Cys Asn Tyr Phe Leu Pro Ser Ser Trp Glu Gly Thr Ala Tyr Thr
    210                 215                 220

Val Ile His Phe Leu Val Gly Phe Val Ile Pro Ser Val Leu Ile Ile
225                 230                 235                 240

Leu Phe Tyr Gln Lys Val Ile Lys Tyr Ile Trp Arg Ile Gly Thr Asp
                245                 250                 255

Gly Arg Thr Val Arg Arg Thr Met Asn Ile Val Pro Arg Thr Lys Val
            260                 265                 270

Lys Thr Ile Lys Met Phe Leu Ile Leu Asn Leu Leu Phe Leu Leu Ser
            275                 280                 285

Trp Leu Pro Phe His Val Ala Gln Leu Trp His Pro His Glu Gln Asp
290                 295                 300

Tyr Lys Lys Ser Ser Leu Val Phe Thr Ala Ile Thr Trp Ile Ser Phe
305                 310                 315                 320

Ser Ser Ser Ala Ser Lys Pro Thr Leu Tyr Ser Ile Tyr Asn Ala Asn
                325                 330                 335

Phe Arg Arg Gly Met Lys Glu Thr Phe Cys Met Ser Ser Met Lys Cys
            340                 345                 350

Tyr Arg Ser Asn Ala Tyr Thr Ile Thr Thr Ser Ser Arg Met Ala Lys
            355                 360                 365

Lys Asn Tyr Val Gly Ile Ser Glu Ile Pro Ser Met Ala Lys Thr Ile
            370                 375                 380

Thr Lys Asp Ser Ile Tyr Asp Ser Phe Asp Arg Glu Ala Lys Glu Lys
385                 390                 395                 400

Lys Leu Ala Trp Pro Ile Asn Ser Asn Pro Asn Thr Phe Val
                405                 410                 415

<210> SEQ ID NO 97
<211> LENGTH: 30
<212> TYPE: DNA
<213> ORGANISM: Artificial Sequence
<220> FEATURE:
<223> OTHER INFORMATION: Novel Sequence

<400> SEQUENCE: 97
ggaaagctta acgatcccca ggagcaacat                                      30

<210> SEQ ID NO 98
<211> LENGTH: 31
<212> TYPE: DNA
<213> ORGANISM: Artificial Sequence
<220> FEATURE:
<223> OTHER INFORMATION: Novel Sequence

<400> SEQUENCE: 98
```
ctgggatcct acgagagcat ttttcacaca g                                31

<210> SEQ ID NO 99
<211> LENGTH: 1842
<212> TYPE: DNA
<213> ORGANISM: Homo sapiens

<400> SEQUENCE: 99
atggggccca ccctagcggt tcccaccccc tatggctgta ttggctgtaa gctaccccag    60
ccagaatacc caccggctct aatcatcttt atgttctgcg cgatggttat caccatcgtt   120
gtagacctaa tcggcaactc catggtcatt ttggctgtga cgaagaacaa gaagctccgg   180
aattctggca acatcttcgt ggtcagtctc tctgtggccg atatgctggt ggccatctac   240
ccatcccctt tgatgctgca tgccatgtcc attggggact gggatctgag ccagttacag   300
tgccagatgg tcggggttcat cacagggctg agtgtggtcg gctccatctt caacatcgtg   360
gcaatcgcta tcaaccgtta ctgctacatc tgccacagcc tccagtacga acggatcttc   420
agtgtgcgca atacctgcat ctacctggtc atcacctgga tcatgaccgt cctggctgtc   480
ctgcccaaca tgtacattgg caccatcgag tacgatcctc gcacctacac ctgcatcttc   540
aactatctga caaccctgt cttcactgtt accatcgtct gcatccactt cgtcctccct   600
ctcctcatcg tgggtttctg ctacgtgagg atctggacca aagtgctggc ggcccgtgac   660
cctgcagggc agaatcctga caaccaactt gctgaggttc gcaattttct aaccatgttt   720
gtgatcttcc tcctctttgc agtgtgctgg tgccctatca cgtgctcac tgtcttggtg   780
gctgtcagtc cgaaggagat ggcaggcaag atccccaact ggctttatct tgcagcctac   840
ttcatagcct acttcaacag ctgcctcaac gctgtgatct acgggctcct caatgagaat   900
ttccgaagag aatactggac catcttccat gctatgcggc accctatcat attcttccct   960
ggcctcatca gtgatattcg tgagatgcag gaggcccgta ccctggcccg cgcccgtgcc  1020
catgctcgcg accaagctcg tgaacaagac cgtgcccatg cctgtcctgc tgtggaggaa  1080
acccgatga atgtccggaa tgttccatta cctggtgatg ctgcagctgg ccaccccgac  1140
cgtgcctctg gccaccctaa gccccattcc agatcctcct ctgcctatcg caaatctgcc  1200
tctacccacc acaagtctgt ctttagccac tccaaggctg cctctggtca cctcaagcct  1260
gtctctggcc actccaagcc tgcctctggt caccccaagt ctgccactgt ctaccctaag  1320
cctgcctctg tccatttcaa gggtgactct gtccatttca agggtgactc tgtccatttc  1380
aagcctgact ctgttcattt caagcctgct tccagcaacc ccaagcccat cactggccac  1440
catgtctctg ctggcagcca ctccaagtct gccttcagtg ctgccaccag ccaccctaaa  1500
cccatcaagc cagctaccag ccatgctgag cccaccactg ctgactatcc caagcctgcc  1560
actaccagcc accctaagcc cgctgctgct gacaaccctg agctctctgc ctcccattgc  1620
cccgagatcc ctgccattgc ccaccctgtg tctgacgaca gtgacctccc tgagtcggcc  1680
tctagccctg ccgctgggcc caccaagcct gctgccagcc agctggagtc tgacaccatc  1740
gctgaccttc ctgaccctac tgtagtcact accagtacca atgattacca tgatgtcgtg  1800
gttgttgatg ttgaagatga tcctgatgaa atggctgtgt ga                     1842

<210> SEQ ID NO 100
<211> LENGTH: 613
<212> TYPE: PRT
<213> ORGANISM: Homo sapiens

<400> SEQUENCE: 100

-continued

```
Met Gly Pro Thr Leu Ala Val Pro Thr Pro Tyr Gly Cys Ile Gly Cys
1               5                   10                  15

Lys Leu Pro Gln Pro Glu Tyr Pro Pro Ala Leu Ile Ile Phe Met Phe
            20                  25                  30

Cys Ala Met Val Ile Thr Ile Val Asp Leu Ile Gly Asn Ser Met
            35                  40                  45

Val Ile Leu Ala Val Thr Lys Asn Lys Lys Leu Arg Asn Ser Gly Asn
            50              55                  60

Ile Phe Val Val Ser Leu Ser Val Ala Asp Met Leu Val Ala Ile Tyr
65                  70                  75                  80

Pro Tyr Pro Leu Met Leu His Ala Met Ser Ile Gly Gly Trp Asp Leu
                85                  90                  95

Ser Gln Leu Gln Cys Gln Met Val Gly Phe Ile Thr Gly Leu Ser Val
            100                 105                 110

Val Gly Ser Ile Phe Asn Ile Val Ala Ile Ala Ile Asn Arg Tyr Cys
            115                 120                 125

Tyr Ile Cys His Ser Leu Gln Tyr Glu Arg Ile Phe Ser Val Arg Asn
            130                 135                 140

Thr Cys Ile Tyr Leu Val Ile Thr Trp Ile Met Thr Val Leu Ala Val
145                 150                 155                 160

Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
            180                 185                 190

Val Cys Ile His Phe Val Leu Pro Leu Leu Ile Val Gly Phe Cys Tyr
            195                 200                 205

Val Arg Ile Trp Thr Lys Val Leu Ala Ala Arg Asp Pro Ala Gly Gln
            210                 215                 220

Asn Pro Asp Asn Gln Leu Ala Glu Val Arg Asn Phe Leu Thr Met Phe
225                 230                 235                 240

Val Ile Phe Leu Leu Phe Ala Val Cys Trp Cys Pro Ile Asn Val Leu
                245                 250                 255

Thr Val Leu Val Ala Val Ser Pro Lys Glu Met Ala Gly Lys Ile Pro
            260                 265                 270

Asn Trp Leu Tyr Leu Ala Ala Tyr Phe Ile Ala Tyr Phe Asn Ser Cys
            275                 280                 285

Leu Asn Ala Val Ile Tyr Gly Leu Leu Asn Glu Asn Phe Arg Arg Glu
            290                 295                 300

Tyr Trp Thr Ile Phe His Ala Met Arg His Pro Ile Ile Phe Phe Pro
305                 310                 315                 320

Gly Leu Ile Ser Asp Ile Arg Glu Met Gln Glu Ala Arg Thr Leu Ala
                325                 330                 335

Arg Ala Arg Ala His Ala Arg Asp Gln Ala Arg Glu Gln Asp Arg Ala
            340                 345                 350

His Ala Cys Pro Ala Val Glu Glu Thr Pro Met Asn Val Arg Asn Val
            355                 360                 365

Pro Leu Pro Gly Asp Ala Ala Gly His Pro Asp Arg Ala Ser Gly
            370                 375                 380

His Pro Lys Pro His Ser Arg Ser Ser Ala Tyr Arg Lys Ser Ala
385                 390                 395                 400

Ser Thr His His Lys Ser Val Phe Ser His Ser Lys Ala Ala Ser Gly
                405                 410                 415
```

```
His Leu Lys Pro Val Ser Gly His Ser Lys Pro Ala Ser Gly His Pro
            420                 425                 430
Lys Ser Ala Thr Val Tyr Pro Lys Pro Ala Ser Val His Phe Lys Gly
        435                 440                 445
Asp Ser Val His Phe Lys Gly Asp Ser Val His Phe Lys Pro Asp Ser
    450                 455                 460
Val His Phe Lys Pro Ala Ser Asn Pro Lys Pro Ile Thr Gly His
465                 470                 475                 480
His Val Ser Ala Gly Ser His Ser Lys Ser Ala Phe Ser Ala Ala Thr
                485                 490                 495
Ser His Pro Lys Pro Ile Lys Pro Ala Thr Ser His Ala Glu Pro Thr
            500                 505                 510
Thr Ala Asp Tyr Pro Lys Pro Ala Thr Thr Ser His Pro Lys Pro Ala
        515                 520                 525
Ala Ala Asp Asn Pro Glu Leu Ser Ala Ser His Cys Pro Glu Ile Pro
    530                 535                 540
Ala Ile Ala His Pro Val Ser Asp Asp Ser Asp Leu Pro Glu Ser Ala
545                 550                 555                 560
Ser Ser Pro Ala Ala Gly Pro Thr Lys Pro Ala Ala Ser Gln Leu Glu
                565                 570                 575
Ser Asp Thr Ile Ala Asp Leu Pro Asp Pro Thr Val Val Thr Thr Ser
            580                 585                 590
Thr Asn Asp Tyr His Asp Val Val Val Asp Val Glu Asp Asp Pro
        595                 600                 605
Asp Glu Met Ala Val
        610

<210> SEQ ID NO 101
<211> LENGTH: 32
<212> TYPE: DNA
<213> ORGANISM: Artificial Sequence
<220> FEATURE:
<223> OTHER INFORMATION: Novel Sequence

<400> SEQUENCE: 101
tccaagcttc gccatgggac ataacgggag ct                              32

<210> SEQ ID NO 102
<211> LENGTH: 30
<212> TYPE: DNA
<213> ORGANISM: Artificial Sequence
<220> FEATURE:
<223> OTHER INFORMATION: Novel Sequence

<400> SEQUENCE: 102
cgtgaattcc aagaatttac aatccttgct                                 30

<210> SEQ ID NO 103
<211> LENGTH: 1548
<212> TYPE: DNA
<213> ORGANISM: Homo sapiens

<400> SEQUENCE: 103
atgggacata acgggagctg gatctctcca aatgccagcg agccgcacaa cgcgtccggc      60
gccgaggctg cgggtgtgaa ccgcagcgcg ctcggggagt tcggcgaggc gcagctgtac     120
cgccagttca ccaccaccgt gcaggtcgtc atcttcatag gctcgctgct cggaaacttc    180
atggtgttat ggtcaacttg ccgcacaacc gtgttcaaat ctgtcaccaa caggttcatt    240
```

-continued

```
aaaaacctgg cctgctcggg gatttgtgcc agcctggtct gtgtgccctt cgacatcatc    300
ctcagcacca gtcctcactg ttgctggtgg atctacacca tgctcttctg caaggtcgtc    360
aaattttgc acaaagtatt ctgctctgtg accatcctca gcttccctgc tattgctttg     420
gacaggtact actcagtcct ctatccactg gagaggaaaa tatctgatgc caagtcccgt    480
gaactggtga tgtacatctg ggcccatgca gtggtggcca gtgtccctgt gtttgcagta    540
accaatgtgg ctgacatcta tgccacgtcc acctgcacgg aagtctggag caactccttg    600
ggccacctgg tgtacgttct ggtgtataac atcaccacgg tcattgtgcc tgtggtggtg    660
gtgttcctct tcttgatact gatccgacgg gccctgagtg ccagccagaa gaagaaggtc    720
atcatagcag cgctccggac cccacagaac accatctcta ttccctatgc ctcccagcgg    780
gaggccgagc tgcacgccac cctgctctcc atggtgatgg tcttcatctt gtgtagcgtg    840
ccctatgcca ccctggtcgt ctaccagact gtgctcaatg tccctgacac ttccgtcttc    900
ttgctgctca ctgctgtttg gctgcccaaa gtctccctgc tggcaaaccc tgttctcttt    960
cttactgtga acaaatctgt ccgcaagtgc ttgatagggga ccctggtgca actacaccac  1020
cggtacagtc gccgtaatgt ggtcagtaca gggagtggca tggctgaggc cagcctggaa   1080
cccagcatac gctcgggtag ccagctcctg gagatgttcc acattgggca gcagcagatc   1140
tttaagccca cagaggatga ggaagagagt gaggccaagt acattggctc agctgacttc   1200
caggccaagg agatatttag cacctgcctg gagggagagc aggggccaca gtttgcgccc   1260
tctgccccac ccctgagcac agtggactct gtatcccagg tggcaccggc agccctgtg    1320
gaacctgaaa cattccctga taagtattcc ctgcagtttg gctttgggcc ttttgagttg   1380
cctcctcagt ggctctcaga gacccgaaac agcaagaagc ggctgcttcc cccttgggc    1440
aacaccccag aagagctgat ccagacaaag gtgcccaagg taggcagggt ggagcggaag   1500
atgagcagaa acaataaagt gagcattttt ccaaaggtgg attcctag                 1548
```

<210> SEQ ID NO 104
<211> LENGTH: 515
<212> TYPE: PRT
<213> ORGANISM: Homo sapiens

<400> SEQUENCE: 104

```
Met Gly His Asn Gly Ser Trp Ile Ser Pro Asn Ala Ser Glu Pro His
1               5                   10                  15

Asn Ala Ser Gly Ala Glu Ala Ala Gly Val Asn Arg Ser Ala Leu Gly
            20                  25                  30

Glu Phe Gly Glu Ala Gln Leu Tyr Arg Gln Phe Thr Thr Thr Val Gln
        35                  40                  45

Val Val Ile Phe Ile Gly Ser Leu Leu Gly Asn Phe Met Val Leu Trp
    50                  55                  60

Ser Thr Cys Arg Thr Thr Val Phe Lys Ser Val Thr Asn Arg Phe Ile
65                  70                  75                  80

Lys Asn Leu Ala Cys Ser Gly Ile Cys Ala Ser Leu Val Cys Val Pro
                85                  90                  95

Phe Asp Ile Ile Leu Ser Thr Ser Pro His Cys Cys Trp Trp Ile Tyr
            100                 105                 110

Thr Met Leu Phe Cys Lys Val Val Lys Phe Leu His Lys Val Phe Cys
        115                 120                 125

Ser Val Thr Ile Leu Ser Phe Pro Ala Ile Ala Leu Asp Arg Tyr Tyr
    130                 135                 140
```

```
Ser Val Leu Tyr Pro Leu Glu Arg Lys Ile Ser Asp Ala Lys Ser Arg
145                 150                 155                 160

Glu Leu Val Met Tyr Ile Trp Ala His Ala Val Val Ala Ser Val Pro
                165                 170                 175

Val Phe Ala Val Thr Asn Val Ala Asp Ile Tyr Ala Thr Ser Thr Cys
            180                 185                 190

Thr Glu Val Trp Ser Asn Ser Leu Gly His Leu Val Tyr Val Leu Val
        195                 200                 205

Tyr Asn Ile Thr Thr Val Ile Val Pro Val Val Val Phe Leu Phe
210                 215                 220

Leu Ile Leu Ile Arg Arg Ala Leu Ser Ala Ser Gln Lys Lys Val
225                 230                 235                 240

Ile Ile Ala Ala Leu Arg Thr Pro Gln Asn Thr Ile Ser Ile Pro Tyr
                245                 250                 255

Ala Ser Gln Arg Glu Ala Glu Leu His Ala Thr Leu Leu Ser Met Val
            260                 265                 270

Met Val Phe Ile Leu Cys Ser Val Pro Tyr Ala Thr Leu Val Val Tyr
            275                 280                 285

Gln Thr Val Leu Asn Val Pro Asp Thr Ser Val Phe Leu Leu Leu Thr
290                 295                 300

Ala Val Trp Leu Pro Lys Val Ser Leu Leu Ala Asn Pro Val Leu Phe
305                 310                 315                 320

Leu Thr Val Asn Lys Ser Val Arg Lys Cys Leu Ile Gly Thr Leu Val
                325                 330                 335

Gln Leu His His Arg Tyr Ser Arg Arg Asn Val Val Ser Thr Gly Ser
            340                 345                 350

Gly Met Ala Glu Ala Ser Leu Glu Pro Ser Ile Arg Ser Gly Ser Gln
            355                 360                 365

Leu Leu Glu Met Phe His Ile Gly Gln Gln Ile Phe Lys Pro Thr
370                 375                 380

Glu Asp Glu Glu Glu Ser Glu Ala Lys Tyr Ile Gly Ser Ala Asp Phe
385                 390                 395                 400

Gln Ala Lys Glu Ile Phe Ser Thr Cys Leu Glu Gly Glu Gln Gly Pro
                405                 410                 415

Gln Phe Ala Pro Ser Ala Pro Pro Leu Ser Thr Val Asp Ser Val Ser
            420                 425                 430

Gln Val Ala Pro Ala Ala Pro Val Glu Pro Glu Thr Phe Pro Asp Lys
            435                 440                 445

Tyr Ser Leu Gln Phe Gly Phe Gly Pro Phe Glu Leu Pro Pro Gln Trp
450                 455                 460

Leu Ser Glu Thr Arg Asn Ser Lys Lys Arg Leu Leu Pro Pro Leu Gly
465                 470                 475                 480

Asn Thr Pro Glu Glu Leu Ile Gln Thr Lys Val Pro Lys Val Gly Arg
                485                 490                 495

Val Glu Arg Lys Met Ser Arg Asn Asn Lys Val Ser Ile Phe Pro Lys
            500                 505                 510

Val Asp Ser
        515

<210> SEQ ID NO 105
<211> LENGTH: 29
<212> TYPE: DNA
<213> ORGANISM: Artificial Sequence
<220> FEATURE:
<223> OTHER INFORMATION: Novel Sequence
```

<400> SEQUENCE: 105
ggagaattca ctaggcgagg cgctccatc        29

<210> SEQ ID NO 106
<211> LENGTH: 30
<212> TYPE: DNA
<213> ORGANISM: Artificial Sequence
<220> FEATURE:
<223> OTHER INFORMATION: Novel Sequence

<400> SEQUENCE: 106
ggaggatcca ggaaacctta ggccgagtcc        30

<210> SEQ ID NO 107
<211> LENGTH: 1164
<212> TYPE: DNA
<213> ORGANISM: Homo sapiens

<400> SEQUENCE: 107

```
atgaatcggc accatctgca ggatcacttt ctggaaatag acaagaagaa ctgctgtgtg       60
ttccgagatg acttcattgc caaggtgttg ccgccggtgt gggggctgga gtttatcttt      120
gggcttctgg gcaatggcct tgccctgtgg attttctgtt ccacctcaa  gtcctggaaa      180
tccagccgga ttttcctgtt caacctggca gtagctgact ttctactgat catctgcctg      240
ccgttcgtga tggactacta tgtgcggcgt tcagactgga actttgggga catcccttgc      300
cggctggtgc tcttcatgtt tgccatgaac cgccagggca gcatcatctt cctcacggtg      360
gtggcggtag acaggtattt ccgggtggtc catccccacc acgccctgaa caagatctcc      420
aattggacag cagccatcat ctcttgcctt ctgtggggca tcactgttgg cctaacagtc      480
cacctcctga agaagaagtt gctgatccag aatggccctg caaatgtgtg catcagcttc      540
agcatctgcc ataccttccg gtggcacgaa gctatgttcc tcctggagtt cctcctgccc      600
ctgggcatca tcctgttctg ctcagccaga attatctgga gcctgcggca gagacaaatg      660
gaccggcatg ccaagatcaa gagagccatc accttcatca tggtggtggc catcgtctttt    720
gtcatctgct tccttcccag cgtggttgtg cggatccgca tcttctggct cctgcacact      780
tcgggcacgc agaattgtga agtgtaccgc tcggtggacc tggcgttctt tatcactctc      840
agcttcaccc tacatgaacag catgctggac cccgtggtgt actacttctc agcccatcc      900
tttcccaact tcttctccac tttgatcaac cgctgcctcc agaggaagat gacaggtgag      960
ccagataata accgcagcac gagcgtcgag ctcacagggg accccaacaa  accagaggc    1020
gctccagagg cgttaatggc caactccggt gagccatgga gccctctta ctgggcccca    1080
acctcaaata accattccaa gaaggggacat tgtcaccaag aaccagcatc tctggagaaa    1140
cagttgggct gttgcatcga gtaa                                           1164
```

<210> SEQ ID NO 108
<211> LENGTH: 387
<212> TYPE: PRT
<213> ORGANISM: Homo sapiens

<400> SEQUENCE: 108

Met Asn Arg His His Leu Gln Asp His Phe Leu Glu Ile Asp Lys Lys
1               5                   10                  15

Asn Cys Cys Val Phe Arg Asp Asp Phe Ile Ala Lys Val Leu Pro Pro
            20                  25                  30

-continued

Val Leu Gly Leu Glu Phe Ile Phe Gly Leu Leu Gly Asn Gly Leu Ala
        35                  40                  45

Leu Trp Ile Phe Cys Phe His Leu Lys Ser Trp Lys Ser Ser Arg Ile
    50                  55                  60

Phe Leu Phe Asn Leu Ala Val Ala Asp Phe Leu Ile Ile Cys Leu
65                  70                  75                  80

Pro Phe Val Met Asp Tyr Tyr Val Arg Arg Ser Asp Trp Asn Phe Gly
                85                  90                  95

Asp Ile Pro Cys Arg Leu Val Leu Phe Met Phe Ala Met Asn Arg Gln
                100                 105                 110

Gly Ser Ile Ile Phe Leu Thr Val Val Ala Val Asp Arg Tyr Phe Arg
                115                 120                 125

Val Val His Pro His His Ala Leu Asn Lys Ile Ser Asn Trp Thr Ala
                130                 135                 140

Ala Ile Ile Ser Cys Leu Leu Trp Gly Ile Thr Val Gly Leu Thr Val
145                 150                 155                 160

His Leu Leu Lys Lys Lys Leu Leu Ile Gln Asn Gly Pro Ala Asn Val
                165                 170                 175

Cys Ile Ser Phe Ser Ile Cys His Thr Phe Arg Trp His Glu Ala Met
                180                 185                 190

Phe Leu Leu Glu Phe Leu Leu Pro Leu Gly Ile Ile Leu Phe Cys Ser
                195                 200                 205

Ala Arg Ile Ile Trp Ser Leu Arg Gln Arg Gln Met Asp Arg His Ala
                210                 215                 220

Lys Ile Lys Arg Ala Ile Thr Phe Ile Met Val Val Ala Ile Val Phe
225                 230                 235                 240

Val Ile Cys Phe Leu Pro Ser Val Val Arg Ile Arg Ile Phe Trp
                245                 250                 255

Leu Leu His Thr Ser Gly Thr Gln Asn Cys Glu Val Tyr Arg Ser Val
                260                 265                 270

Asp Leu Ala Phe Phe Ile Thr Leu Ser Phe Thr Tyr Met Asn Ser Met
                275                 280                 285

Leu Asp Pro Val Val Tyr Tyr Phe Ser Ser Pro Ser Phe Pro Asn Phe
                290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
                340                 345                 350

Trp Ser Pro Ser Tyr Leu Gly Pro Thr Ser Asn Asn His Ser Lys Lys
                355                 360                 365

Gly His Cys His Gln Glu Pro Ala Ser Leu Glu Lys Gln Leu Gly Cys
                370                 375                 380

Cys Ile Glu
385

<210> SEQ ID NO 109
<211> LENGTH: 37
<212> TYPE: DNA
<213> ORGANISM: Artificial Sequence
<220> FEATURE:
<223> OTHER INFORMATION: Novel Sequence

<400> SEQUENCE: 109

| | |
|---|---|
| accatggctt gcaatggcag tgcggccagg gggcact | 37 |

<210> SEQ ID NO 110
<211> LENGTH: 39
<212> TYPE: DNA
<213> ORGANISM: Artificial Sequence
<220> FEATURE:
<223> OTHER INFORMATION: Novel Sequence

<400> SEQUENCE: 110

| | |
|---|---|
| cgaccaggac aaacagcatc ttggtcactt gtctccggc | 39 |

<210> SEQ ID NO 111
<211> LENGTH: 39
<212> TYPE: DNA
<213> ORGANISM: Artificial Sequence
<220> FEATURE:
<223> OTHER INFORMATION: Novel Sequence

<400> SEQUENCE: 111

| | |
|---|---|
| gaccaagatg ctgtttgtcc tggtcgtggt gtttggcat | 39 |

<210> SEQ ID NO 112
<211> LENGTH: 35
<212> TYPE: DNA
<213> ORGANISM: Artificial Sequence
<220> FEATURE:
<223> OTHER INFORMATION: Novel Sequence

<400> SEQUENCE: 112

| | |
|---|---|
| cggaattcag gatggatcgg tctcttgctg cgcct | 35 |

<210> SEQ ID NO 113
<211> LENGTH: 1212
<212> TYPE: DNA
<213> ORGANISM: Homo sapiens

<400> SEQUENCE: 113

| | |
|---|---|
| atggcttgca atggcagtgc ggccagggg cactttgacc ctgaggactt gaacctgact | 60 |
| gacgaggcac tgagactcaa gtacctgggg ccccagcaga cagagctgtt catgcccatc | 120 |
| tgtgccacat acctgctgat cttcgtggtg ggcgctgtgg gcaatgggct gacctgtctg | 180 |
| gtcatcctgc gccacaaggc catgcgcacg cctaccaact actacctctt cagcctggcc | 240 |
| gtgtcggacc tgctggtgct gctggtgggc ctgccctgg agctctatga gatgtggcac | 300 |
| aactacccct tcctgctggg cgttggtggc tgctatttcc gcacgctact gtttgagatg | 360 |
| gtctgcctgg cctcagtgct caacgtcact gccctgagcg tggaacgcta tgtgccgtg | 420 |
| gtgcacccac tccaggccag gtccatggtg acgcgggccc atgtgcgccg agtgcttggg | 480 |
| gccgtctggg gtcttgccat gctctgctcc ctgcccaaca ccagcctgca cggcatccgg | 540 |
| cagctgcacg tgcctgccg ggcccagtg ccagactcag ctgtttgcat gctggtccgc | 600 |
| ccacgggccc tctacaacat ggtagtgcag accaccgcgc tgctcttctt ctgcctgccc | 660 |
| atgccatca tgagcgtgct ctacctgctc attgggctgc gactgcggcg ggagaggctg | 720 |
| ctgctcatgc aggaggccaa gggcagggg tctgcagcag ccaggtccag atacacctgc | 780 |
| aggctccagc agcacgatcg gggccggaga caagtgacca agatgctgtt tgtcctggtc | 840 |
| gtggtgtttg gcatctgctg ggcccgttc cacgccgacc gcgtcatgtg gagcgtcgtg | 900 |
| tcacagtgga cagatggcct gcacctggcc ttccagcacg tgcacgtcat ctccggcatc | 960 |
| ttcttctacc tgggctcggc ggccaacccc gtgctctata gctcatgtc cagccgcttc | 1020 |

```
cgagagacct tccaggaggc cctgtgcctc gggcctgct gccatcgcct cagaccccgc    1080
cacagctccc acagcctcag caggatgacc acaggcagca ccctgtgtga tgtgggctcc    1140
ctgggcagct gggtccaccc cctggctggg aacgatggcc cagaggcgca gcaagagacc    1200
gatccatcct ga                                                         1212
```

<210> SEQ ID NO 114
<211> LENGTH: 403
<212> TYPE: PRT
<213> ORGANISM: Homo sapiens

<400> SEQUENCE: 114

```
Met Ala Cys Asn Gly Ser Ala Ala Arg Gly His Phe Asp Pro Glu Asp
1               5                   10                  15

Leu Asn Leu Thr Asp Glu Ala Leu Arg Leu Lys Tyr Leu Gly Pro Gln
            20                  25                  30

Gln Thr Glu Leu Phe Met Pro Ile Cys Ala Thr Tyr Leu Leu Ile Phe
        35                  40                  45

Val Val Gly Ala Val Gly Asn Gly Leu Thr Cys Leu Val Ile Leu Arg
    50                  55                  60

His Lys Ala Met Arg Thr Pro Thr Asn Tyr Tyr Leu Phe Ser Leu Ala
65                  70                  75                  80

Val Ser Asp Leu Leu Val Leu Val Gly Leu Pro Leu Glu Leu Tyr
                85                  90                  95

Glu Met Trp His Asn Tyr Pro Phe Leu Leu Gly Val Gly Cys Tyr
                100                 105                 110

Phe Arg Thr Leu Leu Phe Glu Met Val Cys Leu Ala Ser Val Leu Asn
            115                 120                 125

Val Thr Ala Leu Ser Val Glu Arg Tyr Val Ala Val His Pro Leu
    130                 135                 140

Gln Ala Arg Ser Met Val Thr Arg Ala His Val Arg Arg Val Leu Gly
145                 150                 155                 160

Ala Val Trp Gly Leu Ala Met Leu Cys Ser Leu Pro Asn Thr Ser Leu
                165                 170                 175

His Gly Ile Arg Gln Leu His Val Pro Cys Arg Gly Pro Val Pro Asp
            180                 185                 190

Ser Ala Val Cys Met Leu Val Arg Pro Arg Ala Leu Tyr Asn Met Val
        195                 200                 205

Val Gln Thr Thr Ala Leu Leu Phe Phe Cys Leu Pro Met Ala Ile Met
    210                 215                 220

Ser Val Leu Tyr Leu Leu Ile Gly Leu Arg Leu Arg Arg Glu Arg Leu
225                 230                 235                 240

Leu Leu Met Gln Glu Ala Lys Gly Arg Gly Ser Ala Ala Arg Ser
                245                 250                 255

Arg Tyr Thr Cys Arg Leu Gln Gln His Asp Arg Gly Arg Arg Gln Val
            260                 265                 270

Thr Lys Met Leu Phe Val Leu Val Val Phe Gly Ile Cys Trp Ala
        275                 280                 285

Pro Phe His Ala Asp Arg Val Met Trp Ser Val Ser Gln Trp Thr
    290                 295                 300

Asp Gly Leu His Leu Ala Phe Gln His Val His Val Ile Ser Gly Ile
305                 310                 315                 320

Phe Phe Tyr Leu Gly Ser Ala Ala Asn Pro Val Leu Tyr Ser Leu Met
                325                 330                 335
```

```
Ser Ser Arg Phe Arg Glu Thr Phe Gln Glu Ala Leu Cys Leu Gly Ala
            340                 345                 350

Cys Cys His Arg Leu Arg Pro Arg His Ser Ser His Ser Leu Ser Arg
            355                 360                 365

Met Thr Thr Gly Ser Thr Leu Cys Asp Val Gly Ser Leu Gly Ser Trp
    370                 375                 380

Val His Pro Leu Ala Gly Asn Asp Gly Pro Glu Ala Gln Gln Glu Thr
385                 390                 395                 400

Asp Pro Ser

<210> SEQ ID NO 115
<211> LENGTH: 30
<212> TYPE: DNA
<213> ORGANISM: Artificial Sequence
<220> FEATURE:
<223> OTHER INFORMATION: Novel Sequence

<400> SEQUENCE: 115
ggaagcttca ggcccaaaga tggggaacat                                    30

<210> SEQ ID NO 116
<211> LENGTH: 30
<212> TYPE: DNA
<213> ORGANISM: Artificial Sequence
<220> FEATURE:
<223> OTHER INFORMATION: Novel Sequence

<400> SEQUENCE: 116
gtggatccac ccgcggagga cccaggctag                                    30

<210> SEQ ID NO 117
<211> LENGTH: 1098
<212> TYPE: DNA
<213> ORGANISM: Homo sapiens

<400> SEQUENCE: 117
atggggaaca tcactgcaga caactcctcg atgagctgta ccatcgacca taccatccac     60
cagacgctgg ccccggtggt ctatgttacc gtgctggtgg tgggcttccc ggccaactgc    120
ctgtccctct acttcggcta cctgcagatc aaggcccgga cgagctgggc gtgtacctg    180 tgcaacctga cggtggccga cctcttctac atctgctcgc tgcccttctg gctgcagtac    240
gtgctgcagc acgacaactg gtctcacggc gacctgtcct gccaggtgtg cggcatcctc    300
ctgtacgaga acatctacat cagcgtgggc ttcctctgct gcatctccgt ggaccgctac    360
ctggctgtgg cccatccctt ccgcttccac cagttccgga ccctgaaggc ggccgtcggc    420
gtcagcgtgg tcatctgggc caaggagctg ctgaccagca tctacttcct gatgcacgag    480
gaggtcatcg aggacgagaa ccagcaccgc gtgtgctttg agcactaccc catccaggca    540
tggcagcgcg ccatcaacta ctaccgcttc ctggtgggct tcctcttccc catctgcctg    600
ctgctggcgt cctaccaggg catcctgcgc gccgtgcgcc ggagccacgg cacccagaag    660
agccgcaagg accagatcca gcggctggtg ctcagcaccg tggtcatctt cctggcctgc    720
ttcctgccct accacgtgtt gctgctggtg cgcagcgtct gggaggccag ctgcgacttc    780
gccaagggcg ttttcaacgc ctaccacttc tccctcctgc tcaccagctt caactgcgtc    840
gccgaccccg tgctctactg cttcgtcagc gagaccaccc accggacctg gcccgcctc    900 cgcgggggcct gcctggcctt cctcacctgc tccaggaccg gccgggccag ggaggcctac    960
```

```
ccgctgggtg cccccgaggc ctccgggaaa agcggggccc agggtgagga gcccgagctg    1020
ttgaccaagc tccacccggc cttccagacc cctaactcgc agggtcggg cgggttcccc     1080 acgggcaggt tggcctag                                                   1098
```

<210> SEQ ID NO 118
<211> LENGTH: 365
<212> TYPE: PRT
<213> ORGANISM: Homo sapiens

<400> SEQUENCE: 118

```
Met Gly Asn Ile Thr Ala Asp Asn Ser Ser Met Ser Cys Thr Ile Asp
1               5                   10                  15

His Thr Ile His Gln Thr Leu Ala Pro Val Val Tyr Val Thr Val Leu
            20                  25                  30

Val Val Gly Phe Pro Ala Asn Cys Leu Ser Leu Tyr Phe Gly Tyr Leu
        35                  40                  45

Gln Ile Lys Ala Arg Asn Glu Leu Gly Val Tyr Leu Cys Asn Leu Thr
    50                  55                  60

Val Ala Asp Leu Phe Tyr Ile Cys Ser Leu Pro Phe Trp Leu Gln Tyr
65                  70                  75                  80

Val Leu Gln His Asp Asn Trp Ser His Gly Asp Leu Ser Cys Gln Val
            85                  90                  95

Cys Gly Ile Leu Leu Tyr Glu Asn Ile Tyr Ile Ser Val Gly Phe Leu
        100                 105                 110

Cys Cys Ile Ser Val Asp Arg Tyr Leu Ala Val Ala His Pro Phe Arg
    115                 120                 125

Phe His Gln Phe Arg Thr Leu Lys Ala Ala Val Gly Val Ser Val Val
130                 135                 140

Ile Trp Ala Lys Glu Leu Leu Thr Ser Ile Tyr Phe Leu Met His Glu
145                 150                 155                 160

Glu Val Ile Glu Asp Glu Asn Gln His Arg Val Cys Phe Glu His Tyr
            165                 170                 175

Pro Ile Gln Ala Trp Gln Arg Ala Ile Asn Tyr Tyr Arg Phe Leu Val
        180                 185                 190

Gly Phe Leu Phe Pro Ile Cys Leu Leu Leu Ala Ser Tyr Gln Gly Ile
    195                 200                 205

Leu Arg Ala Val Arg Arg Ser His Gly Thr Gln Lys Ser Arg Lys Asp
210                 215                 220

Gln Ile Gln Arg Leu Val Leu Ser Thr Val Val Ile Phe Leu Ala Cys
225                 230                 235                 240

Phe Leu Pro Tyr His Val Leu Leu Leu Val Arg Ser Val Trp Glu Ala
            245                 250                 255

Ser Cys Asp Phe Ala Lys Gly Val Phe Asn Ala Tyr His Phe Ser Leu
        260                 265                 270

Leu Leu Thr Ser Phe Asn Cys Val Ala Asp Pro Val Leu Tyr Cys Phe
    275                 280                 285

Val Ser Glu Thr Thr His Arg Asp Leu Ala Arg Leu Arg Gly Ala Cys
290                 295                 300

Leu Ala Phe Leu Thr Cys Ser Arg Thr Gly Arg Ala Arg Glu Ala Tyr
305                 310                 315                 320

Pro Leu Gly Ala Pro Glu Ala Ser Gly Lys Ser Gly Ala Gln Gly Glu
            325                 330                 335

Glu Pro Glu Leu Leu Thr Lys Leu His Pro Ala Phe Gln Thr Pro Asn
        340                 345                 350
```

```
Ser Pro Gly Ser Gly Gly Phe Pro Thr Gly Arg Leu Ala
        355                 360                 365
```

<210> SEQ ID NO 119
<211> LENGTH: 26
<212> TYPE: DNA
<213> ORGANISM: Artificial Sequence
<220> FEATURE:
<223> OTHER INFORMATION: Novel Sequence

<400> SEQUENCE: 119

| | |
|---|---|
| gacctcgagt ccttctacac ctcatc | 26 |

<210> SEQ ID NO 120
<211> LENGTH: 30
<212> TYPE: DNA
<213> ORGANISM: Artificial Sequence
<220> FEATURE:
<223> OTHER INFORMATION: Novel Sequence

<400> SEQUENCE: 120

| | |
|---|---|
| tgctctagat tccagatagg tgaaaacttg | 30 |

<210> SEQ ID NO 121
<211> LENGTH: 1416
<212> TYPE: DNA
<213> ORGANISM: Homo sapiens

<400> SEQUENCE: 121

| | |
|---|---|
| atggatattc tttgtgaaga aaatacttct ttgagctcaa ctacgaactc cctaatgcaa | 60 |
| ttaaatgatg acaacaggct ctacagtaat gactttaact ccggagaagc taacacttct | 120 |
| gatgcattta actggacagt cgactctgaa aatcgaacca acctttcctg tgaagggtgc | 180 |
| ctctcaccgt cgtgtctctc cttacttcat ctccaggaaa aaaactggtc tgctttactg | 240 |
| acagccgtag tgattattct aactattgct ggaaacatac tcgtcatcat ggcagtgtcc | 300 |
| ctagagaaaa agctgcagaa tgccaccaac tatttcctga tgtcacttgc catagctgat | 360 |
| atgctgctgg gtttccttgt catgcccgtg tccatgttaa ccatcctgta tgggtaccgg | 420 |
| tggcctctgc cgagcaagct ttgtgcagtc tggatttacc tggacgtgct cttctccacg | 480 |
| gcctccatca tgcacctctg cgccatctcg ctggaccgct acgtcgccat ccagaatccc | 540 |
| atccaccaca gccgcttcaa ctccagaact aaggcatttc tgaaaatcat tgctgtttgg | 600 |
| accatatcag taggtatatc catgccaata ccagtctttg gctacaggca cgattcgaag | 660 |
| gtctttaagg aggggagttg cttactcgcc gatgataact ttgtcctgat cggctctttt | 720 |
| gtgtcatttt tcattccctt aaccatcatg gtgatcacct actttctaac tatcaagtca | 780 |
| ctccagaaag aagctacttt gtgtgtaagt gatcttggca cacgggccaa attagcttct | 840 |
| ttcagcttcc tccctcagag ttctttgtct tcagaaaagc tcttccagcg gtcgatccat | 900 |
| agggagccag ggtcctacac aggcaggagg actatgcagt ccatcagcaa tgagcaaaag | 960 |
| gcatgcaagg tgctgggcat cgtcttcttc ctgtttgtgg tgatgtggtg cccttttctt | 1020 |
| atcacaaaca tcatggccgt catctgcaaa gagtcctgca atgaggatgt cattggggcc | 1080 |
| ctgctcaatg tgtttgtttg gatcggttat ctctcttcag cagtcaaccc actagtctac | 1140 |
| acactgttca acaagaccta taggtcagcc ttttcacggt atattcagtg tcagtacaag | 1200 |
| gaaaacaaaa aaccattgca gttaatttta gtgaacacaa taccggcttt ggcctacaag | 1260 |
| tctagccaac ttcaaatggg acaaaaaaag aattcaaagc aagatgccaa gacaacagat | 1320 |

-continued

```
aatgactgct caatggttgc tctaggaaag cagtattctg aagaggcttc taaagacaat      1380
agcgacggag tgaatgaaaa ggtgagctgt gtgtga                               1416
```

<210> SEQ ID NO 122
<211> LENGTH: 471
<212> TYPE: PRT
<213> ORGANISM: Homo sapiens

<400> SEQUENCE: 122

```
Met Asp Ile Leu Cys Glu Glu Asn Thr Ser Leu Ser Ser Thr Thr Asn
1               5                   10                  15

Ser Leu Met Gln Leu Asn Asp Asp Asn Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Gly Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
    290                 295                 300

Ser Tyr Thr Gly Arg Arg Thr Met Gln Ser Ile Ser Asn Glu Gln Lys
305                 310                 315                 320

Ala Cys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350
```

```
Cys Asn Glu Asp Val Ile Gly Ala Leu Leu Asn Val Phe Val Trp Ile
            355                 360                 365

Gly Tyr Leu Ser Ser Ala Val Asn Pro Leu Val Tyr Thr Leu Phe Asn
        370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Asn Ser
            420                 425                 430

Lys Gln Asp Ala Lys Thr Thr Asp Asn Asp Cys Ser Met Val Ala Leu
        435                 440                 445

Gly Lys Gln Tyr Ser Glu Glu Ala Ser Lys Asp Asn Ser Asp Gly Val
    450                 455                 460

Asn Glu Lys Val Ser Cys Val
465                 470
```

```
<210> SEQ ID NO 123
<211> LENGTH: 27
<212> TYPE: DNA
<213> ORGANISM: Artificial Sequence
<220> FEATURE:
<223> OTHER INFORMATION: Novel Sequence

<400> SEQUENCE: 123
gacctcgagg ttgcttaaga ctgaagc                                          27

<210> SEQ ID NO 124
<211> LENGTH: 27
<212> TYPE: DNA
<213> ORGANISM: Artificial Sequence
<220> FEATURE:
<223> OTHER INFORMATION: Novel Sequence

<400> SEQUENCE: 124
atttctagac atatgtagct tgtaccg                                          27

<210> SEQ ID NO 125
<211> LENGTH: 1377
<212> TYPE: DNA
<213> ORGANISM: Homo sapiens

<400> SEQUENCE: 125
atggtgaacc tgaggaatgc ggtgcattca ttccttgtgc acctaattgg cctattggtt      60
tggcaatgtg atatttctgt gagcccagta gcagctatag taactgacat tttcaatacc     120
tccgatggtg gacgcttcaa attcccagac ggggtacaaa actggccagc actttcaatc     180
gtcatcataa taatcatgac aataggtggc aacatccttg tgatcatggc agtaagcatg     240
gaaaagaaac tgcacaatgc caccaattac ttcttaatgt ccctagccat tgctgatatg     300
ctagtgggac tacttgtcat gccccctgtct ctcctggcaa tccttttatga ttatgtctgg     360 ccactaccta gatatttgtg ccccgtctgg atttctttag atgtttttatt ttcaacagcg     420 tccatcatgc acctctgcgc tatatcgctg atcggtatg tagcaatacg taatcctatt     480
gagcatagcc gtttcaattc gcggactaag gccatcatga gagattgctat tgtttgggca     540 atttctatag gtgtatcagt tcctatccct gtgattggac tgagggacga agaaaaggtg     600
ttcgtgaaca acacgacgtg cgtgctcaac gacccaaatt tcgttcttat tgggtccttc     660
gtagctttct tcataccgct gacgattatg gtgattacgt attgcctgac catctacgtt     720
```

```
ctgcgccgac aagctttgat gttactgcac ggccacaccg aggaaccgcc tggactaagt    780
ctggatttcc tgaagtgctg caagaggaat acggccgagg aagagaactc tgcaaaccct    840
aaccaagacc agaacgcacg ccgaagaaag aagaaggaga cgtcctag ggcaccatg        900 caggctatca acaatgaaag aaaagcttcg aaagtccttg ggattgtttt ctttgtgttt    960
ctgatcatgt ggtgcccatt tttcattacc aatattctgt ctgttctttg tgagaagtcc   1020
tgtaaccaaa agctcatgga aaagcttctg aatgtgtttg tttggattgg ctatgtttgt   1080
tcaggaatca atcctctggt gtatactctg ttcaacaaaa tttaccgaag gcattctcc    1140 aactatttgc gttgcaatta taaggtagag aaaaagcctc ctgtcaggca gattccaaga   1200
gttgccgcca ctgctttgtc tgggagggag cttaatgtta acatttatcg gcataccaat   1260
gaaccggtga tcgagaaagc cagtgacaat gagcccggta tagagatgca agttgagaat   1320
ttagagttac cagtaaatcc ctccagtgtg gttagcgaaa ggattagcag tgtgtga      1377
```

<210> SEQ ID NO 126
<211> LENGTH: 458
<212> TYPE: PRT
<213> ORGANISM: Homo sapiens

<400> SEQUENCE: 126

```
Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
            20                  25                  30

Ile Val Thr Asp Ile Phe Asn Thr Ser Asp Gly Gly Arg Phe Lys Phe
        35                  40                  45

Pro Asp Gly Val Gln Asn Trp Pro Ala Leu Ser Ile Val Ile Ile Ile
    50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
    210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255
```

-continued

```
Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
    290                 295                 300

Asn Glu Arg Lys Ala Ser Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
    370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
    450                 455
```

<210> SEQ ID NO 127
<211> LENGTH: 30
<212> TYPE: DNA
<213> ORGANISM: Artificial Sequence
<220> FEATURE:
<223> OTHER INFORMATION: Novel Sequence

<400> SEQUENCE: 127
ggtaagcttg gcagtccacg ccaggccttc                            30

<210> SEQ ID NO 128
<211> LENGTH: 30
<212> TYPE: DNA
<213> ORGANISM: Artificial Sequence
<220> FEATURE:
<223> OTHER INFORMATION: Novel Sequence

<400> SEQUENCE: 128
tccgaattct ctgtagacac aaggctttgg                            30

<210> SEQ ID NO 129
<211> LENGTH: 1068
<212> TYPE: DNA
<213> ORGANISM: Homo sapiens

<400> SEQUENCE: 129
atggatcagt ccctgaatc agtgacagaa aactttgagt cgatgattt ggctgaggcc     60 tgttatattg gggacatcgt ggtctttggg actgtgttcc tgtccatatt ctactccgtc    120
atctttgcca ttggcctggt gggaaatttg ttggtagtgt ttgccctcac caacagcaag    180
aagcccaaga gtgtcaccga catttacctc ctgaacctgg ccttgtctga tctgctgttt    240

```
gtagccactt tgcccttctg gactcactat ttgataaatg aaaagggcct ccacaatgcc      300
atgtgcaaat tcactaccgc cttcttcttc atcggctttt ttggaagcat attcttcatc      360
accgtcatca gcattgatag gtacctggcc atcgtcctgg ccgccaactc catgaacaac      420
cggaccgtgc agcatggcgt caccatcagc ctaggcgtct gggcagcagc cattttggtg      480
gcagcacccc agttcatgtt cacaaagcag aaagaaaatg aatgccttgg tgactacccc      540
gaggtcctcc aggaaatctg gccgtgctc cgcaatgtgg aaacaaattt tcttggcttc      600 ctactcccc tgctcattat gagttattgc tacttcagaa tcatccagac gctgttttcc      660
tgcaagaacc acaagaaagc caaagccatt aaactgatcc ttctggtggt catcgtgttt      720
ttcctcttct ggacacccta caacgttatg attttcctgg agacgcttaa gctctatgac      780
ttctttccca gttgtgacat gaggaaggat ctgaggctgg ccctcagtgt gactgagacg      840
gttgcattta gccattgttg cctgaatcct ctcatctatg catttgctgg ggagaagttc      900
agaagatacc tttaccacct gtatgggaaa tgcctggctg tcctgtgtgg gcgctcagtc      960
cacgttgatt tctcctcatc tgaatcacaa aggagcaggc atggaagtgt tctgagcagc     1020
aattttactt accacacgag tgatggagat gcattgctcc ttctctga                  1068
```

<210> SEQ ID NO 130
<211> LENGTH: 355
<212> TYPE: PRT
<213> ORGANISM: Homo sapiens

<400> SEQUENCE: 130

```
Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Phe Gly Thr Val
                20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Leu Leu Pro Leu Ile Met Ser
        195                 200                 205

Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
```

```
225                 230                 235                 240
Phe Leu Phe Trp Thr Pro Tyr Asn Val Met Ile Phe Leu Glu Thr Leu
                245                 250                 255

Lys Leu Tyr Asp Phe Pro Ser Cys Asp Met Arg Lys Asp Leu Arg
            260                 265                 270

Leu Ala Leu Ser Val Thr Glu Thr Val Ala Phe Ser His Cys Cys Leu
            275                 280                 285

Asn Pro Leu Ile Tyr Ala Phe Ala Gly Glu Lys Phe Arg Arg Tyr Leu
            290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

<210> SEQ ID NO 131
<211> LENGTH: 32
<212> TYPE: DNA
<213> ORGANISM: Artificial Sequence
<220> FEATURE:
<223> OTHER INFORMATION: Novel Sequence

<400> SEQUENCE: 131
gatctccagt aggcataagt ggacaattct gg                              32

<210> SEQ ID NO 132
<211> LENGTH: 30
<212> TYPE: DNA
<213> ORGANISM: Artificial Sequence
<220> FEATURE:
<223> OTHER INFORMATION: Novel Sequence

<400> SEQUENCE: 132
ctccttcggt cctcctatcg ttgtcagaag                                 30

<210> SEQ ID NO 133
<211> LENGTH: 30
<212> TYPE: DNA
<213> ORGANISM: Artificial Sequence
<220> FEATURE:
<223> OTHER INFORMATION: Novel Sequence

<400> SEQUENCE: 133
agaaggccaa gatcgcgcgg ctggccctca                                 30

<210> SEQ ID NO 134
<211> LENGTH: 30
<212> TYPE: DNA
<213> ORGANISM: Artificial Sequence
<220> FEATURE:
<223> OTHER INFORMATION: Novel Sequence

<400> SEQUENCE: 134
cggcgccacc gcacgaaaaa gctcatcttc                                 30

<210> SEQ ID NO 135
<211> LENGTH: 33
<212> TYPE: DNA
<213> ORGANISM: Artificial Sequence
```

-continued

```
<220> FEATURE:
<223> OTHER INFORMATION: Novel Sequence

<400> SEQUENCE: 135
gccaagaagc gggtgaagtt cctggtggtg gca                                    33

<210> SEQ ID NO 136
<211> LENGTH: 30
<212> TYPE: DNA
<213> ORGANISM: Artificial Sequence
<220> FEATURE:
<223> OTHER INFORMATION: Novel Sequence

<400> SEQUENCE: 136
caggcggaag gtgaaagtcc tggtcctcgt                                        30

<210> SEQ ID NO 137
<211> LENGTH: 33
<212> TYPE: DNA
<213> ORGANISM: Artificial Sequence
<220> FEATURE:
<223> OTHER INFORMATION: Novel Sequence

<400> SEQUENCE: 137
cggcgcctgc gggccaagcg gctggtggtg gtg                                    33

<210> SEQ ID NO 138
<211> LENGTH: 31
<212> TYPE: DNA
<213> ORGANISM: Artificial Sequence
<220> FEATURE:
<223> OTHER INFORMATION: Novel Sequence

<400> SEQUENCE: 138
ccaagcacaa agccaagaaa gtgaccatca c                                      31

<210> SEQ ID NO 139
<211> LENGTH: 30
<212> TYPE: DNA
<213> ORGANISM: Artificial Sequence
<220> FEATURE:
<223> OTHER INFORMATION: Novel Sequence

<400> SEQUENCE: 139
gcgccggcgc accaaatgct tgctggtggt                                        30

<210> SEQ ID NO 140
<211> LENGTH: 41
<212> TYPE: DNA
<213> ORGANISM: Artificial Sequence
<220> FEATURE:
<223> OTHER INFORMATION: Novel Sequence

<400> SEQUENCE: 140
caaaaagctg aagaaatcta agaagatcat ctttattgtc g                           41

<210> SEQ ID NO 141
<211> LENGTH: 30
<212> TYPE: DNA
<213> ORGANISM: Artificial Sequence
<220> FEATURE:
<223> OTHER INFORMATION: Novel Sequence

<400> SEQUENCE: 141
caagaccaag gcaaaacgca tgatcgccat                                        30
```

<210> SEQ ID NO 142
<211> LENGTH: 30
<212> TYPE: DNA
<213> ORGANISM: Artificial Sequence
<220> FEATURE:
<223> OTHER INFORMATION: Novel Sequence

<400> SEQUENCE: 142
gtcaaggaga agtccaaaag gatcatcatc                                    30

<210> SEQ ID NO 143
<211> LENGTH: 30
<212> TYPE: DNA
<213> ORGANISM: Artificial Sequence
<220> FEATURE:
<223> OTHER INFORMATION: Novel Sequence

<400> SEQUENCE: 143
cgccgcgtgc gggccaagca gctcctgctc                                    30

<210> SEQ ID NO 144
<211> LENGTH: 33
<212> TYPE: DNA
<213> ORGANISM: Artificial Sequence
<220> FEATURE:
<223> OTHER INFORMATION: Novel Sequence

<400> SEQUENCE: 144
cctgataagc gctataaaat ggtcctgttt cga                                33

<210> SEQ ID NO 145
<211> LENGTH: 36
<212> TYPE: DNA
<213> ORGANISM: Artificial Sequence
<220> FEATURE:
<223> OTHER INFORMATION: Novel Sequence

<400> SEQUENCE: 145
gaaagacaaa agagagtcaa gaggatgtct ttattg                             36

<210> SEQ ID NO 146
<211> LENGTH: 33
<212> TYPE: DNA
<213> ORGANISM: Artificial Sequence
<220> FEATURE:
<223> OTHER INFORMATION: Novel Sequence

<400> SEQUENCE: 146
cggagaaaga gggtgaaacg cacagccatc gcc                                33

<210> SEQ ID NO 147
<211> LENGTH: 30
<212> TYPE: DNA
<213> ORGANISM: Artificial Sequence
<220> FEATURE:
<223> OTHER INFORMATION: Novel Sequence

<400> SEQUENCE: 147
aagcttcagc gggccaaggc actggtcacc                                    30

<210> SEQ ID NO 148
<211> LENGTH: 30
<212> TYPE: DNA
<213> ORGANISM: Artificial Sequence
<220> FEATURE:
<223> OTHER INFORMATION: Novel Sequence

<400> SEQUENCE: 148
cagcggcaga aggcaaaaag ggtggccatc                                30

<210> SEQ ID NO 149
<211> LENGTH: 30
<212> TYPE: DNA
<213> ORGANISM: Artificial Sequence
<220> FEATURE:
<223> OTHER INFORMATION: Novel Sequence

<400> SEQUENCE: 149
cggcagaagg cgaagcgcat gatcctcgcg                                30

<210> SEQ ID NO 150
<211> LENGTH: 30
<212> TYPE: DNA
<213> ORGANISM: Artificial Sequence
<220> FEATURE:
<223> OTHER INFORMATION: Novel Sequence

<400> SEQUENCE: 150
gagcgcaaca aggccaaaaa ggtgatcatc                                30

<210> SEQ ID NO 151
<211> LENGTH: 39
<212> TYPE: DNA
<213> ORGANISM: Artificial Sequence
<220> FEATURE:
<223> OTHER INFORMATION: Novel Sequence

<400> SEQUENCE: 151
ggtgtaaaca aaaggctaa aaacacaatt attcttatt                       39

<210> SEQ ID NO 152
<211> LENGTH: 27
<212> TYPE: DNA
<213> ORGANISM: Artificial Sequence
<220> FEATURE:
<223> OTHER INFORMATION: Novel Sequence

<400> SEQUENCE: 152
gagagccagc tcaagagcac cgtggtg                                   27

<210> SEQ ID NO 153
<211> LENGTH: 30
<212> TYPE: DNA
<213> ORGANISM: Artificial Sequence
<220> FEATURE:
<223> OTHER INFORMATION: Novel Sequence

<400> SEQUENCE: 153
ccacaagcaa accagaaaaa tgctggctgt                                30

<210> SEQ ID NO 154
<211> LENGTH: 30
<212> TYPE: DNA
<213> ORGANISM: Artificial Sequence
<220> FEATURE:
<223> OTHER INFORMATION: Novel Sequence

<400> SEQUENCE: 154
catcaagtgt atcatgtgcc aagtacgccc                                30

<210> SEQ ID NO 155

<210> SEQ ID NO 155
<211> LENGTH: 34
<212> TYPE: DNA
<213> ORGANISM: Artificial Sequence
<220> FEATURE:
<223> OTHER INFORMATION: Novel Sequence

<400> SEQUENCE: 155
ctagagagtc agatgaagtg tacagtagtg gcac        34

<210> SEQ ID NO 156
<211> LENGTH: 36
<212> TYPE: DNA
<213> ORGANISM: Artificial Sequence
<220> FEATURE:
<223> OTHER INFORMATION: Novel Sequence

<400> SEQUENCE: 156
cggacaaaag tgaaaactaa aaagatgttc ctcatt      36

<210> SEQ ID NO 157
<211> LENGTH: 33
<212> TYPE: DNA
<213> ORGANISM: Artificial Sequence
<220> FEATURE:
<223> OTHER INFORMATION: Novel Sequence

<400> SEQUENCE: 157
gctgaggttc gcaataaact aaccatgttt gtg         33

<210> SEQ ID NO 158
<211> LENGTH: 29
<212> TYPE: DNA
<213> ORGANISM: Artificial Sequence
<220> FEATURE:
<223> OTHER INFORMATION: Novel Sequence

<400> SEQUENCE: 158
gggaggccga gctgaaagcc accctgctc              29

<210> SEQ ID NO 159
<211> LENGTH: 31
<212> TYPE: DNA
<213> ORGANISM: Artificial Sequence
<220> FEATURE:
<223> OTHER INFORMATION: Novel Sequence

<400> SEQUENCE: 159
caagatcaag agagccaaaa ccttcatcat g           31

<210> SEQ ID NO 160
<211> LENGTH: 31
<212> TYPE: DNA
<213> ORGANISM: Artificial Sequence
<220> FEATURE:
<223> OTHER INFORMATION: Novel Sequence

<400> SEQUENCE: 160
ccggagacaa gtgaagaaga tgctgtttgt c           31

<210> SEQ ID NO 161
<211> LENGTH: 30
<212> TYPE: DNA
<213> ORGANISM: Artificial Sequence
<220> FEATURE:
<223> OTHER INFORMATION: Novel Sequence

<400> SEQUENCE: 161

```
gcaaggacca gatcaagcgg ctggtgctca                                       30
```

<210> SEQ ID NO 162
<211> LENGTH: 34
<212> TYPE: DNA
<213> ORGANISM: Artificial Sequence
<220> FEATURE:
<223> OTHER INFORMATION: Novel Sequence

<400> SEQUENCE: 162

```
caagaaagcc aaagccaaga aactgatcct tctg                                  34
```

<210> SEQ ID NO 163
<211> LENGTH: 1068
<212> TYPE: DNA
<213> ORGANISM: Homo sapiens

<400> SEQUENCE: 163

```
atggaagatt tggaggaaac attatttgaa gaatttgaaa actattccta tgacctagac      60
tattactctc tggagtctga tttggaggag aaagtccagc tgggagttgt tcactgggtc     120
tccctggtgt tatattgttt ggcttttgtt ctgggaattc aggaaatgc  catcgtcatt     180
tggttcacgg ggctcaagtg gaagaagaca gtcaccactc tgtggttcct caatctagcc     240
attgcggatt tcatttttct tctctttctg ccccctgtaca tctcctatgt ggccatgaat     300
ttccactggc cctttggcat ctggctgtgc aaagccaatt ccttcactgc ccagttgaac     360
atgtttgcca gtgttttttt cctgacagtg atcagcctgg accactatat ccacttgatc     420
catcctgtct tatctcatcg gcatcgaacc ctcaagaact ctctgattgt cattatattc     480
atctggcttt tggcttctct aattggcggt cctgccctgt acttccggga cactgtggag     540
ttcaataatc atactctttg ctataacaat tttcagaagc atgatcctga cctcactttg     600
atcaggcacc atgttctgac ttgggtgaaa tttatcattg gctatctctt cccttttgcta    660
acaatgagta tttgctactt gtgtctcatc ttcaaggtga agaagcgaac agtcctgatc     720
tccagtaggc ataagtggac aattctggtt gtggttgtgg cctttgtggt ttgctggact     780
ccttatcacc tgtttagcat tgggagctc  accattcacc acaatagcta ttcccaccat     840
gtgatgcagg ctgaatcccc cctctccact ggtttggcat tcctcaatag ttgcttgaac     900
cccatccttt atgtcctaat tagtaagaag ttccaagctc gcttccggtc ctcagttgct     960
gagatactca gtacacact  gtgggaagtc agctgttctg gcacagtgag tgaacagctc    1020
aggaactcag aaaccaagaa tctgtgtctc ctggaaacag ctcaataa                 1068
```

<210> SEQ ID NO 164
<211> LENGTH: 355
<212> TYPE: PRT
<213> ORGANISM: Homo sapiens

<400> SEQUENCE: 164

```
Met Glu Asp Leu Glu Glu Thr Leu Phe Glu Glu Phe Glu Asn Tyr Ser
1               5                   10                  15

Tyr Asp Leu Asp Tyr Tyr Ser Leu Glu Ser Asp Leu Glu Glu Lys Val
            20                  25                  30

Gln Leu Gly Val Val His Trp Val Ser Leu Val Leu Tyr Cys Leu Ala
        35                  40                  45

Phe Val Leu Gly Ile Pro Gly Asn Ala Ile Val Ile Trp Phe Thr Gly
    50                  55                  60
```

-continued

```
Leu Lys Trp Lys Lys Thr Val Thr Thr Leu Trp Phe Leu Asn Leu Ala
 65                  70                  75                  80

Ile Ala Asp Phe Ile Phe Leu Leu Phe Leu Pro Leu Tyr Ile Ser Tyr
                 85                  90                  95

Val Ala Met Asn Phe His Trp Pro Phe Gly Ile Trp Leu Cys Lys Ala
            100                 105                 110

Asn Ser Phe Thr Ala Gln Leu Asn Met Phe Ala Ser Val Phe Phe Leu
        115                 120                 125

Thr Val Ile Ser Leu Asp His Tyr Ile His Leu Ile His Pro Val Leu
    130                 135                 140

Ser His Arg His Arg Thr Leu Lys Asn Ser Leu Ile Val Ile Ile Phe
145                 150                 155                 160

Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Leu Ile Arg His His Val Leu Thr Trp
        195                 200                 205

Val Lys Phe Ile Ile Gly Tyr Leu Phe Pro Leu Leu Thr Met Ser Ile
    210                 215                 220

Cys Tyr Leu Cys Leu Ile Phe Lys Val Lys Lys Arg Thr Val Leu Ile
225                 230                 235                 240

Ser Ser Arg His Lys Trp Thr Ile Leu Val Val Val Ala Phe Val
                245                 250                 255

Val Cys Trp Thr Pro Tyr His Leu Phe Ser Ile Trp Glu Leu Thr Ile
            260                 265                 270

His His Asn Ser Tyr Ser His His Val Met Gln Ala Gly Ile Pro Leu
        275                 280                 285

Ser Thr Gly Leu Ala Phe Leu Asn Ser Cys Leu Asn Pro Ile Leu Tyr
    290                 295                 300

Val Leu Ile Ser Lys Lys Phe Gln Ala Arg Phe Arg Ser Ser Val Ala
305                 310                 315                 320

Glu Ile Leu Lys Tyr Thr Leu Trp Glu Val Ser Cys Ser Gly Thr Val
                325                 330                 335

Ser Glu Gln Leu Arg Asn Ser Glu Thr Lys Asn Leu Cys Leu Leu Glu
            340                 345                 350

Thr Ala Gln
        355
```

<210> SEQ ID NO 165
<211> LENGTH: 1089
<212> TYPE: DNA
<213> ORGANISM: Homo sapiens

<400> SEQUENCE: 165

```
atgggcaacc acacgtggga gggctgccac gtggactcgc gcgtggacca cctctttccg    60
ccatccctct acatctttgt catcggcgtg gggctgccca ccaactgcct ggctctgtgg   120
gcggcctacc gccaggtgca acagcgcaac gagctgggcg tctacctgat gaacctcagc   180
atcgccgacc tgctgtacat ctgcacgctg ccgctgtggg tggactactt cctgcaccac   240
gacaactgga tccacggccc cgggtcctgc aagctctttg ggttcatctt ctacaccaat   300
atctacatca gcatcgcctt cctgtgctgc atctcggtgg accgctacct ggctgtggcc   360
cacccactcc gcttcgcccg cctgcgccgc gtcaagaccg ccgtggccgt gagctccgtg   420
```

-continued

```
gtctgggcca cggagctggg cgccaactcg gcgcccctgt tccatgacga gctcttccga    480
gaccgctaca accacacctt ctgctttgag aagttcccca tggaaggctg gtggcctgg     540 atgaacctct atcgggtgtt cgtgggcttc ctcttcccgt gggcgctcat gctgctgtcg    600
taccggggca tcctgcgggc cgtgcggggc agcgtgtcca ccgagcgcca ggagaaggcc    660
aagatcgcgc ggctggccct cagcctcatc gccatcgtgc tggtctgctt tgcgccctat    720
cacgtgctct tgctgtcccg cagcgccatc tacctgggcc gccctgggaa ctgcggcttc    780
gaggagcgcg tcttttctgc ataccacagc tcactggctt tcaccagcct caactgtgtg    840
gcggacccca tcctctactg cctggtcaac gagggcgccc gcagcgatgt ggccaaggcc    900
ctgcacaacc tgctccgctt tctggccagc gacaagcccc aggagatggc caatgcctcg    960
ctcaccctgg agaccccact cacctccaag aggaacagca cagccaaagc catgactggc   1020
agctgggcgg ccactccgcc ttcccagggg gaccaggtgc agctgaagat gctgccgcca   1080
gcacaatga                                                           1089
```

<210> SEQ ID NO 166
<211> LENGTH: 362
<212> TYPE: PRT
<213> ORGANISM: Homo sapiens

<400> SEQUENCE: 166

```
Met Gly Asn His Thr Trp Glu Gly Cys His Val Asp Ser Arg Val Asp
1               5                   10                  15
His Leu Phe Pro Pro Ser Leu Tyr Ile Phe Val Ile Gly Val Gly Leu
                20                  25                  30
Pro Thr Asn Cys Leu Ala Leu Trp Ala Ala Tyr Arg Gln Val Gln Gln
            35                  40                  45
Arg Asn Glu Leu Gly Val Tyr Leu Met Asn Leu Ser Ile Ala Asp Leu
        50                  55                  60
Leu Tyr Ile Cys Thr Leu Pro Leu Trp Val Asp Tyr Phe Leu His His
65                  70                  75                  80
Asp Asn Trp Ile His Gly Pro Gly Ser Cys Lys Leu Phe Gly Phe Ile
                85                  90                  95
Phe Tyr Thr Asn Ile Tyr Ile Ser Ile Ala Phe Leu Cys Cys Ile Ser
                100                 105                 110
Val Asp Arg Tyr Leu Ala Val Ala His Pro Leu Arg Phe Ala Arg Leu
            115                 120                 125
Arg Arg Val Lys Thr Ala Val Ala Val Ser Ser Val Val Trp Ala Thr
        130                 135                 140
Glu Leu Gly Ala Asn Ser Ala Pro Leu Phe His Asp Glu Leu Phe Arg
145                 150                 155                 160
Asp Arg Tyr Asn His Thr Phe Cys Phe Glu Lys Phe Pro Met Glu Gly
                165                 170                 175
Trp Val Ala Trp Met Asn Leu Tyr Arg Val Phe Val Gly Phe Leu Phe
                180                 185                 190
Pro Trp Ala Leu Met Leu Leu Ser Tyr Arg Gly Ile Leu Arg Ala Val
            195                 200                 205
Arg Gly Ser Val Ser Thr Glu Arg Gln Glu Lys Ala Lys Ile Ala Arg
        210                 215                 220
Leu Ala Leu Ser Leu Ile Ala Ile Val Leu Val Cys Phe Ala Pro Tyr
225                 230                 235                 240
His Val Leu Leu Leu Ser Arg Ser Ala Ile Tyr Leu Gly Arg Pro Trp
                245                 250                 255
```

```
Asp Cys Gly Phe Glu Glu Arg Val Phe Ser Ala Tyr His Ser Ser Leu
            260                 265                 270

Ala Phe Thr Ser Leu Asn Cys Val Ala Asp Pro Ile Leu Tyr Cys Leu
        275                 280                 285

Val Asn Glu Gly Ala Arg Ser Asp Val Ala Lys Ala Leu His Asn Leu
    290                 295                 300

Leu Arg Phe Leu Ala Ser Asp Lys Pro Gln Glu Met Ala Asn Ala Ser
305                 310                 315                 320

Leu Thr Leu Glu Thr Pro Leu Thr Ser Lys Arg Asn Ser Thr Ala Lys
            325                 330                 335

Ala Met Thr Gly Ser Trp Ala Ala Thr Pro Pro Ser Gln Gly Asp Gln
            340                 345                 350

Val Gln Leu Lys Met Leu Pro Pro Ala Gln
        355                 360
```

```
<210> SEQ ID NO 167
<211> LENGTH: 1002
<212> TYPE: DNA
<213> ORGANISM: Homo sapiens

<400> SEQUENCE: 167
atggagtcct caggcaaccc agagagcacc acctttttt actatgacct tcagagccag      60
ccgtgtgaga accaggcctg ggtctttgct accctcgcca ccactgtcct gtactgcctg    120
gtgtttctcc tcagcctagt gggcaacagc ctggtcctgt gggtcctggt gaagtatgag    180
agcctggagt ccctcaccaa catcttcatc ctcaacctgt gcctctcaga cctggtgttc    240
gcctgcttgt tgcctgtgtg gatctcccca taccactggg gctgggtgct gggagacttc    300
ctctgcaaac tcctcaatat gatcttctcc atcagcctct acagcagcat cttcttcctg    360
accatcatga ccatccaccg ctacctgtcg gtagtgagcc cctctccac cctgcgcgtc    420
cccaccctcc gctgccgggt gctggtgacc atggctgtgt gggtagccag catcctgtcc    480
tccatcctcg acaccatctt ccacaaggtg ctttcttcgg ctgtgattat ttccgaactc    540
acgtggtacc tcacctccgt ctaccagcac aacctcttct cctgctgtc cctggggatt    600
atcctgttct gctacgtgga gatcctcagg accctgttcc gctcacgctc caagcggcgc    660
caccgcacga aaaagctcat cttcgccatc gtggtggcct acttcctcag ctggggtccc    720
tacaacttca ccctgttct gcagacgctg tttcggaccc agatcatccg gagctgcgag    780
gccaaacagc agctagaata cgccctgctc atctgccgca acctcgcctt ctcccactgc    840
tgctttaacc cggtgctcta tgtcttcgtg ggggtcaagt tccgcacaca cctgaaacat    900
gttctccggc agttctggtt ctgccggctg caggcaccca gcccagcctc gatcccccac    960
tcccctggtg ccttcgccta tgagggcgcc tccttctact ga                      1002
```

```
<210> SEQ ID NO 168
<211> LENGTH: 333
<212> TYPE: PRT
<213> ORGANISM: Homo sapiens

<400> SEQUENCE: 168

Met Glu Ser Ser Gly Asn Pro Glu Ser Thr Thr Phe Phe Tyr Tyr Asp
1               5                   10                  15

Leu Gln Ser Gln Pro Cys Glu Asn Gln Ala Trp Val Phe Ala Thr Leu
            20                  25                  30

Ala Thr Thr Val Leu Tyr Cys Leu Val Phe Leu Leu Ser Leu Val Gly
```

```
                35                  40                  45
Asn Ser Leu Val Leu Trp Val Leu Val Lys Tyr Glu Ser Leu Glu Ser
         50                  55                  60
Leu Thr Asn Ile Phe Ile Leu Asn Leu Cys Leu Ser Asp Leu Val Phe
 65                  70                  75                  80
Ala Cys Leu Leu Pro Val Trp Ile Ser Pro Tyr His Trp Gly Trp Val
                 85                  90                  95
Leu Gly Asp Phe Leu Cys Lys Leu Leu Asn Met Ile Phe Ser Ile Ser
                100                 105                 110
Leu Tyr Ser Ser Ile Phe Phe Leu Thr Ile Met Thr Ile His Arg Tyr
            115                 120                 125
Leu Ser Val Val Ser Pro Leu Ser Thr Leu Arg Val Pro Thr Leu Arg
        130                 135                 140
Cys Arg Val Leu Val Thr Met Ala Val Trp Val Ala Ser Ile Leu Ser
145                 150                 155                 160
Ser Ile Leu Asp Thr Ile Phe His Lys Val Leu Ser Ser Gly Cys Asp
                165                 170                 175
Tyr Ser Glu Leu Thr Trp Tyr Leu Thr Ser Val Tyr Gln His Asn Leu
            180                 185                 190
Phe Phe Leu Leu Ser Leu Gly Ile Ile Leu Phe Cys Tyr Val Glu Ile
        195                 200                 205
Leu Arg Thr Leu Phe Arg Ser Arg Ser Lys Arg Arg His Arg Thr Lys
    210                 215                 220
Lys Leu Ile Phe Ala Ile Val Ala Tyr Phe Leu Ser Trp Gly Pro
225                 230                 235                 240
Tyr Asn Phe Thr Leu Phe Leu Gln Thr Leu Phe Arg Thr Gln Ile Ile
                245                 250                 255
Arg Ser Cys Glu Ala Lys Gln Gln Leu Glu Tyr Ala Leu Leu Ile Cys
            260                 265                 270
Arg Asn Leu Ala Phe Ser His Cys Cys Phe Asn Pro Val Leu Tyr Val
        275                 280                 285
Phe Val Gly Val Lys Phe Arg Thr His Leu Lys His Val Leu Arg Gln
    290                 295                 300
Phe Trp Phe Cys Arg Leu Gln Ala Pro Ser Pro Ala Ser Ile Pro His
305                 310                 315                 320
Ser Pro Gly Ala Phe Ala Tyr Glu Gly Ala Ser Phe Tyr
                325                 330

<210> SEQ ID NO 169
<211> LENGTH: 987
<212> TYPE: DNA
<213> ORGANISM: Homo sapiens

<400> SEQUENCE: 169
atggacaacg cctcgttctc ggagccctgg cccgccaacg catcgggccc ggaccccggcg    60 ctgagctgct ccaacgcgtc gactctggcg ccgctgccgg cgccgctggc ggtggctgta   120
ccagttgtct acgcggtgat ctgcgccgtg gtctggcgg gcaactccgc cgtgctgtac    180
gtgttgctgc gggcgccccg catgaagacc gtcaccaacc tgttcatcct caacctggcc   240
atcgccgacg agctcttcac gctggtgctg cccatcaaca tcgccgactt cctgctgcgg   300
cagtggccct tcggggagct catgtgcaag ctcatcgtgg ctatcgacca gtacaacacc   360
ttctccagcc tctacttcct caccgtcatg agcgccgacc gctacctggt ggtgttggcc   420
actgcggagt cgcgccgggt ggccggccgc acctacagcg ccgcgcgcgc ggtgagcctg    480
```

-continued

```
gccgtgtggg ggatcgtcac actcgtcgtg ctgcccttcg cagtcttcgc ccggctagac    540
gacgagcagg gccggcgcca gtgcgtgcta gtctttccgc agcccgaggc cttctggtgg    600
cgcgcgagcc gcctctacac gctcgtgctg ggcttcgcca tccccgtgtc caccatctgt    660
gtcctctata ccaccctgct gtgccggctg catgccatgc ggctggacag ccacgccaag    720
gccctggagc gcgccaagaa gcgggtgaag ttcctggtgg tggcaatcct ggcggtgtgc    780
ctcctctgct ggacgcccta ccacctgagc accgtggtgg cgctcaccac cgacctcccg    840
cagacgccgc tggtcatcgc tatctcctac ttcatcacca gcctgacgta cgccaacagc    900
tgcctcaacc ccttcctcta cgccttcctg gacgccagct ccgcaggaa cctccgccag    960 ctgataactt gccgcgcggc agcctga                                         987
```

<210> SEQ ID NO 170
<211> LENGTH: 328
<212> TYPE: PRT
<213> ORGANISM: Homo sapiens
<400> SEQUENCE: 170

```
Met Asp Asn Ala Ser Phe Ser Glu Pro Trp Pro Ala Asn Ala Ser Gly
  1               5                  10                  15

Pro Asp Pro Ala Leu Ser Cys Ser Asn Ala Ser Thr Leu Ala Pro Leu
             20                  25                  30

Pro Ala Pro Leu Ala Val Ala Val Pro Val Val Tyr Ala Val Ile Cys
         35                  40                  45

Ala Val Gly Leu Ala Gly Asn Ser Ala Val Leu Tyr Val Leu Leu Arg
     50                  55                  60

Ala Pro Arg Met Lys Thr Val Thr Asn Leu Phe Ile Leu Asn Leu Ala
 65                  70                  75                  80

Ile Ala Asp Glu Leu Phe Thr Leu Val Leu Pro Ile Asn Ile Ala Asp
                 85                  90                  95

Phe Leu Leu Arg Gln Trp Pro Phe Gly Glu Leu Met Cys Lys Leu Ile
            100                 105                 110

Val Ala Ile Asp Gln Tyr Asn Thr Phe Ser Ser Leu Tyr Phe Leu Thr
        115                 120                 125

Val Met Ser Ala Asp Arg Tyr Leu Val Val Leu Ala Thr Ala Glu Ser
    130                 135                 140

Arg Arg Val Ala Gly Arg Thr Tyr Ser Ala Ala Arg Ala Val Ser Leu
145                 150                 155                 160

Ala Val Trp Gly Ile Val Thr Leu Val Val Leu Pro Phe Ala Val Phe
                165                 170                 175

Ala Arg Leu Asp Asp Glu Gln Gly Arg Arg Gln Cys Val Leu Val Phe
            180                 185                 190

Pro Gln Pro Glu Ala Phe Trp Trp Arg Ala Ser Arg Leu Tyr Thr Leu
        195                 200                 205

Val Leu Gly Phe Ala Ile Pro Val Ser Thr Ile Cys Val Leu Tyr Thr
    210                 215                 220

Thr Leu Leu Cys Arg Leu His Ala Met Arg Leu Asp Ser His Ala Lys
225                 230                 235                 240

Ala Leu Glu Arg Ala Lys Lys Arg Val Lys Phe Leu Val Val Ala Ile
                245                 250                 255

Leu Ala Val Cys Leu Leu Cys Trp Thr Pro Tyr His Leu Ser Thr Val
            260                 265                 270

Val Ala Leu Thr Thr Asp Leu Pro Gln Thr Pro Leu Val Ile Ala Ile
```

| | | | | 275 | | | | | 280 | | | | | 285 | | |

Ser Tyr Phe Ile Thr Ser Leu Thr Tyr Ala Asn Ser Cys Leu Asn Pro
            290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325

<210> SEQ ID NO 171
<211> LENGTH: 1002
<212> TYPE: DNA
<213> ORGANISM: Homo sapiens

<400> SEQUENCE: 171

| | | | | | |
|---|---|---|---|---|---|
| atgcaggccg | ctgggcaccc | agagcccctt | gacagcaggg | gctccttctc | cctccccacg | 60 |
| atgggtgcca | acgtctctca | ggacaatggc | actggccaca | atgccacctt | ctccgagcca | 120 |
| ctgccgttcc | tctatgtgct | cctgcccgcc | gtgtactccg | ggatctgtgc | tgtggggctg | 180 |
| actggcaaca | cggccgtcat | ccttgtaatc | ctaaggcgc | ccaagatgaa | gacggtgacc | 240 |
| aacgtgttca | tcctgaacct | ggccgtcgcc | gacgggctct | tcacgctggt | actgcctgtc | 300 |
| aacatcgcgg | agcacctgct | gcagtactgg | cccttcgggg | agctgctctg | caagctggtg | 360 |
| ctggccgtcg | accactacaa | catcttctcc | agcatctact | tcctagccgt | gatgagcgtg | 420 |
| gaccgatacc | tggtggtgct | ggccaccgtg | aggtcccgcc | acatgccctg | cgcacctac | 480 |
| cgggggggcga | aggtcgccag | cctgtgtgtc | tggctgggcg | tcacggtcct | ggttctgccc | 540 |
| ttcttctctt | tcgctggcgt | ctacagcaac | gagctgcagg | tcccaagctg | tgggctgagc | 600 |
| ttcccgtggc | ccgagcaggt | ctggttcaag | gccagccgtg | tctacacgtt | ggtcctgggc | 660 |
| ttcgtgctgc | ccgtgtgcac | catctgtgtg | ctctacacag | acctcctgcg | caggctgcgg | 720 |
| gccgtgcggc | tccgctctgg | agccaaggct | ctaggcaagg | ccaggcggaa | ggtgaaagtc | 780 |
| ctggtcctcg | tcgtgctggc | cgtgtgcctc | tctgctggga | cgcccttcca | cctggcctct | 840 |
| gtcgtggccc | tgaccacgga | cctgccccag | accccactgg | tcatcagtat | gtcctacgtc | 900 |
| atcaccagcc | tcacgtacgc | caactcgtgc | ctgaacccct | cctctacgc | ctttctagat | 960 |
| gacaacttcc | ggaagaactt | ccgcagcata | ttgcggtgct | ga | | 1002 |

<210> SEQ ID NO 172
<211> LENGTH: 333
<212> TYPE: PRT
<213> ORGANISM: Homo sapiens

<400> SEQUENCE: 172

Met Gln Ala Ala Gly His Pro Glu Pro Leu Asp Ser Arg Gly Ser Phe
1               5                   10                  15

Ser Leu Pro Thr Met Gly Ala Asn Val Ser Gln Asp Asn Gly Thr Gly
                20                  25                  30

His Asn Ala Thr Phe Ser Glu Pro Leu Pro Phe Leu Tyr Val Leu Leu
            35                  40                  45

Pro Ala Val Tyr Ser Gly Ile Cys Ala Val Gly Leu Thr Gly Asn Thr
        50                  55                  60

Ala Val Ile Leu Val Ile Leu Arg Ala Pro Lys Met Lys Thr Val Thr
65                  70                  75                  80

Asn Val Phe Ile Leu Asn Leu Ala Val Ala Asp Gly Leu Phe Thr Leu
                85                  90                  95

```
Val Leu Pro Val Asn Ile Ala Glu His Leu Leu Gln Tyr Trp Pro Phe
             100                 105                 110
Gly Glu Leu Leu Cys Lys Leu Val Leu Ala Val Asp His Tyr Asn Ile
         115                 120                 125
Phe Ser Ser Ile Tyr Phe Leu Ala Val Met Ser Val Asp Arg Tyr Leu
     130                 135                 140
Val Val Leu Ala Thr Val Arg Ser Arg His Met Pro Trp Arg Thr Tyr
145                 150                 155                 160
Arg Gly Ala Lys Val Ala Ser Leu Cys Val Trp Leu Gly Val Thr Val
                 165                 170                 175
Leu Val Leu Pro Phe Phe Ser Phe Ala Gly Val Tyr Ser Asn Glu Leu
             180                 185                 190
Gln Val Pro Ser Cys Gly Leu Ser Phe Pro Trp Pro Glu Gln Val Trp
         195                 200                 205
Phe Lys Ala Ser Arg Val Tyr Thr Leu Val Leu Gly Phe Val Leu Pro
     210                 215                 220
Val Cys Thr Ile Cys Val Leu Tyr Thr Asp Leu Leu Arg Arg Leu Arg
225                 230                 235                 240
Ala Val Arg Leu Arg Ser Gly Ala Lys Ala Leu Gly Lys Ala Arg Arg
                 245                 250                 255
Lys Val Lys Val Leu Val Leu Val Leu Ala Val Cys Leu Leu Cys
             260                 265                 270
Trp Thr Pro Phe His Leu Ala Ser Val Val Ala Leu Thr Thr Asp Leu
         275                 280                 285
Pro Gln Thr Pro Leu Val Ile Ser Met Ser Tyr Val Ile Thr Ser Leu
     290                 295                 300
Thr Tyr Ala Asn Ser Cys Leu Asn Pro Phe Leu Tyr Ala Phe Leu Asp
305                 310                 315                 320
Asp Asn Phe Arg Lys Asn Phe Arg Ser Ile Leu Arg Cys
                 325                 330
```

<210> SEQ ID NO 173
<211> LENGTH: 1107
<212> TYPE: DNA
<213> ORGANISM: Homo sapiens

<400> SEQUENCE: 173

| | | | | | |
|---|---|---|---|---|---|
| atggtccttg | aggtgagtga | ccaccaagtg | ctaaatgacg | ccgaggttgc | cgccctcctg | 60 |
| gagaacttca | gctcttccta | tgactatgga | gaaaacgaga | gtgactcgtg | ctgtacctcc | 120 |
| ccgcccctgcc | cacaggactt | cagcctgaac | ttcgaccggg | ccttcctgcc | agccctctac | 180 |
| agcctcctct | ttctgctggg | gctgctggc | aacggcgcgg | tggcagccgt | gctgctgagc | 240 |
| cggcggacag | ccctgagcag | caccgacacc | ttcctgctcc | acctagctgt | agcagacacg | 300 |
| ctgctggtgc | tgacactgcc | gctctgggca | gtggacgctg | ccgtccagtg | ggtctttggc | 360 |
| tctggcctct | gcaaagtggc | aggtgccctc | ttcaacatca | acttctacgc | aggagccctc | 420 |
| ctgctggcct | gcatcagctt | tgaccgctac | ctgaacatag | ttcatgccac | ccagctctac | 480 |
| cgccgggggc | cccggcccg | cgtgaccctc | acctgcctgg | ctgtctgggg | gctctgcctg | 540 |
| cttttcgccc | tccagacttt | catcttcctg | tcggcccacc | acgacgagcg | cctcaacgcc | 600 |
| acccactgcc | aatacaactt | cccacaggtg | ggccgcacgg | ctctgcgggt | gctgcagctg | 660 |
| gtggctggct | ttctgctgcc | cctgctggtc | atggcctact | gctatgccca | catcctggcc | 720 |
| gtgctgctgg | tttccagggg | ccagcggcgc | ctgcgggcca | gcggctggt | ggtggtggtc | 780 |

```
gtggtggcct tgccctctg ctggaccccc tatcacctgg tggtgctggt ggacatcctc      840
atggacctgg gcgctttggc ccgcaactgt ggccgagaaa gcaggtaga cgtggccaag      900 tcggtcacct caggcctggg ctacatgcac tgctgcctca acccgctgct ctatgccttt      960 gtagggtca agttccggga gcggatgtgg atgctgctct tgcgcctggg ctgccccaac     1020
cagagagggc tccagaggca gccatcgtct tcccgccggg attcatcctg gtctgagacc     1080
tcagaggcct cctactcggg cttgtga                                         1107
```

<210> SEQ ID NO 174
<211> LENGTH: 368
<212> TYPE: PRT
<213> ORGANISM: Homo sapiens

<400> SEQUENCE: 174

```
Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
    210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Lys Arg Leu
                245                 250                 255

Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
    290                 295                 300

Gly Leu Gly Tyr Met His Cys Cys Leu Asn Pro Leu Leu Tyr Ala Phe
305                 310                 315                 320
```

| | | | | | | | | | | | |
|---|---|---|---|---|---|---|---|---|---|---|---|
|Val|Gly|Val|Lys|Phe|Arg|Glu|Arg|Met|Trp|Met|Leu|Leu|Leu|Arg|Leu|
| | | |325| | | |330| | | |335| | | | |

Gly Cys Pro Asn Gln Arg Gly Leu Gln Arg Gln Pro Ser Ser Ser Arg
              340                 345                 350

Arg Asp Ser Ser Trp Ser Glu Thr Ser Glu Ala Ser Tyr Ser Gly Leu
        355                 360                 365

<210> SEQ ID NO 175
<211> LENGTH: 1074
<212> TYPE: DNA
<213> ORGANISM: Homo sapiens

<400> SEQUENCE: 175

```
atggctgatg actatggctc tgaatccaca tcttccatgg aagactacgt taacttcaac      60
ttcactgact tctactgtga aaaaacaat gtcaggcagt ttgcgagcca tttcctccca      120
cccttgtact ggctcgtgtt catcgtgggt gccttgggca acagtcttgt tatccttgtc     180
tactggtact gcacaagagt gaagaccatg accgacatgt tccttttgaa tttggcaatt     240
gctgacctcc tctttcttgt cactcttccc ttctgggcca ttgctgctgc tgaccagtgg     300
aagttccaga ccttcatgtg caaggtggtc aacagcatgt acaagatgaa cttctacagc     360
tgtgtgttgc tgatcatgtg catcagcgtg gacaggtaca ttgccattgc ccaggccatg     420
agagcacata cttggaggga aaaaggctt ttgtacagca aaatggtttg ctttaccatc     480
tgggtattgg cagctgctct ctgcatccca gaaatcttat acagccaaat caaggaggaa     540
tccggcattg ctatctgcac catggtttac cctagcgatg agagcaccaa actgaagtca     600
gctgtcttga ccctgaaggt cattctgggg ttcttccttc ccttcgtggt catggcttgc     660
tgctatacca tcatcattca caccctgata caagccaaga agtcttccaa gcacaaagcc     720
aagaaagtga ccatcactgt cctgaccgtc tttgtcttgt ctcagtttcc ctacaactgc     780
attttgttgg tgcagaccat tgacgcctat gccatgttca tctccaactg tgccgtttcc     840
accaacattg acatctgctt ccaggtcacc cagaccatcg ccttcttcca cagttgcctg     900
aaccctgttc tctatgtttt tgtgggtgag agattccgcc gggatctcgt gaaaaccctg     960
aagaacttgg gttgcatcag ccaggcccag tgggtttcat ttacaaggag agagggaagc    1020
ttgaagctgt cgtctatgtt gctggagaca acctcaggag cactctccct ctga          1074
7
```

<210> SEQ ID NO 176
<211> LENGTH: 357
<212> TYPE: PRT
<213> ORGANISM: Homo sapiens

<400> SEQUENCE: 176

Met Ala Asp Asp Tyr Gly Ser Glu Ser Thr Ser Ser Met Glu Asp Tyr
1               5                   10                  15

Val Asn Phe Asn Phe Thr Asp Phe Tyr Cys Glu Lys Asn Asn Val Arg
              20                  25                  30

Gln Phe Ala Ser His Phe Leu Pro Pro Leu Tyr Trp Leu Val Phe Ile
          35                  40                  45

Val Gly Ala Leu Gly Asn Ser Leu Val Ile Leu Val Tyr Trp Tyr Cys
      50                  55                  60

Thr Arg Val Lys Thr Met Thr Asp Met Phe Leu Leu Asn Leu Ala Ile
65                  70                  75                  80

Ala Asp Leu Leu Phe Leu Val Thr Leu Pro Phe Trp Ala Ile Ala Ala
                85                  90                  95

-continued

```
Ala Asp Gln Trp Lys Phe Gln Thr Phe Met Cys Lys Val Val Asn Ser
            100                 105                 110
Met Tyr Lys Met Asn Phe Tyr Ser Cys Val Leu Leu Ile Met Cys Ile
            115                 120                 125
Ser Val Asp Arg Tyr Ile Ala Ile Ala Gln Ala Met Arg Ala His Thr
            130                 135                 140
Trp Arg Glu Lys Arg Leu Leu Tyr Ser Lys Met Val Cys Phe Thr Ile
145                 150                 155                 160
Trp Val Leu Ala Ala Ala Leu Cys Ile Pro Glu Ile Leu Tyr Ser Gln
            165                 170                 175
Ile Lys Glu Glu Ser Gly Ile Ala Ile Cys Thr Met Val Tyr Pro Ser
            180                 185                 190
Asp Glu Ser Thr Lys Leu Lys Ser Ala Val Leu Thr Leu Lys Val Ile
            195                 200                 205
Leu Gly Phe Phe Leu Pro Phe Val Val Met Ala Cys Cys Tyr Thr Ile
            210                 215                 220
Ile Ile His Thr Leu Ile Gln Ala Lys Lys Ser Ser Lys His Lys Ala
225                 230                 235                 240
Lys Lys Val Thr Ile Thr Val Leu Thr Val Phe Val Leu Ser Gln Phe
            245                 250                 255
Pro Tyr Asn Cys Ile Leu Leu Val Gln Thr Ile Asp Ala Tyr Ala Met
            260                 265                 270
Phe Ile Ser Asn Cys Ala Val Ser Thr Asn Ile Asp Ile Cys Phe Gln
            275                 280                 285
Val Thr Gln Thr Ile Ala Phe Phe His Ser Cys Leu Asn Pro Val Leu
            290                 295                 300
Tyr Val Phe Val Gly Glu Arg Phe Arg Arg Asp Leu Val Lys Thr Leu
305                 310                 315                 320
Lys Asn Leu Gly Cys Ile Ser Gln Ala Gln Trp Val Ser Phe Thr Arg
            325                 330                 335
Arg Glu Gly Ser Leu Lys Leu Ser Ser Met Leu Leu Glu Thr Thr Ser
            340                 345                 350
Gly Ala Leu Ser Leu
            355

<210> SEQ ID NO 177
<211> LENGTH: 1110
<212> TYPE: DNA
<213> ORGANISM: Homo sapiens

<400> SEQUENCE: 177
atggcctcat cgaccactcg gggcccagg  gtttctgact tatttctgg  gctgccgccg    60 gcggtcacaa ctcccgccaa ccagagcgca gaggcctcgg cgggcaacgg gtcggtggct   120
ggcgcggacg ctccagccgt cacgcccttc cagagcctgc agctggtgca tcagctgaag   180
gggctgatcg tgctgctcta cagcgtcgtg tggtcgtgg  ggctggtggg caactgcctg   240
ctggtgctgg tgatcgcgcg ggtgccgcgg ctgcacaacg tgacgaactt cctcatcggc   300
aacctggcct tgtccgacgt gctcatgtgc accgcctgcg tgccgctcac gctggcctat   360
gccttcgagc acgcggctg  ggtgttcggc ggcggcctgt gccacctggt cttcttcctg   420
cagccggtca ccgtctatgt gtcggtgttc acgctcacca ccatcgcagt ggaccgctac   480
gtcgtgctgg tgcacccgct gaggcgcgca tctcgctgcg cctcagccta cgctgtgctg   540
gccatctggg cgctgtccgc ggtgctggcg ctgccgccg  ccgtgcacac ctatcacgtg   600
```

-continued

```
gagctcaagc cgcacgacgt gcgcctctgc gaggagttct ggggctccca ggagcgccag    660
cgccagctct acgcctgggg gctgctgctg gtcacctacc tgctccctct gctggtcatc    720
ctcctgtctt acgtccgggt gtcagtgaag ctccgcaacc gcgtggtgcc gggctgcgtg    780
acccagagcc aggccgactg gaccgcgct cggcgccggc gcaccaaatg cttgctggtg     840
gtggtcgtgg tggtgttcgc cgtctgctgg ctgccgctgc acgtcttcaa cctgctgcgg    900
gacctcgacc cccacgccat cgacccttac gcctttgggc tggtgcagct gctctgccac    960
tggctcgcca tgagttcggc ctgctacaac cccttcatct acgcctggct gcacgacagc   1020
ttccgcgagg agctgcgcaa actgttggtc gcttggcccc gcaagatagc ccccatggc    1080 cagaatatga ccgtcagcgt ggtcatctga                                    1110
```

<210> SEQ ID NO 178
<211> LENGTH: 369
<212> TYPE: PRT
<213> ORGANISM: Homo sapiens

<400> SEQUENCE: 178

```
Met Ala Ser Ser Thr Thr Arg Gly Pro Arg Val Ser Asp Leu Phe Ser
1               5                   10                  15

Gly Leu Pro Pro Ala Val Thr Pro Ala Asn Gln Ser Ala Glu Ala
            20                  25                  30

Ser Ala Gly Asn Gly Ser Val Ala Gly Ala Asp Ala Pro Ala Val Thr
        35                  40                  45

Pro Phe Gln Ser Leu Gln Leu Val His Gln Leu Lys Gly Leu Ile Val
    50                  55                  60

Leu Leu Tyr Ser Val Val Val Val Gly Leu Val Gly Asn Cys Leu
65                  70                  75                  80

Leu Val Leu Val Ile Ala Arg Val Pro Arg Leu His Asn Val Thr Asn
                85                  90                  95

Phe Leu Ile Gly Asn Leu Ala Leu Ser Asp Val Leu Met Cys Thr Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Ala Ser Arg Cys Ala Ser Ala
                165                 170                 175

Tyr Ala Val Leu Ala Ile Trp Ala Leu Ser Ala Val Leu Ala Leu Pro
            180                 185                 190

Pro Ala Val His Thr Tyr His Val Glu Leu Lys Pro His Asp Val Arg
        195                 200                 205

Leu Cys Glu Glu Phe Trp Gly Ser Gln Glu Arg Gln Arg Gln Leu Tyr
    210                 215                 220

Ala Trp Gly Leu Leu Leu Val Thr Tyr Leu Leu Pro Leu Leu Val Ile
225                 230                 235                 240

Leu Leu Ser Tyr Val Arg Val Ser Val Lys Leu Arg Asn Arg Val Val
                245                 250                 255

Pro Gly Cys Val Thr Gln Ser Gln Ala Asp Trp Asp Arg Ala Arg Arg
            260                 265                 270

Arg Arg Thr Lys Cys Leu Leu Val Val Val Val Val Phe Ala Val
```

```
                275                 280                 285
Cys Trp Leu Pro Leu His Val Phe Asn Leu Leu Arg Asp Leu Asp Pro
        290                 295                 300

His Ala Ile Asp Pro Tyr Ala Phe Gly Leu Val Gln Leu Leu Cys His
305                 310                 315                 320

Trp Leu Ala Met Ser Ser Ala Cys Tyr Asn Pro Phe Ile Tyr Ala Trp
                325                 330                 335

Leu His Asp Ser Phe Arg Glu Glu Leu Arg Lys Leu Leu Val Ala Trp
            340                 345                 350

Pro Arg Lys Ile Ala Pro His Gly Gln Asn Met Thr Val Ser Val Val
        355                 360                 365

Ile
```

<210> SEQ ID NO 179
<211> LENGTH: 1083
<212> TYPE: DNA
<213> ORGANISM: Homo sapiens

<400> SEQUENCE: 179

```
atggacccag aagaaacttc agtttatttg gattattact atgctacgag cccaaactct      60
gacatcaggg agacccactc ccatgttcct tacacctctg tcttccttcc agtcttttac     120
acagctgtgt tcctgactgg agtgctgggg aaccttgttc tcatgggagc gttgcatttc     180
aaacccggca gccgaagact gatcgacatc tttatcatca atctggctgc ctctgacttc     240
attttcttg tcacattgcc tctctgggtg gataaagaag catctctagg actgtggagg     300
acgggctcct tcctgtgcaa agggagctcc tacatgatct ccgtcaatat gcactgcagt     360
gtcctcctgc tcacttgcat gagtgttgac cgctacctgg ccattgtgtg ccagtcgta     420
tccaggaaat tcagaaggac agactgtgca tatgtagtct gtgccagcat ctggtttatc     480
tcctgcctgc tggggttgcc tactcttctg tccagggagc tcacgctgat tgatgataag     540
ccatactgtg cagagaaaaa ggcaactcca attaaactca tatggtccct ggtggcctta     600
attttcacct ttttgtccc tttgttgagc attgtgacct gctactgttg cattgcaagg     660
aagctgtgtg cccattacca gcaatcagga aagcacaaca aaaagctgaa gaaatctaag     720
aagatcatct ttattgtcgt ggcagccttt cttgtctcct ggctgccctt caatactttc     780
aagttcctgg ccattgtctc tgggttgcgg caagaacact atttaccctc agctattctt     840
cagcttggta tggaggtgag tggacccttg gcatttgcca acagctgtgt caaccctttc     900
atttactata tcttcgacag ctacatccgc cgggccattg tccactgctt gtgcccttgc     960
ctgaaaaact atgactttgg gagtagcact gagacatcag atagtcacct cactaaggct    1020
ctctccacct tcattcatgc agaagatttt gccaggagga ggaagaggtc tgtgtcactc    1080
taa                                                                  1083
```

<210> SEQ ID NO 180
<211> LENGTH: 360
<212> TYPE: PRT
<213> ORGANISM: Homo sapiens

<400> SEQUENCE: 180

```
Met Asp Pro Glu Glu Thr Ser Val Tyr Leu Asp Tyr Tyr Tyr Ala Thr
1               5                   10                  15

Ser Pro Asn Ser Asp Ile Arg Glu Thr His Ser His Val Pro Tyr Thr
            20                  25                  30
```

```
Ser Val Phe Leu Pro Val Phe Tyr Thr Ala Val Phe Leu Thr Gly Val
         35                  40                  45

Leu Gly Asn Leu Val Leu Met Gly Ala Leu His Phe Lys Pro Gly Ser
 50                  55                  60

Arg Arg Leu Ile Asp Ile Phe Ile Ile Asn Leu Ala Ala Ser Asp Phe
 65                  70                  75                  80

Ile Phe Leu Val Thr Leu Pro Leu Trp Val Asp Lys Glu Ala Ser Leu
                 85                  90                  95

Gly Leu Trp Arg Thr Gly Ser Phe Leu Cys Lys Gly Ser Ser Tyr Met
                100                 105                 110

Ile Ser Val Asn Met His Cys Ser Val Leu Leu Leu Thr Cys Met Ser
                115                 120                 125

Val Asp Arg Tyr Leu Ala Ile Val Trp Pro Val Val Ser Arg Lys Phe
130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175

Ile Asp Asp Lys Pro Tyr Cys Ala Glu Lys Lys Ala Thr Pro Ile Lys
                180                 185                 190

Leu Ile Trp Ser Leu Val Ala Leu Ile Phe Thr Phe Phe Val Pro Leu
                195                 200                 205

Leu Ser Ile Val Thr Cys Tyr Cys Cys Ile Ala Arg Lys Leu Cys Ala
210                 215                 220

His Tyr Gln Gln Ser Gly Lys His Asn Lys Lys Leu Lys Lys Ser Lys
225                 230                 235                 240

Lys Ile Ile Phe Ile Val Ala Ala Phe Leu Val Ser Trp Leu Pro
                245                 250                 255

Phe Asn Thr Phe Lys Phe Leu Ala Ile Val Ser Gly Leu Arg Gln Glu
                260                 265                 270

His Tyr Leu Pro Ser Ala Ile Leu Gln Leu Gly Met Glu Val Ser Gly
                275                 280                 285

Pro Leu Ala Phe Ala Asn Ser Cys Val Asn Pro Phe Ile Tyr Tyr Ile
290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Thr Ser Asp Ser His
                325                 330                 335

Leu Thr Lys Ala Leu Ser Thr Phe Ile His Ala Glu Asp Phe Ala Arg
                340                 345                 350

Arg Arg Lys Arg Ser Val Ser Leu
355                 360

<210> SEQ ID NO 181
<211> LENGTH: 1020
<212> TYPE: DNA
<213> ORGANISM: Homo sapiens

<400> SEQUENCE: 181
atgaatggcc ttgaagtggc tcccccaggt ctgatcacca acttctccct ggccacggca    60
gagcaatgtg gccaggagac gccactggag aacatgctgt tcgcctcctt ctaccttctg   120
gattttatcc tggctttagt tggcaatacc ctggctctgt ggcttttcat ccagaccac   180 aagtccggga ccccggccaa cgtgttcctg atgcatctgg ccgtggccga cttgtcgtgc   240
```

```
gtgctggtcc tgcccacccg cctggtctac cacttctctg ggaaccactg gccatttggg      300
gaaatcgcat gccgtctcac cggcttcctc ttctacctca acatgtacgc cagcatctac      360
ttcctcacct gcatcagcgc cgaccgtttc ctggccattg tgcacccggt caagtccctc      420
aagctccgca ggcccctcta cgcacacctg gcctgtgcct tcctgtgggt ggtggtggct      480
gtggccatgg ccccgctgct ggtgagccca cagaccgtgc agaccaacca cacggtggtc      540
tgcctgcagc tgtaccggga aaggcctcc caccatgccc tggtgtccct ggcagtggcc       600 ttcacctcc cgttcatcac cacggtcacc tgctacctgc tgatcatccg cagcctgcgg       660
cagggcctgc gtgtggagaa gcgcctcaag accaaggcaa aacgcatgat cgccatagtg      720
ctggccatct tcctggtctg cttcgtgccc taccacgtca accgctccgt ctacgtgctg      780
cactaccgca gccatggggc ctcctgcgcc acccagcgca tcctggccct ggcaaaccgc      840
atcacctcct gcctcaccag cctcaacggg gcactcgacc ccatcatgta tttcttcgtg      900
gctgagaagt tccgccacgc cctgtgcaac ttgctctgtg gcaaaaggct caagggcccg      960
ccccccagct tcgaagggaa aaccaacgag agctcgctga gtgccaagtc agagctgtga     1020
```

<210> SEQ ID NO 182
<211> LENGTH: 339
<212> TYPE: PRT
<213> ORGANISM: Homo sapiens

<400> SEQUENCE: 182

```
Met Asn Gly Leu Glu Val Ala Pro Pro Gly Leu Ile Thr Asn Phe Ser
1               5                  10                  15

Leu Ala Thr Ala Glu Gln Cys Gly Gln Glu Thr Pro Leu Glu Asn Met
            20                  25                  30

Leu Phe Ala Ser Phe Tyr Leu Leu Asp Phe Ile Leu Ala Leu Val Gly
        35                  40                  45

Asn Thr Leu Ala Leu Trp Leu Phe Ile Arg Asp His Lys Ser Gly Thr
    50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
            85                  90                  95

Trp Pro Phe Gly Glu Ile Ala Cys Arg Leu Thr Gly Phe Leu Phe Tyr
        100                 105                 110

Leu Asn Met Tyr Ala Ser Ile Tyr Phe Leu Thr Cys Ile Ser Ala Asp
    115                 120                 125

Arg Phe Leu Ala Ile Val His Pro Val Lys Ser Leu Lys Leu Arg Arg
130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
            165                 170                 175

His Thr Val Val Cys Leu Gln Leu Tyr Arg Glu Lys Ala Ser His His
        180                 185                 190

Ala Leu Val Ser Leu Ala Val Ala Phe Thr Phe Pro Phe Ile Thr Thr
    195                 200                 205

Val Thr Cys Tyr Leu Leu Ile Ile Arg Ser Leu Arg Gln Gly Leu Arg
    210                 215                 220

Val Glu Lys Arg Leu Lys Thr Lys Ala Lys Arg Met Ile Ala Ile Val
225                 230                 235                 240
```

```
Leu Ala Ile Phe Leu Val Cys Phe Val Pro Tyr His Val Asn Arg Ser
                245                 250                 255

Val Tyr Val Leu His Tyr Arg Ser His Gly Ala Ser Cys Ala Thr Gln
            260                 265                 270

Arg Ile Leu Ala Leu Ala Asn Arg Ile Thr Ser Cys Leu Thr Ser Leu
        275                 280                 285

Asn Gly Ala Leu Asp Pro Ile Met Tyr Phe Val Ala Glu Lys Phe
    290                 295                 300

Arg His Ala Leu Cys Asn Leu Cys Gly Lys Arg Leu Lys Gly Pro
305                 310                 315                 320

Pro Pro Ser Phe Glu Gly Lys Thr Asn Glu Ser Ser Leu Ser Ala Lys
                325                 330                 335

Ser Glu Leu

<210> SEQ ID NO 183
<211> LENGTH: 996
<212> TYPE: DNA
<213> ORGANISM: Homo sapiens

<400> SEQUENCE: 183
atgatcaccc tgaacaatca agatcaacct gtcccttta acagctcaca tccagatgaa      60
tacaaaattg cagcccttgt cttctatagc tgtatcttca taattggatt atttgttaac    120
atcactgcat tatgggtttt cagttgtacc accaagaaga gaaccacggt aaccatctat    180
atgatgaatg tggcattagt ggacttgata tttataatga ctttaccctt tcgaatgttt    240
tattatgcaa aagatgaatg gccatttgga gagtacttct gccagattct ggagctctc    300
acagtgtttt acccaagcat tgctttatgg cttcttgcct ttattagtgc tgacagatac    360
atggccattg tacagccgaa gtacgccaaa gaacttaaaa acacgtgcaa agccgtgctg    420
gcgtgtgtgg gagtctggat aatgaccctg accacgacca cccctctgct actgctctat    480
aaagacccag ataaagactc cactcccgcc acctgcctca gatttctga catcatctat    540
ctaaaagctg tgaacgtgct gaacctcact cgactgacta ttttttttctt gattcctttg    600
ttcatcatga ttgggtgcta cttggtcatt attcataatc tccttcacgg caggacgtct    660
aagctgaaac ccaaagtcaa ggagaagtcc aaaaggatca tcatcacgct gctggtgcag    720
gtgctcgtct gctttatgcc cttccacatc tgtttcgctt tcctgatgct gggaacgggg    780
gagaatagtt acaatccctg gggagccttt accaccttcc tcatgaacct cagcacgtgt    840
ctggatgtga ttctctacta catcgtttca aaacaatttc aggctcgagt cattagtgtc    900
atgctatacc gtaattacct tcgaagcatg cgcagaaaaa gtttccgatc tggtagtcta    960
aggtcactaa gcaatataaa cagtgaaatg ttatga                              996

<210> SEQ ID NO 184
<211> LENGTH: 331
<212> TYPE: PRT
<213> ORGANISM: Homo sapiens

<400> SEQUENCE: 184

Met Ile Thr Leu Asn Asn Gln Asp Gln Pro Val Pro Phe Asn Ser Ser
1               5                  10                  15

His Pro Asp Glu Tyr Lys Ile Ala Ala Leu Val Phe Tyr Ser Cys Ile
            20                  25                  30

Phe Ile Ile Gly Leu Phe Val Asn Ile Thr Ala Leu Trp Val Phe Ser
        35                  40                  45
```

```
Cys Thr Thr Lys Lys Arg Thr Thr Val Thr Ile Tyr Met Met Asn Val
 50                  55                  60
Ala Leu Val Asp Leu Ile Phe Ile Met Thr Leu Pro Phe Arg Met Phe
 65                  70                  75                  80
Tyr Tyr Ala Lys Asp Glu Trp Pro Phe Gly Glu Tyr Phe Cys Gln Ile
                 85                  90                  95
Leu Gly Ala Leu Thr Val Phe Tyr Pro Ser Ile Ala Leu Trp Leu Leu
                100                 105                 110
Ala Phe Ile Ser Ala Asp Arg Tyr Met Ala Ile Val Gln Pro Lys Tyr
            115                 120                 125
Ala Lys Glu Leu Lys Asn Thr Cys Lys Ala Val Leu Ala Cys Val Gly
130                 135                 140
Val Trp Ile Met Thr Leu Thr Thr Thr Pro Leu Leu Leu Leu Tyr
145                 150                 155                 160
Lys Asp Pro Asp Lys Asp Ser Thr Pro Ala Thr Cys Leu Lys Ile Ser
                165                 170                 175
Asp Ile Ile Tyr Leu Lys Ala Val Asn Val Leu Asn Leu Thr Arg Leu
            180                 185                 190
Thr Phe Phe Phe Leu Ile Pro Leu Phe Ile Met Ile Gly Cys Tyr Leu
        195                 200                 205
Val Ile Ile His Asn Leu Leu His Gly Arg Thr Ser Lys Leu Lys Pro
210                 215                 220
Lys Val Lys Glu Lys Ser Lys Arg Ile Ile Thr Leu Leu Val Gln
225                 230                 235                 240
Val Leu Val Cys Phe Met Pro Phe His Ile Cys Phe Ala Phe Leu Met
                245                 250                 255
Leu Gly Thr Gly Glu Asn Ser Tyr Asn Pro Trp Gly Ala Phe Thr Thr
                260                 265                 270
Phe Leu Met Asn Leu Ser Thr Cys Leu Asp Val Ile Leu Tyr Tyr Ile
            275                 280                 285
Val Ser Lys Gln Phe Gln Ala Arg Val Ile Ser Val Met Leu Tyr Arg
290                 295                 300
Asn Tyr Leu Arg Ser Met Arg Arg Lys Ser Phe Arg Ser Gly Ser Leu
305                 310                 315                 320
Arg Ser Leu Ser Asn Ile Asn Ser Glu Met Leu
                325                 330

<210> SEQ ID NO 185
<211> LENGTH: 1077
<212> TYPE: DNA
<213> ORGANISM: Homo sapiens

<400> SEQUENCE: 185
atgccctctg tgtctccagc ggggccctcg gccggggcag tccccaatgc caccgcagtg      60
acaacagtgc ggaccaatgc cagcgggctg gaggtgcccc tgttccacct gtttgcccgg     120
ctggacgagg agctgcatgg cacctttcca ggcctgtgcg tggcgctgat ggcggtgcac     180
ggagccatct tcctggcagg gctggtgctc aacgggctgg cgctgtacgt cttctgctgc     240
cgcacccggg ccaagacacc ctcagtcatc tacaccatca acctggtggt gaccgatcta     300
ctggtagggc tgtccctgcc cacgcgcttc gctgtgtact acggcgccag gggctgcctg     360
cgctgtgcct tccgcacgt cctcggttac ttcctcaaca tgcactgctc catcctcttc     420
ctcacctgca tctgcgtgga ccgctacctg gccatcgtgc ggcccgaagg ctcccgccgc     480
tgccgccagc tgcctgtgc cagggccgtg tgcgccttcg tgtggctggc cgccggtgcc     540
```

-continued

```
gtcaccctgt cggtgctggg cgtgacaggc agccggccct gctgccgtgt ctttgcgctg    600
actgtcctgg agttcctgct gcccctgctg gtcatcagcg tgtttaccgg ccgcatcatg    660
tgtgcactgt cgcggccggg tctgctccac cagggtcgcc agcgccgcgt gcgggccaag    720
cagctcctgc tcacggtgct catcatcttt ctcgtctgct tcacgcccct ccacgcccgc    780
caagtggccg tggcgctgtg gcccgacatg ccacaccaca cgagcctcgt ggtctaccac    840
gtggccgtga ccctcagcag cctcaacagc tgcatggacc ccatcgtcta ctgcttcgtc    900
accagtggct tccaggccac cgtccgaggc ctcttcggcc agcacggaga gcgtgagccc    960
agcagcggtg acgtggtcag catgcacagg agctccaagg gctcaggccg tcatcacatc   1020
ctcagtgccg ccctcacgc cctcacccag gccctggcta atgggcccga ggcttag      1077
```

<210> SEQ ID NO 186
<211> LENGTH: 358
<212> TYPE: PRT
<213> ORGANISM: Homo sapiens

<400> SEQUENCE: 186

```
Met Pro Ser Val Ser Pro Ala Gly Pro Ser Ala Gly Ala Val Pro Asn
1               5                   10                  15

Ala Thr Ala Val Thr Thr Val Arg Thr Asn Ala Ser Gly Leu Glu Val
            20                  25                  30

Pro Leu Phe His Leu Phe Ala Arg Leu Asp Glu Glu Leu His Gly Thr
        35                  40                  45

Phe Pro Gly Leu Cys Val Ala Leu Met Ala Val His Gly Ala Ile Phe
    50                  55                  60

Leu Ala Gly Leu Val Leu Asn Gly Leu Ala Leu Tyr Val Phe Cys Cys
65                  70                  75                  80

Arg Thr Arg Ala Lys Thr Pro Ser Val Ile Tyr Thr Ile Asn Leu Val
                85                  90                  95

Val Thr Asp Leu Leu Val Gly Leu Ser Leu Pro Thr Arg Phe Ala Val
            100                 105                 110

Tyr Tyr Gly Ala Arg Gly Cys Leu Arg Cys Ala Phe Pro His Val Leu
        115                 120                 125

Gly Tyr Phe Leu Asn Met His Cys Ser Ile Leu Phe Leu Thr Cys Ile
    130                 135                 140

Cys Val Asp Arg Tyr Leu Ala Ile Val Arg Pro Glu Gly Ser Arg Ala
145                 150                 155                 160

Cys Arg Gln Pro Ala Cys Ala Arg Ala Val Cys Ala Phe Val Trp Leu
                165                 170                 175

Ala Ala Gly Ala Val Thr Leu Ser Val Leu Gly Val Thr Gly Ser Arg
            180                 185                 190

Pro Cys Cys Arg Val Phe Ala Leu Thr Val Leu Glu Phe Leu Leu Pro
        195                 200                 205

Leu Leu Val Ile Ser Val Phe Thr Gly Arg Ile Met Cys Ala Leu Ser
    210                 215                 220

Arg Pro Gly Leu Leu His Gln Gly Arg Gln Arg Val Arg Ala Lys
225                 230                 235                 240

Gln Leu Leu Leu Thr Val Leu Ile Ile Phe Leu Val Cys Phe Thr Pro
                245                 250                 255

Phe His Ala Arg Gln Val Ala Val Ala Leu Trp Pro Asp Met Pro His
            260                 265                 270

His Thr Ser Leu Val Val Tyr His Val Ala Val Thr Leu Ser Ser Leu
```

```
                275                 280                 285
Asn Ser Cys Met Asp Pro Ile Val Tyr Cys Phe Val Thr Ser Gly Phe
        290                 295                 300

Gln Ala Thr Val Arg Gly Leu Phe Gly Gln His Gly Glu Arg Glu Pro
305                 310                 315                 320

Ser Ser Gly Asp Val Val Ser Met His Arg Ser Ser Lys Gly Ser Gly
                325                 330                 335

Arg His His Ile Leu Ser Ala Gly Pro His Ala Leu Thr Gln Ala Leu
                340                 345                 350

Ala Asn Gly Pro Glu Ala
        355
```

<210> SEQ ID NO 187
<211> LENGTH: 1050
<212> TYPE: DNA
<213> ORGANISM: Homo sapiens

<400> SEQUENCE: 187

| | | | | | |
|---|---|---|---|---|---|
| atgaactcca | ccttggatgg | taatcagagc | agccaccctt | tttgcctctt | ggcatttggc | 60 |
| tatttggaaa | ctgtcaattt | tgccttttg | gaagtattga | ttattgtctt | tctaactgta | 120 |
| ttgattattt | ctggcaacat | cattgtgatt | tttgtatttc | actgtgcacc | tttgttgaac | 180 |
| catcacacta | caagttattt | tatccagact | atggcatatg | ctgacctttt | tgttggggtg | 240 |
| agctgcgtgg | tccttctttt | atcactcctc | catcaccccc | ttccagtaga | ggagtccttg | 300 |
| acttgccaga | tatttggttt | tgtagtatca | gttctgaaga | gcgtctccat | ggcttctctg | 360 |
| gcctgtatca | gcattgatag | atacattgcc | attactaaac | tttaaccta | taatactctg | 420 |
| gttacaccct | ggagactacg | cctgtgtatt | ttcctgattt | ggctatactc | gaccctggtc | 480 |
| ttcctgcctt | cctttttcca | ctggggcaaa | cctggatatc | atggagatgt | gtttcagtgg | 540 |
| tgtgcggagt | cctggcacac | cgactcctac | ttcaccctgt | tcatcgtgat | gatgttatat | 600 |
| gccccagcag | cccttattgt | ctgcttcacc | tatttcaaca | tcttccgcat | ctgccaacag | 660 |
| cacacaaagg | atatcagcga | aaggcaagcc | cgcttcagca | gccagagtgg | ggagactggg | 720 |
| gaagtgcagg | cctgtcctga | taagcgctat | aaaatggtcc | tgtttcgaat | cactagtgta | 780 |
| ttttacatcc | tctggttgcc | atatatcatc | tacttcttgt | tggaaagctc | cactggccac | 840 |
| agcaaccgct | tcgcatcctt | cttgaccacc | tggcttgcta | ttagtaacag | tttctgcaac | 900 |
| tgtgtaattt | atagtctctc | caacagtgta | ttccaaagag | gactaaagcg | cctctcaggg | 960 |
| gctatgtgta | cttcttgtgc | aagtcagact | acagccaacg | acccttacac | agttagaagc | 1020 |
| aaaggccctc | ttaatggatg | tcatatctga | | | | 1050 |

<210> SEQ ID NO 188
<211> LENGTH: 349
<212> TYPE: PRT
<213> ORGANISM: Homo sapiens

<400> SEQUENCE: 188

```
Met Asn Ser Thr Leu Asp Gly Asn Gln Ser Ser His Pro Phe Cys Leu
1               5                   10                  15

Leu Ala Phe Gly Tyr Leu Glu Thr Val Asn Phe Cys Leu Leu Glu Val
                20                  25                  30

Leu Ile Ile Val Phe Leu Thr Val Leu Ile Ile Ser Gly Asn Ile Ile
                35                  40                  45

Val Ile Phe Val Phe His Cys Ala Pro Leu Leu Asn His His Thr Thr
```

```
                50              55              60
Ser Tyr Phe Ile Gln Thr Met Ala Tyr Ala Asp Leu Phe Val Gly Val
 65                  70                  75                  80

Ser Cys Val Val Pro Ser Leu Ser Leu Leu His His Pro Leu Pro Val
                 85                  90                  95

Glu Glu Ser Leu Thr Cys Gln Ile Phe Gly Phe Val Val Ser Val Leu
            100                 105                 110

Lys Ser Val Ser Met Ala Ser Leu Ala Cys Ile Ser Ile Asp Arg Tyr
            115                 120                 125

Ile Ala Ile Thr Lys Pro Leu Thr Tyr Asn Thr Leu Val Thr Pro Trp
130                 135                 140

Arg Leu Arg Leu Cys Ile Phe Leu Ile Trp Leu Tyr Ser Thr Leu Val
145                 150                 155                 160

Phe Leu Pro Ser Phe Phe His Trp Gly Lys Pro Gly Tyr His Gly Asp
                165                 170                 175

Val Phe Gln Trp Cys Ala Glu Ser Trp His Thr Asp Ser Tyr Phe Thr
            180                 185                 190

Leu Phe Ile Val Met Met Leu Tyr Ala Pro Ala Ala Leu Ile Val Cys
            195                 200                 205

Phe Thr Tyr Phe Asn Ile Phe Arg Ile Cys Gln Gln His Thr Lys Asp
210                 215                 220

Ile Ser Glu Arg Gln Ala Arg Phe Ser Ser Gln Ser Gly Glu Thr Gly
225                 230                 235                 240

Glu Val Gln Ala Cys Pro Asp Lys Arg Tyr Lys Met Val Leu Phe Arg
                245                 250                 255

Ile Thr Ser Val Phe Tyr Ile Leu Trp Leu Pro Tyr Ile Ile Tyr Phe
            260                 265                 270

Leu Leu Glu Ser Ser Thr Gly His Ser Asn Arg Phe Ala Ser Phe Leu
            275                 280                 285

Thr Thr Trp Leu Ala Ile Ser Asn Ser Phe Cys Asn Cys Val Ile Tyr
290                 295                 300

Ser Leu Ser Asn Ser Val Phe Gln Arg Gly Leu Lys Arg Leu Ser Gly
305                 310                 315                 320

Ala Met Cys Thr Ser Cys Ala Ser Gln Thr Thr Ala Asn Asp Pro Tyr
                325                 330                 335

Thr Val Arg Ser Lys Gly Pro Leu Asn Gly Cys His Ile
            340                 345

<210> SEQ ID NO 189
<211> LENGTH: 1302
<212> TYPE: DNA
<213> ORGANISM: Homo sapiens

<400> SEQUENCE: 189
atgtgttttt ctcccattct ggaaatcaac atgcagtctg aatctaacat tacagtgcga      60
gatgacattg atgacatcaa caccaatatg taccaaccac tatcatatcc gttaagcttt     120
caagtgtctc tcaccggatt tcttatgtta gaaattgtgt tgggacttgg cagcaacctc     180
actgtattgg tactttactg catgaaatcc aacttaatca actctgtcag taacattatt     240
acaatgaatc ttcatgtact tgatgtaata atttgtgtgg gatgtattcc tctaactata     300
gttatccttc tgctttcact ggagagtaac actgctctca tttgctgttt ccatgaggct     360
tgtgtatctt ttgcaagtgt ctcaacagca atcaacgttt ttgctatcac tttggacaga     420
tatgacatct ctgtaaaacc tgcaaaccga attctgacaa tgggcagagc tgtaatgtta     480
```

-continued

```
atgatatcca tttggatttt ttcttttttc tctttcctga ttccttttat tgaggtaaat    540
tttttcagtc ttcaaagtgg aaatacctgg gaaaacaaga cacttttatg tgtcagtaca    600
aatgaatact acactgaact gggaatgtat tatcacctgt tagtacagat cccaatattc    660
tttttcactg ttgtagtaat gttaatcaca tacaccaaaa tacttcaggc tcttaatatt    720
cgaataggca caagattttc aacagggcag aagaagaaag caagaaagaa aaagacaatt    780
tctctaacca cacaacatga ggctacagac atgtcacaaa gcagtggtgg gagaaatgta    840
gtctttggtg taagaacttc agtttctgta ataattgccc tccggcgagc tgtgaaacga    900
caccgtgaac gacgagaaag acaaaagaga gtcaagagga tgtctttatt gattatttct    960
acatttcttc tctgctggac accaatttct gttttaaata ccaccatttt atgtttaggc   1020
ccaagtgacc ttttagtaaa attaagattg tgtttttag tcatggctta tggaacaact   1080
atatttcacc ctctattata tgcattcact agacaaaaat ttcaaaaggt cttgaaaagt   1140
aaaatgaaaa agcgagttgt ttctatagta gaagctgatc ccctgcctaa taatgctgta   1200
atacacaact cttggataga tcccaaaaga aacaaaaaaa ttacctttga agatagtgaa   1260
ataagagaaa aacgtttagt gcctcaggtt gtcacagact ag                       1302
```

<210> SEQ ID NO 190
<211> LENGTH: 433
<212> TYPE: PRT
<213> ORGANISM: Homo sapiens

<400> SEQUENCE: 190

```
Met Cys Phe Ser Pro Ile Leu Glu Ile Asn Met Gln Ser Glu Ser Asn
  1               5                  10                  15

Ile Thr Val Arg Asp Asp Ile Asp Asp Ile Asn Thr Asn Met Tyr Gln
             20                  25                  30

Pro Leu Ser Tyr Pro Leu Ser Phe Gln Val Ser Leu Thr Gly Phe Leu
         35                  40                  45

Met Leu Glu Ile Val Leu Gly Leu Gly Ser Asn Leu Thr Val Leu Val
     50                  55                  60

Leu Tyr Cys Met Lys Ser Asn Leu Ile Asn Ser Val Ser Asn Ile Ile
 65                  70                  75                  80

Thr Met Asn Leu His Val Leu Asp Val Ile Cys Val Gly Cys Ile
                 85                  90                  95

Pro Leu Thr Ile Val Ile Leu Leu Ser Leu Glu Ser Asn Thr Ala
            100                 105                 110

Leu Ile Cys Cys Phe His Glu Ala Cys Val Ser Phe Ala Ser Val Ser
        115                 120                 125

Thr Ala Ile Asn Val Phe Ala Ile Thr Leu Asp Arg Tyr Asp Ile Ser
    130                 135                 140

Val Lys Pro Ala Asn Arg Ile Leu Thr Met Gly Arg Ala Val Met Leu
145                 150                 155                 160

Met Ile Ser Ile Trp Ile Phe Ser Phe Ser Phe Leu Ile Pro Phe
                165                 170                 175

Ile Glu Val Asn Phe Phe Ser Leu Gln Ser Gly Asn Thr Trp Glu Asn
            180                 185                 190

Lys Thr Leu Leu Cys Val Ser Thr Asn Glu Tyr Tyr Thr Glu Leu Gly
        195                 200                 205

Met Tyr Tyr His Leu Leu Val Gln Ile Pro Ile Phe Phe Phe Thr Val
    210                 215                 220
```

```
Val Val Met Leu Ile Thr Tyr Thr Lys Ile Leu Gln Ala Leu Asn Ile
225                 230                 235                 240

Arg Ile Gly Thr Arg Phe Ser Thr Gly Gln Lys Lys Ala Arg Lys
                245                 250                 255

Lys Lys Thr Ile Ser Leu Thr Thr Gln His Glu Ala Thr Asp Met Ser
                260                 265                 270

Gln Ser Ser Gly Gly Arg Asn Val Val Phe Gly Val Arg Thr Ser Val
            275                 280                 285

Ser Val Ile Ile Ala Leu Arg Arg Ala Val Lys Arg His Arg Glu Arg
            290                 295                 300

Arg Glu Arg Gln Lys Arg Val Lys Arg Met Ser Leu Leu Ile Ile Ser
305                 310                 315                 320

Thr Phe Leu Leu Cys Trp Thr Pro Ile Ser Val Leu Asn Thr Thr Ile
                325                 330                 335

Leu Cys Leu Gly Pro Ser Asp Leu Leu Val Lys Leu Arg Leu Cys Phe
                340                 345                 350

Leu Val Met Ala Tyr Gly Thr Thr Ile Phe His Pro Leu Leu Tyr Ala
                355                 360                 365

Phe Thr Arg Gln Lys Phe Gln Lys Val Leu Lys Ser Lys Met Lys Lys
370                 375                 380

Arg Val Val Ser Ile Val Glu Ala Asp Pro Leu Pro Asn Asn Ala Val
385                 390                 395                 400

Ile His Asn Ser Trp Ile Asp Pro Lys Arg Asn Lys Lys Ile Thr Phe
                405                 410                 415

Glu Asp Ser Glu Ile Arg Glu Lys Arg Leu Val Pro Gln Val Val Thr
                420                 425                 430

Asp

<210> SEQ ID NO 191
<211> LENGTH: 1209
<212> TYPE: DNA
<213> ORGANISM: Homo sapiens

<400> SEQUENCE: 191
atgttgtgtc cttccaagac agatggctca gggcactctg gtaggattca ccaggaaact     60
catggagaag ggaaaaggga caagattagc aacagtgaag ggagggagaa tggtgggaga    120
ggattccaga tgaacggtgg gtcgctggag gctgagcatg ccagcaggat gtcagttctc    180
agagcaaagc ccatgtcaaa cagccaacgc ttgctccttc tgtccccagg atcacctcct    240
cgcacgggga gcatctccta catcaacatc atcatgcctt cggtgttcgg caccatctgc    300
ctcctgggca tcatcgggaa ctccacggtc atcttcgcgg tcgtgaagaa gtccaagctg    360
cactggtgca caacgtccc gacatcttc atcatcaacc tctcggtagt agatctcctc    420
tttctcctgg gcatgcccttt catgatccac cagctcatgg gcaatgggt gtggcacttt    480
ggggagacca tgtgcaccct catcacggcc atggatgcca atagtcagtt caccagcacc    540
tacatcctga ccgccatggc cattgaccgc tacctggcca ctgtccaccc catctcttcc    600
acgaagttcc ggaagccctc tgtggccacc ctggtgatct gcctcctgtg ggccctctcc    660
ttcatcagca tcacccctgt gtggctgtat gccagactac tccccttccc aggaggtgca    720
gtgggctgcg gcatacgcct gcccaaccca gacactgacc tctactggtt caccctgtac    780
cagttttttcc tggcctttgc cctgccttt gtggtcatca cagccgcata cgtgaggatc    840
ctgcagcgca tgacgtcctc agtggccccc gcctcccagc gcagcatccg gctgcggaca    900
```

```
aagagggtga acgcacagc catcgccatc tgtctggtct tctttgtgtg ctgggcaccc      960
tactatgtgc tacagctgac ccagttgtcc atcagccgcc cgaccctcac ctttgtctac   1020
ttatacaatg cggccatcag cttgggctat gccaacagct gcctcaaccc ctttgtgtac   1080
atcgtgctct gtgagacgtt ccgcaaacgc ttggtcctgt cggtgaagcc tgcagcccag   1140
gggcagcttc gcgctgtcag caacgctcag acggctgacg aggagaggac agaaagcaaa   1200
ggcacctga                                                           1209
```

<210> SEQ ID NO 192
<211> LENGTH: 402
<212> TYPE: PRT
<213> ORGANISM: Homo sapiens

<400> SEQUENCE: 192

```
Met Leu Cys Pro Ser Lys Thr Asp Gly Ser Gly His Ser Gly Arg Ile
1               5                   10                  15

His Gln Glu Thr His Gly Glu Gly Lys Arg Asp Lys Ile Ser Asn Ser
            20                  25                  30

Glu Gly Arg Glu Asn Gly Gly Arg Gly Phe Gln Met Asn Gly Gly Ser
        35                  40                  45

Leu Glu Ala Glu His Ala Ser Arg Met Ser Val Leu Arg Ala Lys Pro
    50                  55                  60

Met Ser Asn Ser Gln Arg Leu Leu Leu Ser Pro Gly Ser Pro Pro
65                  70                  75                  80

Arg Thr Gly Ser Ile Ser Tyr Ile Asn Ile Met Pro Ser Val Phe
                85                  90                  95

Gly Thr Ile Cys Leu Leu Gly Ile Ile Gly Asn Ser Thr Val Ile Phe
            100                 105                 110

Ala Val Val Lys Lys Ser Lys Leu His Trp Cys Asn Asn Val Pro Asp
        115                 120                 125

Ile Phe Ile Ile Asn Leu Ser Val Val Asp Leu Leu Phe Leu Leu Gly
    130                 135                 140

Met Pro Phe Met Ile His Gln Leu Met Gly Asn Gly Val Trp His Phe
145                 150                 155                 160

Gly Glu Thr Met Cys Thr Leu Ile Thr Ala Met Asp Ala Asn Ser Gln
                165                 170                 175

Phe Thr Ser Thr Tyr Ile Leu Thr Ala Met Ala Ile Asp Arg Tyr Leu
            180                 185                 190

Ala Thr Val His Pro Ile Ser Ser Thr Lys Phe Arg Lys Pro Ser Val
        195                 200                 205

Ala Thr Leu Val Ile Cys Leu Leu Trp Ala Leu Ser Phe Ile Ser Ile
    210                 215                 220

Thr Pro Val Trp Leu Tyr Ala Arg Leu Ile Pro Phe Pro Gly Gly Ala
225                 230                 235                 240

Val Gly Cys Gly Ile Arg Leu Pro Asn Pro Asp Thr Asp Leu Tyr Trp
                245                 250                 255

Phe Thr Leu Tyr Gln Phe Phe Leu Ala Phe Ala Leu Pro Phe Val Val
            260                 265                 270

Ile Thr Ala Ala Tyr Val Arg Ile Leu Gln Arg Met Thr Ser Ser Val
        275                 280                 285

Ala Pro Ala Ser Gln Arg Ser Ile Arg Leu Arg Thr Lys Arg Val Lys
    290                 295                 300

Arg Thr Ala Ile Ala Ile Cys Leu Val Phe Phe Val Cys Trp Ala Pro
305                 310                 315                 320
```

Tyr Tyr Val Leu Gln Leu Thr Gln Leu Ser Ile Ser Arg Pro Thr Leu
                325                 330                 335

Thr Phe Val Tyr Leu Tyr Asn Ala Ala Ile Ser Leu Gly Tyr Ala Asn
            340                 345                 350

Ser Cys Leu Asn Pro Phe Val Tyr Ile Val Leu Cys Glu Thr Phe Arg
        355                 360                 365

Lys Arg Leu Val Leu Ser Val Lys Pro Ala Ala Gln Gly Gln Leu Arg
    370                 375                 380

Ala Val Ser Asn Ala Gln Thr Ala Asp Glu Glu Arg Thr Glu Ser Lys
385                 390                 395                 400

Gly Thr

<210> SEQ ID NO 193
<211> LENGTH: 1128
<212> TYPE: DNA
<213> ORGANISM: Homo sapiens

<400> SEQUENCE: 193

```
atggatgtga cttcccaagc ccggggcgtg ggcctggaga tgtacccagg caccgcgcac      60
gctgcggccc caacaccac ctcccccgag ctcaacctgt cccacccgct cctgggcacc     120
gccctggcca atgggacagg tgagctctcg gagcaccagc agtacgtgat cggcctgttc     180
ctctcgtgcc tctacaccat cttcctcttc cccatcggct ttgtgggcaa catcctgatc     240
ctggtggtga acatcagctt ccgcgagaag atgaccatcc ccgacctgta cttcatcaac     300
ctggcggtgg cggacctcat cctggtggcc gactccctca ttgaggtgtt caacctgcac     360
gagcggtact acgacatcgc cgtcctgtgc accttcatgt cgctcttcct gcaggtcaac     420
atgtacagca gcgtcttctt cctcacctgg atgagcttcg accgctacat cgccctggcc     480
agggccatgc gctgcagcct gttccgcacc aagcaccacg cccggctgag ctgtggcctc     540
atctggatgg catccgtgtc agccacgctg gtgcccttca ccgccgtgca cctgcagcac     600
accgacgagg cctgcttctg tttcgcggat gtccgggagg tgcagtggct cgaggtcacg     660
ctgggcttca tcgtgccctt cgccatcatc ggcctgtgct actccctcat tgtccgggtg     720
ctggtcaggg cgcaccggca ccgtgggctg cggccccggc ggcagaaggc gaaacgcatg     780
atcctcgcgg tggtgctggt cttcttcgtc tgctggctgc cggagaacgt cttcatcagc     840
gtgcacctcc tgcagcggac gcagcctggg gccgctccct gcaagcagtc tttccgccat     900
gcccaccccc tcacgggcca cattgtcaac ctcgccgcct ctccaacag ctgcctaaac     960
cccctcatct acagctttct cggggagacc ttcagggaca agctgaggct gtacattgag    1020
cagaaaacaa atttgccggc cctgaaccgc ttctgtcacg ctgccctgaa ggccgtcatt    1080
ccagacagca ccgagcagtc ggatgtgagg ttcagcagtg ccgtgtga                 1128
```

<210> SEQ ID NO 194
<211> LENGTH: 375
<212> TYPE: PRT
<213> ORGANISM: Homo sapiens

<400> SEQUENCE: 194

Met Asp Val Thr Ser Gln Ala Arg Gly Val Gly Leu Glu Met Tyr Pro
1               5                   10                  15

Gly Thr Ala His Ala Ala Ala Pro Asn Thr Thr Ser Pro Glu Leu Asn
            20                  25                  30

Leu Ser His Pro Leu Leu Gly Thr Ala Leu Ala Asn Gly Thr Gly Glu

```
                 35                   40                  45
Leu Ser Glu His Gln Gln Tyr Val Ile Gly Leu Phe Leu Ser Cys Leu
     50                   55                  60

Tyr Thr Ile Phe Leu Phe Pro Ile Gly Phe Val Gly Asn Ile Leu Ile
 65                   70                  75                  80

Leu Val Val Asn Ile Ser Phe Arg Glu Lys Met Thr Ile Pro Asp Leu
                 85                   90                  95

Tyr Phe Ile Asn Leu Ala Val Ala Asp Leu Ile Leu Val Ala Asp Ser
                100                  105                 110

Leu Ile Glu Val Phe Asn Leu His Glu Arg Tyr Tyr Asp Ile Ala Val
            115                  120                 125

Leu Cys Thr Phe Met Ser Leu Phe Leu Gln Val Asn Met Tyr Ser Ser
    130                  135                 140

Val Phe Phe Leu Thr Trp Met Ser Phe Asp Arg Tyr Ile Ala Leu Ala
145                  150                 155                 160

Arg Ala Met Arg Cys Ser Leu Phe Arg Thr Lys His His Ala Arg Leu
                165                  170                 175

Ser Cys Gly Leu Ile Trp Met Ala Ser Val Ser Ala Thr Leu Val Pro
            180                  185                 190

Phe Thr Ala Val His Leu Gln His Thr Asp Glu Ala Cys Phe Cys Phe
        195                  200                 205

Ala Asp Val Arg Glu Val Gln Trp Leu Glu Val Thr Leu Gly Phe Ile
    210                  215                 220

Val Pro Phe Ala Ile Ile Gly Leu Cys Tyr Ser Leu Ile Val Arg Val
225                  230                 235                 240

Leu Val Arg Ala His Arg His Arg Gly Leu Arg Pro Arg Arg Gln Lys
                245                  250                 255

Ala Lys Arg Met Ile Leu Ala Val Val Leu Val Phe Phe Val Cys Trp
            260                  265                 270

Leu Pro Glu Asn Val Phe Ile Ser Val His Leu Leu Gln Arg Thr Gln
        275                  280                 285

Pro Gly Ala Ala Pro Cys Lys Gln Ser Phe Arg His Ala His Pro Leu
    290                  295                 300

Thr Gly His Ile Val Asn Leu Ala Ala Phe Ser Asn Ser Cys Leu Asn
305                  310                 315                 320

Pro Leu Ile Tyr Ser Phe Leu Gly Glu Thr Phe Arg Asp Lys Leu Arg
                325                  330                 335

Leu Tyr Ile Glu Gln Lys Thr Asn Leu Pro Ala Leu Asn Arg Phe Cys
            340                  345                 350

His Ala Ala Leu Lys Ala Val Ile Pro Asp Ser Thr Glu Gln Ser Asp
        355                  360                 365

Val Arg Phe Ser Ser Ala Val
    370                  375

<210> SEQ ID NO 195
<211> LENGTH: 960
<212> TYPE: DNA
<213> ORGANISM: Homo sapiens

<400> SEQUENCE: 195
atgccattcc caaactgctc agcccccagc actgtggtgg ccacagctgt gggtgtcttg      60
ctggggctgg agtgtgggct gggtctgctg ggcaacgcgg tggcgctgtg gaccttcctg     120
ttccgggtca gggtgtggaa gccgtacgct gtctacctgc tcaacctggc cctggctgac     180
```

```
ctgctgttgg ctgcgtgcct gcctttcctg gccgccttct acctgagcct ccaggcttgg    240
catctgggcc gtgtgggctg ctgggccctg cgcttcctgc tggacctcag ccgcagcgtg    300
gggatggcct tcctggccgc cgtggctttg accggtacc tccgtgtggt ccaccctcgg     360
cttaaggtca acctgctgtc tcctcaggcg gccctggggg tctcgggcct cgtctggctc    420
ctgatggtcg ccctcacctg cccgggcttg ctcatctctg aggccgccca gaactccacc    480
aggtgccaca gtttctactc cagggcagac ggctccttca gcatcatctg caggaagca     540 ctctcctgcc ttcagtttgt cctcccctt ggcctcatcg tgttctgcaa tgcaggcatc     600
atcagggctc tccagaaaag actccgggag cctgagaaac agcccaagct tcagcgggcc    660
aaggcactgg tcaccttggt ggtggtgctg tttgctctgt gctttctgcc ctgcttcctg    720
gccagagtcc tgatgcacat cttccagaat ctggggagct gcagggccct ttgtgcagtg    780 gctcataccct cggatgtcac gggcagcctc acctacctgc acagtgtcgt caaccccgtg    840
gtatactgct tctccagccc caccttcagg agctcctatc ggagggtctt ccacaccctc    900
cgaggcaaag ggcaggcagc agagccccca gatttcaacc ccagagactc ctattcctga    960
```

<210> SEQ ID NO 196
<211> LENGTH: 319
<212> TYPE: PRT
<213> ORGANISM: Homo sapiens

<400> SEQUENCE: 196

```
Met Pro Phe Pro Asn Cys Ser Ala Pro Ser Thr Val Val Ala Thr Ala
1               5                   10                  15

Val Gly Val Leu Leu Gly Leu Glu Cys Gly Leu Gly Leu Leu Gly Asn
            20                  25                  30

Ala Val Ala Leu Trp Thr Phe Leu Phe Arg Val Arg Val Trp Lys Pro
        35                  40                  45

Tyr Ala Val Tyr Leu Leu Asn Leu Ala Leu Ala Asp Leu Leu Leu Ala
    50                  55                  60

Ala Cys Leu Pro Phe Leu Ala Ala Phe Tyr Leu Ser Leu Gln Ala Trp
65                  70                  75                  80

His Leu Gly Arg Val Gly Cys Trp Ala Leu Arg Phe Leu Leu Asp Leu
                85                  90                  95

Ser Arg Ser Val Gly Met Ala Phe Leu Ala Ala Val Ala Leu Asp Arg
            100                 105                 110

Tyr Leu Arg Val His Pro Arg Leu Lys Val Asn Leu Leu Ser Pro
        115                 120                 125

Gln Ala Ala Leu Gly Val Ser Gly Leu Val Trp Leu Leu Met Val Ala
    130                 135                 140

Leu Thr Cys Pro Gly Leu Leu Ile Ser Glu Ala Ala Gln Asn Ser Thr
145                 150                 155                 160

Arg Cys His Ser Phe Tyr Ser Arg Ala Asp Gly Ser Phe Ser Ile Ile
                165                 170                 175

Trp Gln Glu Ala Leu Ser Cys Leu Gln Phe Val Leu Pro Phe Gly Leu
            180                 185                 190

Ile Val Phe Cys Asn Ala Gly Ile Ile Arg Ala Leu Gln Lys Arg Leu
        195                 200                 205

Arg Glu Pro Glu Lys Gln Pro Lys Leu Gln Arg Ala Lys Ala Leu Val
    210                 215                 220

Thr Leu Val Val Val Leu Phe Ala Leu Cys Phe Leu Pro Cys Phe Leu
225                 230                 235                 240
```

Ala Arg Val Leu Met His Ile Phe Gln Asn Leu Gly Ser Cys Arg Ala
                245                 250                 255

Leu Cys Ala Val Ala His Thr Ser Asp Val Thr Gly Ser Leu Thr Tyr
            260                 265                 270

Leu His Ser Val Val Asn Pro Val Tyr Cys Phe Ser Ser Pro Thr
        275                 280                 285

Phe Arg Ser Ser Tyr Arg Arg Val Phe His Thr Leu Arg Gly Lys Gly
    290                 295                 300

Gln Ala Ala Glu Pro Pro Asp Phe Asn Pro Arg Asp Ser Tyr Ser
305                 310                 315

<210> SEQ ID NO 197
<211> LENGTH: 1143
<212> TYPE: DNA
<213> ORGANISM: Homo sapiens

<400> SEQUENCE: 197

| | |
|---|---|
| atggaggaag gtggtgattt tgacaactac tatggggcag acaaccagtc tgagtgtgag | 60 |
| tacacagact ggaaatcctc gggggccctc atccctgcca tctacatgtt ggtcttcctc | 120 |
| ctgggcacca cggaaacgg tctggtgctc tggaccgtgt ttcggagcag ccgggagaag | 180 |
| aggcgctcag ctgatatctt cattgctagc ctggcggtgg ctgacctgac cttcgtggtg | 240 |
| acgctgcccc tgtgggctac ctacacgtac cgggactatg actggccctt gggaccttc | 300 |
| ttctgcaagc tcagcagcta cctcatcttc gtcaacatgt acgccagcgt cttctgcctc | 360 |
| accggcctca gcttcgaccg ctacctggcc atcgtgaggc cagtggccaa tgctcggctg | 420 |
| aggctgcggg tcagcggggc cgtggccacg gcagttcttt gggtgctggc cgccctcctg | 480 |
| gccatgcctg tcatggtgtt acgcaccacc ggggacttgg agaacaccac taaggtgcag | 540 |
| tgctacatgg actactccat ggtggccact gtgagctcag agtgggcctg ggaggtgggc | 600 |
| cttggggtct cgtccaccac cgtgggcttt gtggtgccct tcaccatcat gctgacctgt | 660 |
| tacttcttca tcgcccaaac catcgctggc cacttccgca ggaacgcat cgagggcctg | 720 |
| cggaagcggc gccggcttaa gagcatcatc gtggtgctgg tgtgaccttt gccctgtgc | 780 |
| tggatgccct accacctggt gaagacgctg tacatgctgg gcagcctgct gcactggccc | 840 |
| tgtgactttg acctcttcct catgaacatc ttcccctact gcacctgcat cagctacgtc | 900 |
| aacagctgcc tcaaccccct cctctatgcc tttttcgacc ccgcttccg ccaggcctgc | 960 |
| acctccatgc tctgctgtgg ccagagcagg tgcgcaggca cctcccacag cagcagtggg | 1020 |
| gagaagtcag ccagctactc ttcggggcac agccaggggc ccggcccaa catgggcaag | 1080 |
| ggtggagaac agatgcacga gaaatccatc ccctacagcc aggagaccct tgtggttgac | 1140 |
| tag | 1143 |

<210> SEQ ID NO 198
<211> LENGTH: 380
<212> TYPE: PRT
<213> ORGANISM: Homo sapiens

<400> SEQUENCE: 198

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

| | | | | | | | | | | | |
|---|---|---|---|---|---|---|---|---|---|---|---|
| Val | Leu | Trp | Thr | Val | Phe | Arg | Ser | Ser | Arg | Glu | Lys | Arg | Arg | Ser | Ala |
| 50 | | | | | 55 | | | | | 60 | |
| Asp | Ile | Phe | Ile | Ala | Ser | Leu | Ala | Val | Ala | Asp | Leu | Thr | Phe | Val | Val |
| 65 | | | | | 70 | | | | | 75 | | | | | 80 |
| Thr | Leu | Pro | Leu | Trp | Ala | Thr | Tyr | Thr | Tyr | Arg | Asp | Tyr | Asp | Trp | Pro |
| | | | | 85 | | | | | 90 | | | | | 95 | |
| Phe | Gly | Thr | Phe | Phe | Cys | Lys | Leu | Ser | Ser | Tyr | Leu | Ile | Phe | Val | Asn |
| | | | 100 | | | | | 105 | | | | | 110 | |
| Met | Tyr | Ala | Ser | Val | Phe | Cys | Leu | Thr | Gly | Leu | Ser | Phe | Asp | Arg | Tyr |
| | | 115 | | | | | 120 | | | | | 125 | | |
| Leu | Ala | Ile | Val | Arg | Pro | Val | Ala | Asn | Ala | Arg | Leu | Arg | Leu | Arg | Val |
| | 130 | | | | | 135 | | | | | 140 | | | | |
| Ser | Gly | Ala | Val | Ala | Thr | Ala | Val | Leu | Trp | Val | Leu | Ala | Ala | Leu | Leu |
| 145 | | | | | 150 | | | | | 155 | | | | | 160 |
| Ala | Met | Pro | Val | Met | Val | Leu | Arg | Thr | Thr | Gly | Asp | Leu | Glu | Asn | Thr |
| | | | | 165 | | | | | 170 | | | | | 175 | |
| Thr | Lys | Val | Gln | Cys | Tyr | Met | Asp | Tyr | Ser | Met | Val | Ala | Thr | Val | Ser |
| | | | 180 | | | | | 185 | | | | | 190 | | |
| Ser | Glu | Trp | Ala | Trp | Glu | Val | Gly | Leu | Gly | Val | Ser | Ser | Thr | Thr | Val |
| | | | 195 | | | | | 200 | | | | | 205 | | |
| Gly | Phe | Val | Val | Pro | Phe | Thr | Ile | Met | Leu | Thr | Cys | Tyr | Phe | Phe | Ile |
| 210 | | | | | 215 | | | | | 220 | | | | | |
| Ala | Gln | Thr | Ile | Ala | Gly | His | Phe | Arg | Lys | Glu | Arg | Ile | Glu | Gly | Leu |
| 225 | | | | | 230 | | | | | 235 | | | | | 240 |
| Arg | Lys | Arg | Arg | Arg | Leu | Lys | Ser | Ile | Ile | Val | Val | Leu | Val | Val | Thr |
| | | | | 245 | | | | | 250 | | | | | 255 | |
| Phe | Ala | Leu | Cys | Trp | Met | Pro | Tyr | His | Leu | Val | Lys | Thr | Leu | Tyr | Met |
| | | | 260 | | | | | 265 | | | | | 270 | | |
| Leu | Gly | Ser | Leu | Leu | His | Trp | Pro | Cys | Asp | Phe | Asp | Leu | Phe | Leu | Met |
| | | 275 | | | | | 280 | | | | | 285 | | | |
| Asn | Ile | Phe | Pro | Tyr | Cys | Thr | Cys | Ile | Ser | Tyr | Val | Asn | Ser | Cys | Leu |
| | 290 | | | | | 295 | | | | | 300 | | | | |
| Asn | Pro | Phe | Leu | Tyr | Ala | Phe | Phe | Asp | Pro | Arg | Phe | Arg | Gln | Ala | Cys |
| 305 | | | | | 310 | | | | | 315 | | | | | 320 |
| Thr | Ser | Met | Leu | Cys | Cys | Gly | Gln | Ser | Arg | Cys | Ala | Gly | Thr | Ser | His |
| | | | | 325 | | | | | 330 | | | | | 335 | |
| Ser | Ser | Ser | Gly | Glu | Lys | Ser | Ala | Ser | Tyr | Ser | Ser | Gly | His | Ser | Gln |
| | | | 340 | | | | | 345 | | | | | 350 | | |
| Gly | Pro | Gly | Pro | Asn | Met | Gly | Lys | Gly | Gly | Glu | Gln | Met | His | Glu | Lys |
| | | | 355 | | | | | 360 | | | | | 365 | | |
| Ser | Ile | Pro | Tyr | Ser | Gln | Glu | Thr | Leu | Val | Val | Asp |
| | 370 | | | | | 375 | | | | | 380 |

<210> SEQ ID NO 199
<211> LENGTH: 1119
<212> TYPE: DNA
<213> ORGANISM: Homo sapiens

<400> SEQUENCE: 199

| | | |
|---|---|---|
| atgaactacc cgctaacgct ggaaatggac ctcgagaacc tggaggacct gttctgggaa | 60 |
| ctggacagat tggacaacta taacgacacc tccctggtgg aaaatcatct ctgccctgcc | 120 |
| acagagggtc ccctcatggc ctccttcaag gccgtgttcg tgcccgtggc ctacagcctc | 180 |
| atcttcctcc tgggcgtgat cggcaacgtc ctggtgctgg tgatcctgga gcggcaccgg | 240 |

```
cagacacgca gttccacgga gaccttcctg ttccacctgg ccgtggccga cctcctgctg     300
gtcttcatct tgccctttgc cgtggccgag ggctctgtgg gctgggtcct ggggaccttc     360
ctctgcaaaa ctgtgattgc cctgcacaaa gtcaacttct actgcagcag cctgctcctg     420
gcctgcatcg ccgtggaccg ctacctggcc attgtccacg ccgtccatgc ctaccgccac     480
cgccgcctcc tctccatcca catcacctgt gggaccatct ggctggtggg cttcctcctt     540
gccttgccag agattctctt cgccaaagtc agccaaggcc atcacaacaa ctccctgcca     600
cgttgcacct ctcccaaga gaaccaagca gaaacgcatg cctggttcac ctcccgattc     660
ctctaccatg tggcgggatt cctgctgccc atgctggtga tgggctggtg ctacgtgggg     720
gtagtgcaca ggttgcgcca ggcccagcgg cgccctcagc ggcagaaggc aaaaagggtg     780
gccatcctgg tgacaagcat cttcttcctc tgctggtcac cctaccacat cgtcatcttc     840
ctggacaccc tggcgaggct gaaggccgtg gacaatacct gcaagctgaa tggctctctc     900
cccgtggcca tcaccatgtg tgagttcctg ggcctggccc actgctgcct caaccccatg     960
ctctacactt tcgccggcgt gaagttccgc agtgacctgt cgcggctcct gaccaagctg    1020
ggctgtaccg gccctgcctc cctgtgccag ctcttcccta gctggcgcag gagcagtctc    1080
tctgagtcag agaatgccac ctctctcacc acgttctag                           1119
```

<210> SEQ ID NO 200
<211> LENGTH: 372
<212> TYPE: PRT
<213> ORGANISM: Homo sapiens

<400> SEQUENCE: 200

```
Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
```

|     |     |     |     |     | 210 |     |     |     |     | 215 |     |     |     |     | 220 |     |     |     |     |
|-----|-----|-----|-----|-----|-----|-----|-----|-----|-----|-----|-----|-----|-----|-----|-----|-----|-----|-----|-----|
| Ala | Gly | Phe | Leu | Leu | Pro | Met | Leu | Val | Met | Gly | Trp | Cys | Tyr | Val | Gly |
| 225 |     |     |     |     | 230 |     |     |     |     | 235 |     |     |     |     | 240 |

```
Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Lys Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370
```

<210> SEQ ID NO 201
<211> LENGTH: 1128
<212> TYPE: DNA
<213> ORGANISM: Homo sapiens

<400> SEQUENCE: 201

| atggatgtga cttcccaagc ccggggcgtg ggcctggaga tgtacccagg caccgcgcag | 60 |
|---|---|
| cctgcggccc ccaacaccac ctcccccgag ctcaacctgt cccaccgct cctgggcacc | 120 |
| gccctggcca atgggacagg tgagctctcg gagcaccagc agtacgtgat cggcctgttc | 180 |
| ctctcgtgcc tctacaccat cttcctcttc cccatcggct tgtgggcaa catcctgatc | 240 |
| ctggtggtga acatcagctt ccgcgagaag atgaccatcc ccgacctgta cttcatcaac | 300 |
| ctggcggtgg cggacctcat cctggtggcc gactccctca ttgaggtgtt caacctgcac | 360 |
| gagcggtact acgacatcgc cgtcctgtgc accttcatgt cgctcttcct gcaggtcaac | 420 |
| atgtacagca cgtcttcttc cctcacctgg atgagcttcg accgctacat cgccctggcc | 480 |
| agggccatgc gctgcagcct gttccgcacc aagcaccacg cccggctgag ctgtggcctc | 540 |
| atctggatga catccgtgtc agccacgctg gtgcccttca ccgccgtgca cctgcagcac | 600 |
| accgacgagg cctgcttctg tttcgcggat gtccgggagg tgcagtggct cgaggtcacg | 660 |
| ctgggcttca tcgtgccctt cgccatcatc ggcctgtgct actccctcat tgtccgggtg | 720 |
| ctggtcaggg cgcaccggca ccgtgggctg cggccccggc ggcagaaggc gaagcgcatg | 780 |
| atcctcgcgg tggtgctggt cttcttcgtc tgctggctgc cggagaacgt cttcatcagc | 840 |
| gtgcacctcc tgcagcggac gcagcctggg gccgctccct gcaagcagtc tttccgccat | 900 |
| gcccaccccc tcacgggcca cattgtcaac ctcaccgcct tctccaacag ctgcctaaac | 960 |
| cccctcatct acagctttct cggggagacc ttcagggaca agctgaggct gtacattgag | 1020 |
| cagaaaacaa atttgccggc cctgaaccgc ttctgtcacg ctgccctgaa ggccgtcatt | 1080 |
| ccagacagca ccgagcagtc ggatgtgagg ttcagcagtg ccgtgtag | 1128 |

```
<210> SEQ ID NO 202
<211> LENGTH: 375
<212> TYPE: PRT
<213> ORGANISM: Homo sapiens

<400> SEQUENCE: 202

Met Asp Val Thr Ser Gln Ala Arg Gly Val Gly Leu Glu Met Tyr Pro
1               5                   10                  15

Gly Thr Ala Gln Pro Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Lys Arg Met Ile Leu Ala Val Val Leu Val Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Thr Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375
```

<210> SEQ ID NO 203
<211> LENGTH: 1137
<212> TYPE: DNA
<213> ORGANISM: Homo sapiens

<400> SEQUENCE: 203

```
atggacctgg ggaaaccaat gaaaagcgtg ctggtggtgg ctctccttgt cattttccag      60
gtatgcctgt gtcaagatga ggtcacggac gattacatcg gagacaacac cacagtggac     120
tacactttgt tcgagtcttt tgtgctccaa aggacgtgc ggaactttaa agcctggttc      180
ctccctatca tgtactccat catttgtttc gtgggcctac tgggcaatgg gctggtcgtg     240
ttgacctata tctatttcaa gaggctcaag accatgaccg ataccaccta ctgctcaacctg   300
gcggtggcag acatcctctt cctcctgacc cttcccttct gggcctacag cgcggccaag     360
tcctgggtct tcggtgtcca ctttgcaag ctcatctttg ccatctacaa gatgagcttc      420
ttcagtggca tgctcctact tctttgcatc agcattgacc gctacgtggc catcgtccag     480
gctgtctcag ctcaccgcca ccgtgcccgc gtccttctca tcagcaagct gtcctgtgtg     540
ggcatctgga tactagccac agtgctctcc atcccagagc tcctgtacag tgacctccag     600
aggagcagca gtgagcaagc gatgcgatgc tctctcatca cagagcatgt ggaggccttt     660
atcaccatcc aggtggccca gatggtgatc ggctttctgg tcccctgct ggccatgagc      720
ttctgttacc ttgtcatcat ccgcacctgg ctccaggcac gcaactttga gcgcaacaag     780
gccaaaaagg tgatcatcgc tgtggtcgtg gtcttcatag tcttccagct gcctacaat     840
gggtggtcc tggcccagac ggtggccaac ttcaacatca ccagtagcac ctgtgagctc      900
agtaagcaac tcaacatcgc ctacgacgtc acctacagcc tggcctgcgt ccgctgctgc     960
gtcaacccctt tcttgtacgc cttcatcggc gtcaagttcc gcaacgatct cttcaagctc    1020
ttcaaggacc tgggctgcct cagccaggag cagctccggc agtggtcttc ctgtcggcac    1080
atccggcgct cctccatgag tgtggaggcc gagaccacca ccaccttctc cccatag        1137
```

<210> SEQ ID NO 204
<211> LENGTH: 378
<212> TYPE: PRT
<213> ORGANISM: Homo sapiens

<400> SEQUENCE: 204

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
```

| | | | | | | | | | | | |
|---|---|---|---|---|---|---|---|---|---|---|---|
| | | 130 | | | | 135 | | | | 140 | |
| Leu | Leu | Leu | Leu | Cys | Ile | Ser | Ile | Asp | Arg | Tyr | Val | Ala | Ile | Val | Gln |
| 145 | | | | 150 | | | | 155 | | | | 160 |

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
    195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
            245                 250                 255

Glu Arg Asn Lys Ala Lys Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
370                 375

<210> SEQ ID NO 205
<211> LENGTH: 1086
<212> TYPE: DNA
<213> ORGANISM: Homo sapiens

<400> SEQUENCE: 205

| | | |
|---|---|---|
| atggatatac aaatggcaaa caattttact ccgccctctg caactcctca gggaaatgac | 60 |
| tgtgacctct atgcacatca cagcacggcc aggatagtaa tgcctctgca ttacagcctc | 120 |
| gtcttcatca ttgggctcgt gggaaactta ctagccttgg tcgtcattgt tcaaaacagg | 180 |
| aaaaaaatca actctaccac cctctattca acaaatttgg tgatttctga tatactttt | 240 |
| accacggctt tgcctacacg aatagcctac tatgcaatgg gctttgactg gagaatcgga | 300 |
| gatgccttgt gtaggataac tgcgctagtg ttttacatca acacatatgc aggtgtgaac | 360 |
| tttatgacct gcctgagtat tgaccgcttc attgctgtgg tgcaccctct acgctacaac | 420 |
| aagataaaaa ggattgaaca tgcaaaaggc gtgtgcatat ttgtctggat tctagtatt | 480 |
| gctcagacac tcccactcct catcaaccct atgtcaaagc aggaggctga aaggattaca | 540 |
| tgcatggagt atccaaactt gaagaaact aaatctcttc cctggattct gcttggggca | 600 |
| tgtttcatag gatatgtact tccacttata atcattctca tctgctattc tcagatctgc | 660 |
| tgcaaactct tcagaactgc caaacaaaac ccactcactg agaaatctgg tgtaaacaaa | 720 |

```
aaggctaaaa acacaattat tcttattatt gttgtgtttg ttctctgttt cacaccttac    780
catgttgcaa ttattcaaca tatgattaag aagcttcgtt tctctaattt cctggaatgt    840
agccaaagac attcgttcca gatttctctg cactttacag tatgcctgat gaacttcaat    900
tgctgcatgg accctttat ctacttcttt gcatgtaaag ggtataagag aaaggttatg     960
aggatgctga acggcaagt cagtgtatcg atttctagtg ctgtgaagtc agcccctgaa    1020
gaaaattcac gtgaaatgac agaaacgcag atgatgatac attccaagtc ttcaaatgga   1080
aagtga                                                              1086

<210> SEQ ID NO 206
<211> LENGTH: 361
<212> TYPE: PRT
<213> ORGANISM: Homo sapiens

<400> SEQUENCE: 206

Met Asp Ile Gln Met Ala Asn Asn Phe Thr Pro Pro Ser Ala Thr Pro
 1               5                  10                  15

Gln Gly Asn Asp Cys Asp Leu Tyr Ala His His Ser Thr Ala Arg Ile
                20                  25                  30

Val Met Pro Leu His Tyr Ser Leu Val Phe Ile Ile Gly Leu Val Gly
            35                  40                  45

Asn Leu Leu Ala Leu Val Val Ile Val Gln Asn Arg Lys Lys Ile Asn
 50                  55                  60

Ser Thr Thr Leu Tyr Ser Thr Asn Leu Val Ile Ser Asp Ile Leu Phe
65                  70                  75                  80

Thr Thr Ala Leu Pro Thr Arg Ile Ala Tyr Tyr Ala Met Gly Phe Asp
                85                  90                  95

Trp Arg Ile Gly Asp Ala Leu Cys Arg Ile Thr Ala Leu Val Phe Tyr
            100                 105                 110

Ile Asn Thr Tyr Ala Gly Val Asn Phe Met Thr Cys Leu Ser Ile Asp
        115                 120                 125

Arg Phe Ile Ala Val Val His Pro Leu Arg Tyr Asn Lys Ile Lys Arg
130                 135                 140

Ile Glu His Ala Lys Gly Val Cys Ile Phe Val Trp Ile Leu Val Phe
145                 150                 155                 160

Ala Gln Thr Leu Pro Leu Leu Ile Asn Pro Met Ser Lys Gln Glu Ala
                165                 170                 175

Glu Arg Ile Thr Cys Met Glu Tyr Pro Asn Phe Glu Glu Thr Lys Ser
            180                 185                 190

Leu Pro Trp Ile Leu Leu Gly Ala Cys Phe Ile Gly Tyr Val Leu Pro
        195                 200                 205

Leu Ile Ile Ile Leu Ile Cys Tyr Ser Gln Ile Cys Cys Lys Leu Phe
    210                 215                 220

Arg Thr Ala Lys Gln Asn Pro Leu Thr Glu Lys Ser Gly Val Asn Lys
225                 230                 235                 240

Lys Ala Lys Asn Thr Ile Ile Leu Ile Ile Val Val Phe Val Leu Cys
                245                 250                 255

Phe Thr Pro Tyr His Val Ala Ile Ile Gln His Met Ile Lys Lys Leu
            260                 265                 270

Arg Phe Ser Asn Phe Leu Glu Cys Ser Gln Arg His Ser Phe Gln Ile
        275                 280                 285

Ser Leu His Phe Thr Val Cys Leu Met Asn Phe Asn Cys Cys Met Asp
    290                 295                 300
```

Pro Phe Ile Tyr Phe Phe Ala Cys Lys Gly Tyr Lys Arg Lys Val Met
305                 310                 315                 320

Arg Met Leu Lys Arg Gln Val Ser Val Ser Ile Ser Ser Ala Val Lys
            325                 330                 335

Ser Ala Pro Glu Glu Asn Ser Arg Glu Met Thr Glu Thr Gln Met Met
        340                 345                 350

Ile His Ser Lys Ser Ser Asn Gly Lys
        355                 360

<210> SEQ ID NO 207
<211> LENGTH: 1446
<212> TYPE: DNA
<213> ORGANISM: Homo sapiens

<400> SEQUENCE: 207

| | | | | | |
|---|---|---|---|---|---|
| atgcggtggc | tgtggcccct | ggctgtctct | cttgctgtga | ttttggctgt | ggggctaagc | 60 |
| agggtctctg | ggggtgcccc | cctgcacctg | ggcaggcaca | gagccgagac | ccaggagcag | 120 |
| cagagccgat | ccaagagggg | caccgaggat | gaggaggcca | agggcgtgca | gcagtatgtg | 180 |
| cctgaggagt | gggcggagta | cccccggccc | attcaccctg | ctggcctgca | gccaaccaag | 240 |
| cccttggtgg | ccaccagccc | taaccccgac | aaggatgggg | caccccaga | cagtgggcag | 300 |
| gaactgaggg | gcaatctgac | aggggcacca | gggcagaggc | tacagatcca | gaaccccctg | 360 |
| tatccggtga | ccgagagctc | ctacagtgcc | tatgccatca | tgcttctggc | gctggtggtg | 420 |
| tttgcggtgg | gcattgtggg | caacctgtcg | gtcatgtgca | tcgtgtggca | cagctactac | 480 |
| ctgaagagcg | cctggaactc | catccttgcc | agcctggccc | tctgggattt | tctggtcctc | 540 |
| tttttctgcc | tccctattgt | catcttcaac | gagatcacca | gcagaggct | actgggtgac | 600 |
| gtttcttgtc | gtgccgtgcc | cttcatggag | gtctcctctc | tgggagtcac | gactttcagc | 660 |
| ctctgtgccc | tggcattga | ccgcttccac | gtggccacca | gcaccctgcc | caaggtgagg | 720 |
| cccatcgagc | ggtgccaatc | catcctggcc | aagttggctg | tcatctgggt | gggctccatg | 780 |
| acgctggctg | tgcctgagct | cctgctgtgg | cagctggcac | aggagcctgc | ccccaccatg | 840 |
| ggcaccctgg | actcatgcat | catgaaaccc | tcagccagcc | tgcccgagtc | cctgtattca | 900 |
| ctggtgatga | cctaccagaa | cgcccgcatg | tggtggtact | ttggctgcta | cttctgcctg | 960 |
| cccatcctct | tcacagtcac | ctgccagctg | gtgacatggc | gggtgcgagg | ccctccaggg | 1020 |
| aggaagtcag | agtgcagggc | cagcaagcac | gagcagtgtg | agagccagct | caagagcacc | 1080 |
| gtggtgggcc | tgaccgtggt | ctacgccttc | tgcaccctcc | cagagaacgt | ctgcaacatc | 1140 |
| gtggtggcct | acctctccac | cgagctgacc | gccagaccc | tggacctcct | gggcctcatc | 1200 |
| aaccagttct | ccaccttctt | caagggcgcc | atcacccag | tgctgctcct | ttgcatctgc | 1260 |
| aggccgctgg | ccaggccctt | cctggactgc | tgctgctgct | gctgctgtga | ggagtgcggc | 1320 |
| ggggcttcgg | aggcctctgc | tgccaatggg | tcggacaaca | agctcaagac | cgaggtgtcc | 1380 |
| tcttccatct | acttccacaa | gcccagggag | tcaccccac | tcctgcccct | gggcacacct | 1440 |
| tgctga | | | | | | 1446 |

<210> SEQ ID NO 208
<211> LENGTH: 481
<212> TYPE: PRT
<213> ORGANISM: Homo sapiens

<400> SEQUENCE: 208

Met Arg Trp Leu Trp Pro Leu Ala Val Ser Leu Ala Val Ile Leu Ala

-continued

```
1               5                   10                  15
Val Gly Leu Ser Arg Val Ser Gly Gly Ala Pro Leu His Leu Gly Arg
                20                  25                  30
His Arg Ala Glu Thr Gln Glu Gln Ser Arg Ser Lys Arg Gly Thr
            35                  40                  45
Glu Asp Glu Glu Ala Lys Gly Val Gln Gln Tyr Val Pro Glu Glu Trp
50                  55                  60
Ala Glu Tyr Pro Arg Pro Ile His Pro Ala Gly Leu Gln Pro Thr Lys
65                  70                  75                  80
Pro Leu Val Ala Thr Ser Pro Asn Pro Lys Asp Gly Gly Thr Pro
                85                  90                  95
Asp Ser Gly Gln Glu Leu Arg Gly Asn Leu Thr Gly Ala Pro Gly Gln
                100                 105                 110
Arg Leu Gln Ile Gln Asn Pro Leu Tyr Pro Val Thr Glu Ser Ser Tyr
            115                 120                 125
Ser Ala Tyr Ala Ile Met Leu Leu Ala Leu Val Val Phe Ala Val Gly
    130                 135                 140
Ile Val Gly Asn Leu Ser Val Met Cys Ile Val Trp His Ser Tyr Tyr
145                 150                 155                 160
Leu Lys Ser Ala Trp Asn Ser Ile Leu Ala Ser Leu Ala Leu Trp Asp
                165                 170                 175
Phe Leu Val Leu Phe Phe Cys Leu Pro Ile Val Ile Phe Asn Glu Ile
                180                 185                 190
Thr Lys Gln Arg Leu Leu Gly Asp Val Ser Cys Arg Ala Val Pro Phe
            195                 200                 205
Met Glu Val Ser Ser Leu Gly Val Thr Thr Phe Ser Leu Cys Ala Leu
    210                 215                 220
Gly Ile Asp Arg Phe His Val Ala Thr Ser Thr Leu Pro Lys Val Arg
225                 230                 235                 240
Pro Ile Glu Arg Cys Gln Ser Ile Leu Ala Lys Leu Ala Val Ile Trp
                245                 250                 255
Val Gly Ser Met Thr Leu Ala Val Pro Glu Leu Leu Leu Trp Gln Leu
                260                 265                 270
Ala Gln Glu Pro Ala Pro Thr Met Gly Thr Leu Asp Ser Cys Ile Met
            275                 280                 285
Lys Pro Ser Ala Ser Leu Pro Glu Ser Leu Tyr Ser Leu Val Met Thr
    290                 295                 300
Tyr Gln Asn Ala Arg Met Trp Trp Tyr Phe Gly Cys Tyr Phe Cys Leu
305                 310                 315                 320
Pro Ile Leu Phe Thr Val Thr Cys Gln Leu Val Thr Trp Arg Val Arg
                325                 330                 335
Gly Pro Pro Gly Arg Lys Ser Glu Cys Arg Ala Ser Lys His Glu Gln
                340                 345                 350
Cys Glu Ser Gln Leu Lys Ser Thr Val Val Gly Leu Thr Val Val Tyr
            355                 360                 365
Ala Phe Cys Thr Leu Pro Glu Asn Val Cys Asn Ile Val Val Ala Tyr
    370                 375                 380
Leu Ser Thr Glu Leu Thr Arg Gln Thr Leu Asp Leu Leu Gly Leu Ile
385                 390                 395                 400
Asn Gln Phe Ser Thr Phe Phe Lys Gly Ala Ile Thr Pro Val Leu Leu
                405                 410                 415
Leu Cys Ile Cys Arg Pro Leu Gly Gln Ala Phe Leu Asp Cys Cys Cys
                420                 425                 430
```

```
Cys Cys Cys Cys Glu Glu Cys Gly Gly Ala Ser Glu Ala Ser Ala Ala
            435                 440                 445

Asn Gly Ser Asp Asn Lys Leu Lys Thr Glu Val Ser Ser Ser Ile Tyr
        450                 455                 460

Phe His Lys Pro Arg Glu Ser Pro Pro Leu Leu Pro Leu Gly Thr Pro
465                 470                 475                 480

Cys

<210> SEQ ID NO 209
<211> LENGTH: 1101
<212> TYPE: DNA
<213> ORGANISM: Homo sapiens

<400> SEQUENCE: 209
atgtggaacg cgacgcccag cgaagagccg gggttcaacc tcacactggc cgacctggac      60
tgggatgctt cccccggcaa cgactcgctg ggcgacgagc tgctgcagct cttcccgcg     120 ccgctgctgg cgggcgtcac agccacctgc gtggcactct cgtggtggg tatcgctggc     180 aacctgctca ccatgctggt ggtgtcgcgc ttccgcgagc tgcgcaccac caccaacctc     240
tacctgtcca gcatggcctt ctccgatctg ctcatcttcc tctgcatgcc cctggacctc     300
gttcgcctct ggcagtaccg gccctggaac ttcggcgacc tcctctgcaa actcttccaa     360
ttcgtcagtg agagctgcac ctacgccacg gtgctcacca tcacagcgct gagcgtcgag     420
cgctacttcg ccatctgctt cccactccgg gccaaggtgg tggtcaccaa ggggcgggtg     480
aagctggtca tcttcgtcat ctgggccgtg gccttctgca cgccgggcc catcttcgtg     540 ctagtcgggg tggagcacga aacggcacc gaccccttggg acaccaacga gtgccgcccc     600
accgagtttg cggtgcgctc tggactgctc acggtcatgg tgtgggtgtc cagcatcttc     660
ttcttccttc ctgtcttctg tctcacggtc ctctacagtc tcatcggcag gaagctgtgg     720
cggaggaggc gcggcgatgc tgtcgtgggt gcctcgctca gggaccagaa ccacaagcaa     780
accaagaaaa tgctggctgt agtggtgttt gccttcatcc tctgctggct ccccttccac     840
gtagggcgat atttattttc caaatccttt gagcctggct ccttggagat tgctcagatc     900
agccagtact gcaacctcgt gtcctttgtc ctcttctacc tcagtgctgc catcaacccc     960
attctgtaca acatcatgtc caagaagtac cgggtggcag tgttcagact tctgggattc    1020
gaacccttct cccagagaaa gctctccact ctgaaagatg aaagttctcg ggcctggaca    1080
gaatctagta ttaatacatg a                                               1101

<210> SEQ ID NO 210
<211> LENGTH: 366
<212> TYPE: PRT
<213> ORGANISM: Homo sapiens

<400> SEQUENCE: 210

Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
```

```
                65                  70                  75                  80
            Tyr Leu Ser Ser Met Ala Phe Ser Asp Leu Leu Ile Phe Leu Cys Met
                                85                  90                  95

Pro Leu Asp Leu Val Arg Leu Trp Gln Tyr Arg Pro Trp Asn Phe Gly
                            100                 105                 110

Asp Leu Leu Cys Lys Leu Phe Gln Phe Val Ser Glu Ser Cys Thr Tyr
                        115                 120                 125

Ala Thr Val Leu Thr Ile Thr Ala Leu Ser Val Glu Arg Tyr Phe Ala
                    130                 135                 140

Ile Cys Phe Pro Leu Arg Ala Lys Val Val Thr Lys Gly Arg Val
            145                 150                 155                 160

Lys Leu Val Ile Phe Val Ile Trp Ala Val Ala Phe Cys Ser Ala Gly
                            165                 170                 175

Pro Ile Phe Val Leu Val Gly Val Glu His Glu Asn Gly Thr Asp Pro
                        180                 185                 190

Trp Asp Thr Asn Glu Cys Arg Pro Thr Glu Phe Ala Val Arg Ser Gly
                    195                 200                 205

Leu Leu Thr Val Met Val Trp Val Ser Ser Ile Phe Phe Phe Leu Pro
                210                 215                 220

Val Phe Cys Leu Thr Val Leu Tyr Ser Leu Ile Gly Arg Lys Leu Trp
            225                 230                 235                 240

Arg Arg Arg Arg Gly Asp Ala Val Val Gly Ala Ser Leu Arg Asp Gln
                            245                 250                 255

Asn His Lys Gln Thr Lys Lys Met Leu Ala Val Val Val Phe Ala Phe
                        260                 265                 270

Ile Leu Cys Trp Leu Pro Phe His Val Gly Arg Tyr Leu Phe Ser Lys
                    275                 280                 285

Ser Phe Glu Pro Gly Ser Leu Glu Ile Ala Gln Ile Ser Gln Tyr Cys
                290                 295                 300

Asn Leu Val Ser Phe Val Leu Phe Tyr Leu Ser Ala Ala Ile Asn Pro
            305                 310                 315                 320

Ile Leu Tyr Asn Ile Met Ser Lys Lys Tyr Arg Val Ala Val Phe Arg
                            325                 330                 335

Leu Leu Gly Phe Glu Pro Phe Ser Gln Arg Lys Leu Ser Thr Leu Lys
                        340                 345                 350

Asp Glu Ser Ser Arg Ala Trp Thr Glu Ser Ser Ile Asn Thr
                    355                 360                 365

<210> SEQ ID NO 211
<211> LENGTH: 1842
<212> TYPE: DNA
<213> ORGANISM: Homo sapiens

<400> SEQUENCE: 211
atgcgagccc cgggcgcgct ctcgcccgc atgtcgcggc tactgcttct gctactgctc          60
aaggtgtctg cctcttctgc cctcggggtc gcccctgcgt ccagaaacga aacttgtctg        120
ggggagagct gtgcacctac agtgatccag cgccgcggca gggacgcctg ggaccgggaa        180
aattctgcaa gagacgttct gcgagcccga gcacccaggg aggagcaggg ggcagcgttt        240
cttgcgggac cctcctggga cctgccggcg gccccgggcc gtgacccggc tgcaggcaga        300
ggggcggagg cgtcggcagc cggacccccg ggacctccaa ccaggccacc tggcccctgg        360
aggtggaaag gtgctcgggg tcaggagcct tctgaaactt ggggagaggg aaccccacg        420 gccctccagc tcttccttca gatctcagag gaggaagaga aggtcccag aggcgctggc        480
```

-continued

```
atttccgggc gtagccagga gcagagtgtg aagacagtcc ccggagccag cgatcttttt    540
tactggccaa ggagagccgg gaaactccag ggttcccacc acaagcccct gtccaagacg    600
gccaatggac tggcggggca cgaaggtgg acaattgcac tcccgggccg ggcgctggcc     660
cagaatggat ccttgggtga aggaatccat gagcctgggg gtccccgccg gggaaacagc    720
acgaaccggc gtgtgagact gaagaacccc ttctacccgc tgacccagga gtcctatgga    780
gcctacgcgg tcatgtgtct gtccgtggtg atcttcggga ccggcatcat tggcaacctg    840
gcggtgatgt gcatcgtgtg ccacaactac tacatgcgga gcatctccaa ctccctcttg    900
gccaacctgg ccttctggga ctttctcatc atcttcttct gccttccgct ggtcatcttc    960
cacgagctga ccaagaagtg gctgctggag gacttctcct gcaagatcgt gccctatata   1020
gaggtcgcct ctctgggagt caccactttc accttatgtg ctctgtgcat agaccgcttc   1080
cgtgctgcca ccaacgtaca gatgtactac gaaatgatcg aaaattgttc ctcaacaact   1140
gccaaacttg ctgttatatg ggtgggagct ctattgttag cacttccaga agttgttctc   1200
cgccagctga gcaaggagga tttggggttt agtggccgag ctccggcaga aaggtgcatt   1260
attaagatct ctcctgattt accagacacc atctatgttc tagccctcac ctacgacagt   1320
gcgagactgt ggtggtattt tggctgttac ttttgtttgc ccacgctttt caccatcacc   1380
tgctctctag tgactgcgag gaaaatccgc aaagcagaga aagcctgtac ccgagggaat   1440
aaacggcaga ttcaactaga gagtcagatg aagtgtacag tagtggcact gaccatttta   1500
tatggatttt gcattattcc tgaaaatatc tgcaacattg ttactgccta catggctaca   1560
ggggtttcac agcagacaat ggacctcctt aatatcatca gccagttcct tttgttctt    1620 aagtcctgtg tcaccccagt cctcctttc tgtctctgca aacccttcag tcgggccttc    1680
atggagtgct gctgctgttg ctgtgaggaa tgcattcaga agtcttcaac ggtgaccagt   1740
gatgacaatg acaacgagta caccacggaa ctcgaactct cgcctttcag taccatacgc   1800
cgtgaaatgt ccacttttgc ttctgtcgga actcattgct ga                     1842
```

<210> SEQ ID NO 212
<211> LENGTH: 613
<212> TYPE: PRT
<213> ORGANISM: Homo sapiens

<400> SEQUENCE: 212

```
Met Arg Ala Pro Gly Ala Leu Leu Ala Arg Met Ser Arg Leu Leu Leu
 1               5                  10                  15

Leu Leu Leu Lys Val Ser Ala Ser Ser Ala Leu Gly Val Ala Pro
            20                  25                  30

Ala Ser Arg Asn Glu Thr Cys Leu Gly Glu Ser Cys Ala Pro Thr Val
        35                  40                  45

Ile Gln Arg Arg Gly Arg Asp Ala Trp Gly Pro Gly Asn Ser Ala Arg
    50                  55                  60

Asp Val Leu Arg Ala Arg Ala Pro Arg Glu Glu Gln Gly Ala Ala Phe
65                  70                  75                  80

Leu Ala Gly Pro Ser Trp Asp Leu Pro Ala Ala Pro Gly Arg Asp Pro
                85                  90                  95

Ala Ala Gly Arg Gly Ala Glu Ala Ser Ala Ala Gly Pro Pro Gly Pro
            100                 105                 110

Pro Thr Arg Pro Pro Gly Pro Trp Arg Trp Lys Gly Ala Arg Gly Gln
        115                 120                 125
```

-continued

```
Glu Pro Ser Glu Thr Leu Gly Arg Gly Asn Pro Thr Ala Leu Gln Leu
    130                 135                 140

Phe Leu Gln Ile Ser Glu Glu Glu Lys Gly Pro Arg Gly Ala Gly
145                 150                 155                 160

Ile Ser Gly Arg Ser Gln Glu Gln Ser Val Lys Thr Val Pro Gly Ala
                165                 170                 175

Ser Asp Leu Phe Tyr Trp Pro Arg Arg Ala Gly Lys Leu Gln Gly Ser
            180                 185                 190

His His Lys Pro Leu Ser Lys Thr Ala Asn Gly Leu Ala Gly His Glu
        195                 200                 205

Gly Trp Thr Ile Ala Leu Pro Gly Arg Ala Leu Ala Gln Asn Gly Ser
    210                 215                 220

Leu Gly Glu Gly Ile His Glu Pro Gly Gly Pro Arg Arg Gly Asn Ser
225                 230                 235                 240

Thr Asn Arg Arg Val Arg Leu Lys Asn Pro Phe Tyr Pro Leu Thr Gln
                245                 250                 255

Glu Ser Tyr Gly Ala Tyr Ala Val Met Cys Leu Ser Val Val Ile Phe
            260                 265                 270

Gly Thr Gly Ile Ile Gly Asn Leu Ala Val Met Cys Ile Val Cys His
        275                 280                 285

Asn Tyr Tyr Met Arg Ser Ile Ser Asn Ser Leu Leu Ala Asn Leu Ala
    290                 295                 300

Phe Trp Asp Phe Leu Ile Ile Phe Phe Cys Leu Pro Leu Val Ile Phe
305                 310                 315                 320

His Glu Leu Thr Lys Lys Trp Leu Leu Glu Asp Phe Ser Cys Lys Ile
                325                 330                 335

Val Pro Tyr Ile Glu Val Ala Ser Leu Gly Val Thr Thr Phe Thr Leu
            340                 345                 350

Cys Ala Leu Cys Ile Asp Arg Phe Arg Ala Ala Thr Asn Val Gln Met
        355                 360                 365

Tyr Tyr Glu Met Ile Glu Asn Cys Ser Ser Thr Thr Ala Lys Leu Ala
    370                 375                 380

Val Ile Trp Val Gly Ala Leu Leu Leu Ala Leu Pro Glu Val Val Leu
385                 390                 395                 400

Arg Gln Leu Ser Lys Glu Asp Leu Gly Phe Ser Gly Arg Ala Pro Ala
                405                 410                 415

Glu Arg Cys Ile Ile Lys Ile Ser Pro Asp Leu Pro Asp Thr Ile Tyr
            420                 425                 430

Val Leu Ala Leu Thr Tyr Asp Ser Ala Arg Leu Trp Trp Tyr Phe Gly
        435                 440                 445

Cys Tyr Phe Cys Leu Pro Thr Leu Phe Thr Ile Thr Cys Ser Leu Val
    450                 455                 460

Thr Ala Arg Lys Ile Arg Lys Ala Glu Lys Ala Cys Thr Arg Gly Asn
465                 470                 475                 480

Lys Arg Gln Ile Gln Leu Glu Ser Gln Met Lys Cys Thr Val Val Ala
                485                 490                 495

Leu Thr Ile Leu Tyr Gly Phe Cys Ile Ile Pro Glu Asn Ile Cys Asn
            500                 505                 510

Ile Val Thr Ala Tyr Met Ala Thr Gly Val Ser Gln Gln Thr Met Asp
        515                 520                 525

Leu Leu Asn Ile Ile Ser Gln Phe Leu Leu Phe Phe Lys Ser Cys Val
    530                 535                 540

Thr Pro Val Leu Leu Phe Cys Leu Cys Lys Pro Phe Ser Arg Ala Phe
```

```
                545                 550                 555                 560
Met Glu Cys Cys Cys Cys Cys Glu Glu Cys Ile Gln Lys Ser Ser
                565                 570                 575

Thr Val Thr Ser Asp Asp Asn Asp Asn Glu Tyr Thr Thr Glu Leu Glu
            580                 585                 590

Leu Ser Pro Phe Ser Thr Ile Arg Arg Glu Met Ser Thr Phe Ala Ser
        595                 600                 605

Val Gly Thr His Cys
    610

<210> SEQ ID NO 213
<211> LENGTH: 1248
<212> TYPE: DNA
<213> ORGANISM: Homo sapiens

<400> SEQUENCE: 213 atggttttg ctcacagaat ggataacagc aagccacatt tgattattcc tacacttctg      60
gtgcccctcc aaaaccgcag ctgcactgaa acagccacac tctgccaag ccaatacctg     120 atggaattaa gtgaggagca cagttggatg agcaaccaaa cagaccttca ctatgtgctg    180
aaacccgggg aagtggccac agccagcatc ttctttggga ttctgtggtt gttttctatc    240
ttcggcaatt ccctggtttg tttggtcatc cataggagta ggaggactca gtctaccacc    300
aactactttg tggtctccat ggcatgtgct gaccttctca tcagcgttgc cagcacgcct    360
ttcgtcctgc tccagttcac cactggaagg tggacgctgg gtagtgcaac gtgcaaggtt    420
gtgcgatatt ttcaatatct cactccaggt gtccagatct acgttctcct ctccatctgc    480
atagaccggt tctacaccat cgtctatcct ctgagcttca ggtgtccag agaaaaagcc     540 aagaaaatga ttgcggcatc gtggatcttt gatgcaggct tgtgacccc tgtgctcttt    600 ttctatggct ccaactggga cagtcattgt aactatttcc tcccctcctc ttgggaaggc   660
actgcctaca ctgtcatcca cttcttggtg ggctttgtga ttccatctgt cctcataatt   720
ttattttacc aaaaggtcat aaaatatatt tggagaatag gcacagatgg ccgaacggtg    780
aggaggacaa tgaacattgt ccctcggaca aaagtgaaaa ctaaaaagat gttcctcatt    840
ttaaatctgt tgttttgct ctcctggctg ccttttcatg tagctcagct atggcacccc    900
catgaacaag actataagaa aagttccctt gttttcacag ctatcacatg gatatccttt    960
agttcttcag cctctaaacc tactctgtat tcaatttata tgccaatttt tcggagaggg   1020
atgaaagaga cttttttgcat gtcctctatg aaatgttacc gaagcaatgc ctatactatc   1080
acaacaagtt caaggatggc caaaaaaaac tacgttggca tttcagaaat ccctttccatg   1140 gccaaaacta ttaccaaaga ctcgatctat gactcatttg acagagaagc caaggaaaaa   1200
aagcttgctt ggcccattaa ctcaaatcca ccaaatactt ttgtctaa                 1248

<210> SEQ ID NO 214
<211> LENGTH: 415
<212> TYPE: PRT
<213> ORGANISM: Homo sapiens

<400> SEQUENCE: 214

Met Val Phe Ala His Arg Met Asp Asn Ser Lys Pro His Leu Ile Ile
1               5                  10                  15

Pro Thr Leu Leu Val Pro Leu Gln Asn Arg Ser Cys Thr Glu Thr Ala
            20                  25                  30

Thr Pro Leu Pro Ser Gln Tyr Leu Met Glu Leu Ser Glu Glu His Ser
```

```
                35                  40                  45
Trp Met Ser Asn Gln Thr Asp Leu His Tyr Val Leu Lys Pro Gly Glu
    50                  55                  60
Val Ala Thr Ala Ser Ile Phe Phe Gly Ile Leu Trp Leu Phe Ser Ile
65                  70                  75                  80
Phe Gly Asn Ser Leu Val Cys Leu Val Ile His Arg Ser Arg Arg Thr
                85                  90                  95
Gln Ser Thr Thr Asn Tyr Phe Val Val Ser Met Ala Cys Ala Asp Leu
            100                 105                 110
Leu Ile Ser Val Ala Ser Thr Pro Phe Val Leu Leu Gln Phe Thr Thr
        115                 120                 125
Gly Arg Trp Thr Leu Gly Ser Ala Thr Cys Lys Val Val Arg Tyr Phe
    130                 135                 140
Gln Tyr Leu Thr Pro Gly Val Gln Ile Tyr Val Leu Leu Ser Ile Cys
145                 150                 155                 160
Ile Asp Arg Phe Tyr Thr Ile Val Tyr Pro Leu Ser Phe Lys Val Ser
                165                 170                 175
Arg Glu Lys Ala Lys Met Ile Ala Ala Ser Trp Ile Phe Asp Ala
            180                 185                 190
Gly Phe Val Thr Pro Val Leu Phe Phe Tyr Gly Ser Asn Trp Asp Ser
        195                 200                 205
His Cys Asn Tyr Phe Leu Pro Ser Ser Trp Glu Gly Thr Ala Tyr Thr
    210                 215                 220
Val Ile His Phe Leu Val Gly Phe Val Ile Pro Ser Val Leu Ile Ile
225                 230                 235                 240
Leu Phe Tyr Gln Lys Val Ile Lys Tyr Ile Trp Arg Ile Gly Thr Asp
                245                 250                 255
Gly Arg Thr Val Arg Arg Thr Met Asn Ile Val Pro Arg Thr Lys Val
            260                 265                 270
Lys Thr Lys Lys Met Phe Leu Ile Leu Asn Leu Leu Phe Leu Leu Ser
        275                 280                 285
Trp Leu Pro Phe His Val Ala Gln Leu Trp His Pro His Glu Gln Asp
    290                 295                 300
Tyr Lys Lys Ser Ser Leu Val Phe Thr Ala Ile Thr Trp Ile Ser Phe
305                 310                 315                 320
Ser Ser Ser Ala Ser Lys Pro Thr Leu Tyr Ser Ile Tyr Asn Ala Asn
                325                 330                 335
Phe Arg Arg Gly Met Lys Glu Thr Phe Cys Met Ser Ser Met Lys Cys
            340                 345                 350
Tyr Arg Ser Asn Ala Tyr Thr Ile Thr Thr Ser Ser Arg Met Ala Lys
        355                 360                 365
Lys Asn Tyr Val Gly Ile Ser Glu Ile Pro Ser Met Ala Lys Thr Ile
    370                 375                 380
Thr Lys Asp Ser Ile Tyr Asp Ser Phe Asp Arg Glu Ala Lys Glu Lys
385                 390                 395                 400
Lys Leu Ala Trp Pro Ile Asn Ser Asn Pro Pro Asn Thr Phe Val
                405                 410                 415

<210> SEQ ID NO 215
<211> LENGTH: 1842
<212> TYPE: DNA
<213> ORGANISM: Homo sapiens

<400> SEQUENCE: 215
```

-continued

```
atgggccca  ccctagcggt  tcccacccc   tatggctgta  ttggctgtaa  gctaccccag    60
ccagaatacc  caccggctct  aatcatcttt  atgttctgcg  cgatggttat  caccatcgtt   120
gtagacctaa  tcggcaactc  catggtcatt  ttggctgtga  cgaagaacaa  gaagctccgg   180
aattctggca  acatcttcgt  ggtcagtctc  tctgtggccg  atatgctggt  ggccatctac   240
ccataccctt  tgatgctgca  tgccatgtcc  attgggggct  gggatctgag  ccagttacag   300
tgccagatgg  tcgggttcat  cacagggctg  agtgtggtcg  gctccatctt  caacatcgtg   360
gcaatcgcta  tcaaccgtta  ctgctacatc  tgccacagcc  tccagtacga  acggatcttc   420
agtgtgcgca  atacctgcat  ctacctggtc  atcacctgga  tcatgaccgt  cctggctgtc   480
ctgcccaaca  tgtacattgg  caccatcgag  tacgatcctc  gcacctacac  ctgcatcttc   540
aactatctga  caaccctgt   cttcactgtt  accatcgtct  gcatccactt  cgtcctccct   600
ctcctcatcg  tgggtttctg  ctacgtgagg  atctggacca  agtgctggc   ggcccgtgac   660
cctgcagggc  agaatcctga  caaccaactt  gctgaggttc  gcaataaact  aaccatgttt   720
gtgatcttcc  tcctctttgc  agtgtgctgg  tgccctatca  acgtgctcac  tgtcttggtg   780
gctgtcagtc  cgaaggagat  ggcaggcaag  atccccaact  ggctttatct  tgcagcctac   840
ttcatagcct  acttcaacag  ctgcctcaac  gctgtgatct  acgggctcct  caatgagaat   900
ttccgaagag  aatactggac  catcttccat  gctatgcggc  accctatcat  attcttctct   960
ggcctcatca  gtgatattcg  tgagatgcag  gaggcccgta  ccctggcccg  cgcccgtgcc  1020
catgctcgcg  accaagctcg  tgaacaagac  cgtgcccatg  cctgtcctgc  tgtggaggaa  1080
accccgatga  atgtccggaa  tgttccatta  cctggtgatg  ctgcagctgg  ccaccccgac  1140
cgtgcctctg  gccacctaa   gccccattcc  agatcctcct  ctgcctatcg  caaatctgcc  1200
tctacccacc  acaagtctgt  ctttagccac  tccaaggctg  cctctggtca  cctcaagcct  1260
gtctctggcc  actccaagcc  tgcctctggt  caccccaagt  ctgccactgt  ctaccctaag  1320
cctgcctctg  tccatttcaa  ggctgactct  gtccatttca  agggtgactc  tgtccatttc  1380
aagcctgact  ctgttcattt  caagcctgct  tccagcaacc  ccaagcccat  cactggccac  1440
catgtctctg  ctggcagcca  ctccaagtct  gccttcaatg  ctgccaccag  ccaccctaaa  1500
cccatcaagc  cagctaccag  ccatgctgag  cccaccactg  ctgactatcc  caagcctgcc  1560
actaccagcc  accctaagcc  cgctgctgct  gacaaccctg  agctctctgc  ctcccattgc  1620
cccgagatcc  ctgccattgc  ccaccctgtg  tctgacgaca  gtgacctccc  tgagtcggcc  1680
tctagccctg  ccgctgggcc  caccaagcct  gctgccagcc  agctggagtc  tgacaccatc  1740
gctgaccttc  ctgaccctac  tgtagtcact  accagtacca  atgattacca  tgatgtcgtg  1800
gttgttgatg  ttgaagatga  tcctgatgaa  atggctgtgt  ga                       1842
```

<210> SEQ ID NO 216
<211> LENGTH: 613
<212> TYPE: PRT
<213> ORGANISM: Homo sapiens

<400> SEQUENCE: 216

```
Met Gly Pro Thr Leu Ala Val Pro Thr Pro Tyr Gly Cys Ile Gly Cys
 1               5                  10                  15

Lys Leu Pro Gln Pro Glu Tyr Pro Pro Ala Leu Ile Ile Phe Met Phe
            20                  25                  30

Cys Ala Met Val Ile Thr Ile Val Val Asp Leu Ile Gly Asn Ser Met
        35                  40                  45
```

-continued

```
Val Ile Leu Ala Val Thr Lys Asn Lys Lys Leu Arg Asn Ser Gly Asn
         50                  55                  60

Ile Phe Val Val Ser Leu Ser Val Ala Asp Met Leu Val Ala Ile Tyr
 65                  70                  75                  80

Pro Tyr Pro Leu Met Leu His Ala Met Ser Ile Gly Gly Trp Asp Leu
                 85                  90                  95

Ser Gln Leu Gln Cys Gln Met Val Gly Phe Ile Thr Gly Leu Ser Val
                100                 105                 110

Val Gly Ser Ile Phe Asn Ile Val Ala Ile Ala Ile Asn Arg Tyr Cys
             115                 120                 125

Tyr Ile Cys His Ser Leu Gln Tyr Glu Arg Ile Phe Ser Val Arg Asn
    130                 135                 140

Thr Cys Ile Tyr Leu Val Ile Thr Trp Ile Met Thr Val Leu Ala Val
145                 150                 155                 160

Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
            180                 185                 190

Val Cys Ile His Phe Val Leu Pro Leu Leu Ile Val Gly Phe Cys Tyr
        195                 200                 205

Val Arg Ile Trp Thr Lys Val Leu Ala Ala Arg Asp Pro Ala Gly Gln
    210                 215                 220

Asn Pro Asp Asn Gln Leu Ala Glu Val Arg Asn Lys Leu Thr Met Phe
225                 230                 235                 240

Val Ile Phe Leu Leu Phe Ala Val Cys Trp Cys Pro Ile Asn Val Leu
                245                 250                 255

Thr Val Leu Val Ala Val Ser Pro Lys Glu Met Ala Gly Lys Ile Pro
            260                 265                 270

Asn Trp Leu Tyr Leu Ala Ala Tyr Phe Ile Ala Tyr Phe Asn Ser Cys
        275                 280                 285

Leu Asn Ala Val Ile Tyr Gly Leu Leu Asn Glu Asn Phe Arg Arg Glu
    290                 295                 300

Tyr Trp Thr Ile Phe His Ala Met Arg His Pro Ile Ile Phe Phe Ser
305                 310                 315                 320

Gly Leu Ile Ser Asp Ile Arg Glu Met Gln Glu Ala Arg Thr Leu Ala
                325                 330                 335

Arg Ala Arg Ala His Ala Arg Asp Gln Ala Arg Glu Gln Asp Arg Ala
            340                 345                 350

His Ala Cys Pro Ala Val Glu Glu Thr Pro Met Asn Val Arg Asn Val
        355                 360                 365

Pro Leu Pro Gly Asp Ala Ala Ala Gly His Pro Asp Arg Ala Ser Gly
    370                 375                 380

His Pro Lys Pro His Ser Arg Ser Ser Ala Tyr Arg Lys Ser Ala
385                 390                 395                 400

Ser Thr His His Lys Ser Val Phe Ser His Ser Lys Ala Ala Ser Gly
                405                 410                 415

His Leu Lys Pro Val Ser Gly His Ser Lys Pro Ala Ser Gly His Pro
            420                 425                 430

Lys Ser Ala Thr Val Tyr Pro Lys Pro Ala Ser Val His Phe Lys Ala
        435                 440                 445

Asp Ser Val His Phe Lys Gly Asp Ser Val His Phe Lys Pro Asp Ser
    450                 455                 460

Val His Phe Lys Pro Ala Ser Ser Asn Pro Lys Pro Ile Thr Gly His
```

|     |     |     |     | 465 |     |     |     |     | 470 |     |     |     |     | 475 |     |     |     |     | 480 |
| --- | --- | --- | --- | --- | --- | --- | --- | --- | --- | --- | --- | --- | --- | --- | --- | --- | --- | --- | --- |
| His | Val | Ser | Ala | Gly | Ser | His | Ser | Lys | Ser | Ala | Phe | Asn | Ala | Thr |
|     |     |     |     |     |     |     | 485 |     |     |     |     |     | 490 |     |     |     |     | 495 |

Ser His Pro Lys Pro Ile Lys Pro Ala Thr Ser His Ala Glu Pro Thr
            500                 505                 510

Thr Ala Asp Tyr Pro Lys Pro Ala Thr Thr Ser His Pro Lys Pro Ala
            515                 520                 525

Ala Ala Asp Asn Pro Glu Leu Ser Ala Ser His Cys Pro Glu Ile Pro
            530                 535                 540

Ala Ile Ala His Pro Val Ser Asp Asp Ser Asp Leu Pro Glu Ser Ala
545                 550                 555                 560

Ser Ser Pro Ala Ala Gly Pro Thr Lys Pro Ala Ser Gln Leu Glu
                565                 570                 575

Ser Asp Thr Ile Ala Asp Leu Pro Asp Pro Thr Val Val Thr Thr Ser
            580                 585                 590

Thr Asn Asp Tyr His Asp Val Val Val Asp Val Glu Asp Asp Pro
            595                 600                 605

Asp Glu Met Ala Val
        610

<210> SEQ ID NO 217
<211> LENGTH: 1854
<212> TYPE: DNA
<213> ORGANISM: Homo sapiens

<400> SEQUENCE: 217

| atggggccca | ccctagcggt | tcccacccc  | tatggctgta | ttggctgtaa | gctaccccag | 60   |
| ccagaatacc | caccggctct | aatcatcttt | atgttctgcg | cgatggttat | caccatcgtt | 120  |
| gtagacctaa | tcggcaactc | catggtcatt | ttggctgtga | cgaagaacaa | gaagctccgg | 180  |
| aattctggca | acatcttcgt | ggtcagtctc | tctgtggccg | atatgctggt | ggccatctac | 240  |
| ccataccctt | tgatgctgca | tgccatgtcc | attgggggct | gggatctgag | ccagttacag | 300  |
| tgccagatgg | tcgggttcat | cacagggctg | agtgtggtcg | gctccatctt | caacatcgtg | 360  |
| gcaatcgcta | tcaaccgtta | ctgctacatc | tgccacagcc | tccagtacga | acggatcttc | 420  |
| agtgtgcgca | ataccctgcat | ctacctggtc | atcacctgga | tcatgaccgt | cctggctgtc | 480  |
| ctgcccaaca | tgtacattgg | caccatcgag | tacgatcctc | gcacctacac | ctgcatcttc | 540  |
| aactatctga | caaccctgt  | cttcactgtt | accatcgtct | gcatccactt | cgtcctccct | 600  |
| ctcctcatcg | tgggtttctg | ctacgtgagg | atctggacca | agtgctggc  | ggcccgtgac | 660  |
| cctgcagggc | agaatcctga | caaccaactt | gctgaggttc | gcaataaact | aaccatgttt | 720  |
| gtgatcttcc | tcctctttgc | agtgtgctgg | tgccctatca | acgtgctcac | tgtcttggtg | 780  |
| gctgtcagtc | gaaggagat  | ggcaggcaag | atccccaact | ggctttatct | tgcagcctac | 840  |
| ttcatagcct | acttcaacag | ctgcctcaac | gctgtgatct | acgggctcct | caatgagaat | 900  |
| ttccgaagag | aatactggac | catcttccat | gctatgcggc | accctatcat | attcttctct | 960  |
| ggcctcatca | gtgatattcg | tgagatgcag | gaggcccgta | ccctggcccg | cgcccgtgcc | 1020 |
| catgctcgcg | accaagctcg | tgaacaagac | cgtgcccatg | cctgtcctgc | tgtggaggaa | 1080 |
| accccgatga | atgtccggaa | tgttccatta | cctggtgatg | ctgcagctgg | ccaccccgac | 1140 |
| cgtgcctctg | gccaccctaa | gcccattcc  | agatcctcct | ctgcctatcg | caaatctgcc | 1200 |
| tctacccacc | acaagtctgt | ctttagccac | tccaaggctg | cctctggtca | cctcaagcct | 1260 |

-continued

```
gtctctggcc actccaagcc tgcctctggt caccccaagt ctgccactgt ctaccctaag    1320
cctgcctctg tccatttcaa ggctgactct gtccatttca agggtgactc tgtccatttc    1380
aagcctgact ctgttcattt caagcctgct tccagcaacc ccaagcccat cactggccac    1440
catgtctctg ctggcagcca ctccaagtct gccttcagtg ctgccaccag ccaccctaaa    1500
cccaccactg ccacatcaa gccagctacc agccatgctg agcccaccac tgctgactat    1560
cccaagcctg ccactaccag ccaccctaag cccactgctg ctgacaaccc tgagctctct    1620
gcctcccatt gccccgagat ccctgccatt gccaccctg tgtctgacga cagtgacctc     1680
cctgagtcgg cctctagccc tgccgctggg cccaccaagc tgctgccag ccagctggag      1740 tctgacacca tcgctgacct tcctgaccct actgtagtca ctaccagtac caatgattac    1800
catgatgtcg tggttgttga tgttgaagat gatcctgatg aaatggctgt gtga           1854
```

<210> SEQ ID NO 218
<211> LENGTH: 617
<212> TYPE: PRT
<213> ORGANISM: Homo sapiens

<400> SEQUENCE: 218

```
Met Gly Pro Thr Leu Ala Val Pro Thr Pro Tyr Gly Cys Ile Gly Cys
1               5                   10                  15

Lys Leu Pro Gln Pro Glu Tyr Pro Pro Ala Leu Ile Ile Phe Met Phe
            20                  25                  30

Cys Ala Met Val Ile Thr Ile Val Val Asp Leu Ile Gly Asn Ser Met
        35                  40                  45

Val Ile Leu Ala Val Thr Lys Asn Lys Lys Leu Arg Asn Ser Gly Asn
    50                  55                  60

Ile Phe Val Val Ser Leu Ser Val Ala Asp Met Leu Val Ala Ile Tyr
65                  70                  75                  80

Pro Tyr Pro Leu Met Leu His Ala Met Ser Ile Gly Gly Trp Asp Leu
                85                  90                  95

Ser Gln Leu Gln Cys Gln Met Val Gly Phe Ile Thr Gly Leu Ser Val
            100                 105                 110

Val Gly Ser Ile Phe Asn Ile Val Ala Ile Ala Ile Asn Arg Tyr Cys
        115                 120                 125

Tyr Ile Cys His Ser Leu Gln Tyr Glu Arg Ile Phe Ser Val Arg Asn
    130                 135                 140

Thr Cys Ile Tyr Leu Val Ile Thr Trp Ile Met Thr Val Leu Ala Val
145                 150                 155                 160

Leu Pro Asn Met Tyr Ile Gly Thr Ile Glu Tyr Asp Pro Arg Thr Tyr
                165                 170                 175

Thr Cys Ile Phe Asn Tyr Leu Asn Asn Pro Val Phe Thr Val Thr Ile
            180                 185                 190

Val Cys Ile His Phe Val Leu Pro Leu Ile Val Gly Phe Cys Tyr
        195                 200                 205

Val Arg Ile Trp Thr Lys Val Leu Ala Ala Arg Asp Pro Ala Gly Gln
    210                 215                 220

Asn Pro Asp Asn Gln Leu Ala Glu Val Arg Asn Lys Leu Thr Met Phe
225                 230                 235                 240

Val Ile Phe Leu Leu Phe Ala Val Cys Trp Cys Pro Ile Asn Val Leu
                245                 250                 255

Thr Val Leu Val Ala Val Ser Pro Lys Glu Met Ala Gly Lys Ile Pro
            260                 265                 270
```

```
Asn Trp Leu Tyr Leu Ala Ala Tyr Phe Ile Ala Tyr Phe Asn Ser Cys
            275                 280                 285

Leu Asn Ala Val Ile Tyr Gly Leu Leu Asn Glu Asn Phe Arg Arg Glu
        290                 295                 300

Tyr Trp Thr Ile Phe His Ala Met Arg His Pro Ile Ile Phe Phe Ser
305                 310                 315                 320

Gly Leu Ile Ser Asp Ile Arg Glu Met Gln Ala Arg Thr Leu Ala
                325                 330                 335

Arg Ala Arg Ala His Ala Arg Asp Gln Ala Arg Glu Gln Asp Arg Ala
            340                 345                 350

His Ala Cys Pro Ala Val Glu Glu Thr Pro Met Asn Val Arg Asn Val
            355                 360                 365

Pro Leu Pro Gly Asp Ala Ala Gly His Pro Asp Arg Ala Ser Gly
        370                 375                 380

His Pro Lys Pro His Ser Arg Ser Ser Ala Tyr Arg Lys Ser Ala
385                 390                 395                 400

Ser Thr His His Lys Ser Val Phe Ser His Ser Lys Ala Ala Ser Gly
                405                 410                 415

His Leu Lys Pro Val Ser Gly His Ser Lys Pro Ala Ser Gly His Pro
            420                 425                 430

Lys Ser Ala Thr Val Tyr Pro Lys Pro Ala Ser Val His Phe Lys Ala
            435                 440                 445

Asp Ser Val His Phe Lys Gly Asp Ser Val His Phe Lys Pro Asp Ser
450                 455                 460

Val His Phe Lys Pro Ala Ser Ser Asn Pro Lys Pro Ile Thr Gly His
465                 470                 475                 480

His Val Ser Ala Gly Ser His Ser Lys Ser Ala Phe Ser Ala Ala Thr
                485                 490                 495

Ser His Pro Lys Pro Thr Thr Gly His Ile Lys Pro Ala Thr Ser His
            500                 505                 510

Ala Glu Pro Thr Thr Ala Asp Tyr Pro Lys Pro Ala Thr Thr Ser His
            515                 520                 525

Pro Lys Pro Thr Ala Ala Asp Asn Pro Glu Leu Ser Ala Ser His Cys
        530                 535                 540

Pro Glu Ile Pro Ala Ile Ala His Pro Val Ser Asp Ser Asp Leu
545                 550                 555                 560

Pro Glu Ser Ala Ser Ser Pro Ala Ala Gly Pro Thr Lys Pro Ala Ala
                565                 570                 575

Ser Gln Leu Glu Ser Asp Thr Ile Ala Asp Leu Pro Asp Pro Thr Val
            580                 585                 590

Val Thr Thr Ser Thr Asn Asp Tyr His Asp Val Val Val Asp Val
        595                 600                 605

Glu Asp Asp Pro Asp Glu Met Ala Val
    610                 615

<210> SEQ ID NO 219
<211> LENGTH: 1548
<212> TYPE: DNA
<213> ORGANISM: Homo sapiens

<400> SEQUENCE: 219
atgggacata acgggagctg gatctctcca aatgccagcg agccgcacaa cgcgtccggc       60
gccgaggctg cgggtgtgaa ccgcagcgcg ctcggggagt tcggcgaggc gcagctgtac     120
cgccagttca ccaccaccgt gcaggtcgtc atcttcatag gctcgctgct cggaaacttc     180
```

```
atggtgttat ggtcaacttg ccgcacaacc gtgttcaaat ctgtcaccaa caggttcatt      240
aaaaacctgg cctgctcggg gatttgtgcc agcctggtct gtgtgccctt cgacatcatc      300
ctcagcacca gtcctcactg ttgctggtgg atctacacca tgctcttctg caaggtcgtc      360
aaattttgc acaaagtatt ctgctctgtg accatcctca gcttccctgc tattgctttg       420
gacaggtact actcagtcct ctatccactg gagaggaaaa tatctgatgc caagtcccgt      480
gaactggtga tgtacatctg ggcccatgca gtggtggcca gtgtccctgt gtttgcagta      540
accaatgtgc tgacatcta tgccacgtcc acctgcacgg aagtctggag caactccttg       600
ggccacctgg tgtacgttct ggtgtataac atcaccacgg tcattgtgcc tgtggtggtg      660
gtgttcctct tcttgatact gatccgacgg gccctgagtg ccagccagaa gaagaaggtc      720
atcatagcag cgctccggac cccacagaac accatctcta ttccctatgc ctcccagcgg      780
gaggccgagc tgaaagccac cctgctctcc atggtgatgt cttcatctt gtgtagcgtg       840
ccctatgcca ccctggtcgt ctaccagact gtgctcaatg tccctgacac ttccgtcttc      900
ttgctgctca ctgctgtttg gctgcccaaa gtctccctgc tggcaaaccc tgttctcttt      960
cttactgtga acaaatctgt ccgcaagtgc ttgatagga ccctggtgca actacaccac     1020
cggtacagtc gccgtaatgt ggtcagtaca gggagtggca tggctgaggc cagcctggaa      1080
cccagcatac gctcgggtag ccagctcctg gagatgttcc acattgggca gcagcagatc      1140
tttaagccca cagaggatga ggaagagagt gaggccaagt acattggctc agctgacttc      1200
caggccaagg agatatttag cacctgcctg gagggagagc agggccaca gtttgcgccc      1260
tctgccccac ccctgagcac agtggactct gtatcccagg tggcaccggc agcccctgtg      1320
gaacctgaaa cattccctga taagtattcc ctgcagtttg gctttgggcc ttttgagttg      1380
cctcctcagt ggctctcaga gacccgaaac agcaagaagc ggctgcttcc ccccttgggc      1440
aacaccccag aagagctgat ccagacaaag gtgcccaagg taggcagggt ggagcggaag      1500
atgagcagaa acaataaagt gagcatttt ccaaaggtgg attcctag                    1548
```

<210> SEQ ID NO 220
<211> LENGTH: 515
<212> TYPE: PRT
<213> ORGANISM: Homo sapiens

<400> SEQUENCE: 220

```
Met Gly His Asn Gly Ser Trp Ile Ser Pro Asn Ala Ser Glu Pro His
1               5                   10                  15

Asn Ala Ser Gly Ala Glu Ala Ala Gly Val Asn Arg Ser Ala Leu Gly
            20                  25                  30

Glu Phe Gly Glu Ala Gln Leu Tyr Arg Gln Phe Thr Thr Thr Val Gln
        35                  40                  45

Val Val Ile Phe Ile Gly Ser Leu Leu Gly Asn Phe Met Val Leu Trp
    50                  55                  60

Ser Thr Cys Arg Thr Thr Val Phe Lys Ser Val Thr Asn Arg Phe Ile
65                  70                  75                  80

Lys Asn Leu Ala Cys Ser Gly Ile Cys Ala Ser Leu Val Cys Val Pro
                85                  90                  95

Phe Asp Ile Ile Leu Ser Thr Ser Pro His Cys Cys Trp Trp Ile Tyr
            100                 105                 110

Thr Met Leu Phe Cys Lys Val Val Lys Phe Leu His Lys Val Phe Cys
        115                 120                 125
```

```
Ser Val Thr Ile Leu Ser Phe Pro Ala Ile Ala Leu Asp Arg Tyr Tyr
    130                 135                 140

Ser Val Leu Tyr Pro Leu Glu Arg Lys Ile Ser Asp Ala Lys Ser Arg
145                 150                 155                 160

Glu Leu Val Met Tyr Ile Trp Ala His Ala Val Ala Ser Val Pro
                165                 170                 175

Val Phe Ala Val Thr Asn Val Ala Asp Ile Tyr Ala Thr Ser Thr Cys
            180                 185                 190

Thr Glu Val Trp Ser Asn Ser Leu Gly His Leu Val Tyr Val Leu Val
            195                 200                 205

Tyr Asn Ile Thr Thr Val Ile Val Pro Val Val Val Phe Leu Phe
    210                 215                 220

Leu Ile Leu Ile Arg Arg Ala Leu Ser Ala Ser Gln Lys Lys Lys Val
225                 230                 235                 240

Ile Ile Ala Ala Leu Arg Thr Pro Gln Asn Thr Ile Ser Ile Pro Tyr
                245                 250                 255

Ala Ser Gln Arg Glu Ala Glu Leu Lys Ala Thr Leu Leu Ser Met Val
            260                 265                 270

Met Val Phe Ile Leu Cys Ser Val Pro Tyr Ala Thr Leu Val Val Tyr
        275                 280                 285

Gln Thr Val Leu Asn Val Pro Asp Thr Ser Val Phe Leu Leu Leu Thr
    290                 295                 300

Ala Val Trp Leu Pro Lys Val Ser Leu Leu Ala Asn Pro Val Leu Phe
305                 310                 315                 320

Leu Thr Val Asn Lys Ser Val Arg Lys Cys Leu Ile Gly Thr Leu Val
                325                 330                 335

Gln Leu His His Arg Tyr Ser Arg Arg Asn Val Val Ser Thr Gly Ser
            340                 345                 350

Gly Met Ala Glu Ala Ser Leu Glu Pro Ser Ile Arg Ser Gly Ser Gln
        355                 360                 365

Leu Leu Glu Met Phe His Ile Gly Gln Gln Gln Ile Phe Lys Pro Thr
    370                 375                 380

Glu Asp Glu Glu Glu Ser Glu Ala Lys Tyr Ile Gly Ser Ala Asp Phe
385                 390                 395                 400

Gln Ala Lys Glu Ile Phe Ser Thr Cys Leu Glu Gly Glu Gln Gly Pro
                405                 410                 415

Gln Phe Ala Pro Ser Ala Pro Pro Leu Ser Thr Val Asp Ser Val Ser
            420                 425                 430

Gln Val Ala Pro Ala Ala Pro Val Glu Pro Glu Thr Phe Pro Asp Lys
        435                 440                 445

Tyr Ser Leu Gln Phe Gly Phe Gly Pro Phe Glu Leu Pro Pro Gln Trp
    450                 455                 460

Leu Ser Glu Thr Arg Asn Ser Lys Lys Arg Leu Leu Pro Pro Leu Gly
465                 470                 475                 480

Asn Thr Pro Glu Glu Leu Ile Gln Thr Lys Val Pro Lys Val Gly Arg
                485                 490                 495

Val Glu Arg Lys Met Ser Arg Asn Asn Lys Val Ser Ile Phe Pro Lys
            500                 505                 510

Val Asp Ser
    515

<210> SEQ ID NO 221
<211> LENGTH: 1164
<212> TYPE: DNA
```

<213> ORGANISM: Homo sapiens

<400> SEQUENCE: 221

```
atgaatcggc accatctgca ggatcacttt ctggaaatag acaagaagaa ctgctgtgtg      60
ttccgagatg acttcattgc aaggtgttg ccgccggtgt tggggctgga gtttatcttt     120
gggcttctgg gcaatggcct tgccctgtgg attttctgtt ccacctcaa gtcctggaaa     180
tccagccgga ttttcctgtt caacctggca gtagctgact tctactgat catctgcctg     240
ccgttcgtga tggactacta tgtgcggcgt tcagactgga gtttgggga catcccttgc     300
cggctggtgc tcttcatgtt tgccatgaac cgccagggca gcatcatctt cctcacggtg     360
gtggcggtag acaggtattt ccgggtggtc catccccacc acgccctgaa caagatctcc     420
aattggacag cagccatcat ctcttgcctt ctgtggggca tcactgttgg cctaacagtc     480
cacctcctga agaagaagtt gctgatccag aatggccctg caaatgtgtg catcagcttc     540
agcatctgcc ataccttccg gtggcacgaa gctatgttcc tcctggagtt cctcctgccc     600
ctgggcatca tcctgttctg ctcagccaga attatctgga gcctgcggca gagacaaatg     660
gaccggcatg ccaagatcaa gagagccaaa accttcatca tggtggtggc catcgtctttt     720
gtcatctgct tccttcccag cgtggttgtg cggatccgca tcttctggct cctgcacact     780
tcgggcacgc agaattgtga agtgtaccgc tcggtggacc tggcgttctt tatcactctc     840
agcttcacct acatgaacag catgctggac cccgtggtgt actacttctc cagcccatcc     900
tttcccaact tcttctccac tttgatcaac cgctgcctcc agaggaagat gacaggtgag     960
ccagataata accgcagcac gagcgtcgag ctcacagggg accccaacaa accagaggc    1020
gctccagagg cgttaatggc caactccggt gagccatgga gcccctctta tctgggccca    1080
acctcaaata accattccaa gaagggacat tgtcaccaag aaccagcatc tctggagaaa    1140
cagttgggct gttgcatcga gtaa                                          1164
```

<210> SEQ ID NO 222
<211> LENGTH: 387
<212> TYPE: PRT
<213> ORGANISM: Homo sapiens

<400> SEQUENCE: 222

```
Met Asn Arg His His Leu Gln Asp His Phe Leu Glu Ile Asp Lys Lys
1               5                  10                  15

Asn Cys Cys Val Phe Arg Asp Asp Phe Ile Ala Lys Val Leu Pro Pro
            20                  25                  30

Val Leu Gly Leu Glu Phe Ile Phe Gly Leu Leu Gly Asn Gly Leu Ala
        35                  40                  45

Leu Trp Ile Phe Cys Phe His Leu Lys Ser Trp Lys Ser Ser Arg Ile
    50                  55                  60

Phe Leu Phe Asn Leu Ala Val Ala Asp Phe Leu Ile Ile Cys Leu
65                  70                  75                  80

Pro Phe Val Met Asp Tyr Tyr Val Arg Arg Ser Asp Trp Lys Phe Gly
                85                  90                  95

Asp Ile Pro Cys Arg Leu Val Leu Phe Met Phe Ala Met Asn Arg Gln
            100                 105                 110

Gly Ser Ile Ile Phe Leu Thr Val Val Ala Val Asp Arg Tyr Phe Arg
        115                 120                 125

Val Val His Pro His His Ala Leu Asn Lys Ile Ser Asn Trp Thr Ala
    130                 135                 140
```

-continued

```
Ala Ile Ile Ser Cys Leu Leu Trp Gly Ile Thr Val Gly Leu Thr Val
145                 150                 155                 160

His Leu Leu Lys Lys Lys Leu Leu Ile Gln Asn Gly Pro Ala Asn Val
                165                 170                 175

Cys Ile Ser Phe Ser Ile Cys His Thr Phe Arg Trp His Glu Ala Met
            180                 185                 190

Phe Leu Leu Glu Phe Leu Leu Pro Leu Gly Ile Ile Leu Phe Cys Ser
        195                 200                 205

Ala Arg Ile Ile Trp Ser Leu Arg Gln Arg Gln Met Asp Arg His Ala
210                 215                 220

Lys Ile Lys Arg Ala Lys Thr Phe Ile Met Val Ala Ile Val Phe
225                 230                 235                 240

Val Ile Cys Phe Leu Pro Ser Val Val Arg Ile Arg Ile Phe Trp
                245                 250                 255

Leu Leu His Thr Ser Gly Thr Gln Asn Cys Glu Val Tyr Arg Ser Val
                260                 265                 270

Asp Leu Ala Phe Phe Ile Thr Leu Ser Phe Thr Tyr Met Asn Ser Met
            275                 280                 285

Leu Asp Pro Val Val Tyr Tyr Phe Ser Ser Pro Ser Phe Pro Asn Phe
        290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
                340                 345                 350

Trp Ser Pro Ser Tyr Leu Gly Pro Thr Ser Asn Asn His Ser Lys Lys
            355                 360                 365

Gly His Cys His Gln Glu Pro Ala Ser Leu Glu Lys Gln Leu Gly Cys
        370                 375                 380

Cys Ile Glu
385
```

<210> SEQ ID NO 223
<211> LENGTH: 1212
<212> TYPE: DNA
<213> ORGANISM: Homo sapiens

<400> SEQUENCE: 223

| | |
|---|---|
| atggcttgca atggcagtgc ggccaggggg cactttgacc ctgaggactt gaacctgact | 60 |
| gacgaggcac tgagactcaa gtacctgggg ccccagcaga cagagctgtt catgcccatc | 120 |
| tgtgccacat acctgctgat cttcgtggtg ggcgctgtgg gcaatgggct gacctgtctg | 180 |
| gtcatcctgc gccacaaggc catgcgcacg cctaccaact actacctctt cagcctggcc | 240 |
| gtgtcggacc tgctggtgct gctggtgggc ctgcccctgg agctctatga gatgtggcac | 300 |
| aactacccct tcctgctggg cgttggtggc tgctattccc gcacgctact gtttgagatg | 360 |
| gtctgcctgg cctcagtgct caacgtcact gccctgagcg tggaacgcta tgtggccgtg | 420 |
| gtgcacccac tccaggccag gtccatggtg acgcgggccc atgtgcgccg agtgcttggg | 480 |
| gccgtctggg tcttgccat gctctgctcc ctgcccaaca ccagcctgca cggcatccgg | 540 |
| cagctgcacg tgccctgccg gggcccagtg ccagactcag ctgtttgcat gctggtccgc | 600 |
| ccacgggccc tctacaacat ggtagtgcag accaccgcgc tgctcttctt ctgcctgccc | 660 |
| atggccatca tgagcgtgct ctacctgctc attgggctgc gactgcggcg ggagaggctg | 720 |

-continued

```
ctgctcatgc aggaggccaa gggcaggggc tctgcagcag ccaggtccag atacacctgc      780
aggctccagc agcacgatcg gggccggaga caagtgaaga agatgctgtt tgtcctggtc      840
gtggtgtttg gcatctgctg ggccccgttc cacgccgacc gcgtcatgtg gagcgtcgtg      900
tcacagtgga cagatggcct gcacctggcc ttccagcacg tgcacgtcat ctccggcatc      960
ttcttctacc tgggctcggc ggccaacccc gtgctctata gcctcatgtc cagccgcttc     1020
cgagagacct tccaggaggc cctgtgcctc ggggcctgct gccatcgcct cagaccccgc     1080
cacagctccc acagcctcag caggatgacc acaggcagca ccctgtgtga tgtgggctcc     1140
ctgggcagct gggtccaccc cctggctggg aacgatggcc cagaggcgca gcaagagacc     1200
gatccatcct ga                                                         1212
```

<210> SEQ ID NO 224
<211> LENGTH: 403
<212> TYPE: PRT
<213> ORGANISM: Homo sapiens

<400> SEQUENCE: 224

```
Met Ala Cys Asn Gly Ser Ala Ala Arg Gly His Phe Asp Pro Glu Asp
1               5                   10                  15

Leu Asn Leu Thr Asp Glu Ala Leu Arg Leu Lys Tyr Leu Gly Pro Gln
                20                  25                  30

Gln Thr Glu Leu Phe Met Pro Ile Cys Ala Thr Tyr Leu Leu Ile Phe
            35                  40                  45

Val Val Gly Ala Val Gly Asn Gly Leu Thr Cys Leu Val Ile Leu Arg
        50                  55                  60

His Lys Ala Met Arg Thr Pro Thr Asn Tyr Tyr Leu Phe Ser Leu Ala
65                  70                  75                  80

Val Ser Asp Leu Leu Val Leu Val Gly Leu Pro Leu Glu Leu Tyr
                85                  90                  95

Glu Met Trp His Asn Tyr Pro Phe Leu Leu Gly Val Gly Gly Cys Tyr
                100                 105                 110

Phe Arg Thr Leu Leu Phe Glu Met Val Cys Leu Ala Ser Val Leu Asn
            115                 120                 125

Val Thr Ala Leu Ser Val Glu Arg Tyr Val Ala Val His Pro Leu
        130                 135                 140

Gln Ala Arg Ser Met Val Thr Arg Ala His Val Arg Arg Val Leu Gly
145                 150                 155                 160

Ala Val Trp Gly Leu Ala Met Leu Cys Ser Leu Pro Asn Thr Ser Leu
                165                 170                 175

His Gly Ile Arg Gln Leu His Val Pro Cys Arg Gly Pro Val Pro Asp
            180                 185                 190

Ser Ala Val Cys Met Leu Val Arg Pro Arg Ala Leu Tyr Asn Met Val
        195                 200                 205

Val Gln Thr Thr Ala Leu Leu Phe Phe Cys Leu Pro Met Ala Ile Met
    210                 215                 220

Ser Val Leu Tyr Leu Leu Ile Gly Leu Arg Leu Arg Arg Glu Arg Leu
225                 230                 235                 240

Leu Leu Met Gln Glu Ala Lys Gly Arg Gly Ser Ala Ala Ala Arg Ser
                245                 250                 255

Arg Tyr Thr Cys Arg Leu Gln Gln His Asp Arg Gly Arg Arg Gln Val
            260                 265                 270

Lys Lys Met Leu Phe Val Leu Val Val Phe Gly Ile Cys Trp Ala
```

```
            275                 280                 285
Pro Phe His Ala Asp Arg Val Met Trp Ser Val Ser Gln Trp Thr
    290                 295                 300

Asp Gly Leu His Leu Ala Phe Gln His Val His Val Ile Ser Gly Ile
305                 310                 315                 320

Phe Phe Tyr Leu Gly Ser Ala Ala Asn Pro Val Leu Tyr Ser Leu Met
                325                 330                 335

Ser Ser Arg Phe Arg Glu Thr Phe Gln Glu Ala Leu Cys Leu Gly Ala
            340                 345                 350

Cys Cys His Arg Leu Arg Pro Arg His Ser Ser His Ser Leu Ser Arg
        355                 360                 365

Met Thr Thr Gly Ser Thr Leu Cys Asp Val Gly Ser Leu Gly Ser Trp
    370                 375                 380

Val His Pro Leu Ala Gly Asn Asp Gly Pro Glu Ala Gln Gln Glu Thr
385                 390                 395                 400

Asp Pro Ser

<210> SEQ ID NO 225
<211> LENGTH: 1098
<212> TYPE: DNA
<213> ORGANISM: Homo sapiens

<400> SEQUENCE: 225
atggggaaca tcactgcaga caactcctcg atgagctgta ccatcgacca taccatccac     60
cagacgctgg ccccggtggt ctatgttacc gtgctggtgg tgggcttccc ggccaactgc    120
ctgtccctct acttcggcta cctgcagatc aaggcccgga cgagctgggc cgtgtacctg    180
tgcaacctga cggtggccga cctcttctac atctgctcgc tgcccttctg gctgcagtac    240
gtgctgcagc acgacaactg gtctcacggc gacctgtcct gccaggtgtg cggcatcctc    300
ctgtacagag acatctacat cagcgtgggc ttcctctgct gcatctccgt ggaccgctac    360
ctggctgtgg cccatccctt ccgcttccac cagttccgga ccctgaaggc ggccgtcggc    420
gtcagcgtgg tcatctgggc caaggagctg ctgaccagca tctacttcct gatgcacgag    480
gaggtcatcg aggacgagaa ccagcaccgc gtgtgctttg agcactaccc catccaggca    540
tggcagcgcg ccatcaacta ctaccgcttc ctggtgggct tcctcttccc catctgcctg    600
ctgctggcgt cctaccaggg catcctgcgc gccgtgcgcc ggagccacgg cacccagaag    660
agccgcaagg accagatcaa gcggctggtg ctcagcaccg tggtcatctt cctggcctgc    720
ttcctgccct accacgtgtt gctgctggtg cgcagcgtct gggaggccag ctgcgacttc    780
gccaagggcg tttcaacgc ctaccacttc tccctcctgc tcaccagctt caactgcgtc    840
gccgaccccg tgctctactg cttcgtcagc gagaccaccc accgggacct ggcccgcctc    900
cgcggggcct gctggccttt cctcacctgc tccaggaccg gccgggccag ggaggcctac    960
ccgctgggtg cccccgaggc ctccgggaaa gcggggccc agggtgagga gcccgagctg   1020
ttgaccaagc tccaccgcgc cttccagacc cctaactcgc agggtcggg cgggttcccc   1080 acgggcaggt tggcctag                                                 1098

<210> SEQ ID NO 226
<211> LENGTH: 365
<212> TYPE: PRT
<213> ORGANISM: Homo sapiens

<400> SEQUENCE: 226
```

```
Met Gly Asn Ile Thr Ala Asp Asn Ser Ser Met Ser Cys Thr Ile Asp
1               5                   10                  15

His Thr Ile His Gln Thr Leu Ala Pro Val Val Tyr Val Thr Val Leu
                20                  25                  30

Val Val Gly Phe Pro Ala Asn Cys Leu Ser Leu Tyr Phe Gly Tyr Leu
            35                  40                  45

Gln Ile Lys Ala Arg Asn Glu Leu Gly Val Tyr Leu Cys Asn Leu Thr
    50                  55                  60

Val Ala Asp Leu Phe Tyr Ile Cys Ser Leu Pro Phe Trp Leu Gln Tyr
65                  70                  75                  80

Val Leu Gln His Asp Asn Trp Ser His Gly Asp Leu Ser Cys Gln Val
                85                  90                  95

Cys Gly Ile Leu Leu Tyr Glu Asn Ile Tyr Ile Ser Val Gly Phe Leu
            100                 105                 110

Cys Cys Ile Ser Val Asp Arg Tyr Leu Ala Val Ala His Pro Phe Arg
            115                 120                 125

Phe His Gln Phe Arg Thr Leu Lys Ala Ala Val Gly Val Ser Val Val
    130                 135                 140

Ile Trp Ala Lys Glu Leu Leu Thr Ser Ile Tyr Phe Leu Met His Glu
145                 150                 155                 160

Glu Val Ile Glu Asp Glu Asn Gln His Arg Val Cys Phe Glu His Tyr
                165                 170                 175

Pro Ile Gln Ala Trp Gln Arg Ala Ile Asn Tyr Tyr Arg Phe Leu Val
            180                 185                 190

Gly Phe Leu Phe Pro Ile Cys Leu Leu Leu Ala Ser Tyr Gln Gly Ile
    195                 200                 205

Leu Arg Ala Val Arg Arg Ser His Gly Thr Gln Lys Ser Arg Lys Asp
    210                 215                 220

Gln Ile Lys Arg Leu Val Leu Ser Thr Val Val Ile Phe Leu Ala Cys
225                 230                 235                 240

Phe Leu Pro Tyr His Val Leu Leu Val Arg Ser Val Trp Glu Ala
                245                 250                 255

Ser Cys Asp Phe Ala Lys Gly Val Phe Asn Ala Tyr His Phe Ser Leu
            260                 265                 270

Leu Leu Thr Ser Phe Asn Cys Val Ala Asp Pro Val Leu Tyr Cys Phe
    275                 280                 285

Val Ser Glu Thr Thr His Arg Asp Leu Ala Arg Leu Arg Gly Ala Cys
290                 295                 300

Leu Ala Phe Leu Thr Cys Ser Arg Thr Gly Arg Ala Arg Glu Ala Tyr
305                 310                 315                 320

Pro Leu Gly Ala Pro Glu Ala Ser Gly Lys Ser Gly Ala Gln Gly Glu
            325                 330                 335

Glu Pro Glu Leu Leu Thr Lys Leu His Pro Ala Phe Gln Thr Pro Asn
                340                 345                 350

Ser Pro Gly Ser Gly Gly Phe Pro Thr Gly Arg Leu Ala
            355                 360                 365

<210> SEQ ID NO 227
<211> LENGTH: 1416
<212> TYPE: DNA
<213> ORGANISM: Homo sapiens

<400> SEQUENCE: 227
atggatattc tttgtgaaga aaatacttct ttgagctcaa ctacgaactc cctaatgcaa      60
```

-continued

```
ttaaatgatg acaacaggct ctacagtaat gactttaact ccggagaagc taacacttct    120
gatgcattta actggacagt cgactctgaa aatcgaacca acctttcctg tgaagggtgc    180
ctctcaccgt cgtgtctctc cttacttcat ctccaggaaa aaaactggtc tgctttactg    240
acagccgtag tgattattct aactattgct ggaaacatac tcgtcatcat ggcagtgtcc    300
ctagagaaaa agctgcagaa tgccaccaac tatttcctga tgtcacttgc catagctgat    360
atgctgctgg gtttccttgt catgcccgtg tccatgttaa ccatcctgta tgggtaccgg    420
tggcctctgc cgagcaagct ttgtgcagtc tggatttacc tggacgtgct cttctccacg    480
gcctccatca tgcacctctg cgccatctcg ctggaccgct acgtcgccat ccagaatccc    540
atccaccaca gccgcttcaa ctccagaact aaggcatttc tgaaaatcat tgctgtttgg    600
accatatcag taggtatatc catgccaata ccagtctttg gctacaggac gattcgaag     660 gtctttaagg aggggagttg cttactcgcc gatgataact ttgtcctgat cggctctttt    720
gtgtcatttt tcattccctt aaccatcatg gtgatcacct actttctaac tatcaagtca    780
ctccagaaag aagctacttt tgtgtgtaagt gatcttggca cacgggccaa attagcttct    840
ttcagcttcc tccctcagag ttctttgtct tcagaaaagc tcttccagcg gtcgatccat    900
agggagccag ggtcctacac aggcaggagg actatgcagt ccatcagcaa tgagcaaaag    960
gcaaagaagg tgctgggcat cgtcttcttc ctgtttgtgg tgatgtggtg ccctttcttc    1020
atcacaaaca tcatggccgt catctgcaaa gagtcctgca atgaggatgt cattggggcc    1080
ctgctcaatg tgtttgtttg gatcggttat ctctcttcag cagtcaaccc actagtctac    1140
acactgttca acaagaccta taggtcagcc ttttcacggt atattcagtg tcagtacaag    1200
gaaaacaaaa aaccattgca gttaatttta gtgaacacaa taccggcttt ggcctacaag    1260
tctagccaac ttcaaatggg acaaaaaaag aattcaaagc aagatgccaa gacaacagat    1320
aatgactgct caatggttgc tctaggaaag cagtattctg aagaggcttc taaagacaat    1380
agcgacggag tgaatgaaaa ggtgagctgt gtgtga                             1416
```

<210> SEQ ID NO 228
<211> LENGTH: 471
<212> TYPE: PRT
<213> ORGANISM: Homo sapiens

<400> SEQUENCE: 228

```
Met Asp Ile Leu Cys Glu Glu Asn Thr Ser Leu Ser Ser Thr Thr Asn
1               5                   10                  15

Ser Leu Met Gln Leu Asn Asp Asp Asn Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
```

-continued

```
            130                 135                 140
Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Gly Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
    290                 295                 300

Ser Tyr Thr Gly Arg Arg Thr Met Gln Ser Ile Ser Asn Glu Gln Lys
305                 310                 315                 320

Ala Lys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350

Cys Asn Glu Asp Val Ile Gly Ala Leu Leu Asn Val Phe Val Trp Ile
        355                 360                 365

Gly Tyr Leu Ser Ser Ala Val Asn Pro Leu Val Tyr Thr Leu Phe Asn
    370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Asn Ser
            420                 425                 430

Lys Gln Asp Ala Lys Thr Thr Asp Asn Asp Cys Ser Met Val Ala Leu
        435                 440                 445

Gly Lys Gln Tyr Ser Glu Glu Ala Ser Lys Asp Asn Ser Asp Gly Val
    450                 455                 460

Asn Glu Lys Val Ser Cys Val
465                 470
```

<210> SEQ ID NO 229
<211> LENGTH: 1377
<212> TYPE: DNA
<213> ORGANISM: Homo sapiens

<400> SEQUENCE: 229

```
atggtgaacc tgaggaatgc ggtgcattca ttccttgtgc acctaattgg cctattggtt      60
tggcaatgtg atatttctgt gagcccagta gcagctatag taactgacat tttcaatacc     120
tccgatggtg gacgcttcaa attcccagac ggggtacaaa actggccagc actttcaatc     180
```

-continued

```
gtcatcataa taatcatgac aataggtggc aacatccttg tgatcatggc agtaagcatg      240
gaaaagaaac tgcacaatgc caccaattac ttcttaatgt ccctagccat tgctgatatg      300
ctagtgggac tacttgtcat gcccctgtct ctcctggcaa tcctttatga ttatgtctgg      360
ccactaccta gatatttgtg ccccgtctgg atttctttag atgttttatt ttcaacagcg      420
tccatcatgc acctctgcgc tatatcgctg gatcggtatg tagcaatacg taatcctatt      480
gagcatagcc gtttcaattc gcggactaag gccatcatga agattgctat tgtttgggca      540
atttctatag gtgtatcagt tcctatccct gtgattggac tgagggacga agaaaaggtg      600
ttcgtgaaca acacgacgtg cgtgctcaac gacccaaatt tcgttcttat tgggtccttc      660
gtagctttct tcataccgct gacgattatg gtgattacgt attgcctgac catctacgtt      720
ctgcgccgac aagctttgat gttactgcac ggccacaccg aggaaccgcc tggactaagt      780
ctggatttcc tgaagtgctg caagaggaat acggccgagg aagagaactc tgcaaaccct      840
aaccaagacc agaacgcacg ccgaagaaag aagaaggaga gacgtcctag ggcaccatg       900 caggctatca acaatgaaag aaaagctaag aaagtccttg ggattgtttt ctttgtgttt      960
ctgatcatgt ggtgcccatt tttcattacc aatattctgt ctgttctttg tgagaagtcc     1020
tgtaaccaaa agctcatgga aaagcttctg aatgtgtttg tttggattgg ctatgtttgt     1080
tcaggaatca atcctctggt gtatactctg ttcaacaaaa tttaccgaag ggcattctcc     1140
aactatttgc gttgcaatta taaggtagag aaaaagcctc ctgtcaggca gattccaaga     1200
gttgccgcca ctgctttgtc tgggagggag cttaatgtta acatttatcg gcataccaat     1260
gaaccggtga tcgagaaagc cagtgacaat gagcccggta tagagatgca agttgagaat     1320
ttagagttac cagtaaatcc ctccagtgtg gttagcgaaa ggattagcag tgtgtga       1377
```

<210> SEQ ID NO 230
<211> LENGTH: 458
<212> TYPE: PRT
<213> ORGANISM: Homo sapiens

<400> SEQUENCE: 230

```
Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
            20                  25                  30

Ile Val Thr Asp Ile Phe Asn Thr Ser Asp Gly Gly Arg Phe Lys Phe
        35                  40                  45

Pro Asp Gly Val Gln Asn Trp Pro Ala Leu Ser Ile Val Ile Ile
    50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
```

```
                          165                 170                 175
        Ile Val Trp Ala Ile Ser Ile Gly Val Ser Val Pro Ile Pro Val Ile
                            180                 185                 190

Gly Leu Arg Asp Glu Lys Val Phe Val Asn Asn Thr Thr Cys Val
                        195                 200                 205

Leu Asn Asp Pro Asn Phe Val Leu Ile Gly Ser Phe Ala Phe Phe
                    210                 215                 220

Ile Pro Leu Thr Ile Met Val Ile Thr Tyr Cys Leu Thr Ile Tyr Val
        225                 230                 235                 240

Leu Arg Arg Gln Ala Leu Met Leu Leu His Gly His Thr Glu Glu Pro
                        245                 250                 255

Pro Gly Leu Ser Leu Asp Phe Leu Lys Cys Cys Lys Arg Asn Thr Ala
                        260                 265                 270

Glu Glu Glu Asn Ser Ala Asn Pro Asn Gln Asp Gln Asn Ala Arg Arg
                        275                 280                 285

Arg Lys Lys Lys Glu Arg Arg Pro Arg Gly Thr Met Gln Ala Ile Asn
                    290                 295                 300

Asn Glu Arg Lys Ala Lys Lys Val Leu Gly Ile Val Phe Phe Val Phe
        305                 310                 315                 320

Leu Ile Met Trp Cys Pro Phe Phe Ile Thr Asn Ile Leu Ser Val Leu
                        325                 330                 335

Cys Glu Lys Ser Cys Asn Gln Lys Leu Met Glu Lys Leu Leu Asn Val
                        340                 345                 350

Phe Val Trp Ile Gly Tyr Val Cys Ser Gly Ile Asn Pro Leu Val Tyr
                    355                 360                 365

Thr Leu Phe Asn Lys Ile Tyr Arg Arg Ala Phe Ser Asn Tyr Leu Arg
                    370                 375                 380

Cys Asn Tyr Lys Val Glu Lys Lys Pro Pro Val Arg Gln Ile Pro Arg
        385                 390                 395                 400

Val Ala Ala Thr Ala Leu Ser Gly Arg Glu Leu Asn Val Asn Ile Tyr
                        405                 410                 415

Arg His Thr Asn Glu Pro Val Ile Glu Lys Ala Ser Asp Asn Glu Pro
                        420                 425                 430

Gly Ile Glu Met Gln Val Glu Asn Leu Glu Leu Pro Val Asn Pro Ser
                    435                 440                 445

Ser Val Val Ser Glu Arg Ile Ser Ser Val
            450                 455

<210> SEQ ID NO 231
<211> LENGTH: 1068
<212> TYPE: DNA
<213> ORGANISM: Homo sapiens

<400> SEQUENCE: 231
atggatcagt tccctgaatc agtgacagaa aactttgagt acgatgattt ggctgaggcc      60
tgttatattg gggacatcgt ggtctttggg actgtgttcc tgtccatatt ctactccgtc     120
atctttgcca ttggcctggt gggaaatttg ttggtagtgt ttgccctcac caacagcaag     180
aagcccaaga gtgtcaccga catttacctc ctgaacctgg ccttgtctga tctgctgttt     240
gtagccactt tgcccttctg gactcactat ttgataaatg aaaagggcct ccacaatgcc     300
atgtgcaaat tcactaccgc cttcttcttc atcggctttt ttggaagcat attcttcatc     360
accgtcatca gcattgatag gtacctggcc atcgtcctgg ccgccaactc catgaacaac     420
cggaccgtgc agcatggcgt caccatcagc ctaggcgtct gggcagcagc cattttggtg     480
```

```
gcagcacccc agttcatgtt cacaaagcag aaagaaaatg aatgccttgg tgactacccc      540
gaggtcctcc aggaaatctg gcccgtgctc cgcaatgtgg aaacaaattt tcttggcttc      600
ctactccccc tgctcattat gagttattgc tacttcagaa tcatccagac gctgttttcc      660
tgcaagaacc acaagaaagc caaagccaag aaactgatcc ttctggtggt catcgtgttt      720
ttcctcttct ggacaccta caacgttatg attttcctgg agacgcttaa gctctatgac      780
ttctttccca gttgtgacat gaggaaggat ctgaggctgg ccctcagtgt gactgagacg      840
gttgcattta gccattgttg cctgaatcct ctcatctatg catttgctgg ggagaagttc      900
agaagatacc tttaccacct gtatgggaaa tgcctggctg tcctgtgtgg gcgctcagtc      960
cacgttgatt tctcctcatc tgaatcacaa aggagcaggc atggaagtgt tctgagcagc     1020
aattttactt accacacgag tgatggagat gcattgctcc ttctctga                 1068
```

<210> SEQ ID NO 232
<211> LENGTH: 355
<212> TYPE: PRT
<213> ORGANISM: Homo sapiens

<400> SEQUENCE: 232

```
Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Phe Gly Thr Val
            20                  25                  30

Phe Leu Ser Ile Phe Tyr Ser Val Ile Phe Ala Ile Gly Leu Val Gly
                35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
                100                 105                 110

Phe Phe Gly Ser Ile Phe Phe Ile Thr Val Ile Ser Ile Asp Arg Tyr
            115                 120                 125

Leu Ala Ile Val Leu Ala Ala Asn Ser Met Asn Asn Arg Thr Val Gln
130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
                195                 200                 205

Tyr Cys Tyr Phe Arg Ile Ile Gln Thr Leu Phe Ser Cys Lys Asn His
    210                 215                 220

Lys Lys Ala Lys Ala Lys Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270
```

```
Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
        290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

<210> SEQ ID NO 233
<211> LENGTH: 29
<212> TYPE: DNA
<213> ORGANISM: Artificial Sequence
<220> FEATURE:
<223> OTHER INFORMATION: Novel Sequence

<400> SEQUENCE: 233
ggcttaagag catcatcgtg gtgctggtg                                29

<210> SEQ ID NO 234
<211> LENGTH: 34
<212> TYPE: DNA
<213> ORGANISM: Artificial Sequence
<220> FEATURE:
<223> OTHER INFORMATION: Novel Sequence

<400> SEQUENCE: 234
gtcaccacca gcaccacgat gatgctctta agcc                          34

<210> SEQ ID NO 235
<211> LENGTH: 31
<212> TYPE: DNA
<213> ORGANISM: Artificial Sequence
<220> FEATURE:
<223> OTHER INFORMATION: Novel Sequence

<400> SEQUENCE: 235
caaagaaagt actgggcatc gtcttcttcc t                             31

<210> SEQ ID NO 236
<211> LENGTH: 30
<212> TYPE: DNA
<213> ORGANISM: Artificial Sequence
<220> FEATURE:
<223> OTHER INFORMATION: Novel Sequence

<400> SEQUENCE: 236
tgctctagat tccagatagg tgaaaacttg                               30

<210> SEQ ID NO 237
<211> LENGTH: 50
<212> TYPE: DNA
<213> ORGANISM: Artificial Sequence
<220> FEATURE:
<223> OTHER INFORMATION: Novel Sequence

<400> SEQUENCE: 237 ctagggcac catgcaggct atcaacaatg aaagaaaagc taagaaagtc           50
```

<210> SEQ ID NO 238
<211> LENGTH: 50
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: Novel Sequence

<400> SEQUENCE: 238
caaggacttt cttagctttt ctttcattgt tgatagcctg catggtgccc                50

<210> SEQ ID NO 239
<211> LENGTH: 35
<212> TYPE: DNA
<213> ORGANISM: Artificial Sequence
<220> FEATURE:
<223> OTHER INFORMATION: Novel Sequence

<400> SEQUENCE: 239
cggcggcaga aggcgaaacg catgatcctc gcggt                                35

<210> SEQ ID NO 240
<211> LENGTH: 35
<212> TYPE: DNA
<213> ORGANISM: Artificial Sequence
<220> FEATURE:
<223> OTHER INFORMATION: Novel Sequence

<400> SEQUENCE: 240
accgcgagga tcatgcgttt cgccttctgc cgccg                                35

<210> SEQ ID NO 241
<211> LENGTH: 24
<212> TYPE: DNA
<213> ORGANISM: Artificial Sequence
<220> FEATURE:
<223> OTHER INFORMATION: Novel Sequence

<400> SEQUENCE: 241
gagacatatt atctgccacg gagg                                            24

<210> SEQ ID NO 242
<211> LENGTH: 24
<212> TYPE: DNA
<213> ORGANISM: Artificial Sequence
<220> FEATURE:
<223> OTHER INFORMATION: Novel Sequence

<400> SEQUENCE: 242
ttggcataga aaccggaccc aagg                                            24

<210> SEQ ID NO 243
<211> LENGTH: 28
<212> TYPE: DNA
<213> ORGANISM: Artificial Sequence
<220> FEATURE:
<223> OTHER INFORMATION: Novel Sequence

<400> SEQUENCE: 243
taagaattcc ataaaaatta tggaatgg                                        28

<210> SEQ ID NO 244
<211> LENGTH: 30
<212> TYPE: DNA
<213> ORGANISM: Artificial Sequence
<220> FEATURE:
<223> OTHER INFORMATION: Novel Sequence

<400> SEQUENCE: 244

| ccaggatcca gctgaagtct tccatcattc | 30 |
|---|---|

<210> SEQ ID NO 245
<211> LENGTH: 1071
<212> TYPE: DNA
<213> ORGANISM: Homo sapiens

<400> SEQUENCE: 245

| atgaatgggg tctcggaggg gaccagaggc tgcagtgaca ggcaacctgg ggtcctgaca | 60 |
|---|---|
| cgtgatcgct cttgttccag gaagatgaac tcttccggat gcctgtctga ggaggtgggg | 120 |
| tccctccgcc cactgactgt ggttatcctg tctgcgtcca ttgtcgtcgg agtgctgggc | 180 |
| aatgggctgg tgctgtggat gactgtcttc cgtatgcac gcacggtctc caccgtctgc | 240 |
| ttcttccacc tggcccttgc cgatttcatg ctctcactgt ctctgcccat tgccatgtac | 300 |
| tatattgtct ccaggcagtg gctcctcgga gagtgggcct gcaaactcta catcaccttt | 360 |
| gtgttcctca gctactttgc cagtaactgc ctccttgtct tcatctctgt ggaccgttgc | 420 |
| atctctgtcc tctaccccgt ctgggccctg aaccaccgca ctgtgcagcg ggcgagctgg | 480 |
| ctggcctttg gggtgtggct cctggccgcc gccttgtgct ctgcgcacct gaaattccgg | 540 |
| acaaccagaa aatggaatgg ctgtacgcac tgctacttgg cgttcaactc tgacaatgag | 600 |
| actgcccaga tttggattga aggggtcgtg gagggacaca ttatagggac cattggccac | 660 |
| ttcctgctgg gcttcctggg gcccttagca atcataggca cctgcgccca cctcatccgg | 720 |
| gccaagctct gcgggaggg ctgggtccat gccaaccggc ccgcgaggct gctgctggtg | 780 |
| ctggtgagcg cttctcttat cttctggtcc ccgtttaacg tggtgctgtt ggtccatctg | 840 |
| tggcgacggg tgatgctcaa ggaaatctac caccccgga tgctgctcat cctccaggct | 900 |
| agctttgcct gggctgtgt caacagcagc ctcaaccct tcctctacgt cttcgttggc | 960 |
| agagatttcc aagaaaagtt tttccagtct ttgacttctg ccctggcgag ggcgttttga | 1020 |
| gaggaggagt ttctgtcatc ctgtccccgt ggcaacgccc ccgggaatg a | 1071 |

<210> SEQ ID NO 246
<211> LENGTH: 356
<212> TYPE: PRT
<213> ORGANISM: Homo sapiens

<400> SEQUENCE: 246

Met Asn Gly Val Ser Glu Gly Thr Arg Gly Cys Ser Asp Arg Gln Pro
1               5                   10                  15

Gly Val Leu Thr Arg Asp Arg Ser Cys Ser Arg Lys Met Asn Ser Ser
            20                  25                  30

Gly Cys Leu Ser Glu Glu Val Gly Ser Leu Arg Pro Leu Thr Val Val
        35                  40                  45

Ile Leu Ser Ala Ser Ile Val Val Gly Val Leu Gly Asn Gly Leu Val
    50                  55                  60

Leu Trp Met Thr Val Phe Arg Met Ala Arg Thr Val Ser Thr Val Cys
65                  70                  75                  80

Phe Phe His Leu Ala Leu Ala Asp Phe Met Leu Ser Leu Ser Leu Pro
                85                  90                  95

Ile Ala Met Tyr Tyr Ile Val Ser Arg Gln Trp Leu Leu Gly Glu Trp
            100                 105                 110

```
Ala Cys Lys Leu Tyr Ile Thr Phe Val Phe Leu Ser Tyr Phe Ala Ser
        115                 120                 125

Asn Cys Leu Leu Val Phe Ile Ser Val Asp Arg Cys Ile Ser Val Leu
    130                 135                 140

Tyr Pro Val Trp Ala Leu Asn His Arg Thr Val Gln Arg Ala Ser Trp
145                 150                 155                 160

Leu Ala Phe Gly Val Trp Leu Leu Ala Ala Ala Leu Cys Ser Ala His
                165                 170                 175

Leu Lys Phe Arg Thr Thr Arg Lys Trp Asn Gly Cys Thr His Cys Tyr
            180                 185                 190

Leu Ala Phe Asn Ser Asp Asn Glu Thr Ala Gln Ile Trp Ile Glu Gly
        195                 200                 205

Val Val Glu Gly His Ile Ile Gly Thr Ile Gly His Phe Leu Leu Gly
    210                 215                 220

Phe Leu Gly Pro Leu Ala Ile Ile Gly Thr Cys Ala His Leu Ile Arg
225                 230                 235                 240

Ala Lys Leu Leu Arg Glu Gly Trp Val His Ala Asn Arg Pro Ala Arg
                245                 250                 255

Leu Leu Leu Val Leu Val Ser Ala Phe Phe Ile Phe Trp Ser Pro Phe
            260                 265                 270

Asn Val Val Leu Leu Val His Leu Trp Arg Arg Val Met Leu Lys Glu
        275                 280                 285

Ile Tyr His Pro Arg Met Leu Leu Ile Leu Gln Ala Ser Phe Ala Leu
    290                 295                 300

Gly Cys Val Asn Ser Ser Leu Asn Pro Phe Leu Tyr Val Phe Val Gly
305                 310                 315                 320

Arg Asp Phe Gln Glu Lys Phe Phe Gln Ser Leu Thr Ser Ala Leu Ala
                325                 330                 335

Arg Ala Phe Gly Glu Glu Glu Phe Leu Ser Ser Cys Pro Arg Gly Asn
            340                 345                 350

Ala Pro Arg Glu
        355

<210> SEQ ID NO 247
<211> LENGTH: 32
<212> TYPE: DNA
<213> ORGANISM: Artificial Sequence
<220> FEATURE:
<223> OTHER INFORMATION: Novel Sequence

<400> SEQUENCE: 247
gcagaattcg gcggccccat ggacctgccc cc                                    32

<210> SEQ ID NO 248
<211> LENGTH: 30
<212> TYPE: DNA
<213> ORGANISM: Artificial Sequence
<220> FEATURE:
<223> OTHER INFORMATION: Novel Sequence

<400> SEQUENCE: 248
gctggatccc ccgagcagtg gcgttacttc                                       30

<210> SEQ ID NO 249
<211> LENGTH: 903
<212> TYPE: DNA
<213> ORGANISM: Homo sapiens
```

-continued

```
<400> SEQUENCE: 249
atggacctgc ccccgcagct ctccttcggc ctctatgtgg ccgcctttgc gctgggcttc      60
ccgctcaacg tcctggccat ccgaggcgcg acggcccacg cccggctccg tctcacccct     120
agcctggtct acgccctgaa cctgggctgc tccgacctgc tgctgacagt ctctctgccc     180
ctgaaggcgg tggaggcgct agcctccggg gcctggcctc tgccggcctc gctgtgcccc     240
gtcttcgcgg tggcccactt cttcccactc tatgccggcg ggggcttcct ggccgccctg     300
agtgcaggcc gctacctggg agcagccttc cccttgggct accaagcctt ccggaggccg     360
tgctattcct gggggtgtg cgcggccatc tgggccctcg tcctgtgtca cctgggtctg      420
gtctttgggt tggaggctcc aggaggctgg ctggaccaca gcaacacctc cctgggcatc     480
aacacaccgg tcaacggctc tccggtctgc ctggaggcct gggaccccggc ctctgccggc    540
ccggcccgct tcagcctctc tctcctgctc ttttttctgc ccttggccat cacagccttc     600
tgctacgtgg gctgcctccg ggcactggcc cgctccggcc tgacgcacag gcggaagctg     660
cgggccgcct gggtggccgg cggggccctc ctcacgctgc tgctctgcgt aggacccttac    720
aacgcctcca acgtggccag cttcctgtac cccaatctag gaggctcctg gcggaagctg     780
gggctcatca cggtgcctg gagtgtggtg cttaatccgc tggtgaccgg ttacttggga     840
aggggtcctg gcctgaagac agtgtgtgcg gcaagaacgc aagggggcaa gtcccagaag     900
taa                                                                  903

<210> SEQ ID NO 250
<211> LENGTH: 300
<212> TYPE: PRT
<213> ORGANISM: Homo sapiens

<400> SEQUENCE: 250

Met Asp Leu Pro Pro Gln Leu Ser Phe Gly Leu Tyr Val Ala Ala Phe
  1               5                  10                  15

Ala Leu Gly Phe Pro Leu Asn Val Leu Ala Ile Arg Gly Ala Thr Ala
                 20                  25                  30

His Ala Arg Leu Arg Leu Thr Pro Ser Leu Val Tyr Ala Leu Asn Leu
             35                  40                  45

Gly Cys Ser Asp Leu Leu Leu Thr Val Ser Leu Pro Leu Lys Ala Val
         50                  55                  60

Glu Ala Leu Ala Ser Gly Ala Trp Pro Leu Pro Ala Ser Leu Cys Pro
 65                  70                  75                  80

Val Phe Ala Val Ala His Phe Phe Pro Leu Tyr Ala Gly Gly Gly Phe
                 85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
            115                 120                 125

Ala Ile Trp Ala Leu Val Leu Cys His Leu Gly Leu Val Phe Gly Leu
        130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Phe Phe
            180                 185                 190

Leu Pro Leu Ala Ile Thr Ala Phe Cys Tyr Val Gly Cys Leu Arg Ala
```

```
                195                 200                 205
Leu Ala Arg Ser Gly Leu Thr His Arg Arg Lys Leu Arg Ala Ala Trp
    210                 215                 220

Val Ala Gly Gly Ala Leu Leu Thr Leu Leu Cys Val Gly Pro Tyr
225                 230                 235                 240

Asn Ala Ser Asn Val Ala Ser Phe Leu Tyr Pro Asn Leu Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
                275                 280                 285

Cys Ala Ala Arg Thr Gln Gly Gly Lys Ser Gln Lys
    290                 295                 300

<210> SEQ ID NO 251
<211> LENGTH: 31
<212> TYPE: DNA
<213> ORGANISM: Artificial Sequence
<220> FEATURE:
<223> OTHER INFORMATION: Novel Sequence

<400> SEQUENCE: 251
ctcaagctta ctctctctca ccagtggcca c                              31

<210> SEQ ID NO 252
<211> LENGTH: 24
<212> TYPE: DNA
<213> ORGANISM: Artificial Sequence
<220> FEATURE:
<223> OTHER INFORMATION: Novel Sequence

<400> SEQUENCE: 252
ccctcctccc ccggaggacc tagc                                      24

<210> SEQ ID NO 253
<211> LENGTH: 1041
<212> TYPE: DNA
<213> ORGANISM: Homo sapiens

<400> SEQUENCE: 253
atggatacag gccccgacca gtcctacttc tccggcaatc actggttcgt cttctcggtg      60
taccttctca ctttcctggt ggggctcccc ctcaacctgc tggccctggt ggtcttcgtg     120
ggcaagctgc agcgccgccc ggtggccgtg gacgtgctcc tgctcaacct gaccgcctcg     180
gacctgctcc tgctgctgtt cctgcctttc cgcatggtgg aggcagccaa tgcatgcac      240 tggcccctgc ccttcatcct ctgcccactc tctggattca tcttcttcac caccatctat     300
ctcaccgccc tcttcctggc agctgtgagc attgaacgct tcctgagtgt ggcccaccca     360
ctgtggtaca gacccggcc gaggctgggg caggcaggtc tggtgagtgt ggcctgctgg     420
ctgttggcct ctgctcactg cagcgtggtc tacgtcatag aattctcagg ggacatctcc     480
cacagccagg gcaccaatgg gacctgctac ctggagttcc ggaaggacca gctagccatc     540
ctcctgcccg tgcggctgga gatggctgtg gtcctctttg tggtcccgct gatcatcacc     600
agctactgct acagccgcct ggtgtggatc ctcggcagag ggggcagcca ccgccggcag     660
aggagggtgg cggggctgtt ggcggccacg ctgctcaact tccttgtctg ctttgggccc     720
tacaacgtgt cccatgtcgt gggctatatc tgcggtgaaa gccggcatg gaggatctac     780 gtgacgcttc tcagcaccct gaactcctgt gtcgacccct tgtctactac cttctcctcc     840
```

```
tccgggttcc aagccgactt tcatgagctg ctgaggaggt tgtgtgggct ctggggccag    900
tggcagcagg agagcagcat ggagctgaag gagcagaagg gaggggagga gcagagagcg    960
gaccgaccag ctgaaagaaa gaccagtgaa cactcacagg gctgtggaac tggtggccag   1020
gtggcctgtg ctgaaagcta g                                              1041
```

<210> SEQ ID NO 254
<211> LENGTH: 346
<212> TYPE: PRT
<213> ORGANISM: Homo sapiens

<400> SEQUENCE: 254

```
Met Asp Thr Gly Pro Asp Gln Ser Tyr Phe Ser Gly Asn His Trp Phe
1               5                   10                  15

Val Phe Ser Val Tyr Leu Leu Thr Phe Leu Val Gly Leu Pro Leu Asn
            20                  25                  30

Leu Leu Ala Leu Val Val Phe Val Gly Lys Leu Gln Arg Arg Pro Val
        35                  40                  45

Ala Val Asp Val Leu Leu Leu Asn Leu Thr Ala Ser Asp Leu Leu Leu
    50                  55                  60

Leu Leu Phe Leu Pro Phe Arg Met Val Glu Ala Ala Asn Gly Met His
65                  70                  75                  80

Trp Pro Leu Pro Phe Ile Leu Cys Pro Leu Ser Gly Phe Ile Phe Phe
                85                  90                  95

Thr Thr Ile Tyr Leu Thr Ala Leu Phe Leu Ala Ala Val Ser Ile Glu
            100                 105                 110

Arg Phe Leu Ser Val Ala His Pro Leu Trp Tyr Lys Thr Arg Pro Arg
        115                 120                 125

Leu Gly Gln Ala Gly Leu Val Ser Val Ala Cys Trp Leu Leu Ala Ser
    130                 135                 140

Ala His Cys Ser Val Val Tyr Val Ile Glu Phe Ser Gly Asp Ile Ser
145                 150                 155                 160

His Ser Gln Gly Thr Asn Gly Thr Cys Tyr Leu Glu Phe Arg Lys Asp
                165                 170                 175

Gln Leu Ala Ile Leu Leu Pro Val Arg Leu Glu Met Ala Val Val Leu
            180                 185                 190

Phe Val Val Pro Leu Ile Ile Thr Ser Tyr Cys Tyr Ser Arg Leu Val
        195                 200                 205

Trp Ile Leu Gly Arg Gly Gly Ser His Arg Arg Gln Arg Arg Val Ala
    210                 215                 220

Gly Leu Leu Ala Ala Thr Leu Leu Asn Phe Leu Val Cys Phe Gly Pro
225                 230                 235                 240

Tyr Asn Val Ser His Val Val Gly Tyr Ile Cys Gly Glu Ser Pro Ala
                245                 250                 255

Trp Arg Ile Tyr Val Thr Leu Leu Ser Thr Leu Asn Ser Cys Val Asp
            260                 265                 270

Pro Phe Val Tyr Tyr Phe Ser Ser Gly Phe Gln Ala Asp Phe His
        275                 280                 285

Glu Leu Leu Arg Arg Leu Cys Gly Leu Trp Gly Gln Trp Gln Gln Glu
    290                 295                 300

Ser Ser Met Glu Leu Lys Glu Gln Lys Gly Gly Glu Glu Gln Arg Ala
305                 310                 315                 320

Asp Arg Pro Ala Glu Arg Lys Thr Ser Glu His Ser Gln Gly Cys Gly
                325                 330                 335
```

Thr Gly Gly Gln Val Ala Cys Ala Glu Ser
         340                 345

<210> SEQ ID NO 255
<211> LENGTH: 31
<212> TYPE: DNA
<213> ORGANISM: Artificial Sequence
<220> FEATURE:
<223> OTHER INFORMATION: Novel Sequence

<400> SEQUENCE: 255
tttaagcttc ccctccagga tgctgccgga c                                    31

<210> SEQ ID NO 256
<211> LENGTH: 31
<212> TYPE: DNA
<213> ORGANISM: Artificial Sequence
<220> FEATURE:
<223> OTHER INFORMATION: Novel Sequence

<400> SEQUENCE: 256
ggcgaattct gaaggtccag ggaaactgct a                                    31

<210> SEQ ID NO 257
<211> LENGTH: 993
<212> TYPE: DNA
<213> ORGANISM: Homo sapiens

<400> SEQUENCE: 257
atgctgccgg actggaagag ctccttgatc ctcatggctt acatcatcat cttcctcact     60
ggcctccctg ccaacctcct ggccctgcgg gcctttgtgg ggcggatccg ccagccccag    120
cctgcacctg tgcacatcct cctgctgagc ctgacgctgg ccgacctcct cctgctgctg    180
ctgctgccct tcaagatcat cgaggctgcg tcgaacttcc gctggtacct gcccaaggtc    240
gtctgcgccc tcacgagttt tggcttctac agcagcatct actgcagcac gtggctcctg    300
gcgggcatca gcatcgagcg ctacctggga gtggctttcc ccgtgcagta caagctctcc    360
cgccggcctc tgtatggagt gattgcagct ctggtggcct gggttatgtc ctttggtcac    420
tgcaccatcg tgatcatcgt tcaatacttg aacacgactg agcaggtcag aagtggcaat    480
gaaattacct gctacgagaa cttcaccgat aaccagttgg acgtggtgct gccgtgcgg    540
ctggagctgt gcctggtgct cttcttcatc cccatggcag tcaccatctt ctgctactgg    600
cgttttgtgt ggatcatgct ctcccagccc cttgtggggg cccagaggcg cgccgagcc    660
gtggggctgc tgtggtgac gctgctcaat ttcctggtgt gcttcggacc ttacaacgtg    720
tcccacctgg tggggtatca ccagagaaaa agcccctggt ggcggtcaat agccgtggtg    780
ttcagttcac tcaacgccag tctggacccc ctgctcttct atttctcttc ttcagtggtg    840
cgcagggcat ttgggagagg gctgcaggtg ctgcggaatc agggctcctc cctgttggga    900
cgcagaggca agacacagc agaggggaca aatgaggaca gggtgtggg tcaaggagaa    960
gggatgccaa gttcggactt cactacagag tag                                993

<210> SEQ ID NO 258
<211> LENGTH: 330
<212> TYPE: PRT
<213> ORGANISM: Homo sapiens

<400> SEQUENCE: 258

Met Leu Pro Asp Trp Lys Ser Ser Leu Ile Leu Met Ala Tyr Ile Ile

```
1               5              10              15
Ile Phe Leu Thr Gly Leu Pro Ala Asn Leu Leu Ala Leu Arg Ala Phe
                20              25              30

Val Gly Arg Ile Arg Gln Pro Gln Pro Ala Pro Val His Ile Leu Leu
        35              40              45

Leu Ser Leu Thr Leu Ala Asp Leu Leu Leu Leu Leu Leu Leu Pro Phe
    50              55              60

Lys Ile Ile Glu Ala Ala Ser Asn Phe Arg Trp Tyr Leu Pro Lys Val
65              70              75              80

Val Cys Ala Leu Thr Ser Phe Gly Phe Tyr Ser Ser Ile Tyr Cys Ser
                85              90              95

Thr Trp Leu Leu Ala Gly Ile Ser Ile Glu Arg Tyr Leu Gly Val Ala
                100             105             110

Phe Pro Val Gln Tyr Lys Leu Ser Arg Arg Pro Leu Tyr Gly Val Ile
            115             120             125

Ala Ala Leu Val Ala Trp Val Met Ser Phe Gly His Cys Thr Ile Val
    130             135             140

Ile Ile Val Gln Tyr Leu Asn Thr Thr Glu Gln Val Arg Ser Gly Asn
145             150             155             160

Glu Ile Thr Cys Tyr Glu Asn Phe Thr Asp Asn Gln Leu Asp Val Val
            165             170             175

Leu Pro Val Arg Leu Glu Leu Cys Leu Val Leu Phe Phe Ile Pro Met
            180             185             190

Ala Val Thr Ile Phe Cys Tyr Trp Arg Phe Val Trp Ile Met Leu Ser
        195             200             205

Gln Pro Leu Val Gly Ala Gln Arg Arg Arg Ala Val Gly Leu Ala
    210             215             220

Val Val Thr Leu Leu Asn Phe Leu Val Cys Phe Gly Pro Tyr Asn Val
225             230             235             240

Ser His Leu Val Gly Tyr His Gln Arg Lys Ser Pro Trp Trp Arg Ser
                245             250             255

Ile Ala Val Val Phe Ser Ser Leu Asn Ala Ser Leu Asp Pro Leu Leu
            260             265             270

Phe Tyr Phe Ser Ser Ser Val Val Arg Arg Ala Phe Gly Arg Gly Leu
    275             280             285

Gln Val Leu Arg Asn Gln Gly Ser Ser Leu Leu Gly Arg Arg Gly Lys
    290             295             300

Asp Thr Ala Glu Gly Thr Asn Glu Asp Arg Gly Val Gly Gln Gly Glu
305             310             315             320

Gly Met Pro Ser Ser Asp Phe Thr Thr Glu
                325             330

<210> SEQ ID NO 259
<211> LENGTH: 30
<212> TYPE: DNA
<213> ORGANISM: Artificial Sequence
<220> FEATURE:
<223> OTHER INFORMATION: Novel Sequence

<400> SEQUENCE: 259
cccaagcttc gggcaccatg gacacctccc                                     30

<210> SEQ ID NO 260
<211> LENGTH: 30
<212> TYPE: DNA
<213> ORGANISM: Artificial Sequence
```

<220> FEATURE:
<223> OTHER INFORMATION: Novel Sequence

<400> SEQUENCE: 260
acaggatcca aatgcacagc actggtaagc                              30

<210> SEQ ID NO 261
<211> LENGTH: 25
<212> TYPE: DNA
<213> ORGANISM: Artificial Sequence
<220> FEATURE:
<223> OTHER INFORMATION: Novel Sequence

<400> SEQUENCE: 261
ctataactgg gttacatggt ttaac                                   25

<210> SEQ ID NO 262
<211> LENGTH: 30
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: Novel Sequence

<400> SEQUENCE: 262
tttgaattca catattaatt agagacatgg                              30

<210> SEQ ID NO 263
<211> LENGTH: 2724
<212> TYPE: DNA
<213> ORGANISM: Homo sapiens

<400> SEQUENCE: 263
atggacacct cccggctcgg tgtgctcctg tccttgcctg tgctgctgca gctggcgacc      60
gggggcagct ctcccaggtc tggtgtgttg ctgaggggct gccccacaca ctgtcattgc     120
gagcccgacg gcaggatgtt gctcaggggtg gactgctccg acctgggggct ctcggagctg   180 ccttccaacc tcagcgtctt cacctcctac ctagacctca gtatgaacaa catcagtcag     240
ctgctcccga tcccctgcc cagtctccgc ttcctggagg agttacgtct tgcgggaaac     300
gctctgacat acattcccaa gggagcattc actggccttt acagtcttaa agttcttatg    360
ctgcagaata tcagctaag acacgtaccc acagaagctc tgcagaattt gcgaagcctt     420
caatccctgc gtctggatgc taaccacatc agctatgtgc ccccaagctg tttcagtggc    480
ctgcattccc tgaggcacct gtggctggat gacaatgcgt taacagaaat ccccgtccag    540
gcttttagaa gtttatcggc attgcaagcc atgaccttgg ccctgaacaa atacaccac    600 ataccagact atgcctttgg aaacctctcc agcttggtag ttctacatct ccataacaat    660
agaatccact ccctggggaa gaaatgcttt gatgggctcc acagcctaga gactttagat    720
ttaaattaca ataaccttga tgaattcccc actgcaatta ggacactctc caaccttaaa    780
gaactaggat ttcatagcaa caatatcagg tcgataccctg agaaagcatt tgtaggcaac    840
ccttctctta ttacaataca tttctatgac aatcccatcc aatttgttgg gagatctgct    900
tttcaacatt tacctgaact aagaacactg actctgaatg gtgcctcaca ataactgaa    960 tttcctgatt taactggaac tgcaaacctg gagagtctga ctttaactgg agcacagatc   1020
tcatctcttc ctcaaaccgt ctgcaatcag ttacctaatc tccaagtgct agatctgtct   1080
tacaacctat tagaagattt acccagtttt tcagtctgcc aaaagcttca gaaaattgac   1140

-continued

```
ctaagacata atgaaatcta cgaaattaaa gttgacactt tccagcagtt gcttagcctc    1200
cgatcgctga atttggcttg gaacaaaatt gctattattc accccaatgc attttccact    1260
ttgccatccc taataaagct ggacctatcg tccaacctcc tgtcgtcttt tcctataact    1320
gggttacatg gtttaactca cttaaaatta acaggaaatc atgccttaca gagcttgata    1380
tcatctgaaa actttccaga actcaaggtt atagaaatgc cttatgctta ccagtgctgt    1440
gcatttggag tgtgtgagaa tgcctataag atttctaatc aatggaataa aggtgacaac    1500
agcagtatgg acgaccttca taagaaagat gctggaatgt tcaggctcaa agatgaacgt    1560
gaccttgaag atttcctgct tgactttgag gaagacctga aagcccttca ttcagtgcag    1620
tgttcacctt ccccaggccc cttcaaaccc tgtgaacacc tgcttgatgg ctggctgatc    1680
agaattggag tgtggaccat agcagttctg gcacttactt gtaatgcttt ggtgacttca    1740
acagttttca gatcccctct gtacatttcc cccattaaac tgttaattgg ggtcatcgca    1800
gcagtgaaca tgctcacggg agtctccagt gccgtgctgg ctggtgtgga tgcgttcact    1860
tttggcagct ttgcacgaca tggtgcctgg tgggagaatg gggttggttg ccatgtcatt    1920
ggttttttgt ccattttttgc ttcagaatca tctgttttcc tgcttactct ggcagccctg    1980
gagcgtgggg tctctgtgaa atattctgca aaatttgaaa cgaaagctcc attttctagc    2040
ctgaaagtaa tcattttgct ctgtgccctg ctggccttga ccatggccgc agttcccctg    2100
ctgggtggca gcaagtatgg cgcctcccct ctctgcctgc ctttgccttt tggggagccc    2160
agcaccatgg gctacatggt cgctctcatc ttgctcaatt cccttgctt cctcatgatg    2220 accattgcct acaccaagct ctactgcaat ttggacaagg gagacctgga gaatatttgg    2280
gactgctcta tggtaaaaca cattgccctg ttgctcttca ccaactgcat cctaaactgc    2340
cctgtggctt tcttgtcctt ctcctcttta ataaacctta catttatcag tcctgaagta    2400
attaagttta tccttctggt ggtagtccca cttcctgcat gtctcaatcc ccttctctac    2460
atcttgttca atcctcactt taaggaggat ctggtgagcc tgagaaagca aacctacgtc    2520
tggacaagat caaaacaccc aagcttgatg tcaattaact ctgatgatgt cgaaaaacag    2580
tcctgtgact caactcaagc cttggtaacc tttaccagct ccagcatcac ttatgacctg    2640
cctcccagtt ccgtgccatc accagcttat ccagtgactg agagctgcca tctttcctct    2700
gtggcatttg tcccatgtct ctaa                                           2724
```

<210> SEQ ID NO 264
<211> LENGTH: 907
<212> TYPE: PRT
<213> ORGANISM: Homo sapiens

<400> SEQUENCE: 264

```
Met Asp Thr Ser Arg Leu Gly Val Leu Ser Leu Pro Val Leu Leu
1               5                   10                  15

Gln Leu Ala Thr Gly Gly Ser Ser Pro Arg Ser Gly Val Leu Leu Arg
                20                  25                  30

Gly Cys Pro Thr His Cys His Cys Glu Pro Asp Gly Arg Met Leu Leu
            35                  40                  45

Arg Val Asp Cys Ser Asp Leu Gly Leu Ser Glu Leu Pro Ser Asn Leu
        50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95
```

-continued

```
Leu Ala Gly Asn Ala Leu Thr Tyr Ile Pro Lys Gly Ala Phe Thr Gly
            100                 105                 110
Leu Tyr Ser Leu Lys Val Leu Met Leu Gln Asn Asn Gln Leu Arg His
        115                 120                 125
Val Pro Thr Glu Ala Leu Gln Asn Leu Arg Ser Leu Gln Ser Leu Arg
    130                 135                 140
Leu Asp Ala Asn His Ile Ser Tyr Val Pro Pro Ser Cys Phe Ser Gly
145                 150                 155                 160
Leu His Ser Leu Arg His Leu Trp Leu Asp Asp Asn Ala Leu Thr Glu
                165                 170                 175
Ile Pro Val Gln Ala Phe Arg Ser Leu Ser Ala Leu Gln Ala Met Thr
            180                 185                 190
Leu Ala Leu Asn Lys Ile His His Ile Pro Asp Tyr Ala Phe Gly Asn
        195                 200                 205
Leu Ser Ser Leu Val Val Leu His Leu His Asn Asn Arg Ile His Ser
    210                 215                 220
Leu Gly Lys Lys Cys Phe Asp Gly Leu His Ser Leu Glu Thr Leu Asp
225                 230                 235                 240
Leu Asn Tyr Asn Asn Leu Asp Glu Phe Pro Thr Ala Ile Arg Thr Leu
                245                 250                 255
Ser Asn Leu Lys Glu Leu Gly Phe His Ser Asn Asn Ile Arg Ser Ile
            260                 265                 270
Pro Glu Lys Ala Phe Val Gly Asn Pro Ser Leu Ile Thr Ile His Phe
        275                 280                 285
Tyr Asp Asn Pro Ile Gln Phe Val Gly Arg Ser Ala Phe Gln His Leu
    290                 295                 300
Pro Glu Leu Arg Thr Leu Thr Leu Asn Gly Ala Ser Gln Ile Thr Glu
305                 310                 315                 320
Phe Pro Asp Leu Thr Gly Thr Ala Asn Leu Glu Ser Leu Thr Leu Thr
                325                 330                 335
Gly Ala Gln Ile Ser Ser Leu Pro Gln Thr Val Cys Asn Gln Leu Pro
            340                 345                 350
Asn Leu Gln Val Leu Asp Leu Ser Tyr Asn Leu Leu Glu Asp Leu Pro
        355                 360                 365
Ser Phe Ser Val Cys Gln Lys Leu Gln Lys Ile Asp Leu Arg His Asn
    370                 375                 380
Glu Ile Tyr Glu Ile Lys Val Asp Thr Phe Gln Gln Leu Leu Ser Leu
385                 390                 395                 400
Arg Ser Leu Asn Leu Ala Trp Asn Lys Ile Ala Ile Ile His Pro Asn
                405                 410                 415
Ala Phe Ser Thr Leu Pro Ser Leu Ile Lys Leu Asp Leu Ser Ser Asn
            420                 425                 430
Leu Leu Ser Ser Phe Pro Ile Thr Gly Leu His Gly Leu Thr His Leu
        435                 440                 445
Lys Leu Thr Gly Asn His Ala Leu Gln Ser Leu Ile Ser Ser Glu Asn
    450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Asp Leu His Lys Lys Asp Ala Gly
            500                 505                 510
```

```
Met Phe Gln Ala Gln Asp Glu Arg Asp Leu Glu Asp Phe Leu Leu Asp
            515                 520                 525

Phe Glu Glu Asp Leu Lys Ala Leu His Ser Val Gln Cys Ser Pro Ser
        530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
            580                 585                 590

Lys Leu Leu Ile Gly Val Ile Ala Val Asn Met Leu Thr Gly Val
        595                 600                 605

Ser Ser Ala Val Leu Ala Gly Val Asp Ala Phe Thr Phe Gly Ser Phe
    610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Tyr Ser Ala Lys Phe
            660                 665                 670

Glu Thr Lys Ala Pro Phe Ser Ser Leu Lys Val Ile Ile Leu Leu Cys
        675                 680                 685

Ala Leu Leu Ala Leu Thr Met Ala Ala Val Pro Leu Leu Gly Gly Ser
    690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
            740                 745                 750

Lys Gly Asp Leu Glu Asn Ile Trp Asp Cys Ser Met Val Lys His Ile
        755                 760                 765

Ala Leu Leu Leu Phe Thr Asn Cys Ile Leu Asn Cys Pro Val Ala Phe
    770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
        835                 840                 845

Leu Met Ser Ile Asn Ser Asp Asp Val Glu Lys Gln Ser Cys Asp Ser
    850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905

<210> SEQ ID NO 265
<211> LENGTH: 30
<212> TYPE: DNA
```

<213> ORGANISM: Artificial Sequence
<220> FEATURE:
<223> OTHER INFORMATION: Novel Sequence

<400> SEQUENCE: 265
cggaagctgc gggccaaatg ggtggccggc                                         30

<210> SEQ ID NO 266
<211> LENGTH: 27
<212> TYPE: DNA
<213> ORGANISM: Artificial Sequence
<220> FEATURE:
<223> OTHER INFORMATION: Novel Sequence

<400> SEQUENCE: 266
cagaggaggg tgaaggggct gttggcg                                            27

<210> SEQ ID NO 267
<211> LENGTH: 30
<212> TYPE: DNA
<213> ORGANISM: Artificial Sequence
<220> FEATURE:
<223> OTHER INFORMATION: Novel Sequence

<400> SEQUENCE: 267
ggcggcgccg agccaagggg ctggctgtgg                                         30

<210> SEQ ID NO 268
<211> LENGTH: 32
<212> TYPE: DNA
<213> ORGANISM: Artificial Sequence
<220> FEATURE:
<223> OTHER INFORMATION: Novel Sequence

<400> SEQUENCE: 268
gggactgctc tatgaaaaaa cacattgccc tg                                      32

<210> SEQ ID NO 269
<211> LENGTH: 1071
<212> TYPE: DNA
<213> ORGANISM: Homo sapiens

<400> SEQUENCE: 269
atgaatgggg tctcggaggg gaccagaggc tgcagtgaca ggcaacctgg ggtcctgaca        60
cgtgatcgct cttgttccag gaagatgaac tcttccggat gcctgtctga ggaggtgggg       120
tccctccgcc cactgactgt ggttatcctg tctgcgtcca ttgtcgtcgg agtgctgggc       180
aatgggctgg tgctgtggat gactgtcttc cgtatggcac gcacggtctc caccgtctgc       240
ttcttccacc tggcccttgc cgatttcatg ctctcactgt ctctgcccat tgccatgtac       300
tatattgtct ccaggcagtg gctcctcgga gagtgggcct gcaaactcta catcacccttt      360 gtgttcctca gctactttgc cagtaactgc ctccttgtct tcatctctgt ggaccgttgc       420
atctctgtcc tctaccccgt ctgggcccctg aaccaccgca ctgtgcagcg ggcgagctgg       480
ctggcctttg gggtgtggct cctggccgcc gccttgtgct ctgcgcacct gaaattccgg       540
acaaccagaa aatggaatgg ctgtacgcac tgctacttgg cgttcaactc tgacaatgag       600
actgcccaga tttggattga aggggtcgtg gagggacaca ttatagggac cattggccac       660
ttcctgctgg gcttcctggg gcccttagca atcataggca cctgcgccca cctcatccgg       720
gccaagctct gcgggagggg ctgggtccat gccaaccggc caagaggct gctgctggtg       780 ctggtgagcg ctttctttat cttctggtcc cgtttaacg tggtgctgtt ggtccatctg       840

```
tggcgacggg tgatgctcaa ggaaatctac cacccccgga tgctgctcat cctccaggct    900
agctttgcct tgggctgtgt caacagcagc ctcaacccct tcctctacgt cttcgttggc    960
agagatttcc aagaaaagtt tttccagtct ttgacttctg ccctggcgag ggcgtttgga   1020
gaggaggagt ttctgtcatc ctgtccccgt ggcaacgccc cccgggaatg a            1071
```

<210> SEQ ID NO 270
<211> LENGTH: 356
<212> TYPE: PRT
<213> ORGANISM: Homo sapiens

<400> SEQUENCE: 270

```
Met Asn Gly Val Ser Glu Gly Thr Arg Gly Cys Ser Asp Arg Gln Pro
1               5                   10                  15

Gly Val Leu Thr Arg Asp Arg Ser Cys Ser Arg Lys Met Asn Ser Ser
            20                  25                  30

Gly Cys Leu Ser Glu Glu Val Gly Ser Leu Arg Pro Leu Thr Val Val
        35                  40                  45

Ile Leu Ser Ala Ser Ile Val Gly Val Leu Gly Asn Gly Leu Val
    50                  55                  60

Leu Trp Met Thr Val Phe Arg Met Ala Arg Thr Val Ser Thr Val Cys
65                  70                  75                  80

Phe Phe His Leu Ala Leu Ala Asp Phe Met Leu Ser Leu Ser Leu Pro
                85                  90                  95

Ile Ala Met Tyr Tyr Ile Val Ser Arg Gln Trp Leu Leu Gly Glu Trp
            100                 105                 110

Ala Cys Lys Leu Tyr Ile Thr Phe Val Phe Leu Ser Tyr Phe Ala Ser
        115                 120                 125

Asn Cys Leu Leu Val Phe Ile Ser Val Asp Arg Cys Ile Ser Val Leu
    130                 135                 140

Tyr Pro Val Trp Ala Leu Asn His Arg Thr Val Gln Arg Ala Ser Trp
145                 150                 155                 160

Leu Ala Phe Gly Val Trp Leu Leu Ala Ala Ala Leu Cys Ser Ala His
                165                 170                 175

Leu Lys Phe Arg Thr Thr Arg Lys Trp Asn Gly Cys Thr His Cys Tyr
            180                 185                 190

Leu Ala Phe Asn Ser Asp Asn Glu Thr Ala Gln Ile Trp Ile Glu Gly
        195                 200                 205

Val Val Glu Gly His Ile Ile Gly Thr Ile Gly His Phe Leu Leu Gly
    210                 215                 220

Phe Leu Gly Pro Leu Ala Ile Ile Gly Thr Cys Ala His Leu Ile Arg
225                 230                 235                 240

Ala Lys Leu Leu Arg Glu Gly Trp Val His Ala Asn Arg Pro Lys Arg
                245                 250                 255

Leu Leu Leu Val Leu Val Ser Ala Phe Phe Ile Phe Trp Ser Pro Phe
            260                 265                 270

Asn Val Val Leu Leu Val His Leu Trp Arg Arg Val Met Leu Lys Glu
        275                 280                 285

Ile Tyr His Pro Arg Met Leu Leu Ile Leu Gln Ala Ser Phe Ala Leu
    290                 295                 300

Gly Cys Val Asn Ser Ser Leu Asn Pro Phe Leu Tyr Val Phe Val Gly
305                 310                 315                 320

Arg Asp Phe Gln Glu Lys Phe Phe Gln Ser Leu Thr Ser Ala Leu Ala
                325                 330                 335
```

Arg Ala Phe Gly Glu Glu Glu Phe Leu Ser Ser Cys Pro Arg Gly Asn
            340                 345                 350

Ala Pro Arg Glu
        355

<210> SEQ ID NO 271
<211> LENGTH: 903
<212> TYPE: DNA
<213> ORGANISM: Homo sapiens

<400> SEQUENCE: 271

| | | | | | |
|---|---|---|---|---|---|
| atggacctgc | ccccgcagct | ctccttcggc | ctctatgtgg | ccgcctttgc | gctgggcttc | 60 |
| ccgctcaacg | tcctggccat | ccgaggcgcg | acggcccacg | cccggctccg | tctcacccct | 120 |
| agcctggtct | acgccctgaa | cctgggctgc | tccgacctgc | tgctgacagt | ctctctgccc | 180 |
| ctgaaggcgg | tggaggcgct | agcctccggg | gcctggcctc | tgccggcctc | gctgtgcccc | 240 |
| gtcttcgcgg | tggcccactt | cttcccactc | tatgccggcg | ggggcttcct | ggccgccctg | 300 |
| agtgcaggcc | gctacctggg | agcagccttc | cccttgggct | accaagcctt | ccggaggccg | 360 |
| tgctattcct | gggggtgtg | cgcggccatc | tgggccctcg | tcctgtgtca | cctgggtctg | 420 |
| gtctttgggt | tggaggctcc | aggaggctgg | ctggaccaca | gcaacacctc | cctgggcatc | 480 |
| aacacaccgg | tcaacggctc | tccggtctgc | ctggaggcct | gggaccccgc | ctctgccggc | 540 |
| ccggcccgct | tcagcctctc | tctcctgctc | ttttttctgc | ccttggccat | cacagccttc | 600 |
| tgctacgtgg | gctgcctccg | ggcactggcc | cgctccggcc | tgacgcacag | gcggaagctg | 660 |
| cgggccaaat | gggtggccgg | cggggccctc | ctcacgctgc | tgctctgcgt | aggaccctac | 720 |
| aacgcctcca | acgtggccag | cttcctgtac | cccaatctag | gaggctcctg | gcggaagctg | 780 |
| gggctcatca | cgggtgcctg | gagtgtggtg | cttaatccgc | tggtgaccgg | ttacttggga | 840 |
| aggggtcctg | gcctgaagac | agtgtgtgcg | gcaagaacgc | aaggggggcaa | gtcccagaag | 900 |
| taa | | | | | | 903 |

<210> SEQ ID NO 272
<211> LENGTH: 300
<212> TYPE: PRT
<213> ORGANISM: Homo sapiens

<400> SEQUENCE: 272

Met Asp Leu Pro Pro Gln Leu Ser Phe Gly Leu Tyr Val Ala Ala Phe
1               5                   10                  15

Ala Leu Gly Phe Pro Leu Asn Val Leu Ala Ile Arg Gly Ala Thr Ala
            20                  25                  30

His Ala Arg Leu Arg Leu Thr Pro Ser Leu Val Tyr Ala Leu Asn Leu
        35                  40                  45

Gly Cys Ser Asp Leu Leu Leu Thr Val Ser Leu Pro Leu Lys Ala Val
    50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

```
Ala Ile Trp Ala Leu Val Leu Cys His Leu Gly Leu Val Phe Gly Leu
        130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Lys Trp
    210                 215                 220

Val Ala Gly Gly Ala Leu Leu Thr Leu Leu Leu Cys Val Gly Pro Tyr
225                 230                 235                 240

Asn Ala Ser Asn Val Ala Ser Phe Leu Tyr Pro Asn Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
        275                 280                 285

Cys Ala Ala Arg Thr Gln Gly Gly Lys Ser Gln Lys
        290                 295                 300

<210> SEQ ID NO 273
<211> LENGTH: 1041
<212> TYPE: DNA
<213> ORGANISM: Homo sapiens

<400> SEQUENCE: 273
atggatacag cccccgacca gtcctacttc tccggcaatc actggttcgt cttctcggtg      60
taccttctca ctttcctggt ggggctcccc ctcaacctgc tggccctggt ggtcttcgtg     120
ggcaagctgc agcgccgccc ggtggccgtg acgtgctcc tgctcaacct gaccgcctcg      180
gacctgctcc tgctgctgtt cctgcctttc gcatggtgg aggcagccaa tggcatgcac      240
tggcccctgc ccttcatcct ctgcccactc tctggattca tcttcttcac caccatctat     300
ctcaccgccc tcttcctggc agctgtgagc attgaacgct tcctgagtgt ggcccaccca     360
ctgtggtaca gacccggcc gaggctgggg caggcaggtc tggtgagtgt ggcctgctgg      420
ctgttggcct ctgctcactg cagcgtggtc tacgtcatag aattctcagg ggacatctcc     480
cacagccagg gcaccaatgg gacctgctac ctggagttcc ggaaggacca gctagccatc     540
ctcctgcccg tgcggctgga gatggctgtg gtcctctttg tggtcccgct gatcatcacc     600
agctactgct acagccgcct ggtgtggatc ctcggcagag ggggcagcca ccgccggcag     660
aggagggtga aggggctgtt ggcggccacg ctgctcaact tccttgtctg ctttgggccc     720
tacaacgtgt cccatgtcgt gggctatatc tgcggtgaaa gcccggcatg gaggatctac     780
gtgacgcttc tcagcaccct gaactcctgt gtcgacccct tgtctacta cttctcctcc     840
tccgggttcc aagccgactt tcatgagctg ctgaggaggt tgtgtgggct ctggggccag     900
tggcagcagg agagcagcat ggagctgaag gagcagaagg gagggagga gcagagagcg      960
gaccgaccag ctgaaagaaa gaccagtgaa cactcacagg gctgtggaac tggtggccag    1020
gtggcctgtg ctgaaagcta g                                              1041

<210> SEQ ID NO 274
```

```
<211> LENGTH: 346
<212> TYPE: PRT
<213> ORGANISM: Homo sapiens

<400> SEQUENCE: 274

Met Asp Thr Gly Pro Asp Gln Ser Tyr Phe Ser Gly Asn His Trp Phe
1               5                   10                  15

Val Phe Ser Val Tyr Leu Leu Thr Phe Leu Val Gly Leu Pro Leu Asn
            20                  25                  30

Leu Leu Ala Leu Val Val Phe Val Gly Lys Leu Gln Arg Arg Pro Val
        35                  40                  45

Ala Val Asp Val Leu Leu Leu Asn Leu Thr Ala Ser Asp Leu Leu Leu
50                  55                  60

Leu Leu Phe Leu Pro Phe Arg Met Val Glu Ala Ala Asn Gly Met His
65                  70                  75                  80

Trp Pro Leu Pro Phe Ile Leu Cys Pro Leu Ser Gly Phe Ile Phe Phe
                85                  90                  95

Thr Thr Ile Tyr Leu Thr Ala Leu Phe Leu Ala Ala Val Ser Ile Glu
            100                 105                 110

Arg Phe Leu Ser Val Ala His Pro Leu Trp Tyr Lys Thr Arg Pro Arg
        115                 120                 125

Leu Gly Gln Ala Gly Leu Val Ser Val Ala Cys Trp Leu Leu Ala Ser
130                 135                 140

Ala His Cys Ser Val Val Tyr Val Ile Glu Phe Ser Gly Asp Ile Ser
145                 150                 155                 160

His Ser Gln Gly Thr Asn Gly Thr Cys Tyr Leu Glu Phe Arg Lys Asp
                165                 170                 175

Gln Leu Ala Ile Leu Leu Pro Val Arg Leu Glu Met Ala Val Val Leu
            180                 185                 190

Phe Val Val Pro Leu Ile Ile Thr Ser Tyr Cys Tyr Ser Arg Leu Val
        195                 200                 205

Trp Ile Leu Gly Arg Gly Gly Ser His Arg Arg Gln Arg Arg Val Lys
210                 215                 220

Gly Leu Leu Ala Ala Thr Leu Leu Asn Phe Leu Val Cys Phe Gly Pro
225                 230                 235                 240

Tyr Asn Val Ser His Val Val Gly Tyr Ile Cys Gly Glu Ser Pro Ala
                245                 250                 255

Trp Arg Ile Tyr Val Thr Leu Leu Ser Thr Leu Asn Ser Cys Val Asp
            260                 265                 270

Pro Phe Val Tyr Tyr Phe Ser Ser Gly Phe Gln Ala Asp Phe His
        275                 280                 285

Glu Leu Leu Arg Arg Leu Cys Gly Leu Trp Gly Gln Trp Gln Gln Glu
290                 295                 300

Ser Ser Met Glu Leu Lys Glu Gln Lys Gly Glu Glu Gln Arg Ala
305                 310                 315                 320

Asp Arg Pro Ala Glu Arg Lys Thr Ser Glu His Ser Gln Gly Cys Gly
                325                 330                 335

Thr Gly Gly Gln Val Ala Cys Ala Glu Ser
            340                 345

<210> SEQ ID NO 275
<211> LENGTH: 993
<212> TYPE: DNA
<213> ORGANISM: Homo sapiens

<400> SEQUENCE: 275
```

-continued

```
atgctgccgg actggaagag ctccttgatc ctcatggctt acatcatcat cttcctcact      60
ggcctccctg ccaacctcct ggccctgcgg gcctttgtgg ggcggatccg ccagccccag     120
cctgcacctg tgcacatcct cctgctgagc ctgacgctgg ccgacctcct cctgctgctg     180
ctgctgccct tcaagatcat cgaggctgcg tcgaacttcc gctggtacct gcccaaggtc     240
gtctgcgccc tcacgagttt tggcttctac agcagcatct actgcagcac gtggctcctg     300
gcgggcatca gcatcgagcg ctacctggga gtggctttcc ccgtgcagta caagctctcc     360
cgccggcctc tgtatggagt gattgcagct ctggtggcct gggttatgtc ctttggtcac     420
tgcaccatcg tgatcatcgt tcaatacttg aacacgactg agcaggtcag aagtggcaat     480
gaaattacct gctacgagaa cttcaccgat aaccagttgg acgtggtgct gcccgtgcgg     540
ctggagctgt gcctggtgct cttcttcatc cccatggcag tcaccatctt ctgctactgg     600
cgttttgtgt ggatcatgct ctcccagccc cttgtggggg cccagaggcg cgccgagcc     660
aagggctgg ctgtggtgac gctgctcaat ttcctggtgt gcttcggacc ttacaacgtg      720
tcccacctgg tggggtatca ccagagaaaa agccctggt ggcggtcaat agccgtggtg     780
ttcagttcac tcaacgccag tctggacccc ctgctcttct atttctcttc ttcagtggtg     840
cgcagggcat ttgggagagg gctgcaggtg ctgcggaatc agggctcctc cctgttggga     900
cgcagaggca agacacagc agaggggaca atgaggaca ggggtgtggg tcaaggagaa      960
gggatgccaa gttcggactt cactacagag tag                                 993
```

<210> SEQ ID NO 276
<211> LENGTH: 330
<212> TYPE: PRT
<213> ORGANISM: Homo sapiens

<400> SEQUENCE: 276

```
Met Leu Pro Asp Trp Lys Ser Ser Leu Ile Leu Met Ala Tyr Ile Ile
1               5                   10                  15

Ile Phe Leu Thr Gly Leu Pro Ala Asn Leu Leu Ala Leu Arg Ala Phe
            20                  25                  30

Val Gly Arg Ile Arg Gln Pro Gln Pro Ala Pro Val His Ile Leu Leu
        35                  40                  45

Leu Ser Leu Thr Leu Ala Asp Leu Leu Leu Leu Leu Leu Pro Phe
    50                  55                  60

Lys Ile Ile Glu Ala Ala Ser Asn Phe Arg Trp Tyr Leu Pro Lys Val
65                  70                  75                  80

Val Cys Ala Leu Thr Ser Phe Gly Phe Tyr Ser Ser Ile Tyr Cys Ser
                85                  90                  95

Thr Trp Leu Leu Ala Gly Ile Ser Ile Glu Arg Tyr Leu Gly Val Ala
            100                 105                 110

Phe Pro Val Gln Tyr Lys Leu Ser Arg Arg Pro Leu Tyr Gly Val Ile
        115                 120                 125

Ala Ala Leu Val Ala Trp Val Met Ser Phe Gly His Cys Thr Ile Val
    130                 135                 140

Ile Ile Val Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
            180                 185                 190
```

```
Ala Val Thr Ile Phe Cys Tyr Trp Arg Phe Val Trp Ile Met Leu Ser
            195                 200                 205

Gln Pro Leu Val Gly Ala Gln Arg Arg Arg Ala Lys Gly Leu Ala
        210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
                260                 265                 270

Phe Tyr Phe Ser Ser Ser Val Val Arg Arg Ala Phe Gly Arg Gly Leu
            275                 280                 285

Gln Val Leu Arg Asn Gln Gly Ser Ser Leu Leu Gly Arg Arg Gly Lys
        290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330

<210> SEQ ID NO 277
<211> LENGTH: 2724
<212> TYPE: DNA
<213> ORGANISM: Homo sapiens

<400> SEQUENCE: 277 atggcacct cccggctcgg tgtgctcctg tccttgcctg tgctgctgca gctggcgacc      60
ggggcagct ctcccaggtc tggtgtgttg ctgaggggct gccccacaca ctgtcattgc     120
gagcccgacg gcaggatgtt gctcaggtg gactgctccg acctggggct ctcggagctg     180
ccttccaacc tcagcgtctt cacctcctac ctagacctca gtatgaacaa catcagtcag     240
ctgctcccga tcccctgcc cagtctccgc ttcctggagg agttacgtct tgcgggaaac     300
gctctgacat acattcccaa gggagcattc actggccttt acagtcttaa agttcttatg     360
ctgcagaata atcagctaag acacgtaccc acagaagctc tgcagaattt gcgaagcctt     420
caatccctgc gtctggatgc taaccacatc agctatgtgc ccccaagctg tttcagtggc     480
ctgcattccc tgaggcacct gtggctggat gacaatgcgt aacagaaat ccccgtccag     540
gcttttagaa gtttatcggc attgcaagcc atgaccttgg ccctgaacaa aatacaccac     600
ataccagact atgcctttgg aaacctctcc agcttggtag ttctacatct ccataacaat     660
agaatccact ccctgggaaa gaatgctttt gatgggctcc acagcctaga gactttagat     720
ttaaattaca ataaccttga tgaattcccc actgcaatta ggacactctc caaccttaaa     780
gaactaggat tcatagcaa caatatcagg tcgatacctg agaaagcatt tgtaggcaac     840
ccttctctta ttacaataca tttctatgac aatcccatcc aatttgttgg agatctgct      900
tttcaacatt tacctgaact aagaacactg actctgaatg gtgcctcaca aataactgaa     960
tttcctgatt taactggaac tgcaaacctg gagagtctga ctttaactgg agcacagatc    1020
tcatctcttc ctcaaaccgt ctgcaatcag ttacctaatc tccaagtgct agatctgtct    1080
tacaacctat tagaagattt acccagtttt cagtctgcc aaaagcttca gaaaattgac    1140
ctaagacata tgaaatcta cgaaattaaa gttgacactt ccagcagtt gcttagcctc    1200
cgatcgctga atttggcttg gaacaaaatt gctattattc accccaatgc attttccact    1260
ttgccatccc taataaagct ggacctatcg tccaacctcc tgtcgtcttt tcctataact    1320
```

-continued

```
gggttacatg gtttaactca cttaaaatta acaggaaatc atgccttaca gagcttgata    1380
tcatctgaaa actttccaga actcaaggtt atagaaatgc cttatgctta ccagtgctgt    1440
gcatttggag tgtgtgagaa tgcctataag atttctaatc aatggaataa aggtgacaac    1500
agcagtatgg acgaccttca taagaaagat gctggaatgt ttcaggctca agatgaacgt    1560
gaccttgaag atttcctgct tgactttgag gaagacctga agcccttca ttcagtgcag    1620 tgttcacctt ccccaggccc cttcaaaccc tgtgaacacc tgcttgatgg ctggctgatc    1680
agaattggag tgtggaccat agcagttctg gcacttactt gtaatgcttt ggtgacttca    1740
acagttttca gatcccctct gtacatttcc cccattaaac tgttaattgg ggtcatcgca    1800
gcagtgaaca tgctcacggg agtctccagt gccgtgctgg ctggtgtgga tgcgttcact    1860
tttggcagct ttgcacgaca tggtgcctgg tgggagaatg gggttggttg ccatgtcatt    1920
ggttttttgt ccattttgc ttcagaatca tctgttttcc tgcttactct ggcagccctg    1980
gagcgtgggt tctctgtgaa atattctgca aaatttgaaa cgaaagctcc attttctagc    2040
ctgaaagtaa tcattttgct ctgtgccctg ctggccttga ccatggccgc agttcccctg    2100
ctgggtggca gcaagtatgg cgcctcccct ctctgcctgc ctttgccttt tggggagccc    2160
agcaccatgg gctacatggt cgctctcatc ttgctcaatt cccttt gctt cctcatgatg    2220 accattgcct acaccaagct ctactgcaat ttggacaagg gagacctgga gaatatttgg    2280
gactgctcta tgaaaaaaca cattgccctg ttgctcttca ccaactgcat cctaaactgc    2340
cctgtggctt tcttgtcctt ctcctcttta ataaaccttca catttatcag tcctgaagta    2400 attaagtta tccttctggt ggtagtccca cttcctgcat gtctcaatcc ccttctctac    2460
atcttgttca atcctcactt taaggaggat ctggtgagcc tgagaaagca aacctacgtc    2520
tggacaagat caaaacaccc aagcttgatg tcaattaact ctgatgatgt cgaaaaacag    2580
tcctgtgact caactcaagc cttggtaacc tttaccagct ccagcatcac ttatgacctg    2640
cctcccagtt ccgtgccatc accagcttat ccagtgactg agagctgcca tctttcctct    2700
gtggcatttg tcccatgtct ctaa                                           2724
```

<210> SEQ ID NO 278
<211> LENGTH: 907
<212> TYPE: PRT
<213> ORGANISM: Homo sapiens

<400> SEQUENCE: 278

```
Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125
```

-continued

```
Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
                180                 185                 190

Leu Ala Leu Asn Lys Ile His His Ile Pro Asp Tyr Ala Phe Gly Asn
            195                 200                 205

Leu Ser Ser Leu Val Val Leu His Leu His Asn Asn Arg Ile His Ser
210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
                260                 265                 270

Pro Glu Lys Ala Phe Val Gly Asn Pro Ser Leu Ile Thr Ile His Phe
            275                 280                 285

Tyr Asp Asn Pro Ile Gln Phe Val Gly Arg Ser Ala Phe Gln His Leu
        290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
        355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
                405                 410                 415

Ala Phe Ser Thr Leu Pro Ser Leu Ile Lys Leu Asp Leu Ser Ser Asn
            420                 425                 430

Leu Leu Ser Ser Phe Pro Ile Thr Gly Leu His Gly Leu Thr His Leu
        435                 440                 445

Lys Leu Thr Gly Asn His Ala Leu Gln Ser Leu Ile Ser Ser Glu Asn
    450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
            500                 505                 510

Met Phe Gln Ala Gln Asp Glu Arg Asp Leu Glu Asp Phe Leu Leu Asp
        515                 520                 525

Phe Glu Glu Asp Leu Lys Ala Leu His Ser Val Gln Cys Ser Pro Ser
530                 535                 540
```

-continued

```
Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
            580                 585                 590

Lys Leu Leu Ile Gly Val Ile Ala Ala Val Asn Met Leu Thr Gly Val
        595                 600                 605

Ser Ser Ala Val Leu Ala Gly Val Asp Ala Phe Thr Phe Gly Ser Phe
    610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Tyr Ser Ala Lys Phe
            660                 665                 670

Glu Thr Lys Ala Pro Phe Ser Ser Leu Lys Val Ile Leu Leu Cys
        675                 680                 685

Ala Leu Leu Ala Leu Thr Met Ala Ala Val Pro Leu Leu Gly Gly Ser
690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
            740                 745                 750

Lys Gly Asp Leu Glu Asn Ile Trp Asp Cys Ser Met Lys Lys His Ile
        755                 760                 765

Ala Leu Leu Leu Phe Thr Asn Cys Ile Leu Asn Cys Pro Val Ala Phe
770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
        835                 840                 845

Leu Met Ser Ile Asn Ser Asp Asp Val Glu Lys Gln Ser Cys Asp Ser
850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905
```

<210> SEQ ID NO 279
<211> LENGTH: 32
<212> TYPE: DNA
<213> ORGANISM: Artificial Sequence
<220> FEATURE:
<223> OTHER INFORMATION: Novel Sequence

<400> SEQUENCE: 279

```
catgccaacc ggcccgcgag gctgctgctg gt                                    32
```

<210> SEQ ID NO 280
<211> LENGTH: 32
<212> TYPE: DNA
<213> ORGANISM: Artificial Sequence
<220> FEATURE:
<223> OTHER INFORMATION: Novel Sequence

<400> SEQUENCE: 280

```
accagcagca gcctcgcggg ccggttggca tg                                    32
```

<210> SEQ ID NO 281
<211> LENGTH: 17
<212> TYPE: PRT
<213> ORGANISM: Artificial Sequence
<220> FEATURE:
<223> OTHER INFORMATION: Novel Sequence

<400> SEQUENCE: 281

```
Pro Ala Ala Cys Cys Thr Thr Gly Gly Arg Arg Arg Asp Asp Asp Glu
1               5                   10                  15

Gln
```

<210> SEQ ID NO 282
<211> LENGTH: 17
<212> TYPE: PRT
<213> ORGANISM: Artificial Sequence
<220> FEATURE:
<223> OTHER INFORMATION: Novel Sequence

<400> SEQUENCE: 282

```
Pro Ala Ala Cys Cys Thr Thr Gly Gly Arg Arg Arg Asp Asp Asp Glu
1               5                   10                  15

Lys
```

<210> SEQ ID NO 283
<211> LENGTH: 17
<212> TYPE: PRT
<213> ORGANISM: Artificial Sequence
<220> FEATURE:
<223> OTHER INFORMATION: Novel Sequence

<400> SEQUENCE: 283

```
Pro Ala Ala Cys Cys Thr Thr His Ile Gly Arg Arg Asp Asp Asp Glu
1               5                   10                  15

Lys
```

<210> SEQ ID NO 284
<211> LENGTH: 17
<212> TYPE: PRT
<213> ORGANISM: Artificial Sequence
<220> FEATURE:
<223> OTHER INFORMATION: Novel Sequence

<400> SEQUENCE: 284

```
Pro Ala Asp Glu Glu Thr Thr Gly Gly Arg Arg Arg Asp Asp Asp Glu
1               5                   10                  15

Ala
```

<210> SEQ ID NO 285
<211> LENGTH: 16
<212> TYPE: PRT
<213> ORGANISM: Artificial Sequence
<220> FEATURE:
<223> OTHER INFORMATION: Novel Sequence

<400> SEQUENCE: 285

Pro Leu Leu Lys Phe Met Ser Thr Trp Leu Val Ala Ala Pro Gln Lys
1               5                   10                  15

<210> SEQ ID NO 286
<211> LENGTH: 17
<212> TYPE: PRT
<213> ORGANISM: Artificial Sequence
<220> FEATURE:
<223> OTHER INFORMATION: Novel Sequence

<400> SEQUENCE: 286

Ala Leu Leu Lys Phe Met Ser Thr Trp Glx Leu Val Ala Ala Pro Gln
1               5                   10                  15

Lys

<210> SEQ ID NO 287
<211> LENGTH: 4069
<212> TYPE: DNA
<213> ORGANISM: Homo sapiens

<400> SEQUENCE: 287

```
aagcttgata tcgaattcct gcagcccggg ggatccacta gttctagagc ggccgccacc      60
gcggtggagc tccagctttt gttcccttta gtgaggggtta attgcgcgct agaggatctt    120
tgtgaaggaa ccttacttct gtggtgtgac ataattggac aaactaccta cagagattta    180
aagctctaag gtaaatataa aattttttaag tgtataatgt gttaaactac tgattctaat    240
tgtttgtgta ttttagattc caacctatgg aactgatgaa tgggagcagt ggtggaatgc    300
ctttaatgag gaaaacctgt tttgctcaga gaaatgcca tctagtgatg atgaggctac     360
tgctgactct caacattcta ctcctccaaa aagaagaga aaggtagaag accccaagga     420
cttccttca gaattgctaa gttttttgag tcatgctgtg tttagtaata gaactcttgc     480
ttgctttgct atttacacca caaaggaaaa agctgcactg ctatacaaga aaattatgga    540
aaaatattct gtaaccttta taagtaggca taacagttat aatcataaca tactgttttt    600
tcttactcca cacaggcata gagtgtctgc tattaataac tatgctcaaa aattgtgtac    660
ctttagcttt ttaatttgta aaggggttaa taaggaatat ttgatgtata gtgccttgac    720
tagagatcat aatcagccat accacatttg tagaggtttt acttgcttta aaaaacctcc    780
cacacctccc cctgaacctg aaacataaaa tgaatgcaat tgttgttgtt aacttgttta    840
ttgcagctta taatggttac aaataaagca atagcatcac aaatttcaca ataaagcat    900
ttttttcact gcattctagt tgtggtttgt ccaaactcat caatgtatct tatcatgtct    960
agatcttccg aaatgtgtgt cagttagggt gtggaaagtc cccaggctcc ccagcaggca   1020
gaagtatgca aagcatgcat ctcaattagt cagcaaccag gtgtggaaag tccccaggct   1080
ccccagcagg cagaagtatg caaagcatgc atctcaatta gtcagcaacc atagtcccgc   1140
ccctaactcc gcccatcccg ccctaactc cgcccagttc cgcccattct ccgccccatg    1200
gctgactaat ttttttttatt tatgcagagg ccgaggccgc ctcggcctct gagctattcc   1260
agaagtagtg aggaggcttt tttggaggcc taggcttttg caaaaagctc cctcgagagc   1320
ttggcgtaat catggtcata gctgtttcct gtgtgaaatt gttatccgct cacaattcca   1380
cacaacatac gagccggaag cataaagtgt aaagcctggg gtgcctaatg agtgagctaa   1440
```

-continued

| | |
|---|---|
| ctcacattaa ttgcgttgcg ctcactgccc gctttccagt cgggaaacct gtcgtgccag | 1500 |
| ctgcattaat gaatcggcca acgcgcgggg agaggcggtt tgcgtattgg gcgctcttcc | 1560 |
| gcttcctcgc tcactgactc gctgcgctcg gtcgttcggc tgcggcgagc ggtatcagct | 1620 |
| cactcaaagg cggtaatacg gttatccaca gaatcagggg ataacgcagg aaagaacatg | 1680 |
| tgagcaaaag gccagcaaaa ggccaggaac cgtaaaaagg ccgcgttgct ggcgtttttc | 1740 |
| cataggctcc gcccccctga cgagcatcac aaaaatcgac gctcaagtca gaggtggcga | 1800 |
| aacccgacag gactataaag ataccaggcg tttccccctg gaagctccct cgtgcgctct | 1860 |
| cctgttccga ccctgccgct taccggatac ctgtccgcct ttctcccttc gggaagcgtg | 1920 |
| gcgctttctc aatgctcacg ctgtaggtat ctcagttcgg tgtaggtcgt tcgctccaag | 1980 |
| ctgggctgtg tgcacgaacc ccccgttcag cccgaccgct gcgccttatc cggtaactat | 2040 |
| cgtcttgagt ccaacccggt aagacacgac ttatcgccac tggcagcagc cactggtaac | 2100 |
| aggattagca gagcgaggta tgtaggcggt gctacagagt tcttgaagtg gtggcctaac | 2160 |
| tacggctaca ctagaaggac agtatttggt atctgcgctc tgctgaagcc agttaccttc | 2220 |
| ggaaaaagag ttggtagctc ttgatccggc aaacaaacca ccgctggtag cggtggtttt | 2280 |
| tttgtttgca agcagcagat tacgcgcaga aaaaaaggat ctcaagaaga tcctttgatc | 2340 |
| ttttctacgg ggtctgacgc tcagtggaac gaaaactcac gttaagggat tttggtcatg | 2400 |
| agattatcaa aaaggatctt cacctagatc cttttaaatt aaaaatgaag ttttaaatca | 2460 |
| atctaaagta tatatgagta aacttggtct gacagttacc aatgcttaat cagtgaggca | 2520 |
| cctatctcag cgatctgtct atttcgttca tccatagttg cctgactccc cgtcgtgtag | 2580 |
| ataactacga tacgggaggg cttaccatct ggccccagtg ctgcaatgat accgcgagac | 2640 |
| ccacgctcac cggctccaga tttatcagca ataaaccagc cagccggaag ggccgagcgc | 2700 |
| agaagtggtc ctgcaacttt atccgcctcc atccagtcta ttaattgttg ccgggaagct | 2760 |
| agagtaagta gttcgccagt taatagtttg cgcaacgttg ttgccattgc tacaggcatc | 2820 |
| gtggtgtcac gctcgtcgtt tggtatggct tcattcagct ccggttccca acgatcaagg | 2880 |
| cgagttacat gatcccccat gttgtgcaaa aaagcggtta gctccttcgg tcctccgatc | 2940 |
| gttgtcagaa gtaagttggc cgcagtgtta tcactcatgg ttatggcagc actgcataat | 3000 |
| tctcttactg tcatgccatc cgtaagatgc ttttctgtga ctggtgagta ctcaaccaag | 3060 |
| tcattctgag aatagtgtat gcggcgaccg agttgctctt gcccggcgtc aacacgggat | 3120 |
| aataccgcgc cacatagcag aactttaaaa gtgctcatca ttggaaaacg ttcttcgggg | 3180 |
| cgaaaactct caaggatctt accgctgttg agatccagtt cgatgtaacc cactcgtgca | 3240 |
| cccaactgat cttcagcatc ttttactttc accagcgttt ctgggtgagc aaaaacagga | 3300 |
| aggcaaaatg ccgcaaaaaa gggaataagg gcgacacgga aatgttgaat actcatactc | 3360 |
| ttcctttttc aatattattg aagcatttat cagggttatt gtctcatgcg cgttgacatt | 3420 |
| gattattgac tagttattaa tagtaatcaa ttacggggtc attagttcat agcccatata | 3480 |
| tggagttccg cgttacataa cttacggtaa atggcccgcc tggctgaccg cccaacgacc | 3540 |
| cccgcccatt gacgtcaata atgacgtatg ttcccatagt aacgccaata gggactttcc | 3600 |
| attgacgtca atgggtggac tatttacggt aaactgccca cttggcagta catcaagtgt | 3660 |
| atcatatgcc aagtacgccc cctattgacg tcaatgacgg taaatggccc gcctggcatt | 3720 |
| atgcccagta catgacctta tgggactttc ctacttggca gtacatctac gtattagtca | 3780 |
| tcgctattac catggtgatg cggttttggc agtacatcaa tgggcgtgga tagcggtttg | 3840 |

-continued

```
actcacgggg atttccaagt ctccacccca ttgacgtcaa tgggagtttg ttttggcacc      3900
aaaatcaacg ggactttcca aaatgtcgta acaactccgc cccattgacg caaatgggcg      3960
gtaggcgtgt acggtgggag gtctatataa gcagagctct ctggctaact agagaaccca      4020
ctgcttaact ggcttatcga aattaatacg actcactata gggagaccc               4069
```

<210> SEQ ID NO 288
<211> LENGTH: 4069
<212> TYPE: DNA
<213> ORGANISM: Homo sapiens

<400> SEQUENCE: 288

```
gggtctccct atagtgagtc gtattaattt cgataagcca gttaagcagt gggttctcta        60
gttagccaga gagctctgct tatatagacc tcccaccgta cacgcctacc gcccatttgc       120
gtcaatgggg cggagttgtt acgacatttt ggaaagtccc gttgattttg gtgccaaaac       180
aaactcccat tgacgtcaat ggggtggaga cttggaaatc cccgtgagtc aaaccgctat       240
ccacgcccat tgatgtactg ccaaaaccgc atcaccatgg taatagcgat gactaatacg       300
tagatgtact gccaagtagg aaagtcccat aaggtcatgt actgggcata atgccaggcg       360
ggccatttac cgtcattgac gtcaataggg gcgtacttg gcatatgata cacttgatgt       420
actgccaagt gggcagttta ccgtaaatag tccacccatt gacgtcaatg gaaagtccct       480
attggcgtta ctatgggaac atacgtcatt attgacgtca atgggcgggg tcgttgggc       540 ggtcagccag gcgggccatt taccgtaagt tatgtaacgc ggaactccat atatgggcta       600
tgaactaatg accccgtaat tgattactat taataactag tcaataatca atgtcaacgc       660
gcatgagaca ataaccctga taaatgcttc aataatattg aaaaaggaag agtatgagta       720
ttcaacattt ccgtgtcgcc cttattccct tttttgcggc attttgcctt cctgtttttg       780
ctcacccaga aacgctggtg aaagtaaaag atgctgaaga tcagttgggt gcacgagtgg       840
gttacatcga actggatctc aacagcggta agatccttga gagttttcgc cccgaagaac       900
gttttccaat gatgagcact tttaaagttc tgctatgtgg cgcggtatta tcccgtgttg       960
acgccgggca agagcaactc ggtcgccgca tacactattc tcagaatgac ttggttgagt      1020
actcaccagt cacagaaaag catcttacgg atggcatgac agtaagagaa ttatgcagtg      1080
ctgccataac catgagtgat aacactgcgg ccaacttact tctgacaacg atcggaggac      1140
cgaaggagct aaccgctttt ttgcacaaca tgggggatca tgtaactcgc cttgatcgtt      1200
gggaaccgga gctgaatgaa gccataccaa acgacgagcg tgacaccacg atgcctgtag      1260
caatggcaac aacgttgcgc aaactattaa ctggcgaact acttactcta gcttcccggc      1320
aacaattaat agactggatg gaggcggata aagttgcagg accacttctg cgctcggccc      1380
ttccggctgg ctggtttatt gctgataaat ctggagccgg tgagcgtggg tctcgcggta      1440
tcattgcagc actggggcca gatggtaagc cctcccgtat cgtagttatc tacacgacgg      1500
ggagtcaggc aactatggat gaacgaaata gacagatcgc tgagataggt gcctcactga      1560
ttaagcattg gtaactgtca gaccaagttt actcatatat actttagatt gatttaaaac      1620
ttcattttta atttaaaagg atctaggtga agatcctttt tgataatctc atgaccaaaa      1680
tcccttaacg tgagttttcg ttccactgag cgtcagaccc cgtagaaaag atcaaggat      1740 cttcttgaga tccttttttt ctgcgcgtaa tctgctgctt gcaaacaaaa aaaccaccgc      1800
taccagcggt ggtttgtttg ccggatcaag agctaccaac tctttttccg aaggtaactg      1860
```

```
gcttcagcag agcgcagata ccaaatactg tccttctagt gtagccgtag ttaggccacc    1920
acttcaagaa ctctgtagca ccgcctacat acctcgctct gctaatcctg ttaccagtgg    1980
ctgctgccaa tggcgataag tcgtgtctta ccggggttgga ctcaagacga tagttaccgg    2040
ataaggcgca gcggtcgggc tgaacggggg gttcgtgcac acagcccagc ttggagcgaa    2100
cgacctacac cgaactgaga tacctacagc gtgagcattg agaaagcgcc acgcttcccg    2160
aagggagaaa ggcggacagg tatccggtaa gcggcagggt cggaacagga gagcgcacga    2220
gggagcttcc aggggaaac gcctggtatc tttatagtcc tgtcgggttt cgccacctct    2280
gacttgagcg tcgattttg tgatgctcgt caggggggcg gagcctatgg aaaaacgcca    2340
gcaacgcggc cttttttacgg ttcctggcct tttgctggcc ttttgctcac atgttctttc    2400
ctgcgttatc ccctgattct gtggataacc gtattaccgc ctttgagtga gctgataccg    2460
ctcgccgcag ccgaacgacc gagcgcagcg agtcagtgag cgaggaagcg gaagagcgcc    2520
caatacgcaa accgcctctc cccgcgcgtt ggccgattca ttaatgcagc tggcacgaca    2580
ggtttcccga ctggaaagcg ggcagtgagc gcaacgcaat taatgtgagt tagctcactc    2640
attaggcacc ccaggcttta cactttatgc ttccggctcg tatgttgtgt ggaattgtga    2700
gcggataaca atttcacaca ggaaacagct atgaccatga ttacgccaag ctctcgaggg    2760 agcttttttgc aaaagcctag gcctccaaaa aagcctcctc actacttctg aatagctca    2820 gaggccgagg cggcctcggc ctctgcataa ataaaaaaaa ttagtcagcc atggggcgga    2880
gaatgggcgg aactgggcgg agttagggc gggatgggcg gagttagggg cgggactatg    2940
gttgctgact aattgagatg catgctttgc atacttctgc ctgctgggga gcctggggac    3000
tttccacacc tggttgctga ctaattgaga tgcatgcttt gcatacttct gcctgctggg    3060
gagcctgggg actttccaca ccctaactga cacacatttc ggaagatcta gacatgataa    3120
gatacattga tgagtttgga caaaccacaa ctagaatgca gtgaaaaaa tgctttattt    3180 gtgaaatttg tgatgctatt gctttatttg taaccattat aagctgcaat aaacaagtta    3240
acaacaacaa ttgcattcat tttatgtttc aggttcaggg ggaggtgtgg gaggtttttt    3300
aaagcaagta aaacctctac aaatgtggta tggctgatta tgatctctag tcaaggcact    3360
atacatcaaa tattccttat taccccttt acaaattaaa aagctaaagg tacacaattt    3420
ttgagcatag ttattaatag cagacactct atgcctgtgt ggagtaagaa aaacagtat    3480 gttatgatta taactgttat gcctacttat aaaggttaca gaatattttt ccataatttt    3540
cttgtatagc agtgcagctt tttcctttgt ggtgtaaata gcaaagcaag caagagttct    3600
attactaaac acagcatgac tcaaaaaact tagcaattct gaaggaaagt ccttggggtc    3660
ttctaccttt ctcttctttt ttggaggagt agaatgttga gagtcagcag tagcctcatc    3720
atcactagat ggcatttctt ctgagcaaaa caggttttcc tcattaaagg cattccacca    3780
ctgctcccat tcatcagttc cataggttgg aatctaaaat acacaaacaa ttagaatcag    3840
tagtttaaca cattatacac ttaaaaattt tatatttacc ttagagcttt aaatctctgt    3900
aggtagtttg tccaattatg tcacaccaca gaagtaaggt tccttcacaa agatcctcta    3960
gcgcgcaatt aaccctcact aaagggaaca aaagctggag ctccaccgcg gtggcggccg    4020
ctctagaact agtggatccc ccgggctgca ggaattcgat atcaagctt             4069
```

<210> SEQ ID NO 289
<211> LENGTH: 1273
<212> TYPE: PRT
<213> ORGANISM: Homo sapiens

```
<400> SEQUENCE: 289

Lys Leu Asp Ile Glu Phe Leu Gln Pro Gly Ser Thr Ser Ser Arg
  1               5                  10                  15

Ala Ala Ala Thr Ala Val Glu Leu Gln Leu Leu Phe Pro Leu Val Arg
             20                  25                  30

Val Asn Cys Ala Leu Glu Asp Leu Cys Glu Gly Thr Leu Leu Leu Trp
             35                  40                  45

Cys Asp Ile Ile Gly Gln Thr Thr Tyr Arg Asp Leu Lys Leu Gly Lys
 50                  55                  60

Tyr Lys Ile Phe Lys Cys Ile Met Cys Thr Thr Asp Ser Asn Cys Leu
 65                  70                  75                  80

Cys Ile Leu Asp Ser Asn Leu Trp Asn Met Gly Ala Val Val Glu Cys
                 85                  90                  95

Leu Gly Lys Pro Val Leu Arg Arg Asn Ala Ile Gly Tyr Cys Leu
                100                 105                 110

Ser Thr Phe Tyr Ser Ser Lys Lys Glu Glu Lys Gly Arg Arg Pro Gln
                115                 120                 125

Gly Leu Ser Phe Arg Ile Ala Lys Phe Phe Glu Ser Cys Cys Val Asn
            130                 135                 140

Ser Cys Leu Leu Cys Tyr Leu His His Lys Gly Lys Ser Cys Thr Ala
145                 150                 155                 160

Ile Gln Glu Asn Tyr Gly Lys Ile Phe Cys Asn Leu Tyr Lys Ala Gln
                165                 170                 175

Leu His Thr Val Phe Ser Tyr Ser Thr Gln Ala Ser Val Cys Tyr Leu
                180                 185                 190

Cys Ser Lys Ile Val Tyr Leu Leu Phe Asn Leu Arg Gly Gly Ile Phe
            195                 200                 205

Asp Val Cys Leu Asp Arg Ser Ser Ala Ile Pro His Leu Arg Phe Tyr
            210                 215                 220

Leu Leu Lys Thr Ser His Thr Ser Pro Thr Asn Ile Lys Met Gln Leu
225                 230                 235                 240

Leu Leu Leu Thr Cys Leu Leu Gln Leu Ile Met Val Thr Asn Lys Ala
                245                 250                 255

Ile Ala Ser Gln Ile Ser Gln Ile Lys His Phe Phe His Cys Ile Leu
            260                 265                 270

Val Val Val Cys Pro Asn Ser Ser Met Tyr Leu Ile Met Ser Arg Ser
            275                 280                 285

Ser Glu Met Cys Val Ser Gly Val Glu Ser Pro Gln Ala Pro Gln Gln
            290                 295                 300

Ala Glu Val Cys Lys Ala Cys Ile Ser Ile Ser Gln Pro Gly Val
305                 310                 315                 320

Glu Ser Pro Gln Ala Pro Gln Ala Glu Val Cys Lys Ala Cys Ile
                325                 330                 335

Ser Ile Ser Gln Gln Pro Ser Arg Pro Leu Arg Pro Ser Arg Pro Leu
            340                 345                 350

Arg Pro Val Pro Pro Ile Leu Arg Pro Met Ala Asp Phe Phe Leu Phe
            355                 360                 365

Met Gln Arg Pro Arg Pro Arg Pro Leu Ser Tyr Ser Arg Ser Ser
            370                 375                 380

Glu Glu Ala Phe Leu Glu Ala Ala Phe Ala Lys Ser Ser Leu Glu Ser
385                 390                 395                 400

Leu Ala Ser Trp Ser Leu Phe Pro Val Asn Cys Tyr Pro Leu Thr Ile
```

-continued

```
                        405                 410                     415
Pro His Asn Ile Arg Ala Gly Ser Ile Lys Cys Lys Ala Trp Gly Ala
                420                 425                 430
Val Ser Leu Thr Leu Ile Ala Leu Arg Ser Leu Pro Ala Phe Gln Ser
            435                 440                 445
Gly Asn Leu Ser Cys Gln Leu His Ile Gly Gln Arg Ala Gly Arg Gly
        450                 455                 460
Gly Leu Arg Ile Gly Arg Ser Ser Ala Ser Ser Leu Thr Asp Ser Leu
465                 470                 475                 480
Arg Ser Val Val Arg Leu Arg Ala Val Ser Ala His Ser Lys Ala
                485                 490                 495
Val Ile Arg Leu Ser Thr Glu Ser Gly Asp Asn Ala Gly Lys Asn Met
            500                 505                 510
Ala Lys Gly Gln Gln Lys Ala Arg Asn Arg Lys Lys Ala Ala Leu Leu
        515                 520                 525
Ala Phe Phe His Arg Leu Arg Pro Asp Glu His His Lys Asn Arg
    530                 535                 540
Arg Ser Ser Gln Arg Trp Arg Asn Pro Thr Gly Leu Arg Tyr Gln Ala
545                 550                 555                 560
Phe Pro Pro Gly Ser Ser Leu Val Arg Ser Pro Val Pro Thr Leu Pro
                565                 570                 575
Leu Thr Gly Tyr Leu Ser Ala Phe Leu Pro Ser Gly Ser Val Ala Leu
            580                 585                 590
Ser Gln Cys Ser Arg Cys Arg Tyr Leu Ser Ser Val Val Arg Ser
        595                 600                 605
Lys Leu Gly Cys Val His Glu Pro Pro Val Gln Pro Asp Arg Cys Ala
    610                 615                 620
Leu Ser Gly Asn Tyr Arg Leu Glu Ser Asn Pro Val Arg His Asp Leu
625                 630                 635                 640
Ser Pro Leu Ala Ala Ala Thr Gly Asn Arg Ile Ser Arg Ala Arg Tyr
                645                 650                 655
Val Gly Gly Ala Thr Glu Phe Leu Lys Trp Trp Pro Asn Tyr Gly Tyr
            660                 665                 670
Thr Arg Arg Thr Val Phe Gly Ile Cys Ala Leu Leu Lys Pro Val Thr
        675                 680                 685
Phe Gly Lys Arg Val Gly Ser Ser Ser Gly Lys Gln Thr Thr Ala Gly
    690                 695                 700
Ser Gly Gly Phe Phe Val Cys Lys Gln Gln Ile Thr Arg Arg Lys Lys
705                 710                 715                 720
Gly Ser Gln Glu Asp Pro Leu Ile Phe Ser Thr Gly Ser Asp Ala Gln
                725                 730                 735
Trp Asn Glu Asn Ser Arg Gly Ile Leu Val Met Arg Leu Ser Lys Arg
            740                 745                 750
Ile Phe Thr Ile Leu Leu Asn Lys Ser Phe Lys Ser Ile Ser Ile Tyr
        755                 760                 765
Glu Thr Trp Ser Asp Ser Tyr Gln Cys Leu Ile Ser Glu Ala Pro Ile
    770                 775                 780
Ser Ala Ile Cys Leu Phe Arg Ser Ser Ile Val Ala Leu Pro Val Val
785                 790                 795                 800
Ile Thr Thr Ile Arg Glu Gly Leu Pro Ser Gly Pro Ser Ala Ala Met
                805                 810                 815
Ile Pro Arg Asp Pro Arg Ser Pro Ala Pro Asp Leu Ser Ala Ile Asn
            820                 825                 830
```

-continued

```
Gln Pro Ala Gly Arg Ala Glu Arg Arg Ser Gly Pro Ala Thr Leu Ser
            835                 840                 845
Ala Ser Ile Gln Ser Ile Asn Cys Cys Arg Glu Ala Arg Val Ser Ser
        850                 855                 860
Ser Pro Val Asn Ser Leu Arg Asn Val Val Ala Ile Ala Thr Gly Ile
865                 870                 875                 880
Val Val Ser Arg Ser Ser Phe Gly Met Ala Ser Phe Ser Ser Gly Ser
                885                 890                 895
Gln Arg Ser Arg Arg Val Thr Ser Pro Met Leu Cys Lys Lys Ala Val
            900                 905                 910
Ser Ser Phe Gly Pro Pro Ile Val Val Arg Ser Lys Leu Ala Ala Val
        915                 920                 925
Leu Ser Leu Met Val Met Ala Ala Leu His Asn Ser Leu Thr Val Met
930                 935                 940
Pro Ser Val Arg Cys Phe Ser Val Thr Gly Glu Tyr Ser Thr Lys Ser
945                 950                 955                 960
Phe Glu Cys Met Arg Arg Pro Ser Cys Ser Cys Pro Ala Ser Thr Arg
                965                 970                 975
Asp Asn Thr Ala Pro His Ser Arg Thr Leu Lys Val Leu Ile Ile Gly
            980                 985                 990
Lys Arg Ser Ser Gly Arg Lys Leu Ser Arg Ile Leu Pro Leu Leu Arg
        995                 1000                1005
Ser Ser Ser Met Pro Thr Arg Ala Pro Asn Ser Ser Ala Ser Phe
    1010                1015                1020
Thr Phe Thr Ser Val Ser Gly Ala Lys Thr Gly Arg Gln Asn Ala
    1025                1030                1035
Ala Lys Lys Gly Ile Arg Ala Thr Arg Lys Cys Ile Leu Ile Leu
    1040                1045                1050
Phe Leu Phe Gln Tyr Tyr Ser Ile Tyr Gln Gly Tyr Cys Leu Met
    1055                1060                1065
Arg Val Asp Ile Asp Tyr Leu Val Ile Asn Ser Asn Gln Leu Arg
    1070                1075                1080
Gly His Phe Ile Ala His Ile Trp Ser Ser Ala Leu His Asn Leu
    1085                1090                1095
Arg Met Ala Arg Leu Ala Asp Arg Pro Thr Thr Pro Ala His Arg
    1100                1105                1110
Gln Arg Met Phe Pro Arg Gln Gly Leu Ser Ile Asp Val Asn Gly
    1115                1120                1125
Trp Thr Ile Tyr Gly Lys Leu Pro Thr Trp Gln Tyr Ile Lys Cys
    1130                1135                1140
Ile Ile Cys Gln Val Arg Pro Leu Leu Thr Ser Met Thr Val Asn
    1145                1150                1155
Gly Pro Pro Gly Ile Met Pro Ser Thr Pro Tyr Gly Thr Phe Leu
    1160                1165                1170
Leu Gly Ser Thr Ser Thr Tyr Ser Ser Leu Leu Pro Trp Cys Gly
    1175                1180                1185
Phe Gly Ser Thr Ser Met Gly Val Asp Ser Gly Leu Thr His Gly
    1190                1195                1200
Asp Phe Gln Val Ser Thr Pro Leu Thr Ser Met Gly Val Cys Phe
    1205                1210                1215
Gly Thr Lys Ile Asn Gly Thr Phe Gln Asn Val Val Thr Thr Pro
    1220                1225                1230
```

-continued

```
Pro His Arg Lys Trp Ala Val Gly Val Tyr Gly Gly Arg Ser Ile
    1235                1240                1245

Ala Glu Leu Ser Gly Leu Glu Asn Pro Leu Leu Asn Trp Leu Ile
    1250                1255                1260

Glu Ile Asn Thr Thr His Tyr Arg Glu Thr
    1265                1270

<210> SEQ ID NO 290
<211> LENGTH: 1310
<212> TYPE: PRT
<213> ORGANISM: Homo sapiens

<400> SEQUENCE: 290

Ser Leu Ile Ser Asn Ser Cys Ser Pro Gly Asp Pro Leu Val Leu Glu
1                5                  10                  15

Arg Pro Pro Arg Trp Ser Ser Phe Cys Ser Leu Gly Leu Ile
                20                  25                  30

Ala Arg Arg Ile Phe Val Lys Glu Pro Tyr Phe Cys Gly Val Thr Leu
                35                  40                  45

Asp Lys Leu Pro Thr Glu Ile Ser Ser Lys Val Asn Ile Lys Phe Leu
    50                  55                  60

Ser Val Cys Val Lys Leu Leu Ile Leu Ile Val Cys Val Phe Ile Pro
65                  70                  75                  80

Thr Tyr Gly Thr Asp Glu Trp Glu Gln Trp Trp Asn Ala Phe Asn Glu
                85                  90                  95

Glu Asn Leu Phe Cys Ser Glu Met Pro Ser Ser Asp Asp Glu Ala
                100                 105                 110

Thr Ala Asp Ser Gln His Ser Thr Pro Pro Lys Lys Arg Lys Val
    115                 120                 125

Glu Asp Pro Lys Asp Phe Pro Ser Glu Leu Leu Ser Phe Leu Ser His
    130                 135                 140

Ala Val Phe Ser Asn Arg Thr Leu Ala Cys Phe Ala Ile Tyr Thr Thr
145                 150                 155                 160

Lys Glu Lys Ala Ala Leu Leu Tyr Lys Lys Ile Met Glu Lys Tyr Ser
                165                 170                 175

Val Thr Phe Ile Ser Arg His Asn Ser Tyr Asn His Asn Ile Leu Phe
                180                 185                 190

Phe Leu Thr Pro His Arg His Arg Val Ser Ala Ile Asn Asn Tyr Ala
                195                 200                 205

Gln Lys Leu Cys Thr Phe Ser Phe Leu Ile Cys Lys Gly Val Asn Lys
    210                 215                 220

Glu Tyr Leu Met Tyr Ser Ala Leu Thr Arg Asp His Asn Gln Pro Tyr
225                 230                 235                 240

His Ile Cys Arg Gly Phe Thr Cys Phe Lys Lys Pro Thr Pro Pro
                245                 250                 255

Pro Glu Pro Glu Thr Asn Glu Cys Asn Cys Cys Leu Val Tyr Cys
                260                 265                 270

Ser Leu Trp Leu Gln Ile Lys Gln His His Lys Phe His Lys Ser Ile
                275                 280                 285

Phe Phe Thr Ala Phe Leu Trp Phe Val Gln Thr His Gln Cys Ile Leu
    290                 295                 300

Ser Cys Leu Asp Leu Pro Lys Cys Val Ser Val Arg Val Trp Lys Val
305                 310                 315                 320

Pro Arg Leu Pro Ser Arg Gln Lys Tyr Ala Lys His Ala Ser Gln Leu
                325                 330                 335
```

-continued

```
Val Ser Asn Gln Val Trp Lys Val Pro Arg Leu Pro Ser Arg Gln Lys
            340                 345                 350

Tyr Ala Lys His Ala Ser Gln Leu Val Ser Asn His Ser Pro Ala Pro
            355                 360                 365

Asn Ser Ala His Pro Ala Pro Asn Ser Ala Gln Phe Arg Pro Phe Ser
            370                 375                 380

Ala Pro Trp Leu Thr Asn Phe Phe Tyr Leu Cys Arg Gly Arg Gly Arg
385                 390                 395                 400

Leu Gly Leu Ala Ile Pro Glu Val Val Arg Arg Leu Phe Trp Arg Pro
                405                 410                 415

Arg Leu Leu Gln Lys Ala Pro Ser Arg Ala Trp Arg Asn His Gly His
            420                 425                 430

Ser Cys Phe Leu Cys Glu Ile Val Ile Arg Ser Gln Phe His Thr Thr
            435                 440                 445

Tyr Glu Pro Glu Ala Ser Val Lys Pro Gly Val Pro Asn Glu Ala Asn
            450                 455                 460

Ser His Leu Arg Cys Ala His Cys Pro Leu Ser Ser Arg Glu Thr Cys
465                 470                 475                 480

Arg Ala Ser Cys Ile Asn Glu Ser Ala Asn Ala Arg Gly Glu Ala Val
                485                 490                 495

Cys Val Leu Gly Ala Leu Pro Leu Pro Arg Ser Leu Thr Arg Cys Ala
            500                 505                 510

Arg Ser Phe Gly Cys Gly Glu Arg Tyr Gln Leu Thr Gln Arg Arg Tyr
            515                 520                 525

Gly Tyr Pro Gln Asn Gln Gly Ile Thr Gln Glu Arg Thr Cys Glu Gln
            530                 535                 540

Lys Ala Ser Lys Arg Pro Gly Thr Val Lys Arg Pro Arg Cys Trp Arg
545                 550                 555                 560

Phe Ser Ile Gly Ser Ala Pro Leu Thr Ser Ile Thr Lys Ile Asp Ala
                565                 570                 575

Gln Val Arg Gly Gly Glu Thr Arg Gln Asp Tyr Lys Asp Thr Arg Arg
            580                 585                 590

Phe Pro Leu Glu Ala Pro Ser Cys Ala Leu Leu Phe Arg Pro Cys Arg
            595                 600                 605

Leu Pro Asp Thr Cys Pro Pro Phe Ser Leu Arg Glu Ala Trp Arg Phe
            610                 615                 620

Leu Asn Ala His Ala Val Gly Ile Ser Val Arg Cys Arg Ser Phe Ala
625                 630                 635                 640

Pro Ser Trp Ala Val Cys Thr Asn Pro Pro Phe Ser Pro Thr Ala Ala
                645                 650                 655

Pro Tyr Pro Val Thr Ile Val Leu Ser Pro Thr Arg Asp Thr Thr Tyr
            660                 665                 670

Arg His Trp Gln Gln Pro Leu Val Thr Gly Leu Ala Glu Arg Gly Met
            675                 680                 685

Ala Val Leu Gln Ser Ser Gly Gly Leu Thr Thr Ala Thr Leu Glu
            690                 695                 700

Gly Gln Tyr Leu Val Ser Ala Leu Cys Ser Gln Leu Pro Ser Glu Lys
705                 710                 715                 720

Glu Leu Val Ala Leu Asp Pro Ala Asn Lys Pro Pro Leu Val Ala Val
                725                 730                 735

Val Phe Leu Phe Ala Ser Ser Arg Leu Arg Ala Glu Lys Lys Asp Leu
            740                 745                 750
```

-continued

```
Lys Lys Ile Leu Ser Phe Leu Arg Gly Leu Thr Leu Ser Gly Thr Lys
        755                 760                 765

Thr His Val Lys Gly Phe Trp Ser Asp Tyr Gln Lys Gly Ser Ser Pro
    770                 775                 780

Arg Ser Phe Ile Lys Asn Glu Val Leu Asn Gln Ser Lys Val Tyr Met
785                 790                 795                 800

Ser Lys Leu Gly Leu Thr Val Thr Asn Ala Ser Val Arg His Leu Ser
            805                 810                 815

Gln Arg Ser Val Tyr Phe Val His Pro Leu Pro Asp Ser Pro Ser Cys
            820                 825                 830

Arg Leu Arg Tyr Gly Arg Ala Tyr His Leu Ala Pro Val Leu Gln Tyr
            835                 840                 845

Arg Glu Thr His Ala His Arg Leu Gln Ile Tyr Gln Gln Thr Ser Gln
    850                 855                 860

Pro Glu Gly Pro Ser Ala Glu Val Val Leu Gln Leu Tyr Pro Pro Pro
865                 870                 875                 880

Ser Ser Leu Leu Ile Val Ala Gly Lys Leu Glu Val Val Arg Gln Leu
            885                 890                 895

Ile Val Cys Ala Thr Leu Leu Pro Leu Leu Gln Ala Ser Trp Cys His
            900                 905                 910

Ala Arg Arg Leu Val Trp Leu His Ser Ala Pro Val Pro Asn Asp Gln
            915                 920                 925

Gly Glu Leu His Asp Pro Pro Cys Cys Ala Lys Lys Arg Leu Ala Pro
    930                 935                 940

Ser Val Leu Arg Ser Leu Ser Glu Val Ser Trp Pro Gln Cys Tyr His
945                 950                 955                 960

Ser Trp Leu Trp Gln His Cys Ile Ile Leu Leu Ser Cys His Pro
            965                 970                 975

Asp Ala Phe Leu Leu Val Ser Thr Gln Pro Ser His Ser Glu Asn Ser
            980                 985                 990

Val Cys Gly Asp Arg Val Ala Leu Ala Arg Arg Gln His Gly Ile Ile
            995                1000                1005

Pro Arg His Ile Ala Glu Leu Lys Cys Ser Ser Leu Glu Asn Val
    1010                1015                1020

Leu Arg Gly Glu Asn Ser Gln Gly Ser Tyr Arg Cys Asp Pro Val
    1025                1030                1035

Arg Cys Asn Pro Leu Val His Pro Thr Asp Leu Gln His Leu Leu
    1040                1045                1050

Leu Ser Pro Ala Phe Leu Gly Glu Gln Lys Gln Glu Gly Lys Met
    1055                1060                1065

Pro Gln Lys Arg Glu Gly Arg His Gly Asn Val Glu Tyr Ser Tyr
    1070                1075                1080

Ser Ser Phe Phe Asn Ile Ile Glu Ala Phe Ile Arg Val Ile Val
    1085                1090                1095

Ser Cys Ala Leu Thr Leu Ile Ile Asp Leu Leu Ile Val Ile Asn
    1100                1105                1110

Tyr Gly Val Ile Ser Ser Pro Ile Tyr Gly Val Pro Arg Tyr Ile
    1115                1120                1125

Thr Tyr Gly Lys Trp Pro Ala Trp Leu Thr Ala Gln Arg Pro Pro
    1130                1135                1140

Pro Ile Asp Val Asn Asn Asp Val Cys Ser His Ser Asn Ala Asn
    1145                1150                1155

Arg Asp Phe Pro Leu Thr Ser Met Gly Gly Leu Phe Thr Val Asn
```

-continued

```
            1160                1165                1170

Cys Pro Leu Gly Ser Thr Ser Ser Val Ser Tyr Ala Lys Tyr Ala
    1175                1180                1185

Pro Tyr Arg Gln Arg Met Ala Arg Leu Ala Leu Cys Pro Val His
    1190                1195                1200

Asp Leu Met Gly Leu Ser Tyr Leu Ala Val His Leu Arg Ile Ser
    1205                1210                1215

His Arg Tyr Tyr His Gly Asp Ala Val Leu Ala Val His Gln Trp
    1220                1225                1230

Ala Trp Ile Ala Val Leu Thr Gly Ile Ser Lys Ser Pro Pro His
    1235                1240                1245

Arg Gln Trp Glu Phe Val Leu Ala Pro Lys Ser Thr Gly Leu Ser
    1250                1255                1260

Lys Met Ser Gln Leu Arg Pro Ile Asp Ala Asn Gly Arg Ala Cys
    1265                1270                1275

Thr Val Gly Gly Leu Tyr Lys Gln Ser Ser Leu Ala Asn Arg Thr
    1280                1285                1290

His Cys Leu Thr Gly Leu Ser Lys Leu Ile Arg Leu Thr Ile Gly
    1295                1300                1305

Arg Pro
    1310

<210> SEQ ID NO 291
<211> LENGTH: 1286
<212> TYPE: PRT
<213> ORGANISM: Homo sapiens

<400> SEQUENCE: 291

Gln Ala Tyr Arg Ile Pro Ala Ala Arg Gly Ile His Phe Ser Gly Arg
1               5                   10                  15

His Arg Gly Gly Ala Pro Ala Phe Val Pro Phe Ser Glu Gly Leu Arg
                20                  25                  30

Ala Arg Gly Ser Leu Arg Asn Leu Thr Ser Val Val His Asn Trp Thr
            35                  40                  45

Asn Tyr Leu Gln Arg Phe Lys Ala Leu Arg Ile Asn Phe Val Tyr Asn
        50                  55                  60

Val Leu Asn Tyr Phe Leu Phe Val Tyr Phe Arg Phe Gln Pro Met Glu
65                  70                  75                  80

Leu Met Asn Gly Ser Ser Gly Gly Met Pro Leu Met Arg Lys Thr Cys
                85                  90                  95

Phe Ala Gln Lys Lys Cys His Leu Val Met Met Arg Leu Leu Leu Thr
            100                 105                 110

Leu Asn Ile Leu Leu Leu Gln Lys Arg Arg Glu Arg Lys Thr Pro Arg
        115                 120                 125

Thr Phe Leu Gln Asn Cys Val Phe Met Leu Cys Leu Val Ile Glu
    130                 135                 140

Leu Leu Leu Ala Leu Leu Phe Thr Pro Gln Arg Lys Lys Leu His Cys
145                 150                 155                 160

Tyr Thr Arg Lys Leu Trp Lys Asn Ile Leu Pro Leu Val Gly Ile Thr
                165                 170                 175

Val Ile Ile Ile Thr Tyr Cys Phe Phe Leu Leu His Thr Gly Ile Glu
            180                 185                 190

Cys Leu Leu Leu Ile Thr Met Leu Lys Asn Cys Val Pro Leu Ala Phe
        195                 200                 205
```

```
Phe Val Lys Gly Leu Ile Arg Asn Ile Cys Ile Val Pro Leu Glu Ile
    210                 215                 220
Ile Ile Ser His Thr Thr Phe Val Glu Val Leu Leu Ala Leu Lys Asn
225                 230                 235                 240
Leu Pro His Leu Pro Leu Asn Leu Lys His Lys Met Asn Ala Ile Val
                245                 250                 255
Val Val Asn Leu Phe Ile Ala Ala Tyr Asn Gly Tyr Lys Ser Asn Ser
            260                 265                 270
Ile Thr Asn Phe Thr Asn Lys Ala Phe Phe Ser Leu His Ser Ser Cys
        275                 280                 285
Gly Leu Ser Lys Leu Ile Asn Val Ser Tyr His Val Ile Phe Arg Asn
    290                 295                 300
Val Cys Gln Leu Gly Cys Gly Lys Ser Pro Gly Ser Pro Ala Gly Arg
305                 310                 315                 320
Ser Met Gln Ser Met His Leu Asn Ser Ala Thr Arg Cys Gly Lys Ser
                325                 330                 335
Pro Gly Ser Pro Ala Gly Arg Ser Met Gln Ser Met His Leu Asn Ser
            340                 345                 350
Ala Thr Ile Val Pro Pro Leu Thr Pro Pro Ile Pro Pro Leu Thr Pro
        355                 360                 365
Pro Ser Ser Ala His Ser Pro Pro His Gly Leu Ile Phe Phe Ile Tyr
    370                 375                 380
Ala Glu Ala Glu Ala Ala Ser Ala Ser Glu Leu Phe Gln Lys Gly Gly
385                 390                 395                 400
Phe Phe Gly Gly Leu Gly Phe Cys Lys Lys Leu Pro Arg Glu Leu Gly
                405                 410                 415
Val Ile Met Val Ile Ala Val Ser Cys Val Lys Leu Leu Ser Ala His
            420                 425                 430
Asn Ser Thr Gln His Thr Ser Arg Lys His Lys Val Ser Leu Gly Cys
        435                 440                 445
Leu Met Ser Glu Leu Thr His Ile Asn Cys Val Ala Leu Thr Ala Arg
    450                 455                 460
Phe Pro Val Gly Lys Pro Val Pro Ala Ala Leu Met Asn Arg Pro
465                 470                 475                 480
Thr Arg Gly Glu Arg Arg Phe Ala Tyr Trp Ala Leu Phe Arg Phe Leu
                485                 490                 495
Ala His Leu Ala Ala Leu Gly Arg Ser Ala Ala Ser Gly Ile Ser
            500                 505                 510
Ser Leu Lys Gly Gly Asn Thr Val Ile His Arg Ile Arg Gly Arg Arg
        515                 520                 525
Lys Glu His Val Ser Lys Arg Pro Ala Lys Gly Gln Glu Pro Lys Gly
    530                 535                 540
Arg Val Ala Gly Val Phe Pro Ala Pro Pro Arg Ala Ser Gln Lys
545                 550                 555                 560
Ser Thr Leu Lys Ser Glu Val Ala Lys Pro Asp Arg Thr Ile Lys Ile
                565                 570                 575
Pro Gly Val Ser Pro Trp Lys Leu Pro Arg Ala Leu Ser Cys Ser Asp
            580                 585                 590
Pro Ala Ala Tyr Arg Ile Pro Val Arg Leu Ser Pro Phe Gly Lys Arg
        595                 600                 605
Gly Ala Phe Ser Met Leu Thr Leu Val Ser Gln Phe Gly Val Gly Arg
    610                 615                 620
Ser Leu Gln Ala Gly Leu Cys Ala Arg Thr Pro Arg Ser Ala Arg Pro
```

-continued

```
                625                 630                 635                 640
Leu Arg Leu Ile Arg Leu Ser Ser Val Gln Pro Gly Lys Thr Arg Leu
                    645                 650                 655
Ile Ala Thr Gly Ser Ser His Trp Gln Asp Gln Ser Glu Val Cys Arg
            660                 665                 670
Arg Cys Tyr Arg Val Leu Glu Val Ala Leu Arg Leu His Lys Asp
        675                 680                 685
Ser Ile Trp Tyr Leu Arg Ser Glu Ala Ser Tyr Leu Arg Lys Lys
    690                 695                 700
Ser Trp Leu Leu Ile Arg Gln Thr Asn His Arg Trp Arg Trp Phe
705                 710                 715                 720
Cys Leu Gln Ala Ala Asp Tyr Ala Gln Lys Lys Arg Ile Ser Arg Arg
                    725                 730                 735
Ser Phe Asp Leu Phe Tyr Gly Val Arg Ser Val Glu Arg Lys Leu Thr
                740                 745                 750
Leu Arg Asp Phe Gly His Glu Ile Ile Lys Lys Asp Leu His Leu Asp
            755                 760                 765
Pro Phe Lys Leu Lys Met Lys Phe Ile Asn Leu Lys Tyr Ile Val Asn
    770                 775                 780
Leu Val Gln Leu Pro Met Leu Asn Gln Gly Thr Tyr Leu Ser Asp Leu
785                 790                 795                 800
Ser Ile Ser Phe Ile His Ser Cys Leu Thr Pro Arg Arg Val Asp Asn
                    805                 810                 815
Tyr Asp Thr Gly Gly Leu Thr Ile Trp Pro Gln Cys Cys Asn Asp Thr
                820                 825                 830
Ala Arg Pro Thr Leu Thr Gly Ser Arg Phe Ile Ser Asn Lys Pro Ala
            835                 840                 845
Ser Arg Lys Gly Arg Ala Gln Lys Trp Ser Cys Asn Phe Ile Arg Leu
        850                 855                 860
His Pro Val Tyr Leu Leu Pro Gly Ser Ser Lys Phe Ala Ser Phe Ala
865                 870                 875                 880
Gln Arg Cys Cys His Cys Tyr Arg His Arg Gly Val Thr Leu Val Val
                    885                 890                 895
Trp Tyr Gly Phe Ile Gln Leu Arg Phe Pro Thr Ile Lys Ala Ser Tyr
                900                 905                 910
Met Ile Pro His Val Val Gln Lys Ser Gly Leu Leu Arg Ser Ser Asp
            915                 920                 925
Arg Cys Gln Lys Val Gly Arg Ser Val Ile Thr His Gly Tyr Gly Ser
        930                 935                 940
Thr Ala Phe Ser Tyr Cys His Ala Ile Arg Lys Met Leu Phe Cys Asp
945                 950                 955                 960
Trp Val Leu Asn Gln Val Ile Leu Arg Ile Val Tyr Ala Ala Thr Glu
                    965                 970                 975
Leu Leu Leu Pro Gly Val Asn Thr Gly Tyr Arg Ala Thr Gln Asn Phe
                980                 985                 990
Lys Ser Ala His His Trp Lys Thr Phe Phe Gly Ala Lys Thr Leu Lys
            995                 1000                1005
Asp Leu Thr Ala Val Glu Ile Gln Phe Asp Val Thr His Ser Cys
    1010                1015                1020
Thr Gln Leu Ile Phe Ser Ile Phe Tyr Phe His Gln Arg Phe Trp
    1025                1030                1035
Val Ser Lys Asn Arg Lys Ala Lys Cys Arg Lys Lys Gly Asn Lys
    1040                1045                1050
```

-continued

```
Gly Asp Thr Glu Met Leu Asn Thr His Thr Leu Pro Phe Ser Ile
    1055                1060                1065

Leu Leu Lys His Leu Ser Gly Leu Leu Ser His Ala Arg His Leu
    1070                1075                1080

Leu Thr Ser Tyr Ser Ile Thr Gly Ser Leu Val His Ser Pro Tyr
    1085                1090                1095

Met Glu Phe Arg Val Thr Leu Thr Val Asn Gly Pro Pro Gly Pro
    1100                1105                1110

Pro Asn Asp Pro Arg Pro Leu Thr Ser Ile Met Thr Tyr Val Pro
    1115                1120                1125

Ile Val Thr Pro Ile Gly Thr Phe His Arg Gln Trp Val Asp Tyr
    1130                1135                1140

Leu Arg Thr Ala His Leu Ala Val His Gln Val Tyr His Met Pro
    1145                1150                1155

Ser Thr Pro Pro Ile Asp Val Asn Asp Gly Lys Trp Pro Ala Trp
    1160                1165                1170

His Tyr Ala Gln Tyr Met Thr Leu Trp Asp Phe Pro Thr Trp Gln
    1175                1180                1185

Tyr Ile Tyr Val Leu Val Ile Ala Ile Thr Met Val Met Arg Phe
    1190                1195                1200

Trp Gln Tyr Ile Asn Gly Arg Gly Arg Phe Asp Ser Arg Gly Phe
    1205                1210                1215

Pro Ser Leu His Pro Ile Asp Val Asn Gly Ser Leu Phe Trp His
    1220                1225                1230

Gln Asn Gln Arg Asp Phe Pro Lys Cys Arg Asn Asn Ser Ala Pro
    1235                1240                1245

Leu Thr Gln Met Gly Gly Arg Arg Val Arg Trp Glu Val Tyr Ile
    1250                1255                1260

Ser Arg Ala Leu Trp Leu Thr Arg Glu Pro Thr Ala Leu Ala Tyr
    1265                1270                1275

Arg Asn Tyr Asp Ser Leu Gly Asp
    1280                1285

<210> SEQ ID NO 292
<211> LENGTH: 1293
<212> TYPE: PRT
<213> ORGANISM: Homo sapiens

<400> SEQUENCE: 292

Trp Val Ser Leu Val Val Leu Ile Ser Ile Ser Gln Leu Ser Ser Gly
1               5                   10                  15

Phe Ser Ser Pro Glu Ser Ser Ala Tyr Ile Asp Leu Pro Pro Tyr Thr
                20                  25                  30

Pro Thr Ala His Leu Arg Gln Trp Gly Gly Val Thr Thr Phe Trp
            35                  40                  45

Lys Val Pro Leu Ile Leu Val Pro Lys Gln Thr Pro Ile Asp Val Asn
        50                  55                  60

Gly Val Glu Thr Trp Lys Ser Pro Val Lys Pro Leu Ser Thr Pro Ile
65                  70                  75                  80

Asp Val Leu Pro Lys Pro His His Gly Asn Ser Asp Asp Tyr Val
                85                  90                  95

Asp Val Leu Pro Ser Arg Lys Val Pro Gly His Val Leu Gly Ile Met
            100                 105                 110

Pro Gly Gly Pro Phe Thr Val Ile Asp Val Asn Arg Gly Arg Thr Trp
```

```
              115                 120                 125
    His Met Ile His Leu Met Tyr Cys Gln Val Gly Ser Leu Pro Ile Val
        130                 135                 140

His Pro Leu Thr Ser Met Glu Ser Pro Tyr Trp Arg Tyr Tyr Gly Asn
    145                 150                 155                 160

Ile Arg His Tyr Arg Gln Trp Ala Gly Val Val Gly Arg Ser Ala Arg
                    165                 170                 175

Arg Ala Ile Tyr Arg Lys Leu Cys Asn Ala Glu Leu His Ile Trp Ala
                    180                 185                 190

Met Asn Pro Arg Asn Leu Leu Leu Ile Thr Ser Gln Ser Met Ser Thr
                195                 200                 205

Arg Met Arg Gln Pro Met Leu Gln Tyr Lys Arg Lys Ser Met Ser Ile
        210                 215                 220

Gln His Phe Arg Val Ala Leu Ile Pro Phe Phe Ala Ala Phe Cys Leu
    225                 230                 235                 240

Pro Val Phe Ala His Pro Glu Thr Leu Val Lys Val Lys Asp Ala Glu
                    245                 250                 255

Asp Gln Leu Gly Ala Arg Val Gly Tyr Ile Glu Leu Asp Leu Asn Ser
                260                 265                 270

Gly Lys Ile Leu Glu Ser Phe Arg Pro Glu Glu Arg Phe Pro Met Met
            275                 280                 285

Ser Thr Phe Lys Val Leu Leu Cys Gly Ala Val Leu Ser Arg Val Asp
        290                 295                 300

Ala Gly Gln Glu Gln Leu Gly Arg Arg Ile His Tyr Ser Gln Asn Asp
    305                 310                 315                 320

Leu Val Glu Tyr Ser Pro Val Thr Glu Lys His Leu Thr Asp Gly Met
                    325                 330                 335

Thr Val Arg Glu Leu Cys Ser Ala Ala Ile Thr Met Ser Asp Asn Thr
                340                 345                 350

Ala Ala Asn Leu Leu Leu Thr Thr Ile Gly Gly Pro Lys Glu Leu Thr
            355                 360                 365

Ala Phe Leu His Asn Met Gly Asp His Val Thr Arg Leu Asp Arg Trp
        370                 375                 380

Glu Pro Glu Leu Asn Glu Ala Ile Pro Asn Asp Glu Arg Asp Thr Thr
    385                 390                 395                 400

Met Pro Val Ala Met Ala Thr Thr Leu Arg Lys Leu Leu Thr Gly Glu
                    405                 410                 415

Leu Leu Thr Leu Ala Ser Arg Gln Gln Leu Ile Asp Trp Met Glu Ala
                420                 425                 430

Asp Lys Val Ala Gly Pro Leu Leu Arg Ser Ala Leu Pro Ala Gly Trp
            435                 440                 445

Phe Ile Ala Asp Lys Ser Gly Ala Gly Glu Arg Gly Ser Arg Gly Ile
        450                 455                 460

Ile Ala Ala Leu Gly Pro Asp Gly Lys Pro Ser Arg Ile Val Val Ile
    465                 470                 475                 480

Tyr Thr Thr Gly Ser Gln Ala Thr Met Asp Glu Arg Asn Arg Gln Ile
                    485                 490                 495

Ala Glu Ile Gly Ala Ser Leu Ile Lys His Trp Leu Ser Asp Gln Val
                500                 505                 510

Tyr Ser Tyr Ile Leu Ile Asp Leu Lys Leu His Phe Phe Lys Arg Ile
            515                 520                 525

Val Lys Ile Leu Phe Asp Asn Leu Met Thr Lys Ile Pro Arg Glu Phe
        530                 535                 540
```

-continued

```
Ser Phe His Ala Ser Asp Pro Val Glu Lys Ile Lys Gly Ser Ser Asp
545                 550                 555                 560

Pro Phe Leu Arg Val Ile Cys Cys Leu Gln Thr Lys Lys Pro Pro
            565                 570                 575

Leu Pro Ala Val Val Cys Leu Pro Asp Gln Glu Leu Pro Thr Leu Phe
            580                 585                 590

Pro Lys Val Thr Gly Phe Ser Arg Ala Gln Ile Pro Asn Thr Val Leu
            595                 600                 605

Leu Val Pro Leu Gly His His Phe Lys Asn Ser Val Ala Pro Pro Thr
            610                 615                 620

Tyr Leu Ala Leu Leu Ile Leu Leu Pro Val Ala Ala Ser Gly Asp
625                 630                 635                 640

Lys Ser Cys Leu Thr Gly Leu Asp Ser Arg Arg Leu Pro Asp Lys Ala
            645                 650                 655

Gln Arg Ser Gly Thr Gly Ser Cys Thr Gln Pro Ser Leu Glu Arg
            660                 665                 670

Thr Thr Tyr Thr Glu Leu Arg Tyr Leu Gln Arg Glu His Glu Ser Ala
            675                 680                 685

Thr Leu Pro Glu Gly Arg Lys Ala Asp Arg Tyr Pro Val Ser Gly Arg
            690                 695                 700

Val Gly Thr Gly Glu Arg Thr Arg Glu Leu Pro Gly Gly Asn Ala Trp
705                 710                 715                 720

Tyr Leu Tyr Ser Pro Val Gly Phe Arg His Leu Leu Glu Arg Arg Phe
            725                 730                 735

Leu Cys Ser Ser Gly Gly Arg Ser Leu Trp Lys Asn Ala Ser Asn Ala
            740                 745                 750

Ala Phe Leu Arg Phe Leu Ala Phe Cys Trp Pro Phe Ala His Met Phe
            755                 760                 765

Phe Pro Ala Leu Ser Pro Asp Ser Val Asp Asn Arg Ile Thr Ala Phe
            770                 775                 780

Glu Ala Asp Thr Ala Arg Arg Ser Arg Thr Thr Glu Arg Ser Glu Ser
785                 790                 795                 800

Val Ser Glu Glu Ala Glu Glu Arg Pro Ile Arg Lys Pro Pro Leu Pro
            805                 810                 815

Ala Arg Trp Pro Ile His Cys Ser Trp His Asp Arg Phe Pro Asp Trp
            820                 825                 830

Lys Ala Gly Ser Glu Arg Asn Ala Ile Asn Val Ser Leu Thr His Ala
            835                 840                 845

Pro Gln Ala Leu His Phe Met Leu Pro Ala Arg Met Leu Cys Gly Ile
850                 855                 860

Val Ser Gly Gln Phe His Thr Gly Asn Ser Tyr Asp His Asp Tyr Ala
865                 870                 875                 880

Lys Leu Ser Arg Glu Leu Phe Ala Lys Ala Ser Lys Lys Ala Ser
            885                 890                 895

Ser Leu Leu Leu Glu Leu Arg Gly Arg Gly Leu Gly Leu Cys Ile
            900                 905                 910

Asn Lys Lys Asn Ser Ala Met Gly Arg Met Gly Gly Thr Gly Arg
            915                 920                 925

Ser Gly Arg Asp Gly Arg Ser Gly Arg Asp Tyr Gly Cys Leu Ile Glu
            930                 935                 940

Met His Ala Leu His Thr Ser Ala Cys Trp Gly Ala Trp Gly Leu Ser
945                 950                 955                 960
```

-continued

```
Thr Pro Gly Cys Leu Ile Glu Met His Ala Leu His Thr Ser Ala Cys
            965                 970                 975

Trp Gly Ala Trp Gly Leu Ser Thr Pro Leu Thr His Ile Ser Glu Asp
            980                 985                 990

Leu Asp Met Ile Arg Tyr Ile Asp Glu Phe Gly Gln Thr Thr Thr Arg
            995                1000                1005

Met Gln Lys Lys Cys Phe Ile Cys Glu Ile Cys Asp Ala Ile Ala
   1010                1015                1020

Leu Phe Val Thr Ile Ile Ser Cys Asn Lys Gln Val Asn Asn Asn
   1025                1030                1035

Asn Cys Ile His Phe Met Phe Gln Val Gln Gly Glu Val Trp Glu
   1040                1045                1050

Val Phe Ser Lys Asn Leu Tyr Lys Cys Gly Met Ala Asp Tyr Asp
   1055                1060                1065

Leu Ser Arg His Tyr Thr Ser Asn Ile Pro Tyr Pro Leu Tyr Lys
   1070                1075                1080

Leu Lys Ser Arg Tyr Thr Ile Phe Glu His Ser Tyr Gln Thr Leu
   1085                1090                1095

Tyr Ala Cys Val Glu Glu Lys Thr Val Cys Tyr Asp Tyr Asn Cys
   1100                1105                1110

Tyr Ala Tyr Leu Arg Leu Gln Asn Ile Phe Pro Phe Ser Cys Ile
   1115                1120                1125

Ala Val Gln Leu Phe Pro Leu Trp Cys Lys Gln Ser Lys Gln Glu
   1130                1135                1140

Phe Tyr Tyr Thr Gln His Asp Ser Lys Asn Leu Ala Ile Leu Lys
   1145                1150                1155

Glu Ser Pro Trp Gly Leu Leu Pro Phe Ser Ser Phe Leu Glu Glu
   1160                1165                1170

Asn Val Glu Ser Gln Gln Pro His His His Met Ala Phe Leu Leu
   1175                1180                1185

Ser Lys Thr Gly Phe Pro His Arg His Ser Thr Thr Ala Pro Ile
   1190                1195                1200

His Gln Phe His Arg Leu Glu Ser Lys Ile His Lys Gln Leu Glu
   1205                1210                1215

Ser Val Val His Ile Ile His Leu Lys Ile Leu Tyr Leu Pro Ser
   1220                1225                1230

Phe Lys Ser Leu Val Val Cys Pro Ile Met Ser His His Arg Ser
   1235                1240                1245

Lys Val Pro Ser Gln Arg Ser Ser Ser Ala Gln Leu Thr Leu Thr
   1250                1255                1260

Lys Gly Asn Lys Ser Trp Ser Ser Thr Ala Val Ala Ala Ala Leu
   1265                1270                1275

Glu Leu Val Asp Pro Pro Gly Cys Arg Asn Ser Ile Ser Ser Leu
   1280                1285                1290

<210> SEQ ID NO 293
<211> LENGTH: 1279
<212> TYPE: PRT
<213> ORGANISM: Homo sapiens

<400> SEQUENCE: 293

Gly Leu Pro Ile Val Ser Arg Ile Asn Phe Asp Lys Pro Val Lys Gln
1               5                  10                  15

Trp Val Leu Leu Ala Arg Glu Leu Cys Leu Tyr Arg Pro Pro Thr Val
                20                  25                  30
```

```
His Ala Tyr Arg Pro Phe Ala Ser Met Gly Arg Ser Cys Tyr Asp Ile
         35                  40                  45

Leu Glu Ser Pro Val Asp Phe Gly Ala Lys Thr Asn Ser His Arg Gln
 50                  55                  60

Trp Gly Gly Asp Leu Glu Ile Pro Val Ser Gln Thr Ala Ile His Ala
 65                  70                  75                  80

His Cys Thr Ala Lys Thr Ala Ser Pro Trp Arg Leu Ile Arg Arg Cys
                 85                  90                  95

Thr Ala Lys Glu Ser Pro Ile Arg Ser Cys Thr Gly His Asn Ala Arg
             100                 105                 110

Arg Ala Ile Tyr Arg His Arg Gln Gly Ala Tyr Leu Ala Tyr Asp Thr
         115                 120                 125

Leu Asp Val Leu Pro Ser Gly Gln Phe Thr Val Asn Ser Pro Pro Ile
130                 135                 140

Asp Val Asn Gly Lys Ser Leu Leu Ala Leu Leu Trp Glu His Thr Ser
145                 150                 155                 160

Leu Leu Thr Ser Met Gly Gly Arg Trp Ala Val Ser Gln Ala Gly
                 165                 170                 175

His Leu Pro Val Met Arg Gly Thr Pro Tyr Met Gly Tyr Glu Leu Met
             180                 185                 190

Thr Pro Leu Ile Thr Ile Asn Asn Ser Ile Ile Asn Val Asn Ala His
         195                 200                 205

Glu Thr Ile Thr Leu Ile Asn Ala Ser Ile Ile Leu Lys Lys Glu Glu
         210                 215                 220

Tyr Glu Tyr Ser Thr Phe Pro Cys Arg Pro Tyr Ser Leu Phe Cys Gly
225                 230                 235                 240

Ile Leu Pro Ser Cys Phe Cys Ser Pro Arg Asn Ala Gly Glu Ser Lys
                 245                 250                 255

Arg Cys Arg Ser Val Gly Cys Thr Ser Gly Leu His Arg Thr Gly Ser
             260                 265                 270

Gln Gln Arg Asp Pro Glu Phe Ser Pro Arg Arg Thr Phe Ser Asn Asp
         275                 280                 285

Glu His Phe Ser Ser Ala Met Trp Arg Gly Ile Ile Pro Cys Arg Arg
290                 295                 300

Ala Arg Ala Thr Arg Ser Pro His Thr Leu Phe Ser Glu Leu Gly Val
305                 310                 315                 320

Leu Thr Ser His Arg Lys Ala Ser Tyr Gly Trp His Asp Ser Lys Arg
                 325                 330                 335

Ile Met Gln Cys Cys His Asn His Glu His Cys Gly Gln Leu Thr Ser
             340                 345                 350

Asp Asn Asp Arg Arg Thr Glu Gly Ala Asn Arg Phe Ala Gln His
         355                 360                 365

Gly Gly Ser Cys Asn Ser Pro Ser Leu Gly Thr Gly Ala Glu Ser His
         370                 375                 380

Thr Lys Arg Arg Ala His His Asp Ala Cys Ser Asn Gly Asn Val
385                 390                 395                 400

Ala Gln Thr Ile Asn Trp Arg Thr Thr Tyr Ser Ser Phe Pro Ala Thr
                 405                 410                 415

Ile Asn Arg Leu Asp Gly Gly Ser Cys Arg Thr Thr Ser Ala Leu
             420                 425                 430

Gly Pro Ser Gly Trp Leu Val Tyr Cys Ile Trp Ser Arg Ala Trp Val
         435                 440                 445
```

```
Ser Arg Tyr His Cys Ser Thr Gly Ala Arg Trp Ala Leu Pro Tyr Arg
    450                 455                 460
Ser Tyr Leu His Asp Gly Glu Ser Gly Asn Tyr Gly Thr Lys Thr Asp
465                 470                 475                 480
Arg Asp Arg Cys Leu Thr Asp Ala Leu Val Thr Val Arg Pro Ser Leu
                485                 490                 495
Leu Ile Tyr Thr Leu Asp Phe Lys Thr Ser Phe Leu Ile Lys Asp Leu
            500                 505                 510
Gly Glu Asp Pro Phe Ser His Asp Gln Asn Pro Leu Thr Val Phe Val
        515                 520                 525
Pro Leu Ser Val Arg Pro Arg Lys Asp Gln Arg Ile Phe Leu Arg
    530                 535                 540
Ser Phe Phe Ser Ala Arg Asn Leu Leu Leu Ala Asn Lys Lys Thr Thr
545                 550                 555                 560
Ala Thr Ser Gly Gly Leu Phe Ala Gly Ser Arg Ala Thr Asn Ser Phe
                565                 570                 575
Ser Glu Gly Asn Trp Leu Gln Gln Ser Ala Asp Thr Lys Tyr Cys Pro
            580                 585                 590
Ser Ser Val Ala Val Arg Pro Leu Gln Glu Leu Cys Ser Thr
        595                 600                 605
Ala Tyr Ile Pro Arg Ser Ala Asn Pro Val Thr Ser Gly Cys Cys Gln
    610                 615                 620
Trp Arg Val Val Ser Tyr Arg Val Gly Leu Lys Thr Ile Val Thr Gly
625                 630                 635                 640
Gly Ala Ala Val Gly Leu Asn Gly Gly Phe Val His Thr Ala Gln Leu
                645                 650                 655
Gly Ala Asn Asp Leu His Arg Thr Glu Ile Pro Thr Ala Ala Leu Arg
            660                 665                 670
Lys Arg His Ala Ser Arg Arg Glu Lys Gly Gly Gln Val Ser Gly Lys
        675                 680                 685
Arg Gln Gly Arg Asn Arg Arg Ala His Glu Gly Ala Ser Arg Gly Lys
    690                 695                 700
Arg Leu Val Ser Leu Ser Cys Arg Val Ser Pro Leu Thr Ala Ser
705                 710                 715                 720
Ile Phe Val Met Leu Val Arg Gly Ala Glu Pro Met Glu Lys Arg Gln
                725                 730                 735
Gln Arg Gly Leu Phe Thr Val Pro Gly Leu Leu Leu Ala Phe Cys Ser
            740                 745                 750
His Val Leu Ser Cys Val Ile Pro Phe Cys Gly Pro Tyr Tyr Arg Leu
        755                 760                 765
Val Ser Tyr Arg Ser Pro Gln Pro Asn Asp Arg Ala Gln Arg Val Ser
    770                 775                 780
Glu Arg Gly Ser Gly Arg Ala Pro Asn Thr Gln Thr Ala Ser Pro Arg
785                 790                 795                 800
Ala Leu Ala Asp Ser Leu Met Gln Leu Ala Arg Gln Val Ser Arg Leu
                805                 810                 815
Glu Ser Gly Gln Ala Gln Arg Asn Cys Glu Leu Ala His Ser Leu Gly
            820                 825                 830
Thr Pro Gly Phe Thr Leu Tyr Ala Ser Gly Ser Tyr Val Val Trp Asn
        835                 840                 845
Cys Glu Arg Ile Thr Ile Ser His Arg Lys Gln Leu Pro Leu Arg Gln
    850                 855                 860
Ala Leu Glu Gly Ala Phe Cys Lys Ser Leu Gly Leu Gln Lys Ser Leu
```

```
865                 870                875                 880
Leu Thr Thr Ser Gly Ile Ala Gln Arg Pro Arg Pro Arg Pro Leu
                885                 890                 895

His Lys Lys Lys Leu Val Ser His Gly Ala Glu Asn Gly Arg Asn Trp
        900                 905                 910

Ala Glu Leu Gly Ala Gly Trp Ala Glu Leu Gly Ala Gly Leu Trp Leu
        915                 920                 925

Leu Thr Asn Asp Ala Cys Phe Ala Tyr Phe Cys Leu Leu Gly Ser Leu
    930                 935                 940

Gly Thr Phe His Thr Trp Leu Leu Thr Asn Asp Ala Cys Phe Ala Tyr
945                 950                 955                 960

Phe Cys Leu Leu Gly Ser Leu Gly Thr Phe His Thr Leu Thr Asp Thr
                965                 970                 975

His Phe Gly Arg Ser Arg His Asp Lys Ile His Val Trp Thr Asn His
            980                 985                 990

Asn Asn Ala Val Lys Lys Met Leu Tyr Leu Asn Leu Cys Tyr Cys Phe
        995                 1000                1005

Ile Cys Asn His Tyr Lys Leu Gln Thr Ser Gln Gln Gln Leu His
    1010                1015                1020

Ser Phe Tyr Val Ser Gly Ser Gly Gly Gly Val Gly Gly Phe Leu
    1025                1030                1035

Lys Gln Val Lys Pro Leu Gln Met Trp Tyr Gly Leu Ser Leu Val
    1040                1045                1050

Lys Ala Leu Tyr Ile Lys Tyr Ser Leu Leu Thr Pro Leu Gln Ile
    1055                1060                1065

Lys Lys Leu Lys Val His Asn Phe Ala Leu Leu Ile Ala Asp Thr
    1070                1075                1080

Leu Cys Leu Cys Gly Val Arg Lys Asn Ser Met Leu Leu Leu Leu
    1085                1090                1095

Cys Leu Leu Ile Lys Val Thr Glu Tyr Phe Ser Ile Ile Phe Leu
    1100                1105                1110

Tyr Ser Ser Ala Ala Phe Ser Phe Val Val Ile Ala Lys Gln Ala
    1115                1120                1125

Arg Val Leu Leu Leu Asn Thr Ala Leu Lys Lys Leu Ser Asn Ser
    1130                1135                1140

Glu Gly Lys Ser Leu Gly Ser Ser Thr Phe Leu Phe Phe Phe Gly
    1145                1150                1155

Gly Val Glu Cys Glu Ser Ala Val Ala Ser Ser Leu Asp Gly
    1160                1165                1170

Ile Ser Ser Glu Gln Asn Arg Phe Ser Ser Leu Lys Ala Phe His
    1175                1180                1185

His Cys Ser His Ser Ser Val Pro Val Gly Ile Asn Thr Gln Thr
    1190                1195                1200

Ile Arg Ile Ser Ser Leu Thr His Tyr Thr Leu Lys Asn Phe Ile
    1205                1210                1215

Phe Thr Leu Glu Leu Ile Ser Val Gly Ser Leu Ser Asn Tyr Val
    1220                1225                1230

Thr Pro Gln Lys Gly Ser Phe Thr Lys Ile Leu Arg Ala Ile Asn
    1235                1240                1245

Pro His Arg Glu Gln Lys Leu Glu Leu His Arg Gly Gly Gly Arg
    1250                1255                1260

Ser Arg Thr Ser Gly Ser Pro Gly Leu Gln Glu Phe Asp Ile Lys
    1265                1270                1275
```

Leu

<210> SEQ ID NO 294
<211> LENGTH: 1284
<212> TYPE: PRT
<213> ORGANISM: Homo sapiens

<400> SEQUENCE: 294

```
Gly Ser Pro Tyr Ser Glu Ser Tyr Phe Arg Ala Ser Ala Val Gly Ser
1               5                   10                  15
Leu Val Ser Gln Arg Ala Leu Leu Ile Thr Ser His Arg Thr Arg Leu
            20                  25                  30
Pro Pro Ile Cys Val Asn Gly Ala Glu Leu Leu Arg His Phe Gly Lys
        35                  40                  45
Ser Arg Phe Trp Cys Gln Asn Lys Leu Pro Leu Thr Ser Met Gly Trp
    50                  55                  60
Arg Leu Gly Asn Pro Arg Glu Ser Asn Arg Tyr Pro Arg Pro Leu Met
65                  70                  75                  80
Tyr Cys Gln Asn Arg Ile Thr Met Val Ile Ala Met Thr Asn Thr Met
                85                  90                  95
Tyr Cys Gln Val Gly Lys Ser His Lys Val Met Tyr Trp Ala Cys Gln
            100                 105                 110
Ala Gly His Leu Pro Ser Leu Thr Ser Ile Gly Gly Val Leu Gly Ile
        115                 120                 125
Tyr Thr Cys Thr Ala Lys Trp Ala Val Tyr Arg Lys Ser Thr His Arg
    130                 135                 140
Gln Trp Lys Val Pro Ile Gly Val Thr Met Gly Thr Tyr Val Ile Ile
145                 150                 155                 160
Asp Val Asn Gly Arg Gly Ser Leu Gly Gly Gln Pro Gly Gly Pro Phe
                165                 170                 175
Thr Val Ser Tyr Val Thr Arg Asn Ser Ile Tyr Gly Leu Thr Asn Asp
            180                 185                 190
Pro Val Ile Asp Tyr Tyr Leu Val Asn Asn Gln Cys Gln Arg Ala Asp
        195                 200                 205
Asn Asn Pro Asp Lys Cys Phe Asn Asn Ile Glu Lys Gly Arg Val Val
    210                 215                 220
Phe Asn Ile Ser Val Ser Pro Leu Phe Pro Phe Leu Arg His Phe Ala
225                 230                 235                 240
Phe Leu Phe Leu Leu Thr Gln Lys Arg Trp Lys Lys Met Leu Lys Ile
                245                 250                 255
Ser Trp Val His Glu Trp Val Thr Ser Asn Trp Ile Ser Thr Ala Val
            260                 265                 270
Arg Ser Leu Arg Val Phe Ala Pro Lys Asn Val Phe Gln Ala Leu Leu
        275                 280                 285
Lys Phe Cys Tyr Val Ala Arg Tyr Tyr Pro Val Leu Thr Pro Gly Lys
    290                 295                 300
Ser Asn Ser Val Ala Ala Tyr Thr Ile Leu Arg Met Thr Trp Leu Ser
305                 310                 315                 320
Thr His Gln Ser Gln Lys Ser Ile Leu Arg Met Ala Gln Glu Asn Tyr
                325                 330                 335
Ala Val Leu Pro Pro Val Ile Thr Leu Arg Pro Thr Tyr Phe Gln Arg
            340                 345                 350
Ser Glu Asp Arg Arg Ser Pro Leu Phe Cys Thr Thr Trp Gly Ile Met
        355                 360                 365
```

-continued

```
Leu Ala Leu Ile Val Gly Asn Arg Ser Met Lys Pro Tyr Gln Thr Thr
    370                 375                 380

Ser Val Thr Pro Arg Cys Leu Gln Trp Gln Gln Arg Cys Ala Asn Tyr
385                 390                 395                 400

Leu Ala Asn Tyr Leu Leu Pro Gly Asn Asn Thr Gly Trp Arg Arg
            405                 410                 415

Ile Lys Leu Gln Asp His Phe Cys Ala Arg Pro Phe Arg Leu Ala Gly
            420                 425                 430

Leu Leu Leu Ile Asn Leu Glu Pro Val Ser Val Gly Leu Ala Val Ser
        435                 440                 445

Leu Gln His Trp Gly Gln Met Val Ser Pro Pro Val Ser Leu Ser Thr
    450                 455                 460

Arg Arg Gly Val Arg Gln Leu Trp Met Asn Glu Ile Asp Arg Ser Leu
465                 470                 475                 480

Arg Val Pro His Leu Ser Ile Gly Asn Cys Gln Thr Lys Phe Thr His
            485                 490                 495

Ile Tyr Phe Arg Leu Ile Asn Phe Ile Phe Asn Leu Lys Gly Ser Arg
            500                 505                 510

Arg Ser Phe Leu Ile Ile Ser Pro Lys Ser Leu Asn Val Ser Phe Arg
        515                 520                 525

Ser Thr Glu Arg Gln Thr Pro Lys Arg Ser Lys Asp Leu Leu Glu Ile
    530                 535                 540

Leu Phe Phe Cys Ala Ser Ala Ala Cys Lys Gln Lys Asn His Arg Tyr
545                 550                 555                 560

Gln Arg Trp Phe Val Cys Arg Ile Lys Ser Tyr Gln Leu Phe Phe Arg
            565                 570                 575

Arg Leu Ala Ser Ala Glu Arg Arg Tyr Gln Ile Leu Ser Phe Cys Ser
            580                 585                 590

Arg Ser Ala Thr Thr Ser Arg Thr Leu His Arg Leu His Thr Ser Leu
        595                 600                 605

Cys Ser Cys Tyr Gln Trp Leu Leu Pro Val Ala Ile Ser Arg Val Leu
    610                 615                 620

Pro Gly Trp Thr Gln Asp Asp Ser Tyr Arg Ile Arg Arg Ser Gly Arg
625                 630                 635                 640

Ala Glu Arg Gly Val Arg Ala His Ser Pro Ala Trp Ser Glu Arg Pro
            645                 650                 655

Thr Pro Asn Asp Thr Tyr Ser Val Ser Ile Glu Lys Ala Pro Arg Phe
            660                 665                 670

Pro Lys Gly Glu Arg Arg Thr Gly Ile Arg Ala Ala Gly Ser Glu Gln
        675                 680                 685

Glu Ser Ala Arg Gly Ser Phe Gln Gly Glu Thr Pro Gly Ile Phe Ile
    690                 695                 700

Val Leu Ser Gly Phe Ala Thr Ser Asp Leu Ser Val Asp Phe Cys Asp
705                 710                 715                 720

Ala Arg Gln Gly Gly Gly Ala Tyr Gly Lys Thr Pro Ala Thr Arg Pro
            725                 730                 735

Phe Tyr Gly Ser Trp Pro Phe Ala Gly Leu Leu Leu Thr Cys Ser Phe
            740                 745                 750

Leu Arg Tyr Pro Leu Ile Leu Trp Ile Thr Val Leu Pro Pro Leu Ser
        755                 760                 765

Glu Leu Ile Pro Leu Ala Ala Ala Glu Arg Pro Ser Ala Ala Ser Gln
    770                 775                 780
```

-continued

```
Ala Arg Lys Arg Lys Ser Ala Gln Tyr Ala Asn Arg Leu Ser Pro Arg
785                 790                 795                 800

Val Gly Arg Phe Ile Asn Ala Ala Gly Thr Thr Gly Phe Pro Thr Gly
                805                 810                 815

Lys Arg Ala Val Ser Ala Thr Gln Leu Met Val Ser Ser Leu Ile Arg
                820                 825                 830

His Pro Arg Leu Tyr Thr Leu Cys Phe Arg Leu Val Cys Cys Val Glu
                835                 840                 845

Leu Ala Asp Asn Asn Phe Thr Gln Glu Thr Ala Met Thr Met Ile Thr
850                 855                 860

Pro Ser Ser Arg Gly Ser Phe Leu Gln Lys Pro Arg Pro Pro Lys Lys
865                 870                 875                 880

Pro Pro His Tyr Phe Trp Asn Ser Ser Glu Ala Glu Ala Ala Ser Ala
                885                 890                 895

Ser Ala Ile Lys Lys Ile Ser Gln Pro Trp Gly Gly Glu Trp Ala Glu
                900                 905                 910

Leu Gly Gly Val Arg Gly Gly Met Gly Gly Val Arg Gly Gly Thr Met
                915                 920                 925

Val Ala Asp Leu Arg Cys Met Leu Cys Ile Leu Leu Pro Ala Gly Glu
930                 935                 940

Pro Gly Asp Phe Pro His Leu Val Ala Asp Leu Arg Cys Met Leu Cys
945                 950                 955                 960

Ile Leu Leu Pro Ala Gly Glu Pro Gly Asp Phe Pro His Pro Asn His
                965                 970                 975

Thr Phe Arg Lys Ile Thr Asp Thr Leu Met Ser Leu Asp Lys Pro Gln
                980                 985                 990

Leu Glu Cys Ser Glu Lys Asn Ala  Leu Phe Val Lys Phe  Val Met Leu
                995                 1000                1005

Leu Leu  Tyr Leu Pro Leu Ala  Ala Ile Asn Lys Leu  Thr Thr Thr
    1010                1015                1020

Ile Ala  Phe Ile Leu Cys Phe  Arg Phe Arg Gly Arg  Cys Gly Arg
    1025                1030                1035

Phe Phe  Lys Ala Ser Lys Thr  Ser Thr Asn Val Val  Trp Leu Ile
    1040                1045                1050

Met Ile  Ser Ser Gln Gly Thr  Ile His Gln Ile Phe  Leu Ile Asn
    1055                1060                1065

Pro Phe  Thr Asn Lys Ala Lys  Gly Thr Gln Phe Leu  Ser Ile Val
    1070                1075                1080

Ile Asn  Ser Arg His Ser Met  Pro Val Trp Ser Lys  Lys Lys Gln
    1085                1090                1095

Tyr Val  Met Ile Ile Thr Val  Met Pro Thr Tyr Lys  Gly Tyr Arg
    1100                1105                1110

Ile Phe  Phe His Asn Phe Leu  Val Gln Cys Ser Phe  Phe Leu Cys
    1115                1120                1125

Gly Val  Asn Ser Lys Ala Ser  Lys Ser Ser Ile Thr  Lys His Ser
    1130                1135                1140

Met Thr  Gln Lys Thr Gln Phe  Arg Lys Val Leu Gly  Val Phe Tyr
    1145                1150                1155

Leu Ser  Leu Leu Phe Trp Arg  Ser Arg Met Leu Arg  Val Ser Ser
    1160                1165                1170

Ser Leu  Ile Ile Thr Arg Trp  His Phe Phe Ala Lys  Gln Val Phe
    1175                1180                1185

Leu Ile  Lys Gly Ile Pro Pro  Leu Leu Pro Phe Ile  Ser Ser Ile
```

-continued

```
                1190              1195              1200

Gly Trp Asn Leu Lys Tyr Thr Asn Asn Asn Gln Phe Asn Thr Leu
    1205             1210             1215

Tyr Thr Lys Phe Tyr Ile Tyr Leu Arg Ala Leu Asn Leu Cys Arg
    1220             1225             1230

Phe Val Gln Leu Cys His Thr Thr Glu Val Arg Phe Leu His Lys
    1235             1240             1245

Asp Pro Leu Ala Arg Asn Pro Ser Leu Lys Gly Thr Lys Ala Gly
    1250             1255             1260

Ala Pro Pro Arg Trp Arg Pro Leu Asn Trp Ile Pro Arg Ala Ala
    1265             1270             1275

Gly Ile Arg Tyr Gln Ala
    1280
```

What is claimed is:

1. A method for creating a non-endogenous, constitutively active version of an endogenous human G protein coupled receptor (GPCR), said endogenous GPCR comprising a transmembrane 6 region and an intracellular loop 3 region, the method consisting essentially of:

(a) selecting an endogenous human GPCR comprising a proline residue in the transmembrane-6 region;

(b) identifying the endogenous 16$^{th}$ amino acid residue from the proline residue of step (a), in a carboxy-terminus to amino-terminus direction;

(c) altering only the identified amino acid residue of step (b) to a non-endogenous amino acid residue to create a non-endogenous version of the endogenous human GPCR; and (d) determining if the non-endogenous version of the endogenous human GPCR of step (c) is constitutively active by measuring a difference in an intracellular signal measured for the non-endogenous version as compared with a signal induced by the endogenous human GPCR.

2. The method of claim 1 wherein the amino acid residue that is two residues from said proline residue in the transmembrane 6 region, in a carboxy-terminus to amino-terminus direction, is tryptophan.

* * * * *